(12) United States Patent
Nishitani et al.

(10) Patent No.: US 9,334,289 B2
(45) Date of Patent: May 10, 2016

(54) CEPHEM COMPOUND HAVING CATECHOL OR PSEUDO-CATECHOL STRUCTURE

(75) Inventors: Yasuhiro Nishitani, Toyonaka (JP); Toshiaki Aoki, Toyonaka (JP); Jun Sato, Toyonaka (JP); Kenji Yamawaki, Toyonaka (JP); Katsuki Yokoo, Toyonaka (JP); Masayuki Sano, Toyonaka (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 14/113,459

(22) PCT Filed: Apr. 25, 2012

(86) PCT No.: PCT/JP2012/061053
§ 371 (c)(1),
(2), (4) Date: Dec. 10, 2013

(87) PCT Pub. No.: WO2012/147773
PCT Pub. Date: Nov. 1, 2012

(65) Prior Publication Data
US 2014/0088302 A1  Mar. 27, 2014

(30) Foreign Application Priority Data

Apr. 28, 2011 (JP) .................................. 2011-101530
Jun. 27, 2011 (JP) .................................. 2011-142005

(51) Int. Cl.
| | | |
|---|---|---|
| C07D 501/16 | (2006.01) | |
| C07D 501/60 | (2006.01) | |
| C07D 501/18 | (2006.01) | |
| C07D 501/46 | (2006.01) | |
| C07D 519/06 | (2006.01) | |
| C07D 519/00 | (2006.01) | |

(52) U.S. Cl.
CPC ............ *C07D 501/60* (2013.01); *C07D 501/18* (2013.01); *C07D 501/46* (2013.01); *C07D 519/00* (2013.01); *C07D 519/06* (2013.01)

(58) Field of Classification Search
CPC .................................................. C07D 501/16
See application file for complete search history.

(56) References Cited

U.S. PATENT DOCUMENTS

| | | |
|---|---|---|
| 3,966,719 A | 6/1976 | Barth |
| 4,039,532 A | 8/1977 | Barth |
| 4,045,436 A | 8/1977 | Barth |
| 4,045,437 A | 8/1977 | Barth |
| 4,110,327 A | 8/1978 | Saikawa et al. |
| 4,327,097 A | 4/1982 | Saikawa et al. |
| 4,410,522 A | 10/1983 | Saikawa et al. |
| 4,684,641 A | 8/1987 | Greengrass et al. |
| 5,028,427 A | 7/1991 | Finch |
| 5,126,336 A | 6/1992 | Imae et al. |
| 5,143,910 A | 9/1992 | Onoue et al. |
| 5,378,697 A | 1/1995 | Chantot et al. |
| 5,538,963 A | 7/1996 | Chantot et al. |
| 5,621,095 A | 4/1997 | Chantot et al. |
| 2011/0190254 A1* | 8/2011 | Nishitani et al. ............... 514/202 |
| 2013/0079319 A1 | 3/2013 | Yamawaki et al. |
| 2013/0096299 A1 | 4/2013 | Kusano et al. |
| 2013/0102583 A1 | 4/2013 | Hisakawa et al. |

FOREIGN PATENT DOCUMENTS

| | | |
|---|---|---|
| CN | 101108858 A | 1/2008 |
| DE | 2 355 209 | 5/1974 |
| EP | 0 114 752 | 8/1984 |
| EP | 0 168 177 | 1/1986 |
| EP | 0 207 447 | 1/1987 |
| EP | 0 211 656 | 2/1987 |
| EP | 0 237 735 A2 | 9/1987 |
| EP | 0 305 111 | 3/1989 |
| EP | 0 345 671 | 12/1989 |
| EP | 0 472 060 | 2/1992 |
| EP | 1 489 084 | 12/2004 |
| GB | 1 449 290 | 9/1976 |
| GB | 1 455 016 | 11/1976 |

(Continued)

OTHER PUBLICATIONS

Yamano et al. Appl. Micro. Biotech, 1994, 40 (6) pp. 892-897.
Takeda et al. The Journal of Antibiotics, 2008, 61(1), pp. 36-39.
Hashizume et al. The Journal of Antibiotics, 1990, 43 (12), pp. 1617-1620.
Weissberger et al. The Journal of Antibiotics, 1989, 42 (5), pp. 795-806,.
Branch et al. The Journal of Antibiotics, 1987, 40 (5), pp. 646-651.
Fletcher et al. American Review of Respiratory Disease, 1990, 141 (3), pp. 672-677.
Yoshida et al. The Journal of Antibiotics, 1986, 39, pp. 76-89.
Blaszczak et al. *Journal of Medicinal Chemistry*, vol. 33, No. 6, pp. 1656-1662 (1990).

(Continued)

*Primary Examiner* — Noble Jarrell
*Assistant Examiner* — John S Kenyon
(74) *Attorney, Agent, or Firm* — Hamre, Schumann, Mueller & Larson, P.C.

(57) ABSTRACT

The present invention provides a novel compound which has a wide antimicrobial spectrum, and in particular exhibits potent antimicrobial activity against beta-lactamase producing Gram negative bacteria. Specifically, the present invention provides a compound of the formula (I):

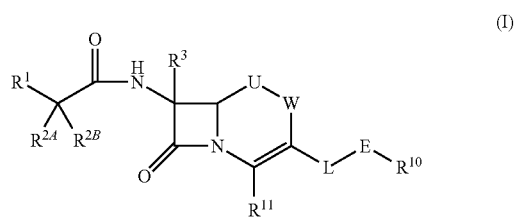

wherein each symbol is as defined in the specification, or an amino-protected compound when the amino group is present on the ring in the 7-side chain, or a pharmaceutically acceptable salt thereof, and a pharmaceutical composition comprising the same.

26 Claims, No Drawings

(56) References Cited

FOREIGN PATENT DOCUMENTS

| | | |
|---|---|---|
| GB | 1 520 479 | 8/1978 |
| GB | 1 520 480 | 8/1978 |
| JP | 57-118588 | 7/1982 |
| JP | 62-30788 | 2/1987 |
| JP | 2-15090 | 1/1990 |
| JP | 2-28185 | 1/1990 |
| JP | 2-117678 | 5/1990 |
| JP | 4-364189 | 12/1992 |
| JP | 5-213971 | 8/1993 |
| WO | WO 92/21683 | 12/1992 |
| WO | WO 2006/104141 | 10/2006 |
| WO | WO 2007/096740 | 8/2007 |
| WO | WO 2007096740 A2 * | 8/2007 |
| WO | WO 2007/119511 | 10/2007 |

OTHER PUBLICATIONS

Smith et al. The Journal of Antibiotics, vol. 48, No. 1, pp. 73-82 (1994).

Long et al. The Journal of Antibiotics, vol. 61, No. 10, pp. 595-602 (2008).

Naito et al. The Journal of Antibiotics, vol. 39, No. 8, pp. 1092-1107 (1986).

Extended European Search Report issued in corresponding European Patent Application No. 12 777 752.2 on Jul. 2, 2015 (15 pages).

* cited by examiner

CEPHEM COMPOUND HAVING CATECHOL OR PSEUDO-CATECHOL STRUCTURE

TECHNICAL FIELD

The compounds of the subject invention are related to Cephem compounds, which have a wide antimicrobial spectrum, in particular exhibit potent antimicrobial activity against beta-lactamase producing Gram negative bacteria, and pharmaceutical compositions comprising the same.

BACKGROUND ART

To date, a variety of beta-lactam drugs have been developed and beta-lactam drugs have become clinically extremely important antimicrobial drugs. However, there are increasing number of bacterial types which have obtained resistance against beta-lactam drugs by producing beta-lactamase, which degrade beta-lactam drugs.

According to the Ambler molecular classification, beta-lactamases are largely classified into four classes. Specifically, these are Class A (TEM type, SHV type, CTX-M type, KPC type and the like), Class B (IMP type, VIM type, L-1 type and the like), Class C (AmpC type) and Class D (OXA type and the like). Amongst these, Classes A, C and D types are largely classified into serine-beta-lactamase, on the other hand, Class B type is classified into metallo-beta-lactamase. It has been known that both have respectively different mechanisms to each other in terms of hydrolysis of beta-lactam drugs.

Recently, clinical problem has been occurring due to the existence of Gram negative bacteria which have become highly resistant to a number of beta-lactam drugs including Cephems and Carbapenems by producing Class A (ESBL) and D types serine-beta-lactamases which have an extended substrate spectrum, and Class B type metallo-beta-lactamase which have an extended substrate spectrum. Particularly, metallo-beta-lactamase is known to be one of the causes of obtaining multidrug-resistance in Gram negative bacteria. Cephem compounds which exhibit intermediate activity against metallo-beta-lactamase producing Gram negative bacteria are known (e.g., Patent Document 1 and Non-Patent Document 1). However, there is a demand for development of Cephem compounds which exhibit more potent antimicrobial activity, in particular more effective against a variety of beta-lactamase producing Gram negative bacteria.

One of the known antimicrobials having high anti-Gram negative bactericidal activity is Cephem compounds having a catechol group intramolecularly (e.g., Non-patent Documents 2-4). The action thereof is that the catechol group forms a chelate with $Fe^{3+}$, thereby the compound is efficiently incorporated into the bacterial body through the $Fe^{3+}$ transportation system on the cellular membrane (tonB-dependent iron transport system). Therefore, research has been conducted on compounds having catechol or similar structure thereto, on the 3-side chain or 7-side chain moiety on the Cephem backbone.

Patent Documents 2-8 and Non-patent Document 5 describe compounds having a partial structure of the 7-side chain and a quaternary salt structure on the Cephem backbone. However, these documents merely describe a pyridinium structure, and merely disclose compounds having a formamide group at the 7-position in most cases. Furthermore, for example, most compounds disclosed in Patent Document 2 have a penicillin structure.

Non-patent document 1 and Patent Documents 8-12 and 15 describe catechol type derivatives having a catechol group on the 3-side chain moiety on the Cephem backbone. Patent Documents 10, 11, 13, and 14 describe pseudo-catechol type derivatives having a hydroxypyridone group on the 3-side chain moiety on the Cephem backbone. Patent Documents 16 and 17 disclose Cephem compounds having a quaternary ammonium group, but do not describe a catechol type derivative.

Moreover, in the above documents, which describe Cephem compounds having a catechol group in their structure, there is no description of Class B type metallo-beta-lactamase, and specific antimicrobial activity against a wide variety of Gram negative bacteria including Class B type.

Non-Patent Document 7 describes that penicilin compounds having a tetrazolyl group at position 3 of the penicilin skeleton has superior stability against beta-lactamase. However, a Cephem compound having a tetrazolyl group at position 4 of the penicilin skeleton is not disclosed in this document.

Patent Documents 18, 19, 20 and Non-Patent Document 6 describe Cephem compounds having a tetrazolyl group at position 4 of the penicilin skeleton. However, a compound having a quaternary ammonium group at the 3-side chain is not disclosed in these documents.

On the other hand, the present applicant filed an application of Cephem compounds having catechol type substituents (Patent Documents 21 to 24). Of these documents, Patent Documents 22 to 24 were open to public inspection before the priority date of the present application. However, these applications do not disclose a compound having a tetrazolyl group at position 4 of the cephem skeleton.

PRIOR ART DOCUMENT

Patent Document

[Patent Document 1]
International Publication No. 2007/119511 pamphlet
[Patent Document 2]
German Patent Publication No. 2519400
[Patent Document 3]
Japanese Laid-Open Publication No. 57-118588
[Patent Document 4]
European Patent Application Publication No. 114752
[Patent Document 5]
European Patent Application Publication No. 168177
[Patent Document 6]
European Patent Application Publication No. 211656
[Patent Document 7]
European Patent Application Publication No. 305111
[Patent Document 8]
Japanese Laid-Open Publication No. 4-364189
[Patent Document 9]
Japanese Laid-Open Publication No. 3-173893
[Patent Document 10]
Japanese Laid-Open Publication No. 2-15090
[Patent Document 11]
Japanese Laid-Open Publication No. 2-28187
[Patent Document 12]
Japanese Laid-Open Publication No. 2-117678
[Patent Document 13]
Japanese Laid-Open Publication No. 6-510523
[Patent Document 14]
Japanese Laid-Open Publication No. 5-213971
[Patent Document 15]
Japanese Laid-Open Publication No. 2-28185
[Patent Document 16]
International Publication No. 2007/096740 pamphlet

[Patent Document 17]
International Publication No. 2003/078440 pamphlet
[Patent Document 18]
U.S. Pat. No. 4,039,532
[Patent Document 19]
U.S. Pat. No. 3,966,719
[Patent Document 20]
European Patent Application Publication No. 207447
[Patent Document 21]
International Publication No. 2010/050468 pamphlet
[Patent Document 22]
International Publication No. 2011/125966 pamphlet
[Patent Document 23]
International Publication No. 2011/125967 pamphlet
[Patent Document 24]
International Publication No. 2011/136268 pamphlet Non-Patent Document

[Non-patent document 1]
Applied Microbiology and Biotechnology (1994), 40(6), 892-7
[Non-patent document 2]
The Journal of Antibiotics, vol. 61, pp. 36-39 (2008)
[Non-patent document 3]
The Journal of Antibiotics, vol. 43, pp. 1617-1620 (1990)
[Non-patent document 4]
The Journal of Antibiotics, vol. 42, pp. 795-806 (1989)
[Non-patent document 5]
The Journal of Antibiotics, vol. 40, pp. 646-651 (1987)
[Non-patent document 6]
American Review of Respiratory Disease (1990), 141(3), 672-7
[Non-patent document 7]
The Journal of Antibiotics, Vol. 39, pp. 76-89 (1986)

SUMMARY OF INVENTION

Problems to be Solved by the Invention

The subject invention provides Cephem compounds which exhibit potent antimicrobial spectrum against a variety of bacteria including Gram negative bacteria and/or Gram positive bacteria. Preferably, the subject invention provides Cephem compounds which exhibit potent antimicrobial activity against beta-lactamase producing Gram negative bacteria. More preferably, the subject invention provides Cephem compounds which exhibit potent antimicrobial activity against multidrug-resistant bacteria, in particular, Class B type metallo-beta-lactamase producing Gram negative bacteria. Still more preferably, the subject invention provides Cephem compounds which exhibit effective antimicrobial activity against extended-spectrum beta-lactamase (ESBL) producing bacteria. Furthermore, the subject invention provides Cephem compounds having antimicrobial activity against strains resistant to Cephem compounds having carboxyl group at position 4.

Means for Solving the Problem

The subject invention provides Cephem compounds which have solved the above-mentioned problems by having the following characteristics in structure:

(Item 1)
A compound of the formula (I):

[Chemical Formula 1]

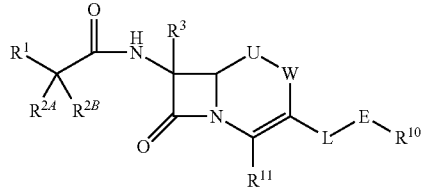

or an amino-protected compound when the amino group is present on the ring in the 7-side chain, or a pharmaceutically acceptable salt thereof,
wherein
W is —CH$_2$—, —S— or —O—;
a) U is —CH$_2$—, —S—, —S(═O)— or —O— when W is —CH$_2$—; or
b) U is —CH$_2$— when H is —S— or —O—;
L is —CH$_2$—, —CH═CH—, —CH$_2$—CH═CH— or —CH═CH—CH$_2$—;
R$^1$ is a substituted or unsubstituted carbocyclic group or a substituted or unsubstituted heterocyclic group;
with regard to R$^{2A}$ and R$^{2B}$,
a) R$^{2A}$ is a hydrogen atom, a substituted or unsubstituted amino group, —SO$_3$H, a substituted or unsubstituted amino sulfonyl group, carboxyl group, a substituted or unsubstituted (lower alkyl)oxycarbonyl group, a substituted or unsubstituted carbamoyl group, hydroxyl group, or a substituted carbonyloxy group; and R$^{23}$ is a hydrogen atom, or
b) R$^{2A}$ and R$^{2B}$ are taken together to form a substituted or unsubstituted methylidene group or a substituted or unsubstituted hydroxyimino group;
R$^3$ is a hydrogen atom, —OCH$_3$ or —NH—CH(═O);
R$^{11}$ is a bioisoster of carboxyl ion (—COO$^-$);
E is a substituted or unsubstituted divalent group having at least one quaternary ammonium ion;
R$^{10}$ is —R$^{22}$ or a group represented by the formula:

[Chemical Formula 2]

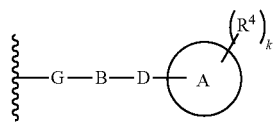

wherein ring A is a benzene ring, or a 6-membered aromatic heterocyclic group having 1-3 nitrogen atoms;
k is an integer from 2 to 5;
each R$^4$ is independently a hydrogen atom, halogen, hydroxyl group, —CN, —C(═O)—R$^5$, —C(═O)—OH, —C(═O)—OR$^5$, or —OR$^5$;
R$^5$ is a lower alkyl group or halo(lower)alkyl group; and
G is a single bond, a substituted or unsubstituted lower alkylene group, a substituted or unsubstituted alkenylene group or a substituted or unsubstituted alkynylene group;
B is a single bond or a 5- or 6-membered heterocyclic group containing at least 1-3 nitrogen atoms;
D is a single bond, —C(═O)—, —O—C(═O)—, —C(═O)—O—, —NR$^6$—, —NR$^6$—C(═O)—, —C(═O)—NR$^6$—, —NR$^6$—C(═O)—NR$^6$—, —O—, —S—, —S(═O)—, —S(═O)$_2$—NR$^6$—, —NR$^6$—S(═O)$_2$—, —NR$^6$—CH$_2$—, —CH$_2$—NR$^6$— or —S(═O)$_2$—;

each $R^6$ is independently a hydrogen atom or a substituted or unsubstituted lower alkyl group;

$R^{12}$ is a hydrogen atom, halogen, hydroxyl group, —$SO_3H$, a substituted or unsubstituted amino group, a substituted or unsubstituted carboxyl group, a substituted or unsubstituted carbamoyl group, a substituted or unsubstituted acyl group, a substituted or unsubstituted amino sulfonyl group, a substituted or unsubstituted lower alkyl group, a substituted or unsubstituted lower alkenyl group, a substituted or unsubstituted lower alkynyl group, a substituted or unsubstituted non-aromatic carbocyclic group or a substituted or unsubstituted non-aromatic heterocyclic group.

(Item 2)

The compound or an amino-protected compound when the amino group is present on the ring in the 7-side chain, or a pharmaceutically acceptable salt thereof according to Item 1, wherein $R^{10}$ is a group represented by the formula:

[Chemical Formula 3]

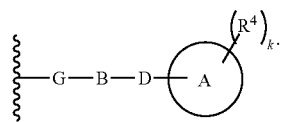

(Item 3)

The compound or an amino-protected compound when the amino group is present on the ring in the 7-side chain, or a pharmaceutically acceptable salt thereof according to Item 1, wherein $R^{10}$ is $R^{12}$ wherein $R^{12}$ is as defined in Item 1.

(Item 4)

The compound or an amino-protected compound when the amino group is present on the ring in the 7-side chain, or a pharmaceutically acceptable salt thereof according to Item 1 or 2, wherein G is a single bond, —$CH_2$—, —$CH_2$—$CH_2$—, —$CH_2$—$CH_2$—$CH_2$—, —CH=CH—, —CH=CH—$CH_2$—, —$CH_2$—CH=CH—, —$CH_2$—CH($CH_3$)—, —CH—CH($^i$Pr)— or —$CH_2$—CH(Ph)— wherein $^i$Pr is isopropyl group and Ph is phenyl group.

(Item 5)

The compound or an amino-protected compound when the amino group is present on the ring in the 7-side chain, or a pharmaceutically acceptable salt thereof according to Item 1, 2 or 4, wherein B is a single bond or a group represented by the formula:

[Chemical Formula 4]

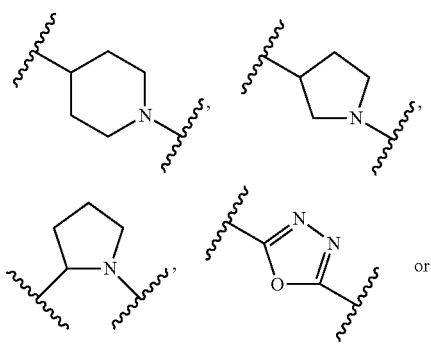

-continued

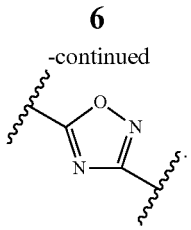

wherein the bond of the left side is attached to G and the bond of the right side is attached to D.

(Item 6)

The compound or an amino-protected compound when the amino group is present on the ring in the 7-side chain, or a pharmaceutically acceptable salt thereof according to any one of Items 1, 2 4, or 5, wherein 0 is a single bond, —C(=O)—, —O—C(=O)—, —C(=O)—O—, —$NR^6$—, —$NR^6$—C(=O)—$NR^6$—, —$NR^6$—C(=O)— or —C(=O)—$NR^6$— wherein $R^6$ is as defined in Item 1.

(Item 7)

The compound or an amino-protected compound when the amino group is present on the ring in the 7-side chain, or a pharmaceutically acceptable salt thereof according to any one of items 1, 2, 4 or 5, wherein the formula:

[Chemical Formula 5]

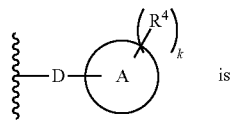 is

[Chemical Formula 6]

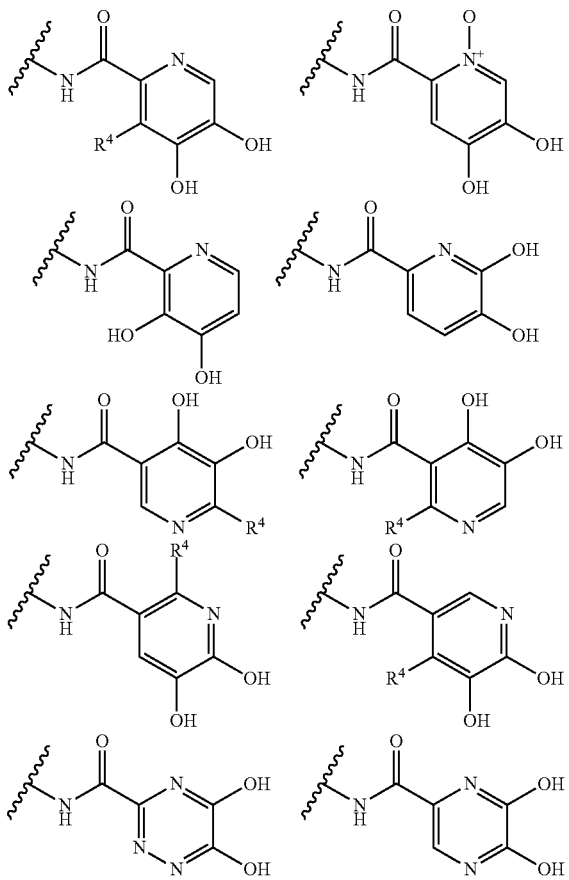

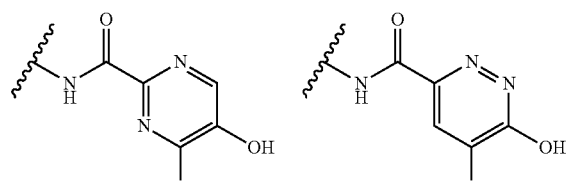
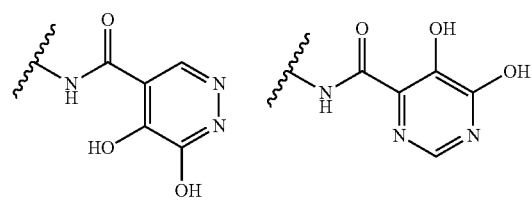
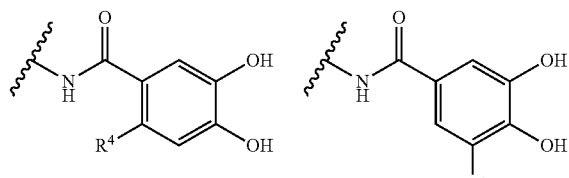
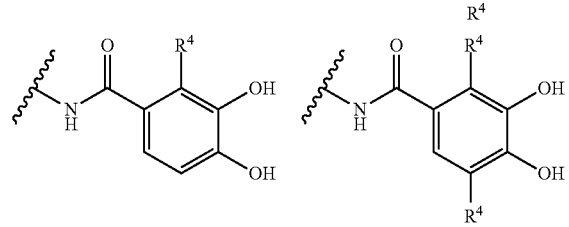
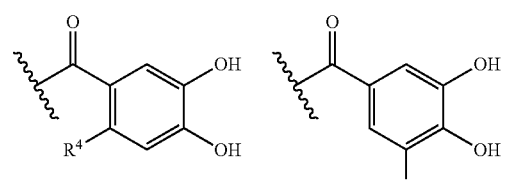
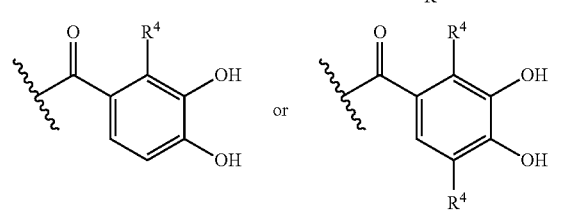

wherein each $R^4$ is independently hydrogen, halogen, hydroxyl group, —CN, —C(=O)—$R^5$, —C(=O)—OH, —C(O)—$OR^5$ or —$OR^5$; and $R^5$ is as defined in Item 1.

(Item 8)

The compound or an amino-protected compound when the amino group is present on the ring in the 7-side chain, or a pharmaceutically acceptable salt thereof according to Item 7, wherein the formula:

[Chemical Formula 7]

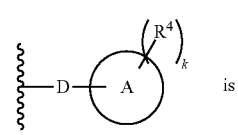 is

[Chemical Formula 8]

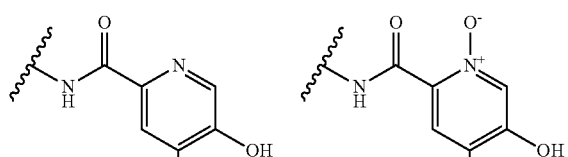
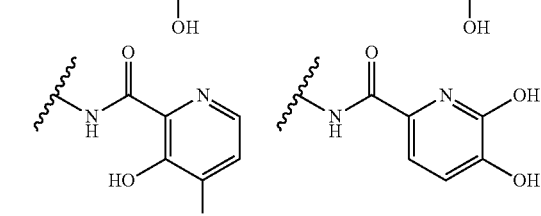
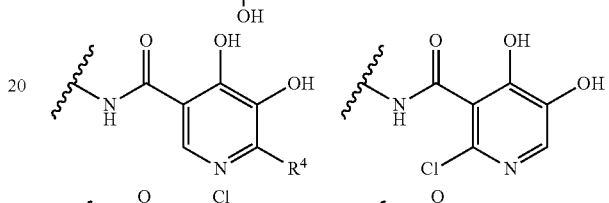
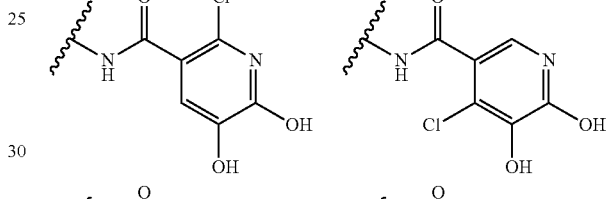
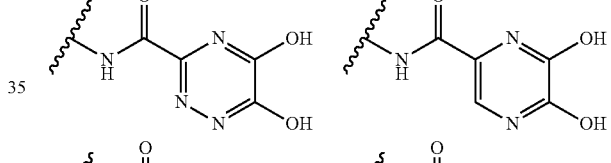
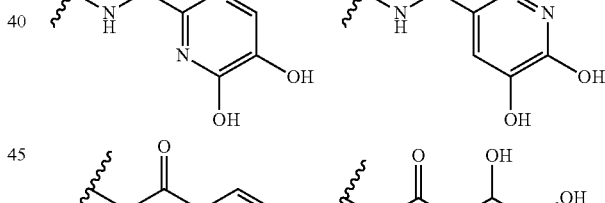
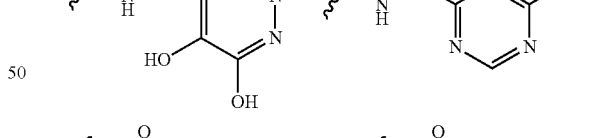
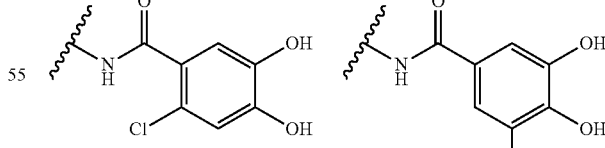
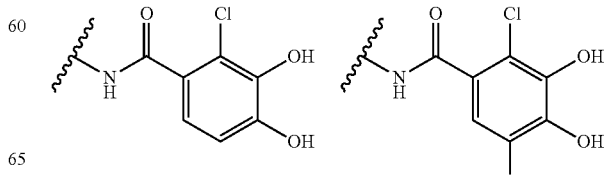

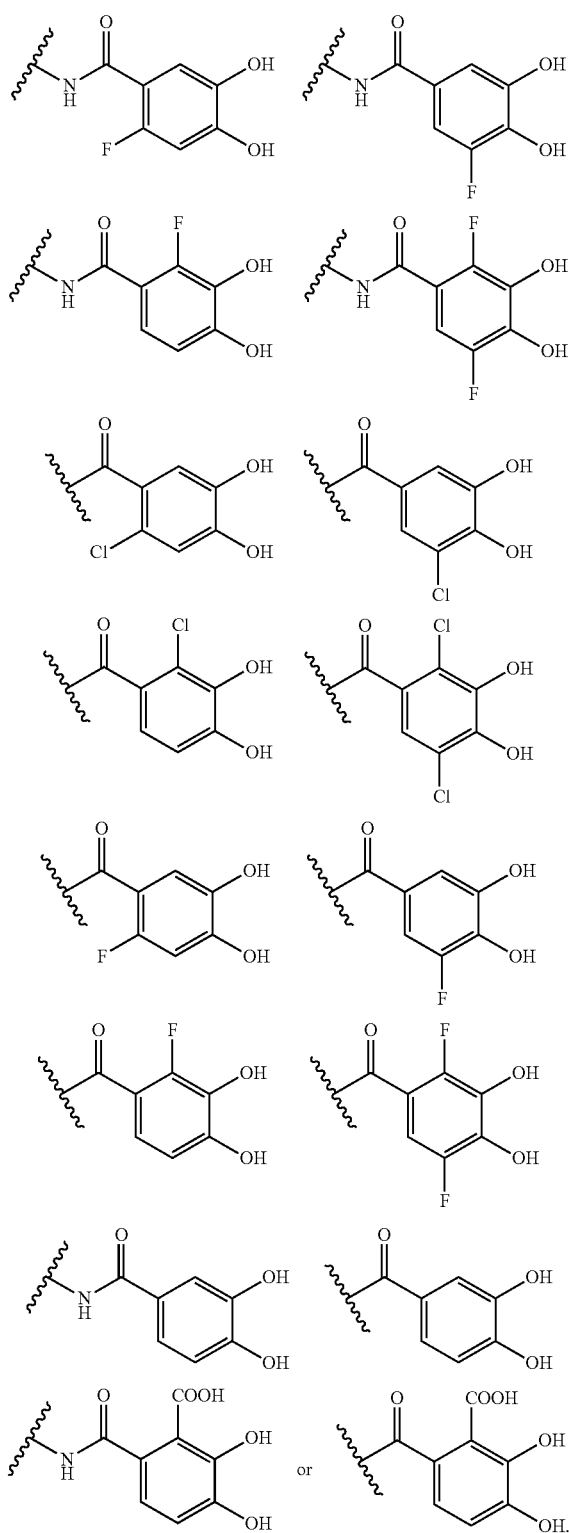
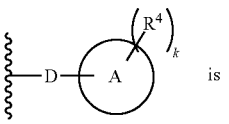
[Chemical Formula 9]
is
[Chemical Formula 10]
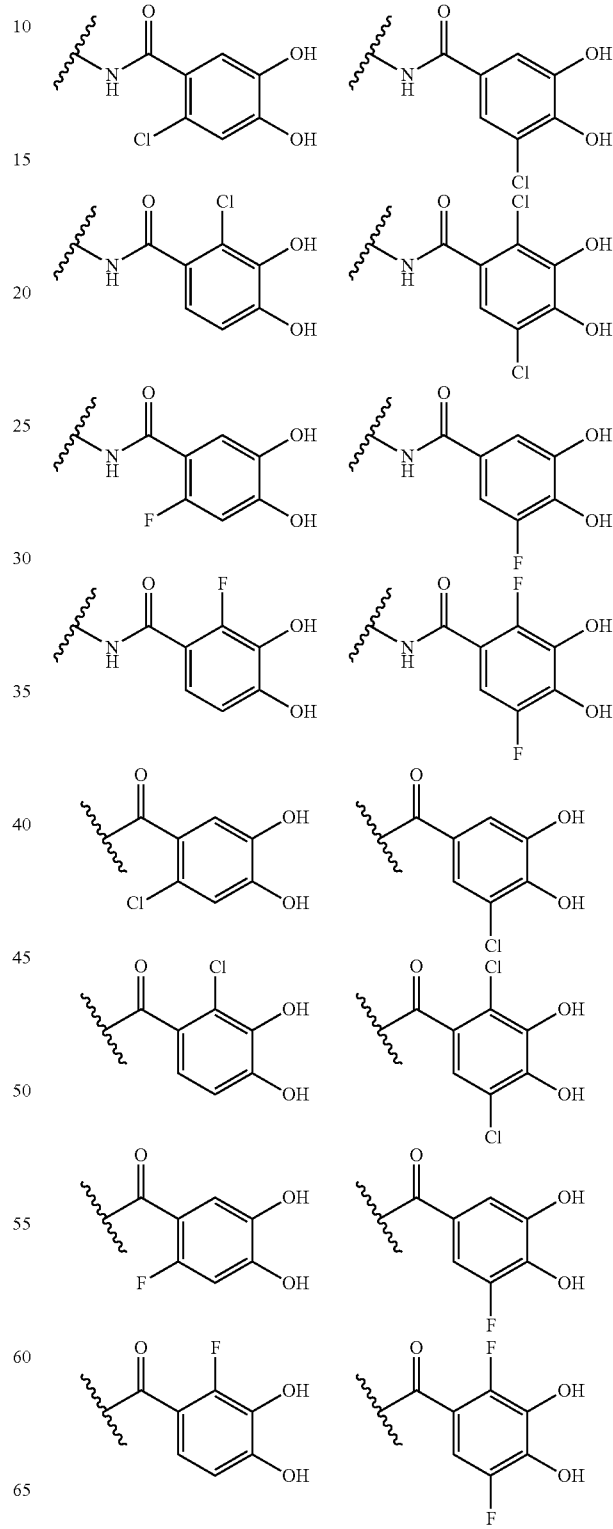
(Item 9)
The compound or an amino-protected compound when the amino group is present on the ring in the 7-side chain, or a pharmaceutically acceptable salt thereof according to Item 7, wherein the formula:

-continued

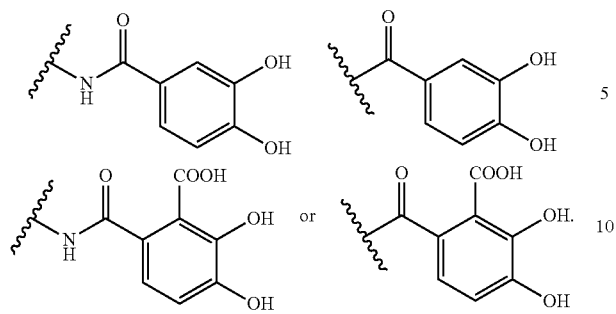

(Item 10)

The compound or an amino-protected compound when the amino group is present on the ring in the 7-side chain, or a pharmaceutically acceptable salt thereof according to any one of items 1 to 9, wherein E is a substituted or unsubstituted, saturated or unsaturated, monocyclic or fused cyclic quaternary ammonium group having at least one nitrogen atom represented by the formula:

[Chemical Formula 11]

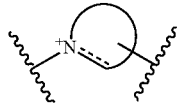

wherein the dashed line is a bond in the ring;

the bond to the cationic nitrogen atom binds to L, and the other bond binds to $R^{10}$;

provided, when a cationic nitrogen atom binds to $R^{10}$, the dashed line is absent, and when a cationic nitrogen atom does not bind to $R^{10}$, the dashed line is a single bond between the cationic nitrogen atom and a neighboring atom or an lower alkylene group connecting the cationic nitrogen atom and any ring member atom other than said neighboring atom.

(Item 11)

The compound or an amino-protected compound when the amino group is present on the ring in the 7-side chain, or a pharmaceutically acceptable salt thereof according to any one of Items 1 to 9, wherein E is a group selected from the following formulae which are substituted or unsubstituted on the ring:

[Chemical Formula 12]

(1)

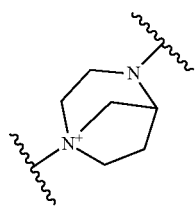

-continued (2)

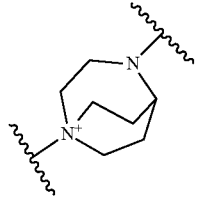

(3)

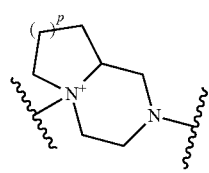

(4)

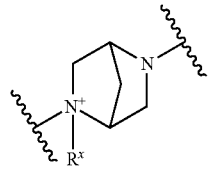

(5)

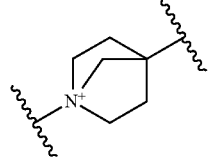

(6)

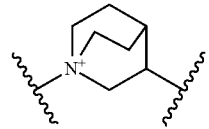

(7)

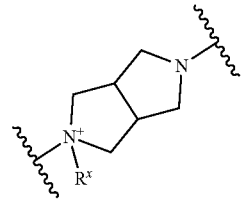

(8)

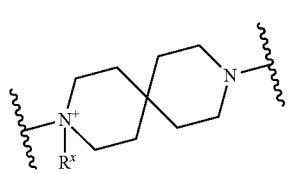

(9)

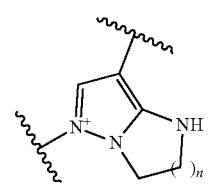

-continued

(26) 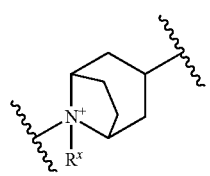
(27) 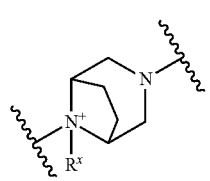
(28) 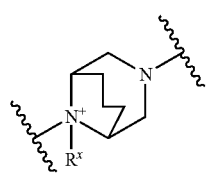
(29) 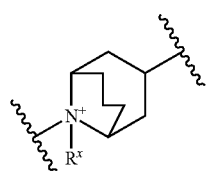
(30) 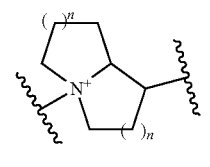
(31) 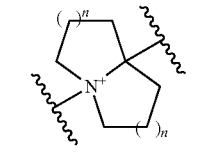
(32) 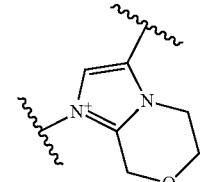
(33) 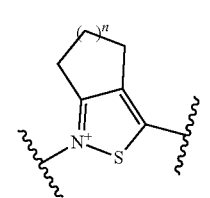
(34) 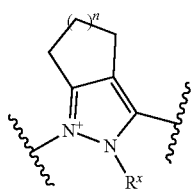
(35) 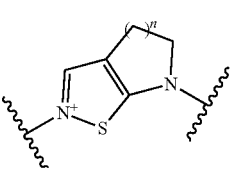
(36) 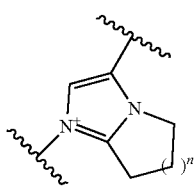
(37) 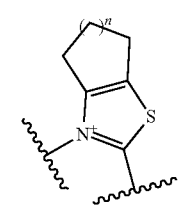
(38) 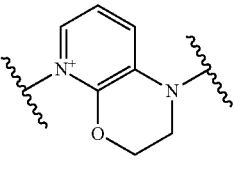
(39) 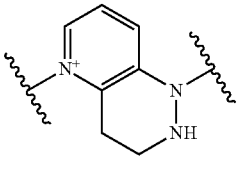
(40) 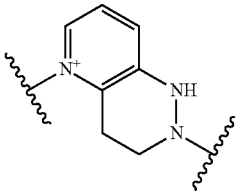
[Chemical Formula 14]
(41) 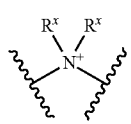

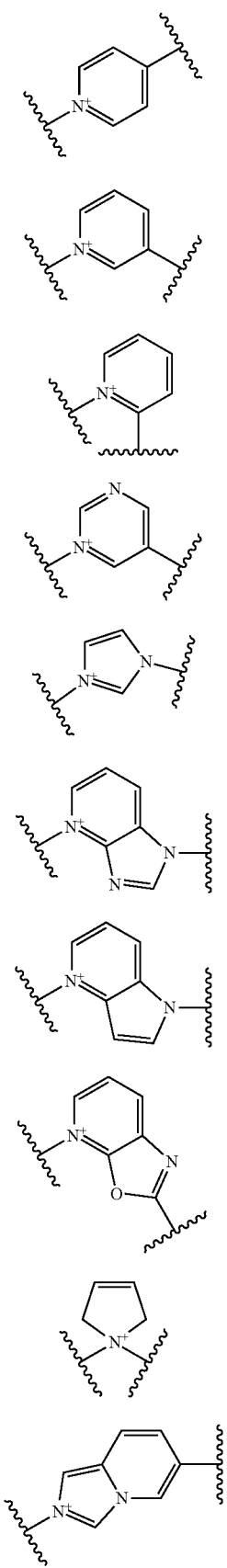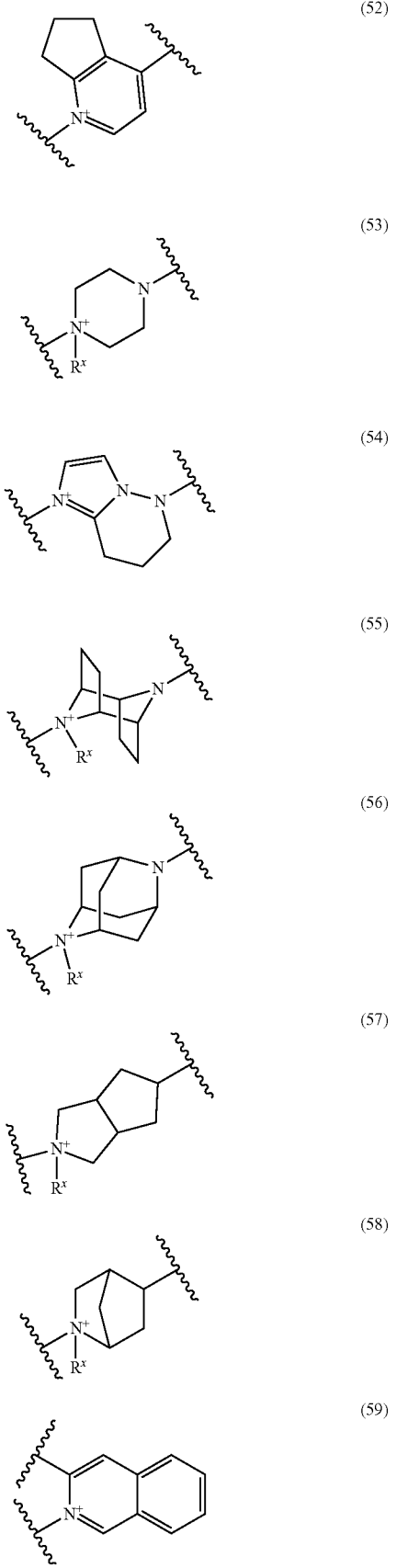

-continued

(60) 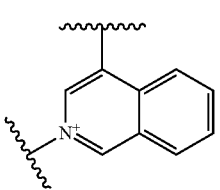

[Chemical Formula 15]

(61) 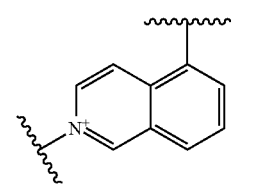

(62) 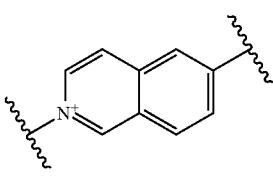

(63) 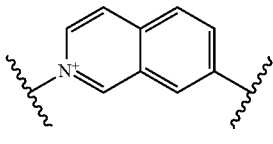

(64) 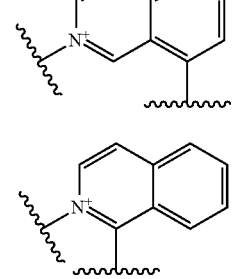

(65) 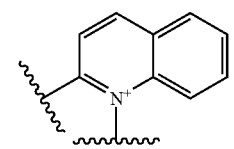

(66) 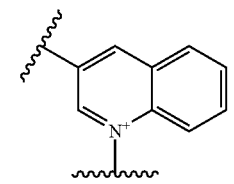

(67) 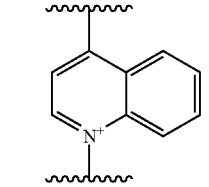

(68)

-continued

(69) 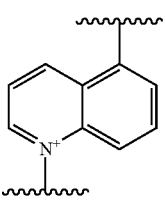

(70) 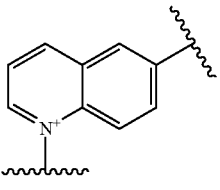

(71) 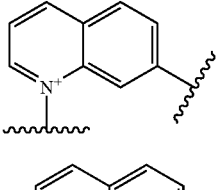

(72) 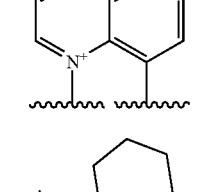

(73) 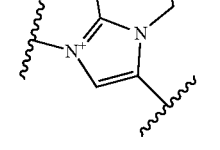

(74) 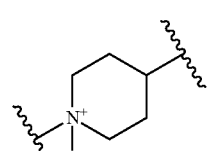

(75) 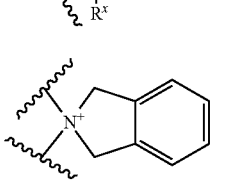 or

(76) 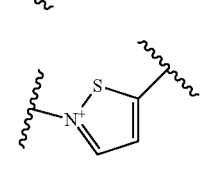

wherein the bond to the quaternary nitrogen atom binds to L, and the other bond binds to $R^{10}$; p is an integer from 1 to 3; n is an integer of 1 or 2; $R^X$ is a substituted or unsubstituted lower alkyl group.

(Item 12)

The compound or an amino-protected compound when the amino group is present on the ring in the 7-side chain, or a pharmaceutically acceptable salt thereof according to Item 11, wherein E is selected from the group consisting of the formulae (1) to (7), (10) to (12), (14), (25) to (29), (31), (41) to (44), (47), (50), (52), (53), (64) and (73).

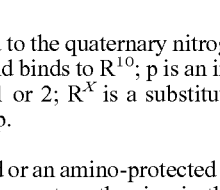

(Item 13)

The compound or an amino-protected compound when the amino group is present on the ring in the 7-side chain, or a pharmaceutically acceptable salt thereof according to Item 11, wherein E is selected from the group consisting of the formulae (3), (10) to (12), (26) to (28), (31), (41), (42), (53), (64) and (73).

(Item 14)

The compound or an amino-protected compound when the amino group is present on the ring in the 7-side chain, or a pharmaceutically acceptable salt thereof according to any one of Items 1 to 9, wherein E is a group selected from the following formulae which are substituted or unsubstituted on the ring:

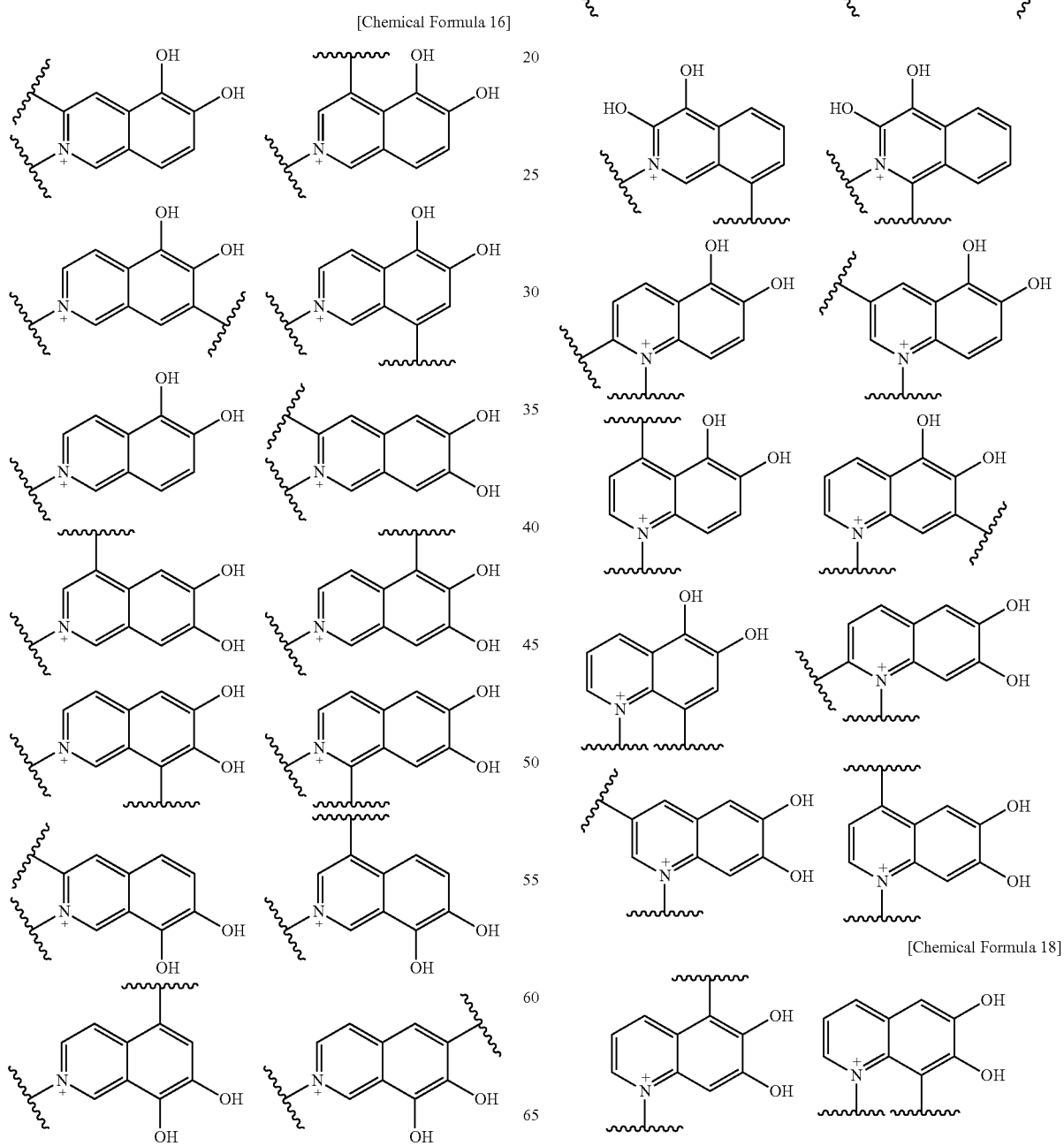

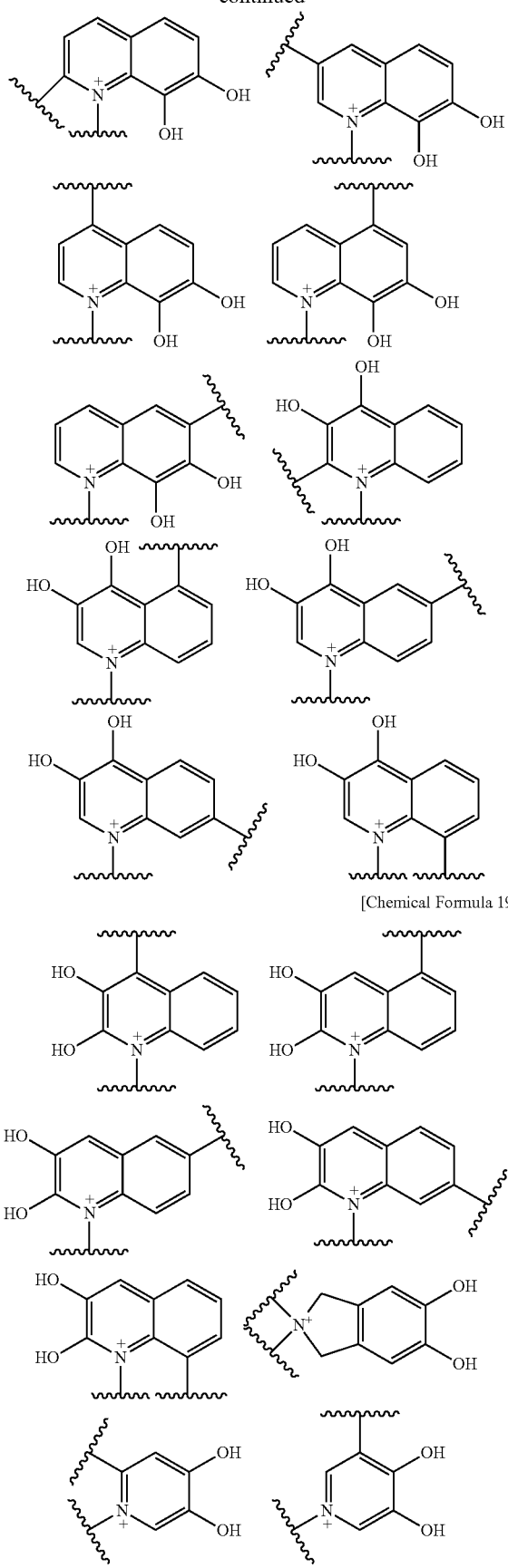

[Chemical Formula 19]

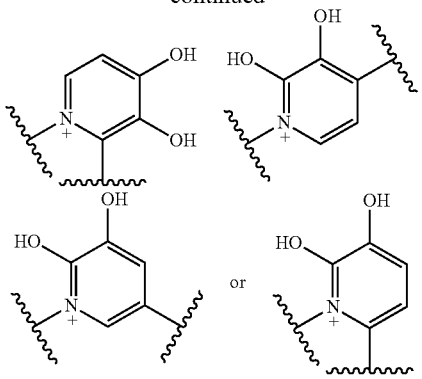

wherein the bond to the quaternary nitrogen atom binds to L, and the other bond binds to $R^{10}$.

(Item 15)

The compound or an amino-protected compound when the amino group is present on the ring in the 7-side chain, or a pharmaceutically acceptable salt thereof according to Item 1, wherein E-$R^{10}$ is a group selected from the following formulae which are substituted or unsubstituted on the ring:

[Chemical Formula 20]

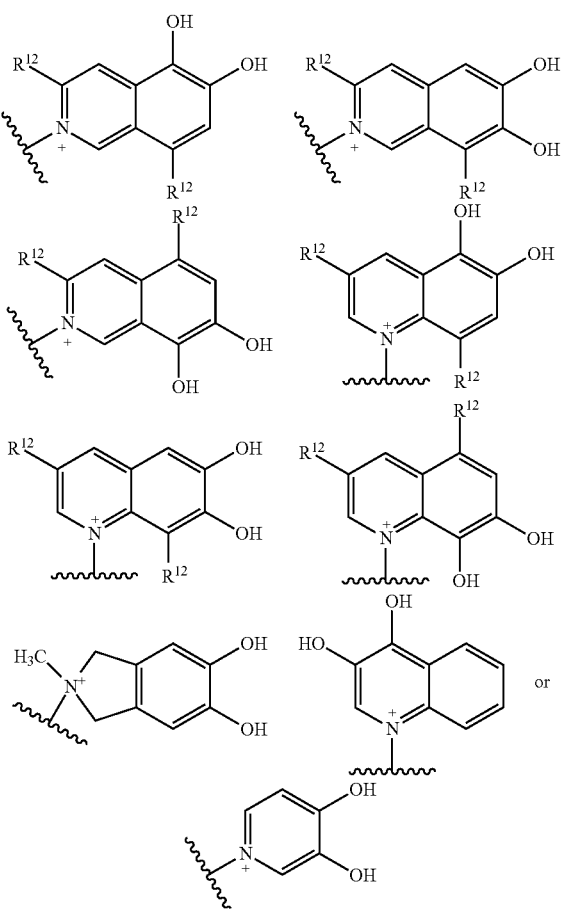

wherein the bond to the quaternary nitrogen atom binds to L, and the other bond binds to $R^{10}$.

(Item 16)

The compound or an amino-protected compound when the amino group is present on the ring in the 7-side chain, or a pharmaceutically acceptable salt thereof according to Item 1, wherein $E-R^{10}$ is

[Chemical Formula 21]

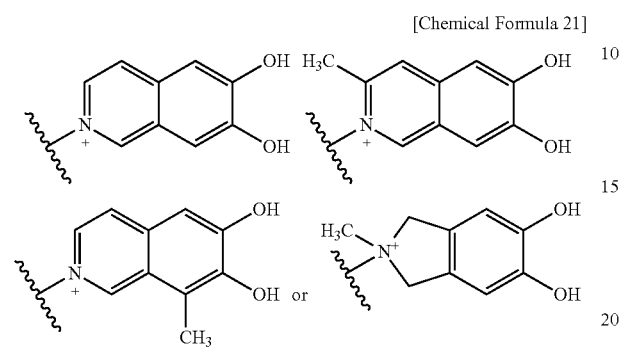

wherein the bond to the quaternary nitrogen atom binds to L.

(Item 17)

The compound or an amino-protected compound when the amino group is present on the ring in the 7-side chain, or a pharmaceutically acceptable salt thereof according to any one of Items 1 to 16, wherein the bioisoster of carboxyl ion (—COO⁻) is selected from —SO₃⁻, —S(=O)₂—N⁻—R¹³, —PO⁻—(OR¹³), —PO₂⁻—(OR¹³), —N⁻—C(=C)—R¹³, —C(=O)—N⁻—OR¹³, —C(=O)—NH—N⁻—S(=O)₂—R¹³, —C(=O)—N⁻—S(=O)₂—R¹³, —C(=O)—CH=C(O⁻)—R¹³, —N⁻—S(=O)₂—R¹³, —C(=O)—N⁻—S(=O)₂—R¹³, —N⁻—S(=O)₂—R¹³, —C(=O)—N⁻—C(=O)—R¹³, —C(=O)—N⁻—S(=O)₂—R¹³, —N⁻—C(=O)—R¹³,

[Chemical Formula 22]

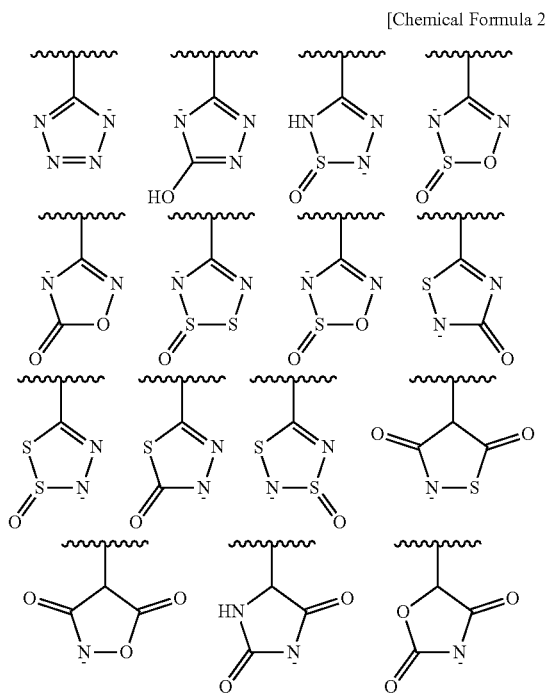

[Chemical formula 23]

[Chemical Formula 24]

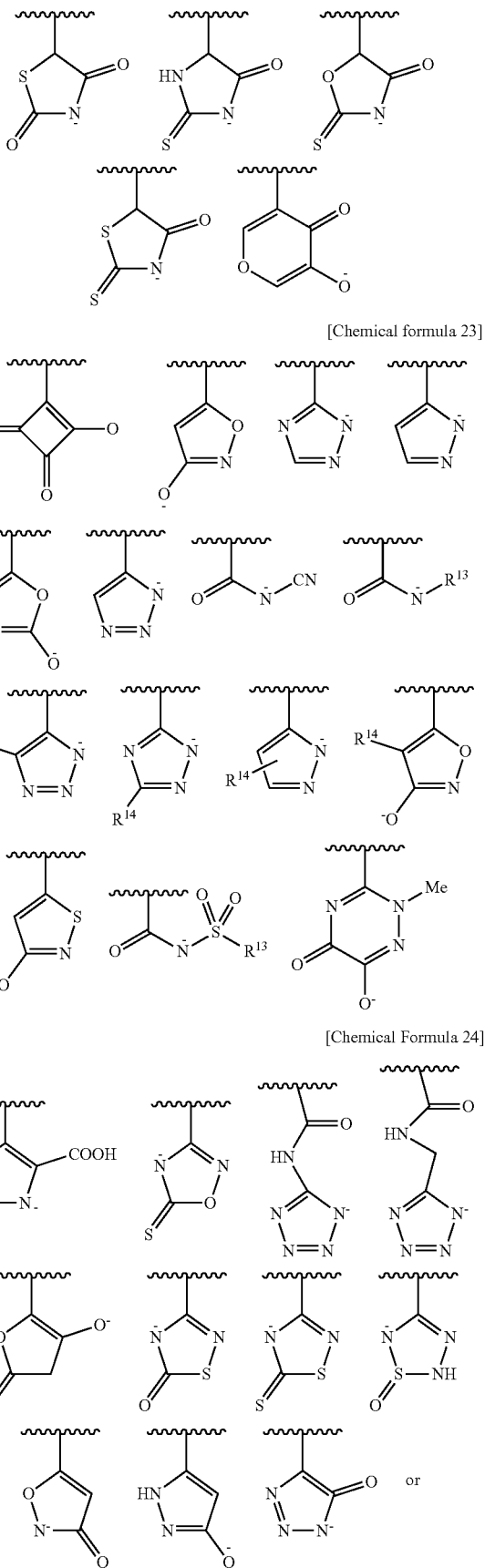

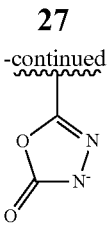

wherein R[13] is selected from the group consisting of hydrogen, hydroxyl group, halogen, a substituted or unsubstituted lower alkyl group, a substituted or unsubstituted lower alkenyl group, a substituted or unsubstituted lower alkynyl group, a substituted or unsubstituted lower alkoxy group, a substituted or unsubstituted amino group, (lower alkenyl)oxy group, a substituted or unsubstituted aryloxy group, cyano, nitro, imino, mercapto, (lower alkyl)thio group, (lower alkyl)sulphonyl group, a substituted or unsubstituted carbocyclic group, a substituted or unsubstituted heterocyclic group and —$CO_2R^{17}$ wherein $R^{17}$ is hydrogen, lower alkyl group or lower alkenyl group; and $R^{14}$ is an electron-withdrawing group.

(Item 18)

The compound or an amino-protected compound when the amino group is present on the ring in the 7-side chain, or a pharmaceutically acceptable salt thereof according to Item 17, wherein the bioisoster of carboxyl ion (—COO⁻) is

[Chemical Formula 25]

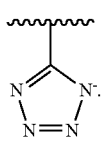

(Item 19)

The compound or an amino-protected compound when the amino group is present on the ring in the 7-side chain, or a pharmaceutically acceptable salt thereof according to any one of Items 1 to 18, wherein U is —S—.

(Item 20)

The compound or an amino-protected compound when the amino group is present on the ring in the 7-side chain, or a pharmaceutically acceptable salt thereof according to any one of Items 1 to 19, wherein W is —$CH_2$—.

(Item 21)

The compound or an amino-protected compound when the amino group is present on the ring in the 7-side chain, or a pharmaceutically acceptable salt thereof according to any one of Items 1 to 20, wherein $R^3$ is a hydrogen atom or —$OCH_3$.

(Item 22)

The compound or an amino-protected compound when the amino group is present on the ring in the 7-side chain, or a pharmaceutically acceptable salt thereof according to any one of Items 1 to 21, wherein $R^1$ is a substituted or unsubstituted phenyl.

(Item 23)

The compound or an amino-protected compound when the amino group is present on the ring in the 7-side chain, or a pharmaceutically acceptable salt thereof according to any one of Items 1 to 21, wherein $R^1$ is represented by the formula:

[Chemical Formula 26]

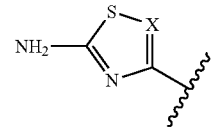

wherein X is N, C(—H) or C(—Cl).

(Item 24)

The compound or an amino-protected compound when the amino group is present on the ring in the 7-side chain, or a pharmaceutically acceptable salt thereof according to Item 23, wherein X is N.

(Item 25)

The compound or an amino-protected compound when the amino group is present on the ring in the 7-side chain, or a pharmaceutically acceptable salt thereof according to Item 23, wherein X is C(—H) or C(—Cl).

(Item 26)

The compound or an amino-protected compound when the amino group is present on the ring in the 7-side chain, or a pharmaceutically acceptable salt thereof according to any one of Items 1 to 25, wherein $R^{2A}$ is a hydrogen atom, a substituted or unsubstituted amino group, —$SO_3H$, a substituted or unsubstituted amino sulphonyl group, carboxyl group, a substituted or unsubstituted carbamoyl group, hydroxyl group, or substituted carbonyloxy group, and $R^{2B}$ is a hydrogen atom.

(Item 27)

The compound or an amino-protected compound when the amino group is present on the ring in the 7-side chain, or a pharmaceutically acceptable salt thereof according to any one of Items 1 to 26, wherein $R^{2A}$ is a substituted amino group shown below:

[Chemical Formula 27]

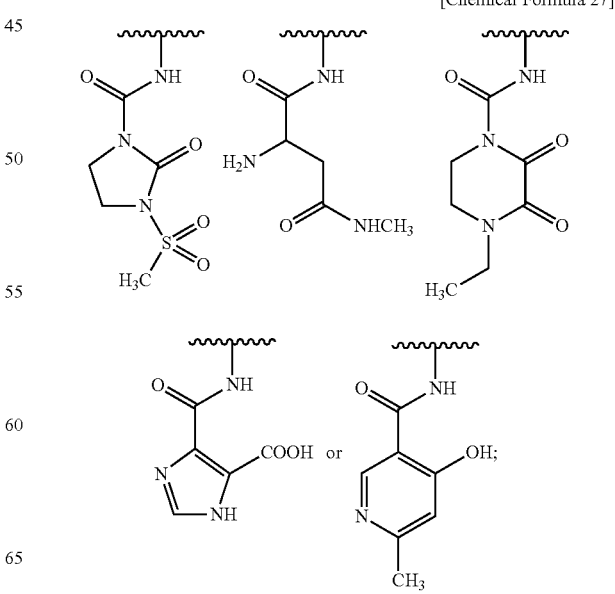

a substituted amino sulfonyl group shown below:

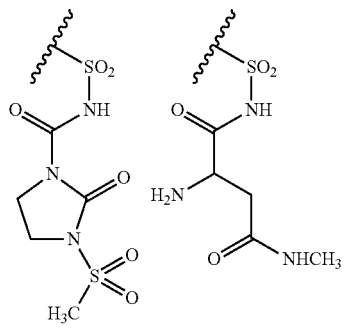

[Chemical Formula 28]

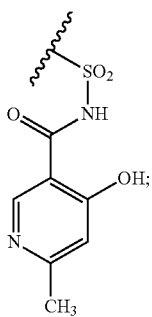

wherein ring B represents a substituted or unsubstituted heterocyclic group;

a substituted carbonyloxy group shown below:

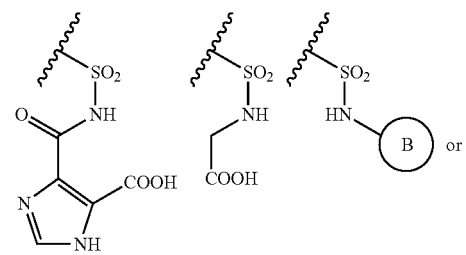

[Chemical Formula 29]

wherein ring B represents a substituted or unsubstituted heterocyclic group; or a substituted carbonyloxy group shown below:

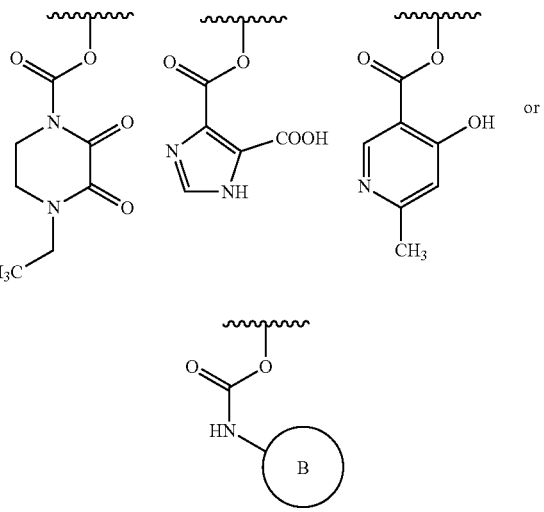

[Chemical Formula 30]

wherein ring B represents a substituted or unsubstituted heterocyclic group.

(Item 28)

The compound or an amino-protected compound when the amino group is present on the ring in the 7-side chain, or a pharmaceutically acceptable salt thereof according to any one of Items 1 to 25, wherein $R^{2A}$ and $R^{2B}$ are taken together to form a substituted methylidene group shown below:

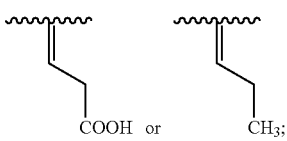

[Chemical Formula 31]

a substituted hydroxyimino group shown below:

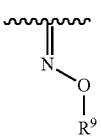

[Chemical Formula 32]

wherein $R^9$ is a substituted or unsubstituted lower alkyl group.

(Item 29)

The compound or an amino-protected compound when the amino group is present on the ring in the 7-side chain, or a pharmaceutically acceptable salt thereof according to any one of items 1 to 25, wherein $R^{2A}$ and $R^{2B}$ are taken together to form a substituted hydroxyimino group shown below:

[Chemical Formula 33]

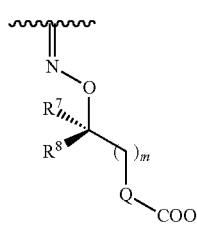

wherein $R^7$ and $R^8$ are each independently a hydrogen atom, halogen, hydroxyl group, carboxyl group, a substituted or unsubstituted lower alkyl group, a substituted or unsubstituted carbocyclic group, or a substituted or unsubstituted heterocyclic group, or $R^7$ and $R^8$ may be taken together with a neighboring atom to form a substituted or unsubstituted carbocyclic group or a substituted or unsubstituted heterocyclic group;

Q is a single bond, a substituted or unsubstituted carbocyclic group or a substituted or unsubstituted heterocyclic group; and m is an integer from 0 to 3.

(Item 30)

A pharmaceutical composition, which comprises a compound or an amino-protected compound when the amino group is present on the ring in the 7-side chain, or a pharmaceutically acceptable salt thereof according to any one of Items 1 to 29.

(Item 31)

The pharmaceutical composition according to Item 30, which possesses antimicrobial activity.

(Item 32)

A compound of the formula:

[Chemical Formula 34]

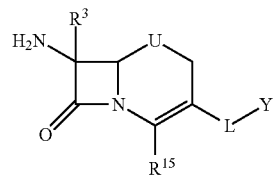

or a salt thereof,
wherein
Y is a leaving group;
U, $R^3$ and L are as defined in claim 1;
the group of the formula:

[Chemical Formula 35]

Is a group of the following formula:

[Chemical Formula 36]

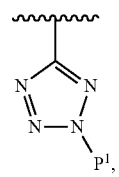

a group of the formula:

[Chemical Formula 37]

$P^1$ is a protecting group.

(Item 33)

The compound according to Claim 32, or a salt thereof, wherein $P^1$ is benzhydryl group, p-methoxybenzyl group, trityl group, 2,6-dimethoxybenzyl group, methoxymethyl group, benzyloxymethyl group or 2-(trimethylsilyl)ethoxymethyl group.

(Item 34)

A compound of the formula:

[Chemical Formula 38]

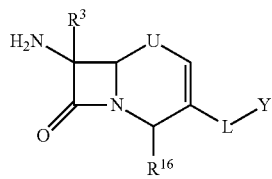

or a salt thereof,
wherein
Y is a leaving group;
U, $R^3$ and L are as defined in claim 1;
the group of the formula:

[Chemical Formula 39]

is a group of the following formula:

[Chemical Formula 40]

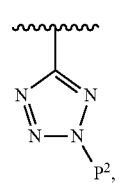

a group of the following formula:

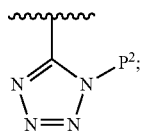

[Chemical Formula 41]

P² is a protecting group.
(Item 35)
The compound according to Claim 34, or a salt thereof, wherein P² is benzhydryl group, p-methoxybenzyl group, trityl group, 2,6-dimethoxybenzyl group, methoxymethyl group, benzyloxymethyl group or 2-(trimethylsilyl)ethoxymethyl group.
(Item 36)
A method for the treatment of infection, which comprises administering a compound according to any one of Items 1 to 29, an ester thereof, or an amino-protected compound when the amino group is present on the ring in the 7-side chain or a pharmaceutically acceptable salt, or a solvate thereof.
(Item 37)
The compound according to any one of Items 1 to 29, an ester thereof, or an amino-protected compound when the amino group is present on the ring in the 7-side chain or a pharmaceutically acceptable salt, or a solvate thereof for the treatment of infection.

Effects of the Invention

The compounds of the subject invention are useful as a pharmaceutical product in that the compounds have at least one of the following features:
1) The compounds exhibit potent antimicrobial spectrum against a variety of bacteria including Gram negative bacteria and/or Gram positive bacteria;
2) the compounds exhibit potent antimicrobial activity against beta-lactamase producing Gram negative bacteria;
3) the compounds exhibit potent antimicrobial activity against multidrug-resistant bacteria, in particular, Class B type metallo-beta-lactamase producing Gram negative bacteria;
4) the compounds exhibit potent antimicrobial activity against extended-spectrum beta-lactamase (ESBL) producing bacteria;
5) the compounds do not exhibit cross resistance with known Cephem drugs and/or Carbapenem drugs; and
6) the compounds do not exhibit side effects such as fever after administration into the body.

EMBODIMENTS FOR CARRYING OUT THE INVENTION

Hereinafter, the subject invention is described with showing embodiments. It should be understood that, throughout the present specification, the expression of a singular form (for example, in the English language, "a", "an", "the", and the like; and in other languages, corresponding articles, adjectives, and the like) includes the concept of its plural form unless specified otherwise. Furthermore, it should be understood that the terms used herein are used in a meaning normally used in the art unless specified otherwise. Thus, unless defined otherwise, all technical and scientific terms used herein have the same meaning as those generally understood by those skilled in the art in the field to which the subject invention pertains. If there is a contradiction, the present specification (including definitions) precedes. Each specific definition of terms specifically used herein is described below.

Each term in the present specification is used alone or in combination with another word, and defined as below.

"Halogen" includes fluorine, chlorine, bromine and iodine. Preferably, halogen is fluorine, chlorine or bromine, and more preferably is chlorine.

"Lower alkyl group" includes linear or branched alkyl group having 1-8 carbons, preferably 1-6 carbons, and more preferably 1-4 carbons, and includes, for example, methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, and the like.

"Lower alkylene group" includes linear alkylene group having 1-8 carbons, preferably 1-6 carbons, more preferably 1-4 carbons, and most preferably one or two carbons, and includes, for example, methylene, ethylene, n-propylene, n-butylene, n-pentylene, n-hexylene, and the like.

"Lower alkenylene group" includes linear alkenylene group having 2-8 carbons, preferably 2-6 carbons, more preferably 2-4 carbons, and at least one double bond at any position, and includes, for example, vinylene, allylene, propenylene, butenylene, prenylene, butadienylene, pentenylene, pentadienylene, hexenylene, hexadienylene, and the like.

"Lower alkynylene group" includes linear alkynylene group having 2-8 carbons, preferably 2-6 carbons, more preferably 2-4 carbons, and at least one triple bond at any position, and includes, for example, ethynylene, propynylene, buthynylene, pentynylene, hexynylene, and the like.

"Halo(lower)alkyl group" refers to a group in which at least one position of said "lower alkyl group" is substituted with the above "halogen", and includes, for example, monofluoromethyl, difluoromethyl, trifluoromethyl, monochloromethyl, dichloromethyl, trichloromethyl, monobromomethyl, monofluoroethyl, monochloroethyl, chlorodifluoromethyl, and the like. Preferably, halo(lower)alkyl group is trifluoromethyl, or trichloromethyl.

Substituents of "a substituted or unsubstituted amino group" or "substituted or unsubstituted carbamoyl group" include substituted or unsubstituted lower alkyl (e.g., methyl, ethyl, isopropyl, benzyl, carbamoylalkyl (e.g., carbamoylmethyl), mono- or di-(lower)alkylcarbamoyl(lower)alkyl (e.g., dimethylcarbamoylethyl), hydroxy(lower)alkyl, heterocycle (lower)alkyl (e.g., morpholinoethyl, tetrahydropyranylethyl), alkoxycarbonyl(lower)alkyl (e.g., ethoxycarbonylmethyl, ethoxycarbonylethyl), mono- or di-(lower)alkylamino (lower)alkyl (e.g., dimethylaminoethyl)); (lower)alkoxy (lower)alkyl (e.g., methoxyethyl, ethoxymethyl, ethoxyethyl, isopropoxyethyl, and the like);
acyl (e.g., formyl, substituted or unsubstituted lower alkylcarbonyl (e.g., acetyl, propionyl, butylyl, isobutylyl, valeryl, isovaleryl, pivaloyl, hexanoyl, octanoyl, methoxyethylcarbonyl, 2,2,2-trifluoroethylcarbonyl, alkoxycarbonylacetyl (e.g., ethoxycarbonylmethylcarbonyl), (lower)alkoxy(lower)alkylcarbonyl (e.g., methoxyethylcarbonyl), (lower)alkylcarbamoyl(lower)alkylcarbonyl (e.g., methylcarbamoylethylcarbonyl), substituted or unsubstituted arylcarbonyl (e.g., benzoyl, toluoyl); substituted or unsubstituted arylalkyl (e.g., benzyl, 4-fluorobenzyl);
hydroxy;
substituted or unsubstituted lower alkylsulfonyl (e.g., methanesulfonyl, ethanesulionyl, isopropylsulfonyl, 2,2,2-trifluoroethanesulfonyl, benzylsulfonyl, methoxyethylsulfonyl);

arylsulfonyl optionally having a lower alkyl or halogen as a substituent (e.g., benzenesulfonyl, toluenesulfonyl, 4-fluorobenzenesulfonyl), cycloalkyl (e.g., cyclopropyl);

aryl optionally having a lower alkyl as a substituent (e.g., phenyl, tolyl);

lower alkylaminosulfonyl (e.g., methylaminosulfonyl, dimethylaminosulfonyl);

lower alkylaminocarbonyl (e.g., dimethylaminocarbonyl);

lower alkoxycarbonyl (e.g., ethoxycarbonyl);

cycloalkylcarbonyl (e.g., cyclopropylcarbonyl, cyclohexylcarbonyl);

substituted or unsubstituted sulfamoyl (e.g., sulfamoyl, methylsulfamoyl, dimethylsulfamoyl);

lower alkylcarbonylamino (e.g., methylcarbonylamino); heterocycle (e.g., morpholino, tetrahydropyranyl);

substituted or unsubstituted amino (e.g., mono- or di-alkylamino (e.g., dimethylamino), formylamino), and the like.

The above "substituted amino group" or "substituted carbamoyl group" may be mono-substituted or di-substituted with these substituent groups.

"Lower alkenyl group" refers to a linear or branched alkenyl having 2 to 8 carbons and having one or more double bonds on said "lower alkyl group". Examples thereof include vinyl, 1-propenyl, 2-propenyl, 1-butenyl, 2-butenyl, 3-butenyl, 1,3-butadienyl, 3-methyl-2-butenyl, and the like. Preferred is alkenyl having 2 to 6 carbons, more preferably 2 to 4 carbons.

With regard to an amino group of "a substituted or unsubstituted amino group" or "substituted or unsubstituted carbamoyl group", two substituents of the amino group may be taken together with the adjacent nitrogen atom to form a nitrogen-containing heterocycle which optionally includes a sulfur atom and/or an oxygen atom in the ring (preferably, the heterocycle is a 5- to 7-membered ring, and is preferably saturated). The heterocycle is substituted or unsubstituted with oxo or hydroxy. When a sulfur atom forms the heterocycle, said sulfur atom may be substituted with oxo. Examples thereof include 5- or 6-membered rings such as piperazinyl, piperidino, morpholino, pyrrolidino, 2-oxopiperidino, 2-oxopyrrolidino, 4-hydroxymorpholino, and the like.

Substituents of "a substituted or unsubstituted lower alkyl group" include at least one group selected from Substituent Group Alpha. When substitution is carried out with a plurality of Substituent Group Alpha, the plurality of Substituent Group Alpha may be the same or different.

Substituents of "a substituted or unsubstituted lower alkylene group", "a substituted or unsubstituted lower alkenylene group" and "a substituted or unsubstituted lower alkynylene group" include at least one group selected from Substituent Group Alpha. When substitution is carried out with a plurality of substituents, the substituents may be the same or different.

Substituents of "a substituted or unsubstituted aminosulfonyl group" include a substituted lower alkyl and at least one group selected from Substituent Group Alpha.

Substituents of "a substituted or unsubstituted lower alkyloxycarbonyl group" include at least one group selected from Substituent Group Alpha.

Substituents of "a substituted carbonyloxy group" meaning "—O—C(=O)-substituent" include a substituted or unsubstituted lower alkyl, a substituted or unsubstituted lower alkenyl, a substituted or unsubstituted lower alkynyl, a substituted or unsubstituted carbocyclic group, a substituted or unsubstituted heterocyclic group, an amino having a heterocyclic group as a substituent, and at least one group selected from Substituent Group Alpha.

Substituents of "a substituted or unsubstituted carboxyl group" include a substituted or unsubstituted lower alkyl, a substituted or unsubstituted lower alkenyl, a substituted or unsubstituted lower alkynyl, a substituted or unsubstituted carbocyclic group, a substituted or unsubstituted heterocyclic group.

"Substituted or unsubstituted acyl group" means a carbonyl group substituted or unsubstituted with a substituted or unsubstituted lower alkyl, a substituted or unsubstituted lower alkenyl, a substituted or unsubstituted lower alkynyl, a substituted or unsubstituted carbocyclic group, a substituted or unsubstituted heterocyclic group.

Substituents of "a substituted or unsubstituted, saturated or unsaturated, monocyclic or fused cyclic quaternary ammonium group" include a substituted or unsubstituted lower alkyl, at least one group selected from Substituent Group Alpha, or two or more substituents that are taken together to form a carbocyclic group or heterocyclic group.

Here, "Substituent Group Alpha" is a group consisting of halogen, hydroxy, lower alkoxy, hydroxy(lower)alkoxy, (lower)alkoxy(lower)alkoxy, carboxy, amino, acylamino, lower(alkyl)amino, imino, hydroxyimino, lower(alkoxy) imino, lower(alkyl)thio, carbanoyl, lower(alkyl)carbamoyl, hydroxy(lower)alkylcarbamoyl, sulfamoyl, lower(alkyl)sulfamoyl, lower(alkyl)sulfinyl, cyano, nitro, a carbocyclic group, and a heterocyclic group.

The lower alkyl moiety in "lower alkoxy group", "hydroxy (lower)alkoxy group", "(lower)alkoxy(lower)alkoxy group", "lower (alkyl)amino group", "lower (alkoxy)imino group", "lower (alkyl)thio group", "lower (alkyl)carbamoyl group", "hydroxy(lower)alkylcarbamoyl group", and "lower (alkyl) sulfamoyl group", "lower(alkyl)sulfinyl group", "lower (alkyl)oxycarbonyl group", "lower (alkyl)sulfonyl group", is defined the same as the above "lower alkyl group".

The lower alkenyl moiety in "lower(alkenyl)oxy group", is defined the same as the above "lower alkenyl group".

The aryl moiety in "aryloxy group", is defined the same as "aryl" defined below.

Preferred embodiments of substituents in "a substituted or unsubstituted lower alkyl" include a fluorine atom, a chlorine atom, a bromine atom, hydroxy, carboxy, methoxy, ethoxy, hydroxymethoxy, hydroxyethoxy, methoxymethoxy, methoxyethoxy, amino, acetylamino, methylamino, dimethylamino, imino, hydroxyimino, methoxyimino, methylthio, carbamoyl, methylcarbamoyl, hydroxymethylcarbamoyl, sulfamoyl, methylsulfamoyl, lower alkylsulfamoyl, cyano, nitro, phenyl, cyclopropyl, cyclobutyl, cyclohexyl, pyridyl, morpholinyl, and the like.

Preferred embodiments of "substituted or unsubstituted lower alkyl" include methyl, ethyl, isopropyl, tert-butyl, monochloromethyl, dichloromethyl, trichloromethyl, carboxymethyl, carboxyethyl, carbamoylmethyl, carbamoylethyl, hydroxymethyl, hydroxyethyl, methoxymethyl, ethoxymethyl, methoxyethyl, ethoxyethyl, methylthiomethyl, ethylthiomethyl, benzyl, phenethyl, 4-hydroxybenzyl, 4-methoxybenzyl, 4-carboxybenzyl, and the like.

"Carbocyclic group" includes cycloalkyl, cycloalkenyl, aryl and non-aromatic fused carbocyclic groups, and the like.

"Cycloalkyl" is a carbocyclic group having 3-10 carbons, preferably 3-8 carbons, more preferably 4-8 carbons, and includes, for example, cyclopropyl, cyclobutyl, cyclopentyl, cyclohexyl, cycloheptyl, cyclooctyl, cyclononyl, cyclodecyl, and the like.

"Cycloalkenyl" includes those in which the ring of the cycloalkyl has at least one double bond at any position(s), and specifically includes, for example, cyclopropenyl, cyclobutenyl, cyclopentenyl, cyclohexenyl, cycloheptynyl, cyclooctynyl, and cyclohexadienyl, and the like.

"Aryl" includes phenyl, naphthyl, anthryl, phenanthryl, and the like, and in particular, phenyl is preferable.

"Aromatic carbocycle" means a ring derived from aryl as described above.

"Aromatic heterocycle" means a aromatic ring, which is monocyclic or bicyclic or more, having same or different one or more hetero atom selected independently from O, S or N.

The aromatic heterocyclic group which is bicyclic or more includes those wherein a monocyclic or bicyclic or more aromatic heterocyle is condensed with "aromatic carbocyle" described above.

"Non-aromatic carbocyclic group" includes those selected from the above "cycloalkyl" and "cycloalkenyl" and specifically includes cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptynyl, cyclooctynyl, and cyclohexadienyl and the like.

"Non-aromatic fused carbocyclic group" includes a group in which one or more cyclic group selected from said "cycloalkyl" and "cycloalkenyl" is fused to said "cycloalkyl" "cycloalkenyl" and "aryl", and specifically includes, for example, indanyl, indenyl, tetrahydronaphthyl, and fluorenyl, and the like.

"Heterocyclic group" includes heterocyclic groups having at least one hetero atom arbitrarily selected from O, S, and N, in the ring thereof, and specifically includes, for example, 5- or 6-membered heteroaryl such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl, thienyl, and the like; bicyclic fused heterocyclic groups such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzotriazolyl, benzisoxazolyl, benzoxazolyl, benzoxadiazolyl, benzisothiazolyl, benzothiazolyl, benzcthiadiazolyl, benzofuryl, isobenzofuryl, benzcthienyl, benzotriazolyl, imidazopyridyl, pyrazolopyridine, triazolopyridyl, imidazothiazolyl, pyrazinopyridazinyl, quinazolinyl, quinolyl, isoquinolyl, naphthyridinyl, dihydrobenzofuryl, tetrahydroquinolyl, tetrahydroisoquinolyl, dihydrobenzoxazine, tetrahydrobenzothienyl, and the like; tricyclic fused heterocyclic groups such as carbazolyl, acridinyl, xanthenyl, phenothiadinyl, phenoxathiinyl, phenoxazinyl, dlbenzofuryl, imidazoquinolyl, and the like; non-aromatic heterocyclic groups such as dioxanyl, thiiranyl, oxiranyl, oxathiolanyl, azetidinyl, thianyl, thiazolidine, pyrrolidinyl, pyrrolinyl, imidazolidinyl, imidazolinyl, pyrazolidinyl, pyrazolinyl, piperidyl, piperazinyl, morpholinyl, thiomorpholinyl, thiomorpholino, dihydropyridyl, dihyrobenzimidazolyl, tetrahydropyridyl, tetrahydrofuryl, tetrahydropyranyl, tetrahydrothiazolyl, tetrahydroisothiazolyl, dihydrooxazinyl, hexahydroazepinyl, tetrahydrodiazepinyl, and the like. Preferably, heterocyclic group is a 5- or 6-membered heteroaryl or non-aromatic heterocyclic group, and more preferably, a 5- or 6-membered heteroaryl.

"Non-aromatic heterocyclic group" means a group which does not show aromatic character of the "heterocyclic group".

Substituents of "a substituted or unsubstituted carbocyclic group" and "a substituted or unsubstituted heterocyclic group", "a substituted or unsubstituted non-aromatic carbocyclic group", "a substituted or unsubstituted non-aromatic heterocyclic group" include substituted or unsubstituted lower alkyl, and at least one group selected from Substituent Group Alpha.

Preferred embodiments of substituents in "a substituted or unsubstituted carbocyclic group", "a substituted or unsubstituted heterocyclic group", "a substituted or unsubstituted non-aromatic carbocyclic group" and "a substituted or unsubstituted non-aromatic heterocyclic group" include methyl, ethyl, isopropyl, tert-butyl, a fluorine atom, a chlorine atom, a bromine atom, hydroxy, carboxy, methoxy, ethoxy, hydroxymethoxy, hydroxyethoxy, methoxymethoxy, methoxyethoxy, amino, acetylamino, methylamino, dimethylamino, imino, hydroxyimino, methoxyimino, methylthio, carbamoyl, methylcarbamoyl, hydroxymethylcarbamoyl, sulfamoyl, methylsulfamoyl, lower alkylsulfamoyl, cyano, nitro, phenyl, cyclopropyl, cyclobutyl, cyclohexyl, pyridyl, morpholinyl, and the like.

"6-membered aromatic heterocyclic group having 1-3 nitrogen atoms" includes pyridine, pyrimidine, pyridazine, pyrazine, 1,3,5-triazine, 1,2,4-triazine, 1,2,3-triazine, and the like.

"5- or 6-membered aromatic heterocyclic group having 1-3 nitrogen atoms" includes pyrrolyl, imidazolyl, pyrazolyl, pyridyl, pyridazinyl, pyrimidinyl, pyrazinyl, triazolyl, triazinyl, isoxazolyl, oxazolyl, oxadiazolyl, isothiazolyl, thiazolyl, thiadiazolyl, furyl, thienyl, and the like.

Examples or embodiments of each site of Formula (I) are provided below. However, the scope of the subject invention is not limited to those described below.

"W" is —$CH_2$—, —S— or —O—. Preferably "W" is —$CH_2$—.

"U" is —$CH_2$—, —S—, —S(=O)— or —O— when "W" is —$CH_2$—. Preferably, "U" is —S— or —S(=O)—, more preferably "U" is —S—.

"U" is —$CH_2$— when "W" is —S— or —O—.

"L" is —$CH_2$—, —CH=CH—, —$CH_2$—CH=CH— or —CH=CH—$CH_2$—. Preferably, "L" is —$CH_2$—. Binding pattern of double bond between carbon atoms in L may be cis or trans, or mixture thereof.

Examples of "a substituted or unsubstituted carbocyclic group or substituted or unsubstituted heterocyclic group" of $R^1$ include phenyl and hydroxyphenyl; phenyl which have a halogen as a substituent; aminothiazole; aminothiazole which have a halogen as a substituent; aminothiadiazole; thiophene; furan; benzothiazole; pyridine; pyrimidine; pyridazine; aminopyridine; and the like. Preferred Examples includes the groups as follows:

[Chemical Formula 42]

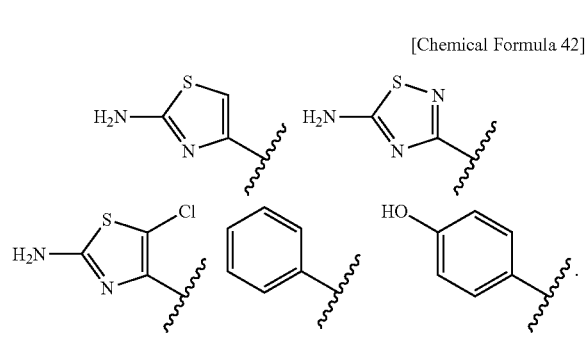

When $R^{2B}$ is hydrogen atom, examples of $R^{2A}$ include hydrogen atom, substituted or unsubstituted amino group, —COOH, —$SO_3H$, substituted or unsubstituted aminosulfonyl group, carboxyl group, substituted or unsubstituted carbamoyl group, hydroxyl group, or substituted carbonyloxy group, and the like. For example, preferred examples of

[Chemical Formula 43]

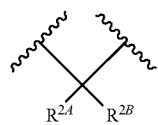

include a substituted amino group shown below:

[Chemical Formula 44]

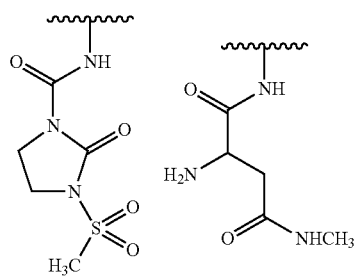

a substituted aminosulfonyl group shown below:

[Chemical Formula 45]

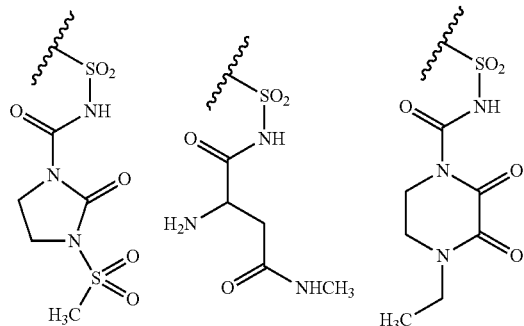

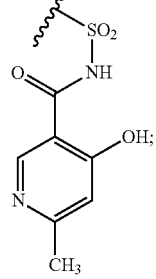

wherein ring B represents a substituted or unsubstituted heterocyclic group;
a substituted carbamoyl group shown below:

[Chemical Formula 46]

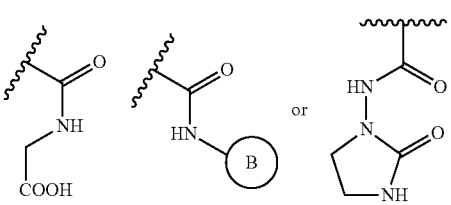

wherein ring B represents a substituted or unsubstituted heterocyclic group; or
a substituted carbonyloxy group shown below:

[Chemical Formula 47]

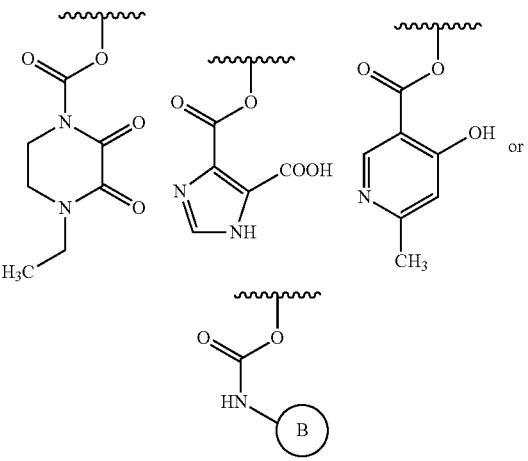

wherein ring B represents a substituted or unsubstituted.
Alternatively, $R^{2A}$ and $R^{2B}$ may be taken together to form a substituted methylidene group shown below:

[Chemical Formula 48]

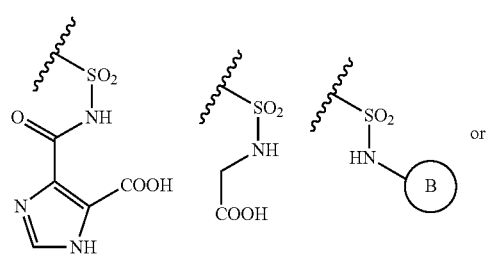

wherein $R^9$ is a substituted or unsubstituted lower alkyl, preferably

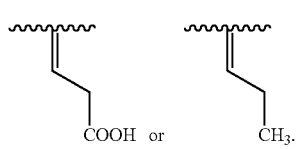

Also, $R^{2A}$ and $R^{2B}$ may be taken together to form a substituted or unsubstituted hydroxyimino group shown below:

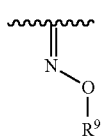

wherein $R^9$ is as defined above.

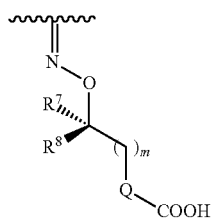

wherein each symbol is as defined above is preferred.

Examples of "$R^7$ and $R^8$" includes a hydrogen atom, a fluorine atom, a chlorine atom, hydroxy, carboxy, methyl, ethyl, isopropyl, tert-butyl, monofluoromethyl, difluoromethyl, trifluoromethyl, carboxymethyl, carboxyethyl, carbamoylmethyl, carbamoylethyl, hydroxymethyl, hydroxyethyl, methoxymethyl, ethoxymethyl, methoxyethyl, ethoxyethyl, methylthiomethyl, ethylthiomethyl, benzyl, 4-hydroxybenzyl, 4-methoxybenzyl, 4-carboxybenzyl, 3,4-dihydroxybenzyl, phenyl, 4-hydroxyphenyl, 3,4-dihydroxyphenyl, naphthyl, cyclopropyl, cyclobutyl, cyclopentyl, cyclohexyl, pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl, thienyl, and the like.

Preferred combinations of $R^7$ and $R^8$ include, as ($R^7$, $R^8$), (a hydrogen atom, a hydrogen atom), (methyl, a hydrogen atom), (a hydrogen atom, methyl), (methyl, methyl), (ethyl, a hydrogen atom), (a hydrogen atom, ethyl), (ethyl, ethyl), (phenyl, a hydrogen atom), (a hydrogen atom, phenyl), (dihydroxyphenyl, a hydrogen atom), (a hydrogen atom, dihydroxyphenyl), (carboxymethyl, a hydrogen atom), (a hydrogen atom, carboxymethyl), (carboxyethyl, a hydrogen atom), (a hydrogen atom, carboxyethyl), (hydroxyethyl, a hydrogen atom), (a hydrogen atom, hydroxylethyl), (carbamoylmethyl, a hydrogen atom), (a hydrogen atom, carbamoylmethyl), (trifluoromethyl, a hydrogen atom), (carboxy, a hydrogen atom), (carbamoylethyl, a hydrogen atom), (benzyl, a hydrogen atom), (dihydroxybenzyl, a hydrogen atom), and the like.

Preferred examples of the above substituted hydroxyimino group include groups shown bellow:

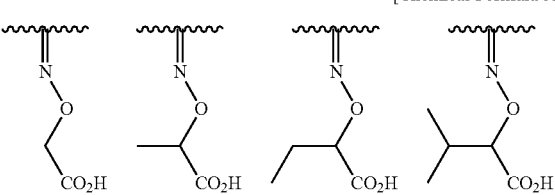
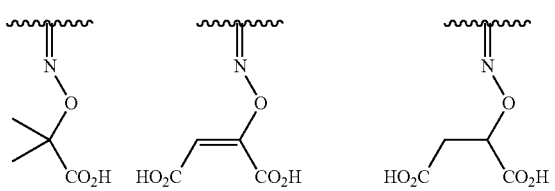
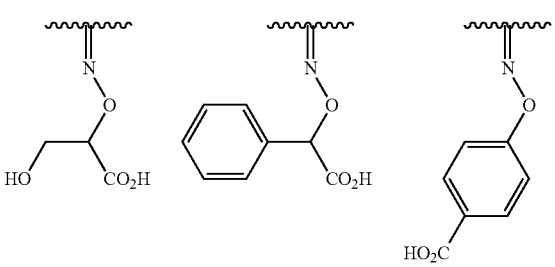
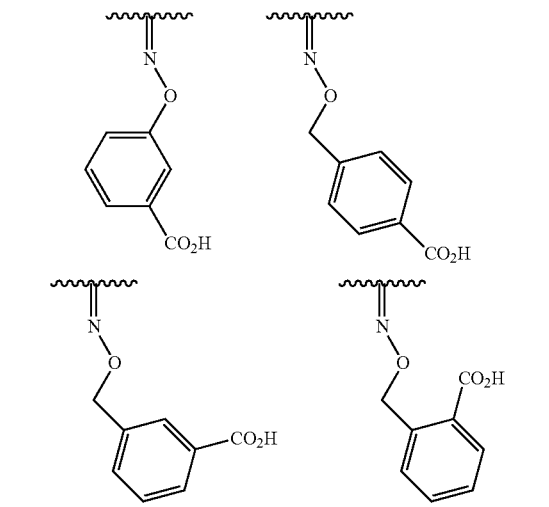
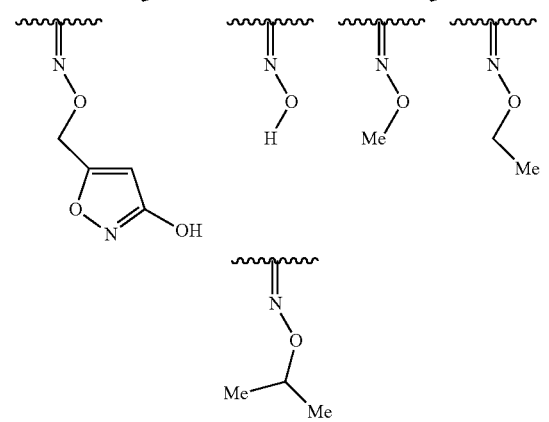

More preferred examples of the above substituted hydroxyimino group include groups shown bellow:

[Chemical Formula 53]

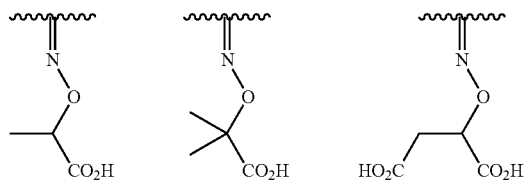

In the case where "$R^7$ and $R^8$ may be taken together with a neighboring atom to form a substituted or unsubstituted carbocyclic group or a substituted or unsubstituted heterocyclic group", $R^7$ and $R^8$ in the formula:

[Chemical Formula 54]

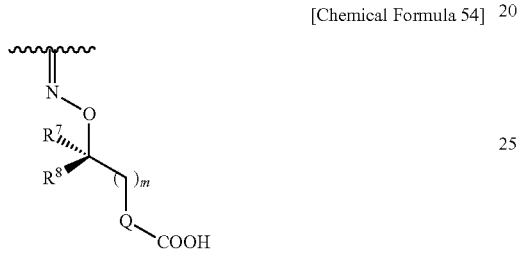

wherein each symbol is as defined above is preferred, may form cycloalkane, cycloalkene, or a non-aromatic heterocycle substituted or unsubstituted on the ring with a group selected from Substituent Group Alpha. For example,

[Chemical Formula 55]

can be a formula shown below:

[Chemical Formula 56]

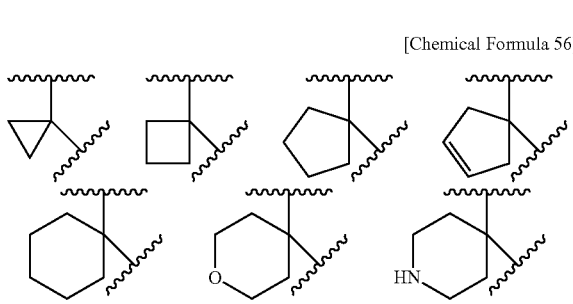

substituted or unsubstituted on the ring with a group selected from Substituent Group Alpha.

Examples of "Q" include a single bond, phenyl, pyridyl, and the like. A single bond is particularly preferable.

"m" is preferably an integer of 0 or 1, and 0 is particularly preferable.

Preferred examples of this embodiment include:

[Chemical Formula 57]

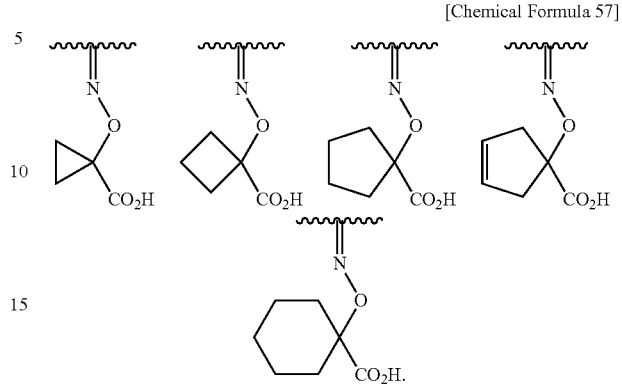

The term "bioisoster" as used herein refers to a group having chemical and physical similarities that provides similar biological properties. Accordingly, "a bioisoster of carboxyl ion (—COO$^-$)" of the subject invention refers to any group that provides biological properties similar to those provided by carboxy ion, specifically refers to a group that is comparatively similar to "carboxyl ion (—COO$^-$)" in its chemical structure, that is expected for physical properties, such as acidity, water solubility and/or disposition, equivalent to those of "carboxyl ion (—COO$^-$)", and that has an acidic proton. Said acidic proton moiety may form a salt, such as an alkali metal salt (e.g., sodium salt). Examples can be found in literatures, such as J. Med. Chem. 1992, 35, 1176-1183; J. Med. Chem. 1993, 36, 2485-2493; J. Med. Chem. 1992, 35, 3691-3698; J. Med. Chem. 1995, 38, 617-628; Med. Res. Rev. 1983, 3, 91-118; J. Med. Chem. 2001, 44, 1560-1563; Bioorganic & Medicinal Chemistry Letters, Vol. 4, No. 1, 41-44, 1994. Preferably, it is selected from —SO$_3^-$, —SO$_2$—N$^-$—R$^{13}$, —PO$^-$—(OR$^{13}$), —PO$_2^-$—(OR$^{13}$), —N$^-$—CO—R$^{13}$, —CO—N$^-$—OR$^{13}$, —CO—NH—N$^-$—SO$_2$—R$^{13}$, —CO—N$^-$—SO$_2$—R$^{13}$, —CO—CH=C(O$^-$)—R$^{13}$, —N$^-$—SO$_2$—R$^{13}$, —CO—N$^-$—SO$_2$—R$^{13}$, —N$^-$—SO$_2$—R$^{13}$, —CO—N$^-$—CO—R$^{13}$, —CO—N$^-$—SO$_2$—R$^{13}$, —N$^-$—CO—R$^{13}$

[Chemical Formula 58]

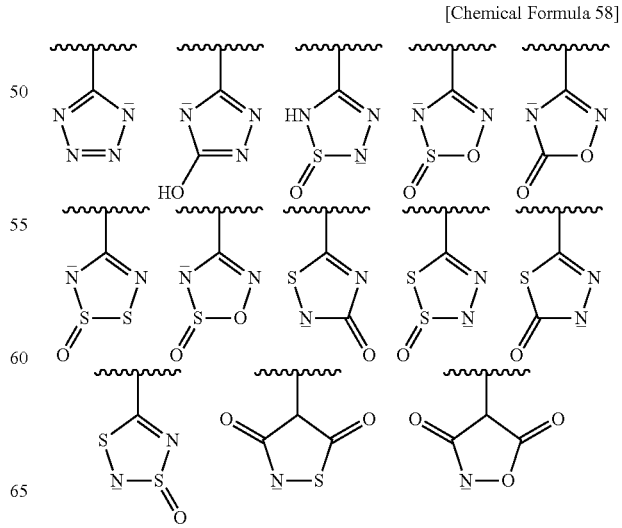

-continued

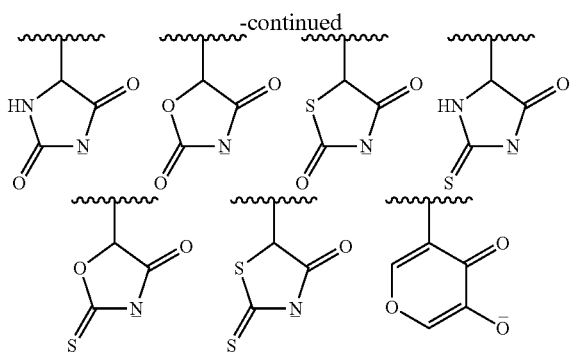

[Chemical Formula 59]

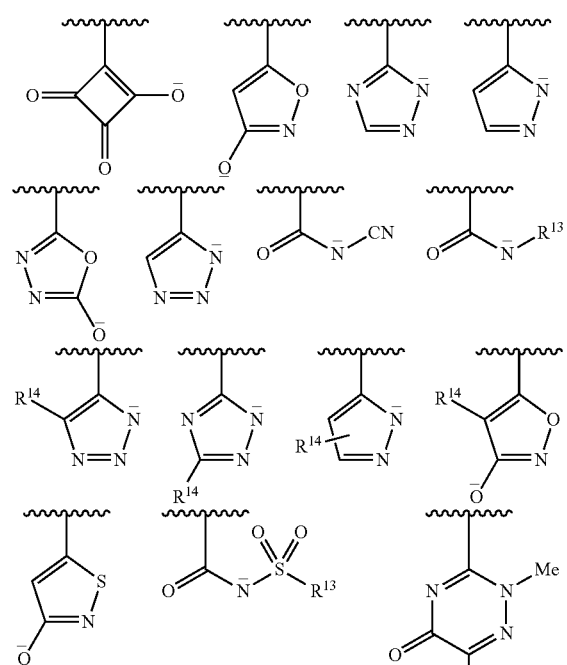

[Chemical Formula 60]

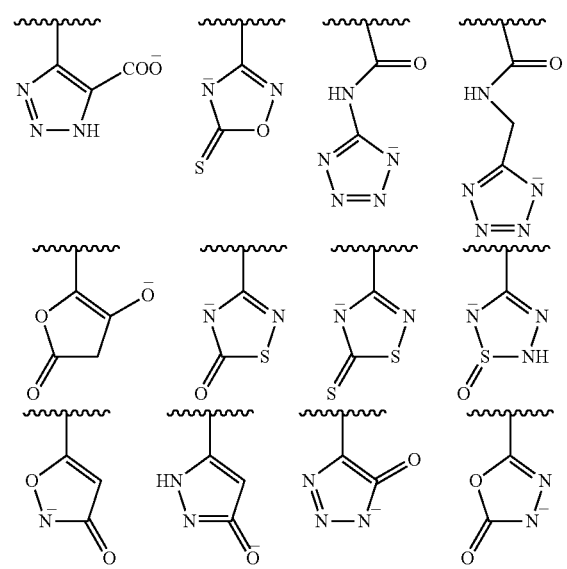

wherein $R^{13}$ is selected from the group consisting of hydrogen, hydroxyl group, halogen, a substituted or unsubstituted lower alkyl group, a substituted or unsubstituted lower alkenyl group, a substituted or unsubstituted lower alkynyl group, a substituted or unsubstituted lower alkoxy group, a substituted or unsubstituted amino group, (lower alkenyl)oxy group, a substituted or unsubstituted aryloxy group, cyano, nitro, imino, mercapto, (lower alkyl)thio group, (lower alkyl) sulphonyl group, a substituted or unsubstituted carbocyclic group, a substituted or unsubstituted heterocyclic group and —$CO_2R^{17}$ wherein $R^{17}$ is hydrogen, lower alkyl group or lower alkenyl group; and $R^{14}$ is an electron-withdrawing group.

[Chemical Formula 61]

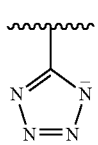

is more preferable.

$R^{14}$ is not limited so long as it is an electron-withdrawing group. Preferred examples of $R^{14}$ include fluorine, —$CHF_2$, —$CF_3$, —$CONH_2$, —CN, —C=N—OH, —$SO_2CH_3$ or —$SO_2NH_2$.

"$R^3$" is preferably a hydrogen atom or —$OCH_3$, and more preferably a hydrogen atom.

E is a substituted or unsubstituted divalent group having at least one quaternary ammonium ion and is preferably selected from the above formulae (1) to (73) substituted or unsubstituted on the ring. Groups "selected from the formulae (1) to (73) substituted or unsubstituted on the ring" include those wherein a hydrogen atom on the carbon atom in the cyclic group is replaced with a substituted or unsubstituted lower alkyl or with same or different one or more group selected from Substituent Group Alpha. Preferred embodiments of such substitutent include methyl, ethyl, isopropyl, tert-butyl, fluorine atom, chlorine atom, bromine atom, hydroxyl, carboxyl, methoxy, ethoxy, hydroxymethoxy, hydroxyethoxy, methoxymethoxy, methoxyethoxy, amino, acetylamino, methylamino, dimethylamino, imino, hydroxyimino, methoxyimino, methylthio, carbanoyl, methylcarbamoyl, hydroxymethylcarbamoyl, sulfamoyl, methylsulfamoyl, (lower)alkylsulfamoyl, cyano, nitro, phenyl, cyclopropyl, cyclobutyl, cyclohexyl, pyridyl, morpholinyl, and the like. More Preferred embodiments include a ring unsubstituted or mono- or di-substituted with a hydroxyl group. Such ring mono- or di-substituted with a hydroxyl group may be substituted additionally with another substituent.

E is "an optionally substituted divalent group having at least one quaternary ammonium ion", and more preferred examples of E include a group selected from the following formulae which are substituted or unsubstituted on the ring:

[Chemical Formula 62]

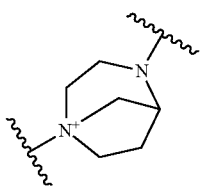

(1)

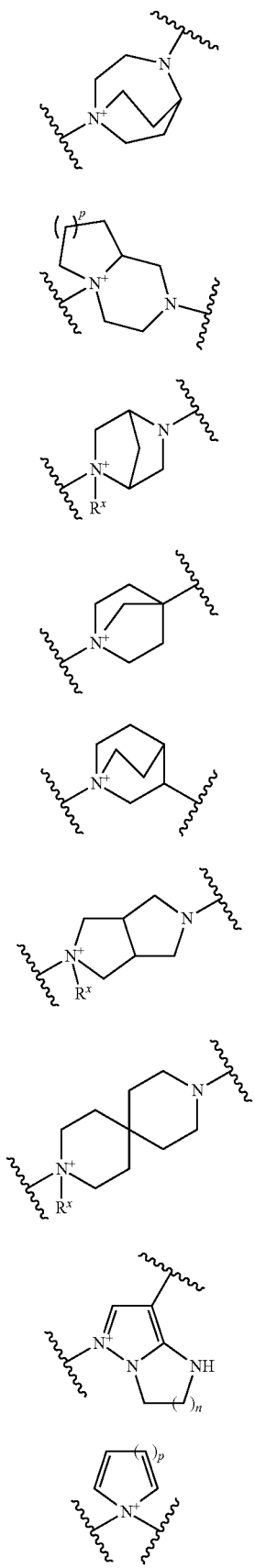
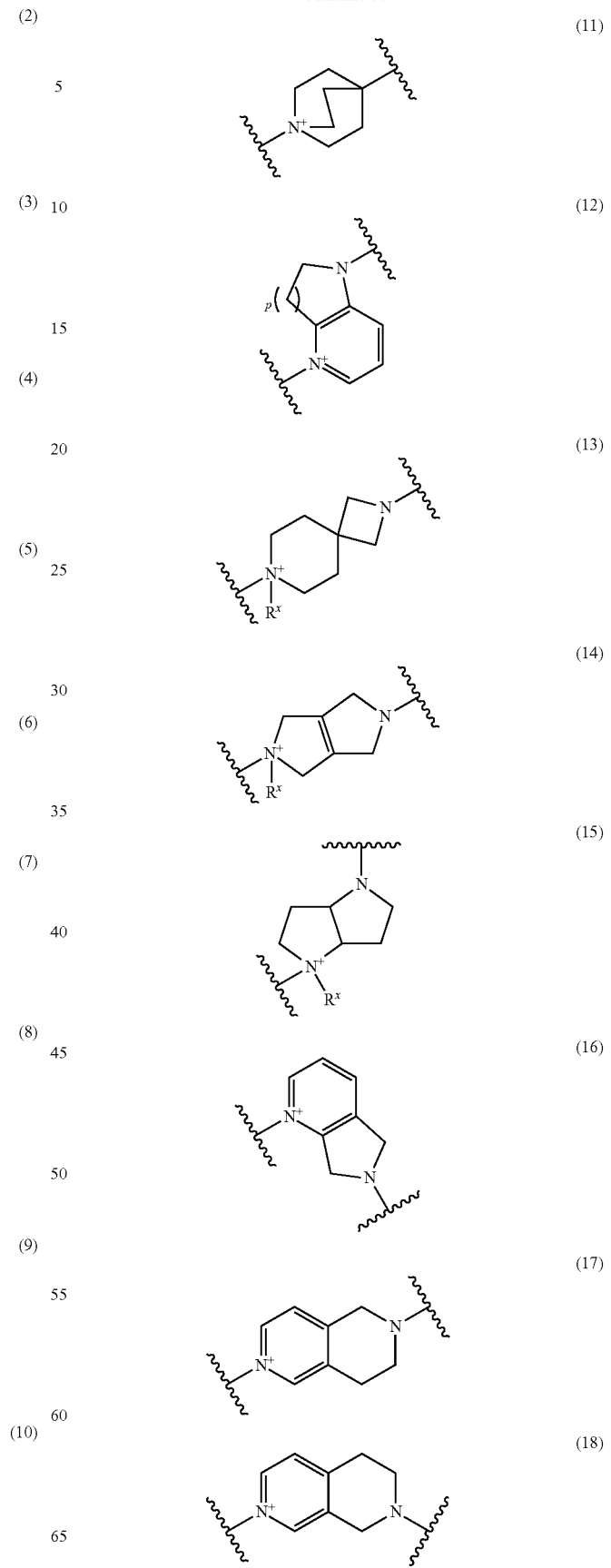

-continued
(19) 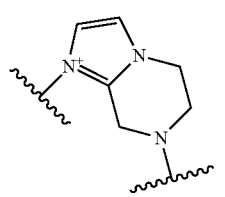
(20) 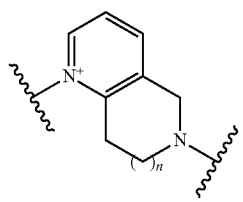
[Chemical Formula 63]
(21) 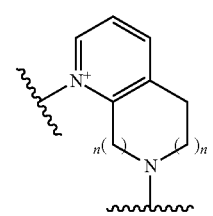
(22) 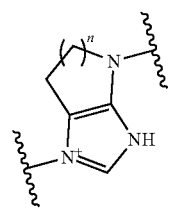
(23) 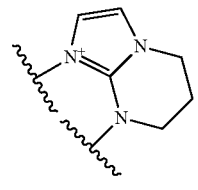
(24) 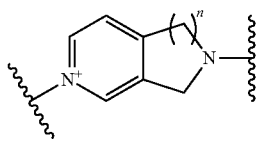
(25) 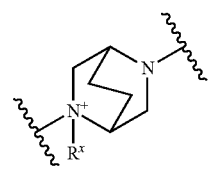
(26) 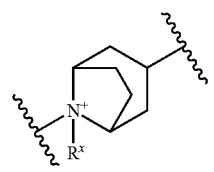
-continued
(27) 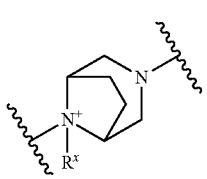
(28) 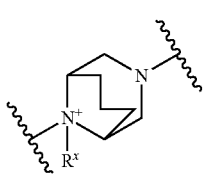
(29) 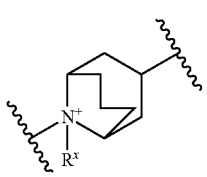
(30) 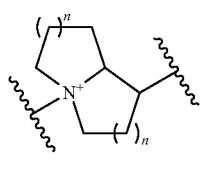
(31) 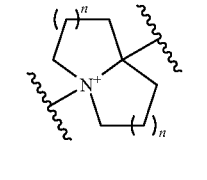
(32) 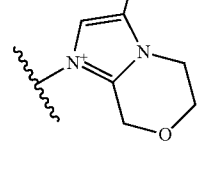
(33) 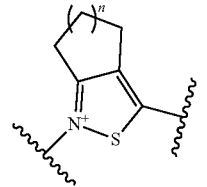
(34) 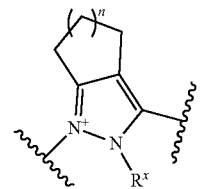

-continued
(35) 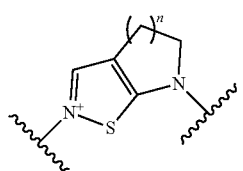
(36) 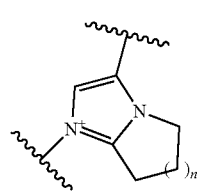
(37) 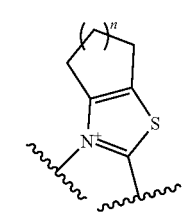
(38) 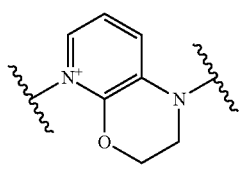
(39) 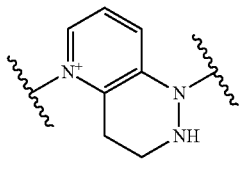
(40) 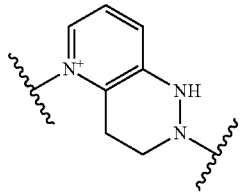
[Chemical Formula 64]
(41) 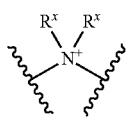
(42) 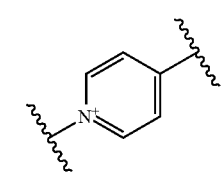
-continued
(43) 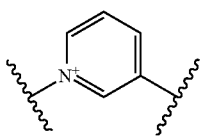
(44) 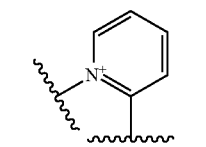
(45) 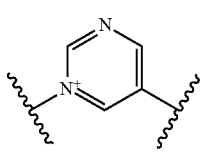
(46) 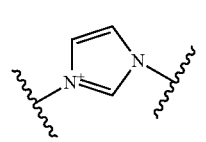
(47) 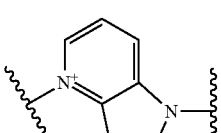
(48) 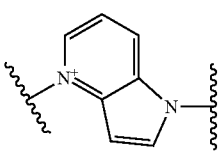
(49) 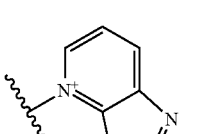
(50) 
(51) 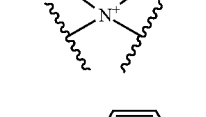
(52) 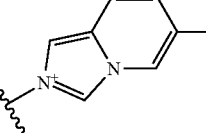

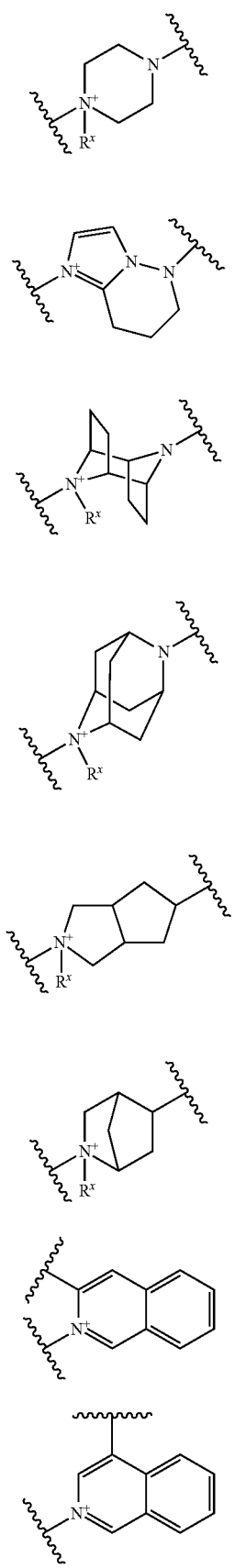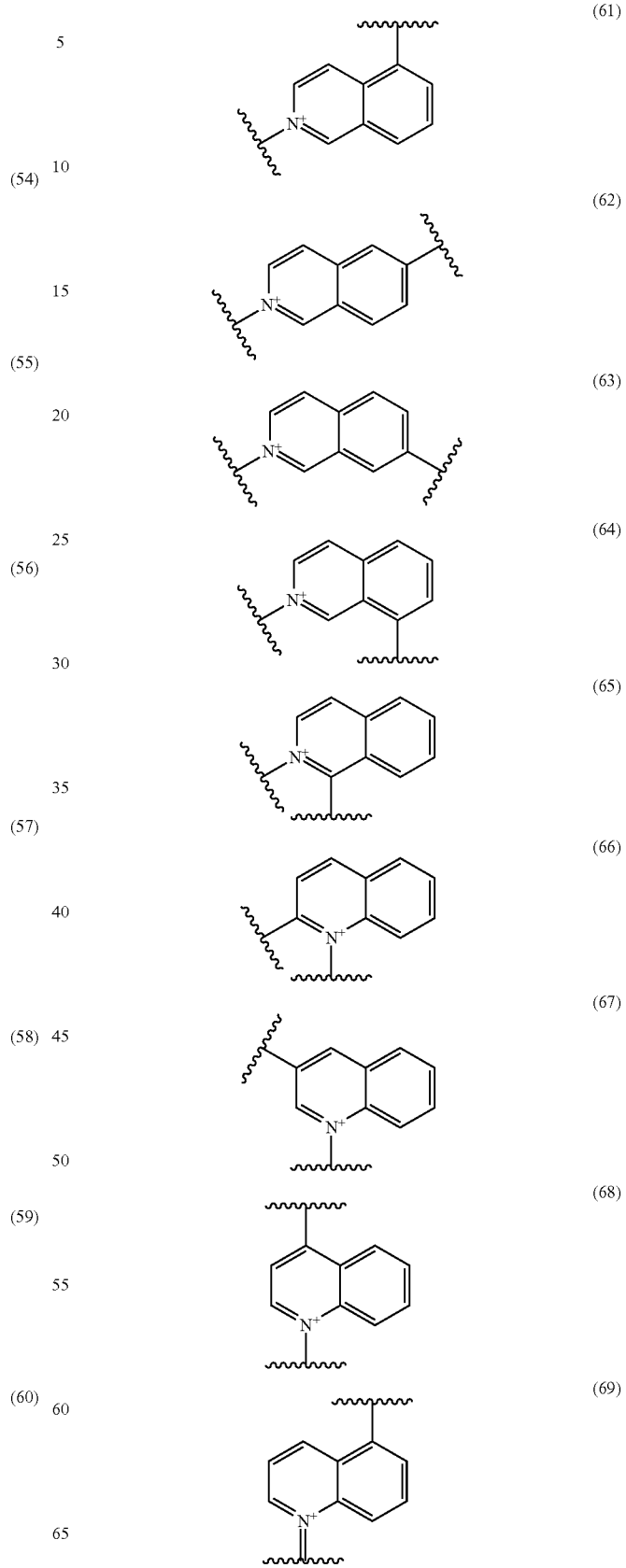

-continued

(70)
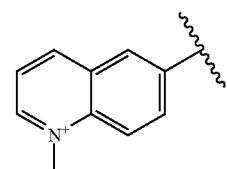

(71)
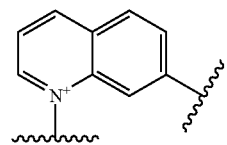

(72)
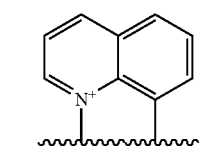

(73)
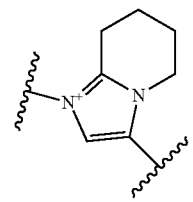

(74)
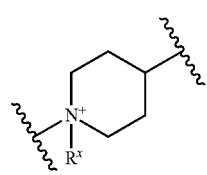

(75)
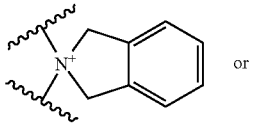 or

(76)
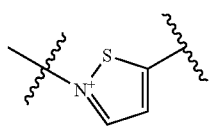

wherein the bond to the quaternary nitrogen atom binds to L, and the other bond binds to $R^{10}$; p is an integer from 1 to 3; n is an integer of 1 or 2; each $R^X$ is independently a substituted or unsubstituted lower alkyl group.

Among the above formulae, a group selected from the group consisting of the formulae (1) to (7), (10) to (12), (14), (25) to (29), (31), (41) to (44), (47), (50), (52), (53), (64) and (73) is more preferable.

Particularly, a group selected from the group consisting of the formulae (3), (10) to (12), (26) to (28), (31), (41), (42), (53), (64) and (73) is preferable.

Also, the following groups are preferable:

[Chemical Formula 66]

(3)
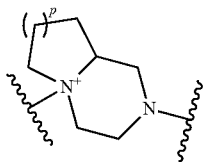

(10)
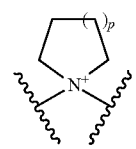

(11)
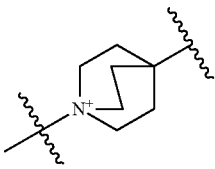

(26)
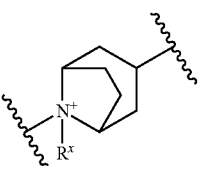

(41)
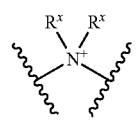

(36)
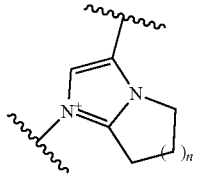

(42)
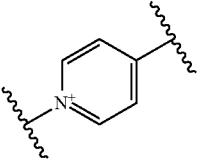

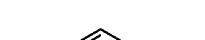

(43)
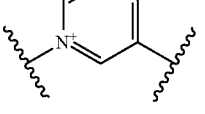

(44)
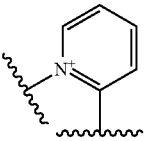

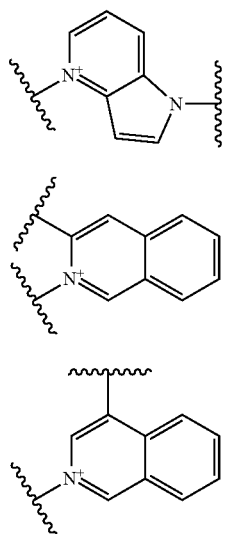

wherein each symbol is as defined above.

In the subject invention, E is a substituted or unsubstituted divalent group having at least one quaternary ammonium ion and divided in two embodiments as follows.

1) E contains an aromatic carbocyclic group or an aromatic heterocyclic group wherein a hydroxyl group binds to each of two adjacent carbon atoms on the aromatic ring; and 2) E contains neither an aromatic carbocyclic group nor an aromatic heterocyclic group or E contains an aromatic carbocyclic group or an aromatic heterocyclic group but a hydroxyl group does not bind to each of two adjacent carbon atoms on the aromatic ring.

In the embodiment that E contains an aromatic carbocyclic group or an aromatic heterocyclic group wherein a hydroxyl group binds to each of two adjacent carbon atoms on the aromatic ring, preferable examples of E include:

[Chemical Formula 67]

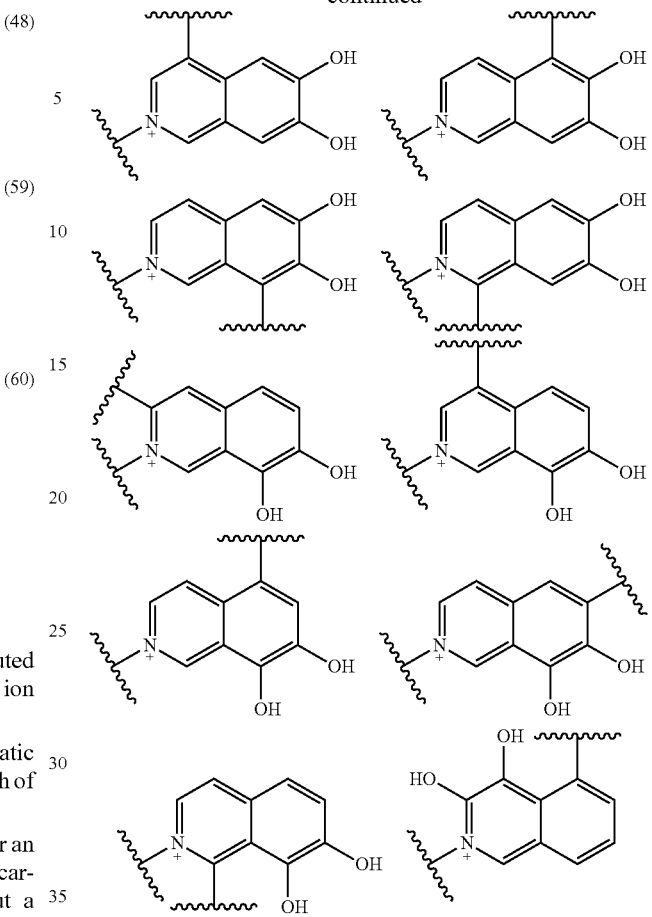

[Chemical Formula 68]

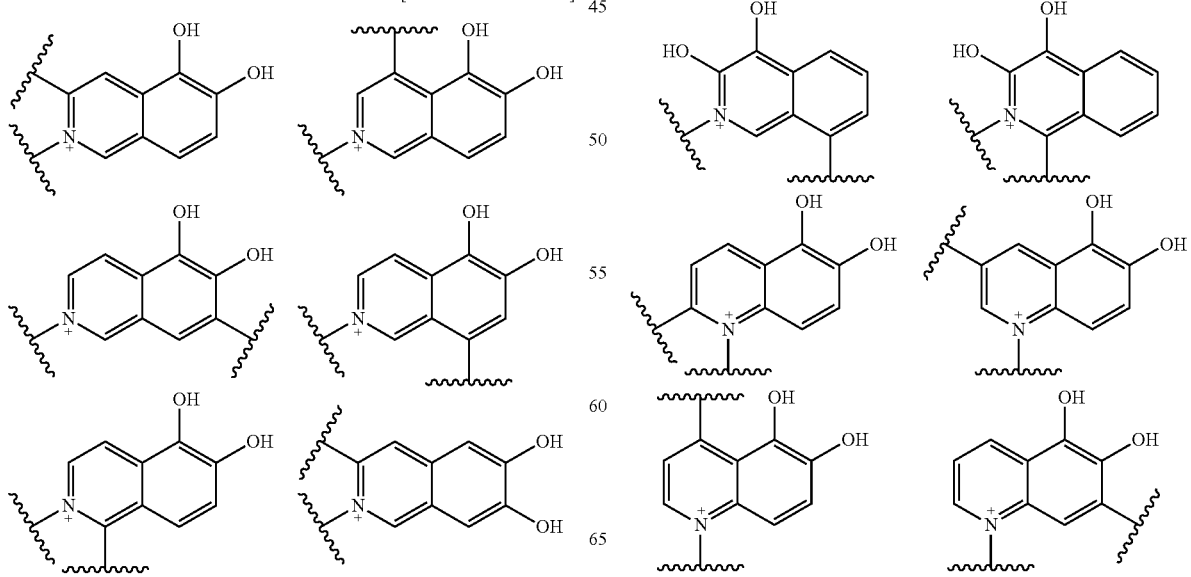

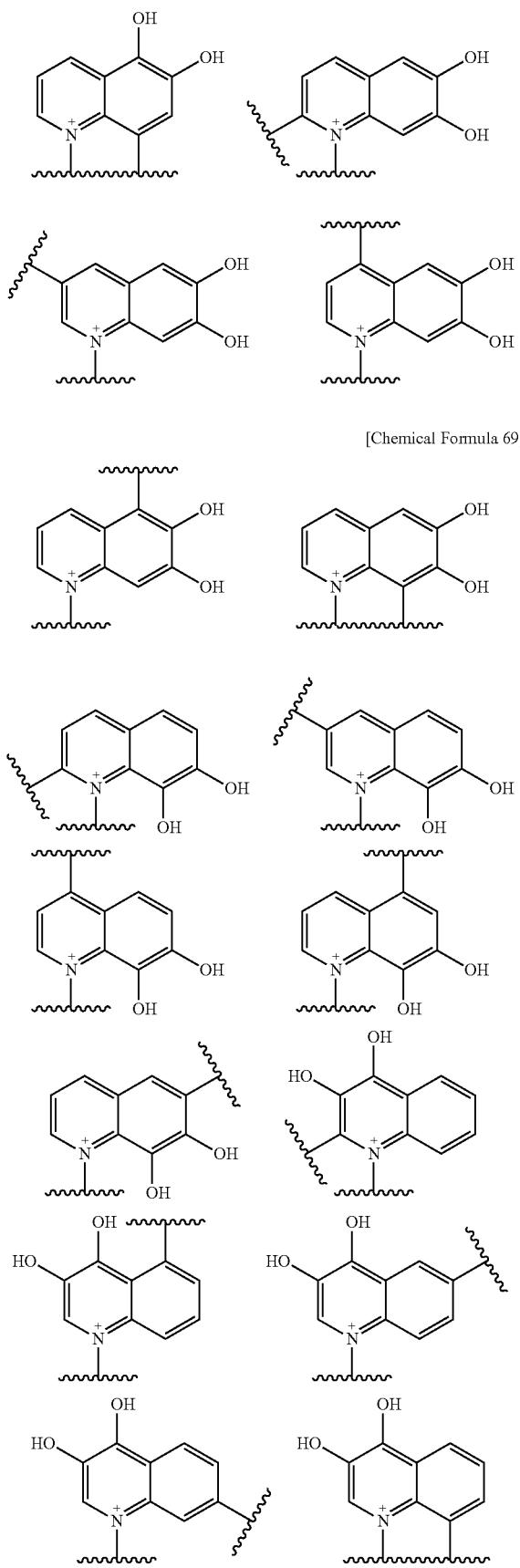
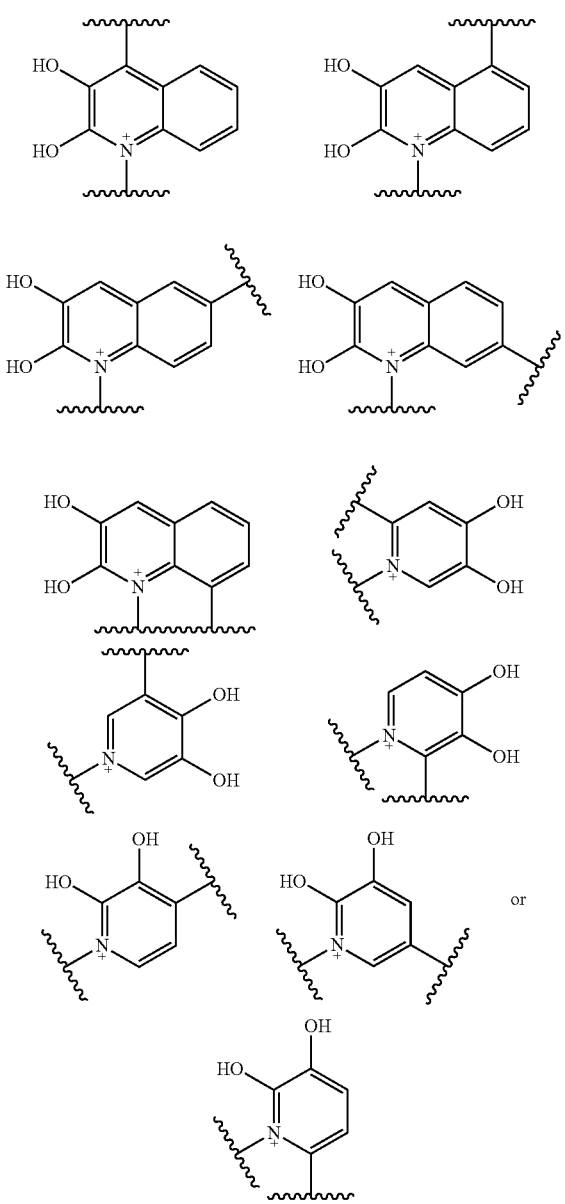
wherein the bond to the quaternary nitrogen atom binds to L, and the other bond binds to $R^{10}$.
Preferred examples of E-$R^{10}$ when E contains an aromatic carbocyclic group or an aromatic heterocyclic group wherein a hydroxyl group binds to each of two adjacent carbon atoms on the aromatic ring include:
[Chemical Formula 71]
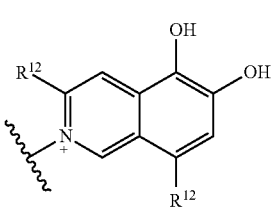

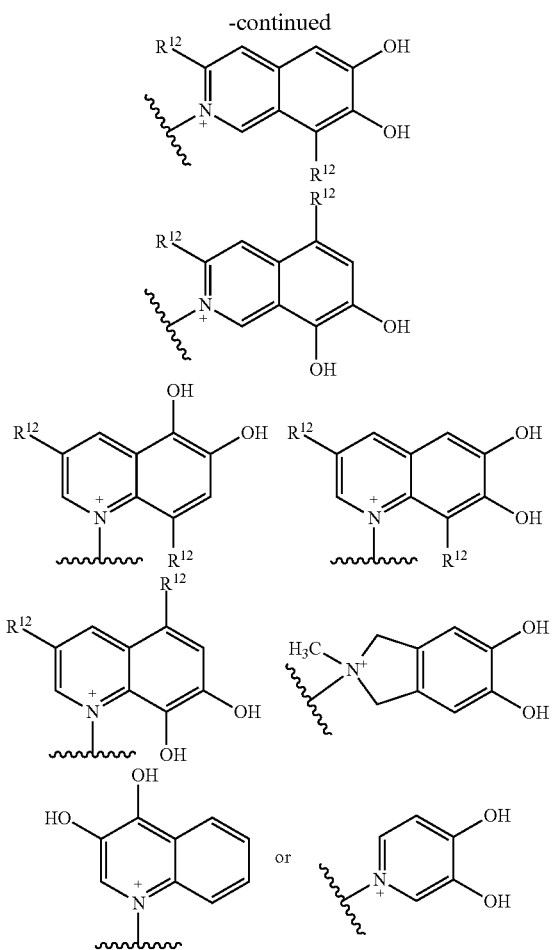

wherein the bond to the quaternary nitrogen atom binds to L, and $R^{12}$ is as defined in Item 1.

Still more preferred examples of E-$R^{10}$ when E contains an aromatic carbocyclic group or an aromatic heterocyclic group wherein a hydroxyl group binds to each of two adjacent carbon atoms on the aromatic ring include:

[Chemical Formula 72]

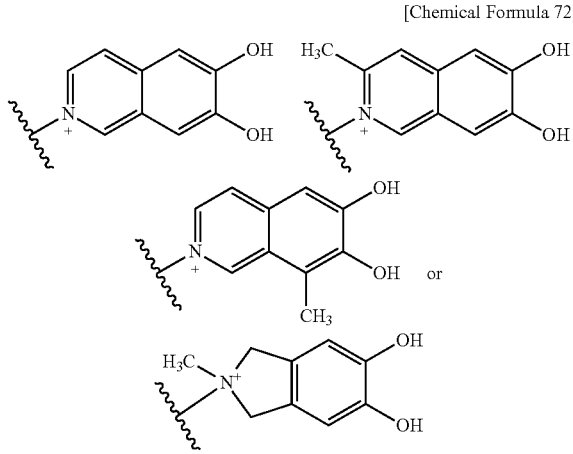

wherein the bond to the quaternary nitrogen atom binds to L.
Examples of $R^{12}$ when $R^{10}$ is —$R^{12}$ include hydrogen atom, halogen, hydroxyl group, —$SO_3H$, a substituted or unsubstituted amino group, a substituted or unsubstituted carboxyl group, a substituted or unsubstituted carbamoyl group, a substituted or unsubstituted acyl group, a substituted or unsubstituted amino sulfonyl group, a substituted or unsubstituted alkyl group, a substituted or unsubstituted alkenyl group, a substituted or unsubstituted alkynyl group, a substituted or unsubstituted non-aromatic carbocyclic group or a substituted or unsubstituted non-aromatic heterocyclic group. Preferably, $R^{12}$ is hydrogen atom or an optionally substituted alkyl group.

Preferred embodiments wherein $R^{10}$ is a group represented by the formula:

[Chemical Formula 73]

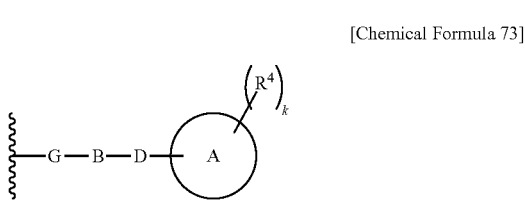

are provided below.

G is preferably a single bond or a substituted or unsubstituted lower alkylene group, and more preferably a single bond, methylene or ethylene.

B is preferably a single bond or a group represented by the formula:

[Chemical Formula 74]

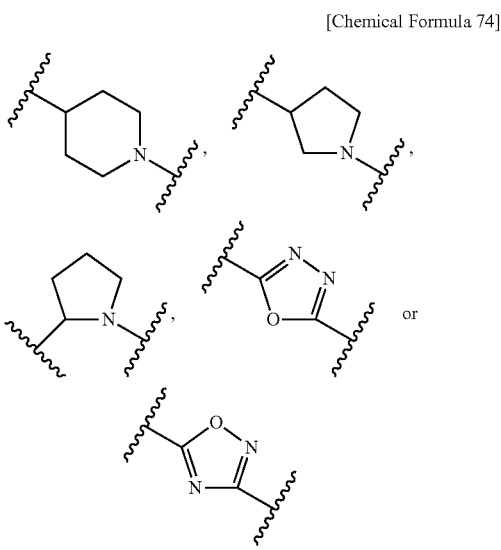

wherein the bond of the left side is attached to G and the bond of the right side is attached to D.

B is more preferably a single bond.

D is preferably a single bond, —C(=O)—, —O—C(=O)—, —C(=O)—O—, —NH—, —NH—C(=O)—, —C(=O)—NH—, —NH—C(=O)—NH—, —O—, —S—, —S(=O)—, —S(=O)$_2$—NH—, —NH—S(=O)$_2$—, —NH—CH$_2$—, —CH$_2$—NH— or —S(=O)$_2$—, and more preferably —C(=O)— or —NH—C(=O)—.

Preferable examples of "-E-G-B-D-" include the formulae as shown below:

[Chemical Formula 75]
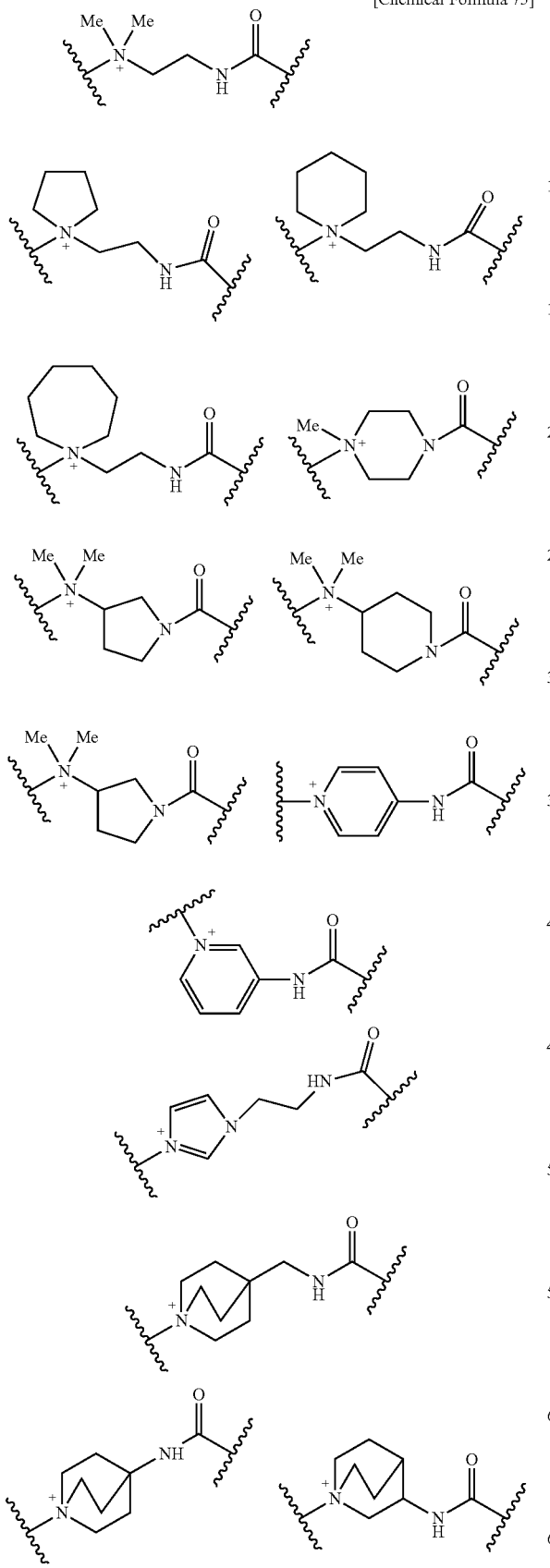
[Chemical Formula 76]
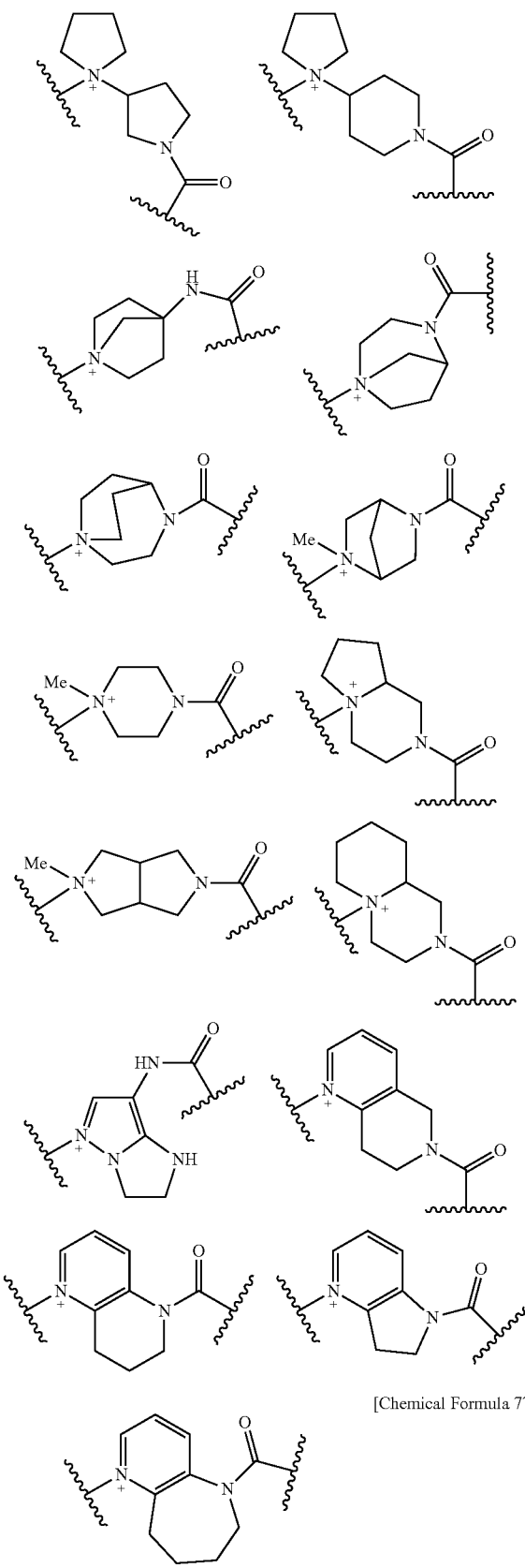
[Chemical Formula 77]

-continued
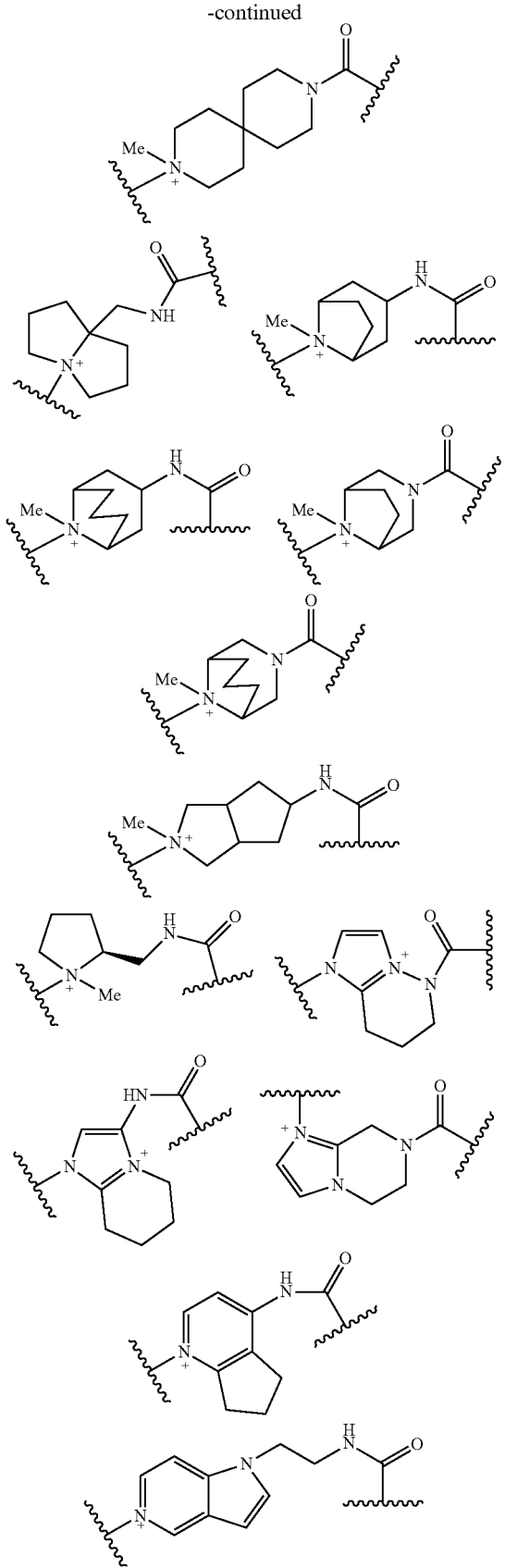
wherein Me represents methyl group.
Preferred examples of a group of the formula:
[Chemical Formula 78]
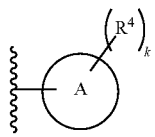
Include the formulae as shown below:
[Chemical Formula 79]
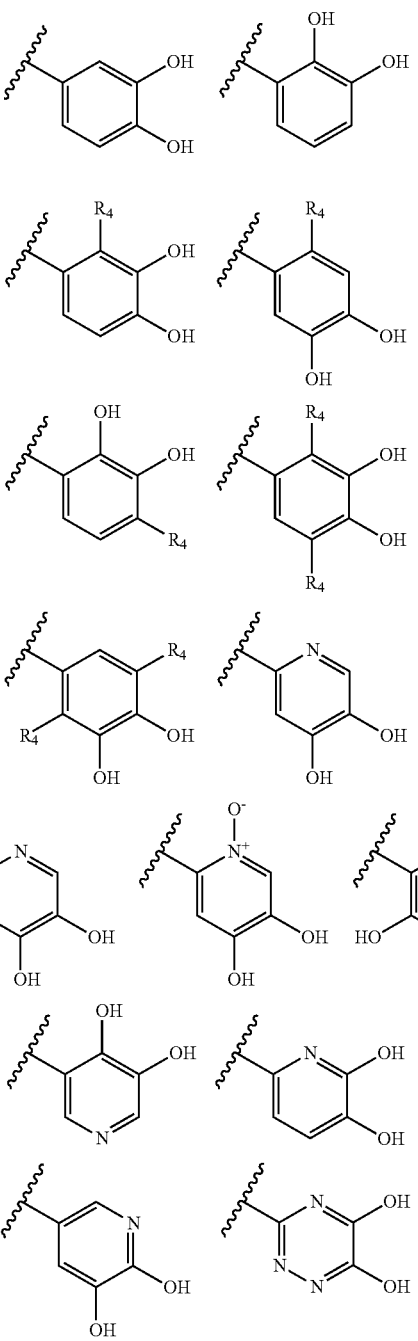

-continued
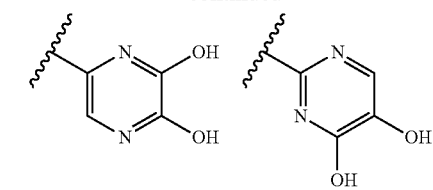
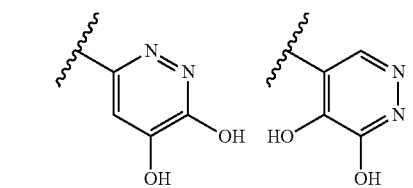
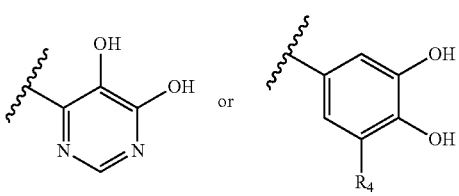 or
wherein each $R^4$ is independently hydrogen atom, halogen, hydroxyl group, —CN, —C(=O)—$R^5$, —C(=O)—OH, —C(=O)—$OR^5$ or —$OR^5$.
Preferred examples of a group of the formula:
[Chemical Formula 80]
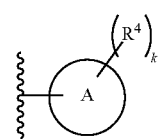
include the formulae as shown below:
[Chemical Formula 81]
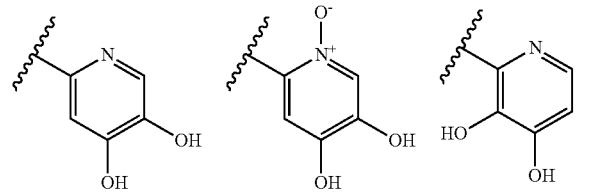
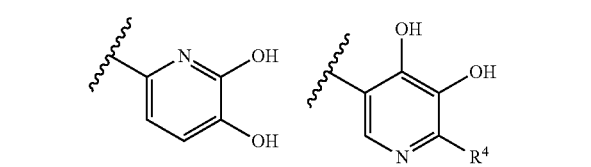
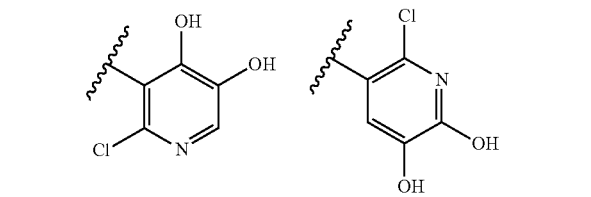
-continued
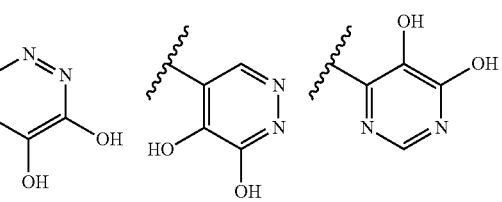
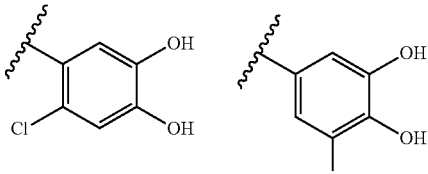
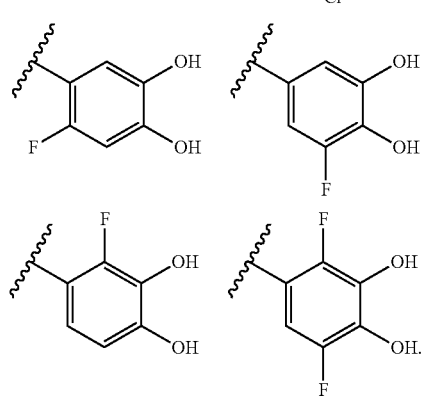
More preferable examples of a group of the formula:
[Chemical Formula 82]
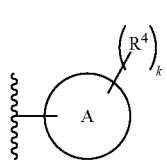

include the formulae as shown below:

[Chemical Formula 83]

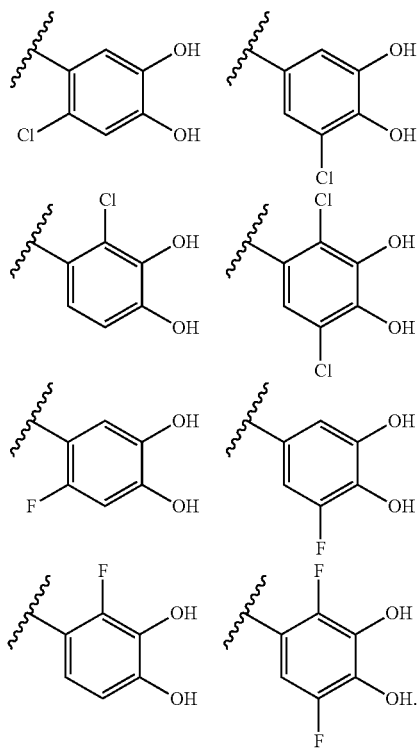

Examples of "R⁴" include hydrogen atom, chlorine atom, fluorine atom, bromine atom, cyano, hydroxy, carboxy, acetyl, methoxy, ethoxy, trifluoromethyl, and the like. Preferably, R⁴ is a hydrogen atom, hydroxy, carboxy, methoxy, fluorine atom, trifluoromethyl, or chlorine atom. Particularly preferably, at least two R⁴ are hydroxyl groups and bind respectively to adjacent carbon atoms on ring A.

"k" is an integer of 2 to 5. As ring A is a benzene ring or a 6-membered aromatic heterocyclic group having 1-3 nitrogen atoms, for example, k is 5 when the ring A is a benzene ring, and k is 2 when the ring A is a 6-membered aromatic heterocyclic group having 3 nitrogen atoms.

The nomenclature of the substitution position on the Cephem skeleton of Formula (C) is as follows. As used herein, 3-side chain, 4-side chain and 7-side chain respectively refer to groups binding to the 3-position, 4-position and the 7-position of the Cephem skeleton as shown below

[Chemical Formula 84]

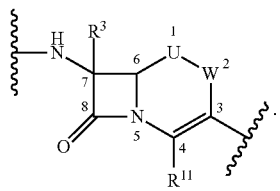

Esters of Formula (I) preferably include those esters at the 7-side chain. Esters at the carboxyl group on the 7-side chain include compounds having a structure in which the carboxyl group of a substituted or unsubstituted amino group, substituted or unsubstituted aminosulfonyl group, carboxyl group, substituted or unsubstituted (lower)alkyloxycarbonyl group, substituted or unsubstituted carbamoyl group, substituted carbonyloxy group, or the like at the terminal of R¹, R²ᴬ or R²ᴮ shown in the formula:

[Chemical Formula 85]

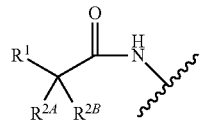

wherein each symbol is as defined above, is esterified (for example, in the case of carboxyl (—COOH), such esters are represented by the structural formula —COORᵃ, which is shown with Rᵃ representing an ester residue such as a carboxyl-protecting group or the like); and the like. Such esters include those esters that are easily metabolized in the body to form a carboxylic state.

The aforementioned protecting groups for a carboxyl group or the like may be of any group as long as it can be protected and/or deprotected by a method described in Protective Groups in Organic Synthesis, written by T. W. Greene, John Wiley & Sons Inc. (1991), or the like. Examples thereof include lower alkyl (e.g., methyl, ethyl, t-butyl), (lower)alkylcarbonyloxymethyl (e.g., pivaloyl), substituted or unsubstituted aralkyl (e.g., benzyl, benzhydryl, phenethyl, p-methoxybenzyl, p-nitrobenzyl), silyl groups (t-butyldimethylsilyl, diphenyl(t-butyl)silyl), and the like.

Amino-protected compounds at the amino on the 7-side chain of Formula (I) refer to the structures in which the amino on the ring has been protected, as shown in the formula:

[Chemical Formula 86]

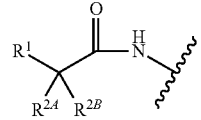

wherein each symbol is as defined above; and when R¹ and/or R²ᴬ has an amino group, the protected compound is represented by the formula —NHRᶜ wherein Rᶜ represents an amino-protecting group. Such amino-protecting groups include those groups that are readily metabolized in the body to form amino. The aforementioned amino-protecting groups may be of any group as long as it can be protected and/or deprotected by a method described in Protective Groups in Organic Synthesis, written by T. W. Greene, John Wiley & Sons Inc. (1991), or the like. Examples thereof include (lower)alkoxycarbonyl (e.g., t-butoxycarbonyl, benzyloxycarbonyl, p-nitrobenzyloxycarbonyl), substituted or unsubstituted aralkanoyl (e.g., benzoyl, p-nitrobenzoyl), acyl (e.g., formyl, chloroacetyl), and the like.

The Compound (I) of the subject invention is not limited to particular isomers, but includes any possible isomers (e.g., keto-enol isomer, imine-enamine isomer, diastereoisomer, optical isomer, rotamer, etc.), racemates and a mixture thereof.

For example,

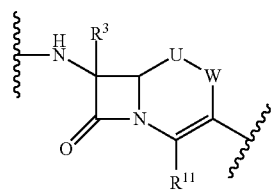
[Chemical Formula 87]

in Formula (I) includes

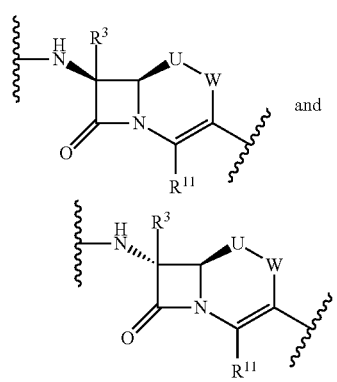
[Chemical Formula 88]

and

The compound (I) of the subject invention can form a zwitter ion between a quaternary ammonium ion on the group "E" and a substituent on the 4-side chain (i.e., a bioisoster of —COO⁻). For example, when the substituent at the 4-position is tetrazolyl group:

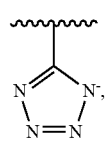
[Chemical Formula 89]

which is negatively charged, but it may take the structure

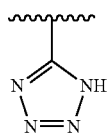
[Chemical Formula 90]

by receiving a proton from another moiety in Formula (I), and such structure should be included in the compound (I) of the subject invention. The same is true in another bioisoster of carboxyl ion (—COO⁻).

For example, the formula:

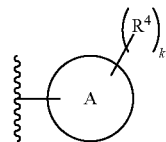
[Chemical Formula 91]

wherein each symbol is as defined above, in Formula (I) includes the following resonance structures:

[Chemical Formula 92]

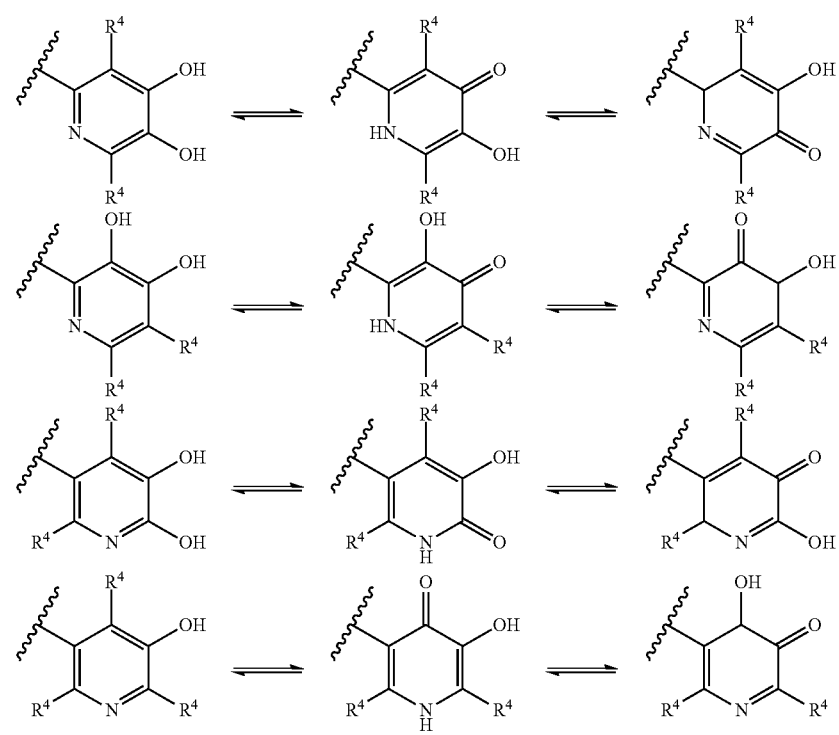

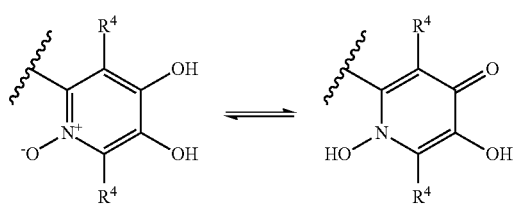

wherein R⁴ is as defined above.

Also, the group "E" in Formula (I), for example, includes the following resonance structures:

[Chemical Formula 93]

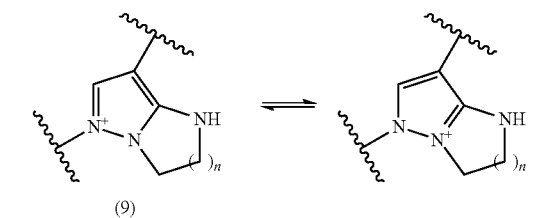

(9)

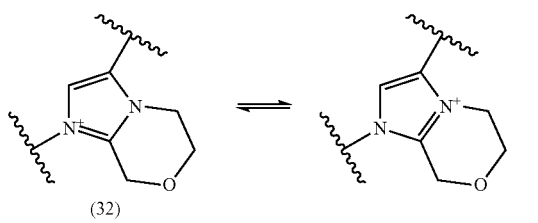

(32)

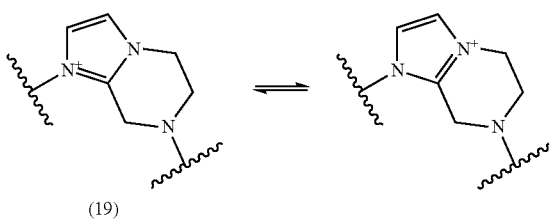

(19)

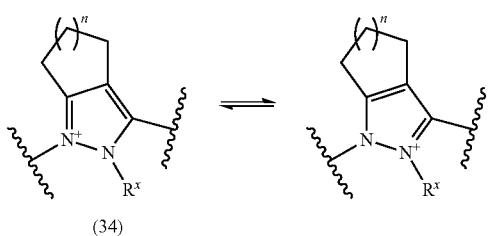

(34)

-continued

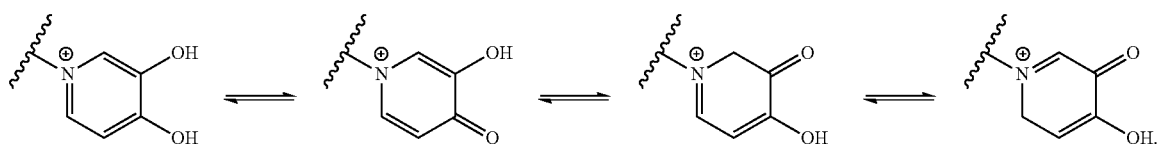

(22)

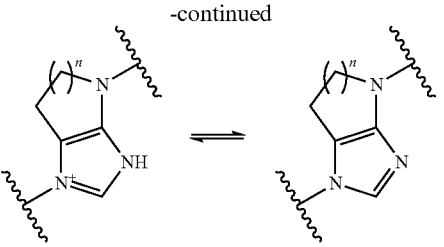

(23)

wherein each symbol is as defined above.

At least one hydrogen atom, carbon atom and/or another atom may be replaced with an isotope of said hydrogen atom, carbon atom and/or another atom. Examples of such isotope include hydrogen, carbon, nitrogen, oxygen, sulfur, fluorine, iodine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$ and $^{36}Cl$. The compound of Formula (I) include compounds having an atom replaced with such isotope. Such compound replaced with an isotope are useful as a pharmaceutical product, and such compound include all of radiolabeled compound of Formula (I). Also, the subject invention includes any method of radioactive labeling for the production of such radiolabeled compound, and thus, it is useful in a research for metabolic pharmacokinetics, binding assay and/or as a diagnostic tool.

A radiolabeled compound of Formula (I) may be prepared according to the technique well known in the art. For example, tritium can be introduced into a specific compound of Formula (I) by catalytic dehalogenation using tritium to prepare a tritium-labeled compound of Formula (I). This method comprises reaction of a precursor which is a compound of Formula (I) appropriately halogenated with tritium gas in the presence of appropriate catalyst, such as Pd/C, in the presence or absence of a base. For another method for the preparation of a tritium-labeled compound, see the literature, Isotopes in the Physical and Biomedical Sciences, Vol. 1, Labeled Compounds (Part A), Chapter 6 (1987). $^{14}C$-labeled compound can be prepared using a starting material having $^{14}C$.

Salts of a compound of Formula (I) include those formed with an inorganic or organic acid by a carboxyl group in the 7-side chain and/or an amino group in the 7-side chain; and those formed with a counter anion by a quaternary amine moiety in the 3-side chain.

Pharmaceutically acceptable salts of a compound of Formula (I) include, for example, salts formed with alkali metal (e.g. lithium, sodium, potassium, etc.), alkaline earth metal (e.g. calcium, barium, etc.), magnesium, transition metal (e.g. zinc, ferrum, etc.), ammonia, organic base (e.g. trimethylamine, triethylamine, dicyclohexylamine, ethanolamine, diethanolamine, triethanolamine, meglumine, diethanolamine, ethylenediamine, pyrydine, picoline, quinoline, etc.) and amino acid, or salts formed with inorganic acid (e.g. hydrochloric acid, sulphuric acid, nitric acid, carbonic acid, hydrobromic acid, phosphoric acid, hydroiodic acid, etc.), and organic acid (e.g. formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulphonic acid, p-toluenesulfonic acid, methanesulphonic acid, ethanesulphonic acid, etc, particularly, salts formed with hydrochloric acid, sulphuric acid, phosphoric acid, tartaric acid, methanesulphonic acid. These salts can be formed according to the conventional method.

The compound of Formula (I) or pharmaceutically acceptable salts thereof may form a solvate (e.g., hydrate) and/or a crystalline polymorphism, and the subject invention also includes such solvates and crystalline polymorphisms. In such "solvate", any number of solvent molecules (e.g., water molecule, etc.) may be coordinated to the compound of Formula (I). By leaving the compound of Formula (I) or pharmaceutically acceptable salt thereof in the atmosphere, it may absorb moisture to adhere with absorbed water or form a hydrate thereof. Also, a crystalline polymorphism of the compound of Formula (I) or pharmaceutically acceptable salt thereof can be formed by recrystallization.

The compound of Formula (I) or pharmaceutically acceptable salt thereof may form a prodrug, and the subject invention includes such prodrugs. Prodrug is a derivative of the compound of the invention having a group chemically- or metabolically-degradable to be transformed into a pharmacologically active compound by solvolysis or under physiological condition in vivo. Prodrug includes compounds which can be transformed into the compound of Formula (I) by enzymatically oxidization, reduction or hydrolysis under physiological condition in vivo, or transformed into the compound of Formula (I) by hydrolysis with gastric acid, etc. Methods for selection and production of appropriate prodrug derivative can be found, for example, in Design of Prodrugs, Elsevier, Amsterdam 1985.

Prodrug may be active compound in itself.

When the compound of Formula (I) or pharmaceutically acceptable salt thereof has a hydroxyl group, acyloxy derivatives or sulfonyloxy derivatives can be prepared as a prodrug. For example, such compound having a hydroxyl group may be reacted with an appropriate acyl halide, acid anhydride or an appropriate sulfonyl chloride, sulfonyl anhydride, mixed anhydride, etc., or may be reacted using a coupling agent, such as for examples, those having $CH_3COO—$, $C_2H_5COO—$, t-BuCOO—, $C_{15}H_{31}COO—$, PhCOO—, (m-NaOOCPh)COO—, $NaOOCCHCH_2CH_2COO—$, $CH_3CH(NH_2)COO—$, $CH_2N(CH_3)_2COO—$, $CH—SO_3—$, $CH_3CH_2SO_3—$, $CF_3SO_3—$, $CH_2FSO_3—$, $CF_3CH_2SO_3—$, p-$CH_3$—O-$PhSO_3—$, $PhSO_3—$, p-$CH_3PhSO_3—$.

For the synthesis of a compound of Formula (I), a compound of the formula:

[Chemical Formula 94]

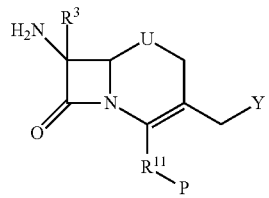

wherein Y is a leaving group, U, $R^3$ and $R^{11}$ are as defined above, and P is a protecting group as defined above, or a pharmaceutically acceptable salt thereof is preferred as an intermediate.

The leaving group includes halogen (Cl, Br, I, F), methanesulfonyloxy, p-toluenesulfonyloxy, trifluoromethanesulfonyloxy, etc.

As described in the following General Synthesis and Examples, an intermediate compound described above is attached with side chain moieties at the 3-, 4- and 7-positions of the cephem skeleton to obtain a compound of Formula (I). Examples of the protecting group "P" include those described in the following General Synthesis, and preferably, benzhydryl group, p-methoxybenzyl group, trityl group, 2,6-dimethoxybenzyl group, methoxymethyl group, benzyloxymethyl group or 2-(trimethylsilyl)ethoxymethyl group, etc.

(General Synthesis Method)

The compounds represented by Formula (I) of the subject invention can be manufactured, for example, by a general synthesis method described below:

Scheme 1

[Chemical Formula 95]

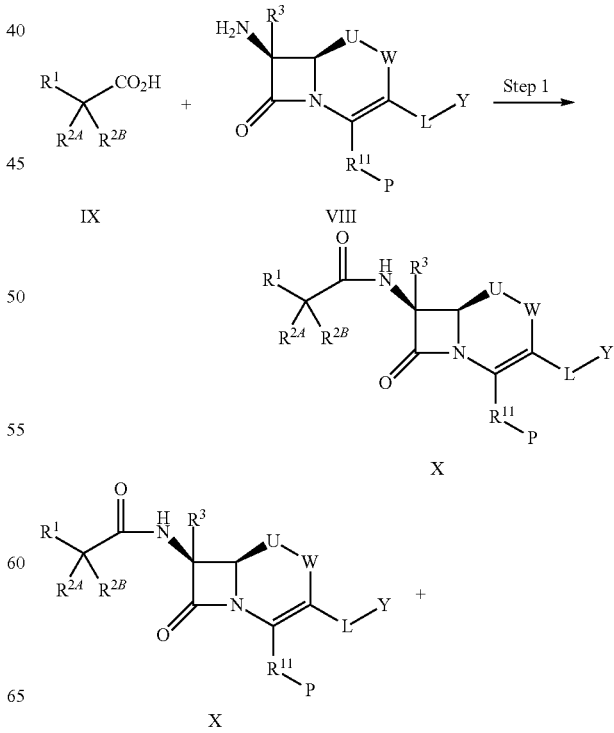

-continued

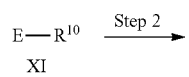

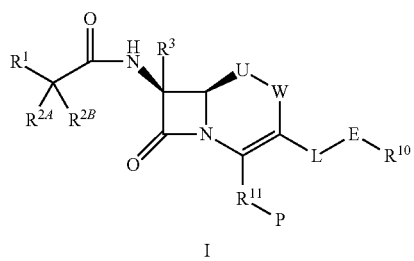

I wherein W, U, $R^1$, $R^{2A}$, $R^{2B}$, $R^3$, $R^{10}$, $R^{11}$, L and E are as defined above, P is a protecting group, and Y is a leaving group (e.g., a halogen (Cl, Br, I, F), methanesulfonyloxy, p-toluenesulformyloxy, trifluoromethanesulfonyloxy, etc.

1) Formation of 7-Side Chain: Synthesis of Compound (X)

Step 1

Compound (X) may be obtained by subjecting Compound (VIII) to a condensation reaction with Compound (IX). The reaction solvents include, for example, ethers (e.g., anisole, dioxane, tetrahydrofuran, diethyl ether, tert-butyl methyl ether, diisopropyl ether), esters (e.g., ethyl formate, ethyl acetate, n-butyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), nitros (e.g., nitromethane, nitroethane, nitrobenzene), dimethylsulfoxide, and water, or a mixed solvent selected from two or more of these solvents. The reaction temperature is usually in the range of from about −100° C. to 100° C., preferably in the range of from about −80° C. to 20° C., more preferably in the range of from about −60° C. to −20° C. The reaction time may vary according to the reagents, solvents or reaction temperature to be employed, and usually, is 0.5 to 24 hours.

2) Formation of the 3-Side Chain; Synthesis of Compound (I)

Step 2

Compound (I) may be obtained by reacting Compound (X) with Compound (XI), followed by deprotecting by a method well-known to those skilled in the art. The reaction solvents include, for example, ethers (e.g., anisole, dioxane, tetrahydrofuran, diethyl ether, tert-butyl methyl ether, diisopropyl ether), esters (e.g., ethyl formate, ethyl acetate, n-butyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), nitros (e.g., nitromethane, nitroethane, nitrobenzene), dimethylsulfoxide, and water, or a mixed solvent selected from two or more of these solvents.

The reaction temperature is usually in the range of from about −100° C. to 100° C., preferably in the range of from about −80° C. to 50° C., more preferably in the range of from about −40° C. to 0° C. The reaction time may vary according to the reagents, solvents or reaction temperature to be employed, and usually, is 0.5 to 24 hours.

If Compound of Formula (I) has a tetrazole ring at 4-position, Compound (VIII) used in the above Scheme 1 can be prepared according to Scheme 2.

Scheme 2

[Chemical Formula 96]

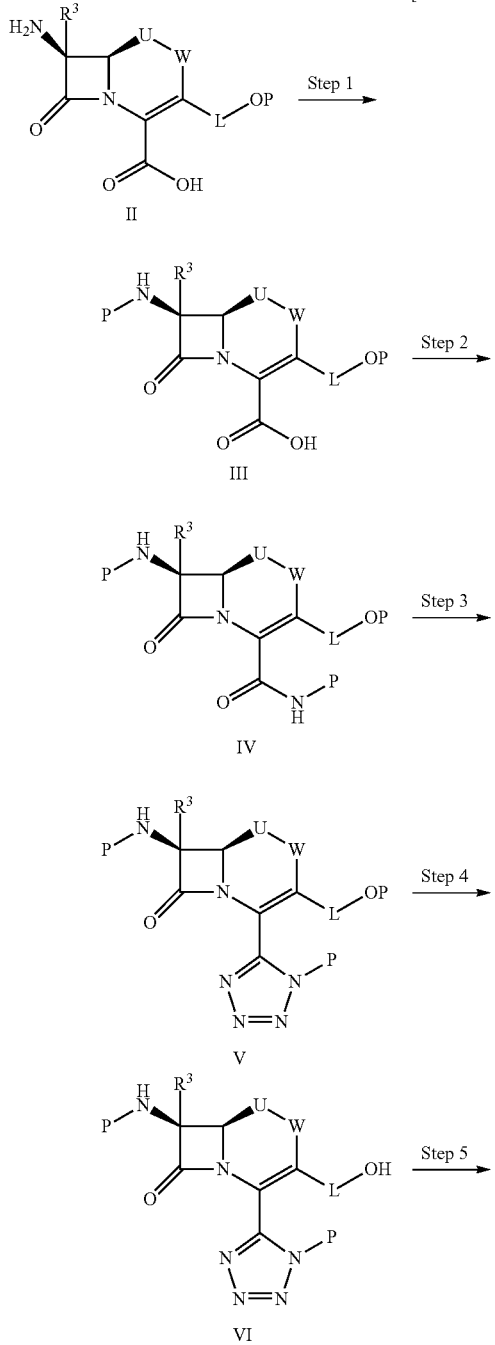

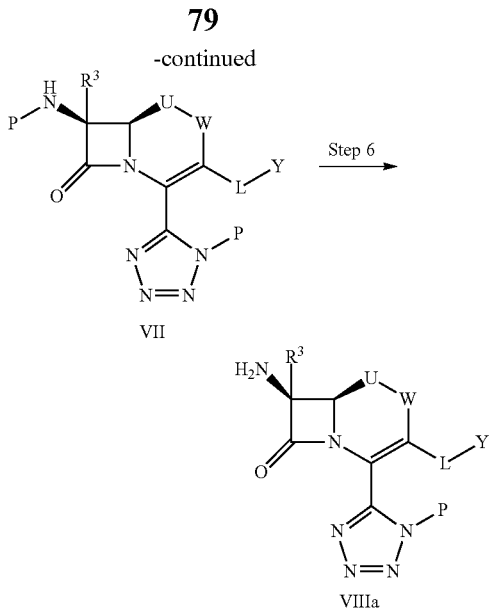

wherein W, U, $R^3$ and L are as defined above, P is a protecting group, and Y is a leaving group (e.g., a halogen (Cl, Br, I, F), methanesulfonyloxy, p-toluenesulfonyloxy, trifluoromethanesulfonyloxy, etc.

Step 1

Compound (III) is obtained by protecting an amino group on the 7-side chain of Compound (II) with a protecting group by a method well-known to those skilled in the art. The protecting groups to be used include the amino-protecting groups as exemplified below.

Step 2

Compound (IV) is obtained by amination of a carboxyl group at 4-position of Compound (III) by a method well-known to those skilled in the art. This amination may be carried out by using an amine compound which is previously protected by a protecting group, or alternatively, an amino group on the 4-side chain may be protected after the amination. The protecting groups to be used include the amino-protecting groups as exemplified below.
The reaction solvents include, for example, ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, and water, or a mixed solvent of these solvents.
The reaction temperature is usually in the range of from about −100° C. to 100° C., preferably in the range of from about −80° C. to 50° C., more preferably in the range of from about −80° C. to −40° C. The reaction time may vary according to the reagents, solvents or reaction temperature to be employed, but usually is 0.5 to 24 hours.

Step 3

Compound (V) is obtained by reacting Compound (IV) with, for example, hydrogen azide, trimethylsilyl azide (TMSN$_3$), or hydrazoates (e.g., sodium azide, tetra-n-butylammonium azide, and tetramethylguanidinium azide) to form a tetrazole ring.
Trimethylsilyl azide is generally used in an amount of about 1 to 100 moles, preferably in an amount of 1 to 30 moles, for 1 mole of Compound (IV). The reaction solvents include, for example, water, alcohols (e.g., methanol, ethanol, etc.), carboxylic acids (e.g., acetic acid, etc.). The reaction temperature is usually in the range of from about 0° C. to 100° C., preferably in the range of from about 10° C. to 90° C., more preferably in the range of from about 10° C. to 50° C. The reaction time may vary according to the reagents, solvents or reaction temperature to be employed, but usually is 0.5 to 24 hours.

Step 4

Compound (VI) is obtained by subjecting Compound (V) to a deprotection reaction by a method well-known to those skilled in the art.

Step 5

Compound (VII) is obtained by halogenating a hydroxyl group on the 3-side chain of Compound (VI). The halogenating agents to be used include, for example, phosgene, and triphosgene. The reaction solvents include, for example, ethers (e.g., anisole, dioxane, tetrahydrofuran, diethyl ether, tert-butyl methyl ether, diisopropyl ether), esters (e.g., ethyl formate, ethyl acetate, n-butyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), nitros (e.g., nitromethane, nitorethane, nitrobenzene), dimethylsulfoxide, and water, or a mixed solvent selected from two or more of these solvents. The reaction temperature is usually in the range of from about −100° C. to 100° C., preferably in the range of from about −80° C. to 50° C., more preferably in the range of from about −20° C. to 30° C. The reaction time may vary according to the reagents, solvents or reaction temperature to be employed, but usually is 0.5 to 24 hours.

Step 6

Compound (VII) is subjected to deprotection of an amino-protecting group at 7-position by a method well-known to those skilled in the art to obtain Compound (VIIIa).
Alternatively, the compounds represented by Formula (I) can be prepared by the following synthesis method.

Scheme 3

[Chemical Formula 97]

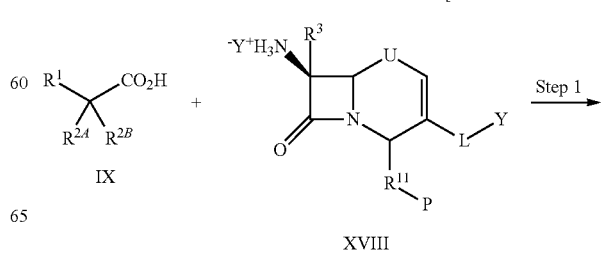

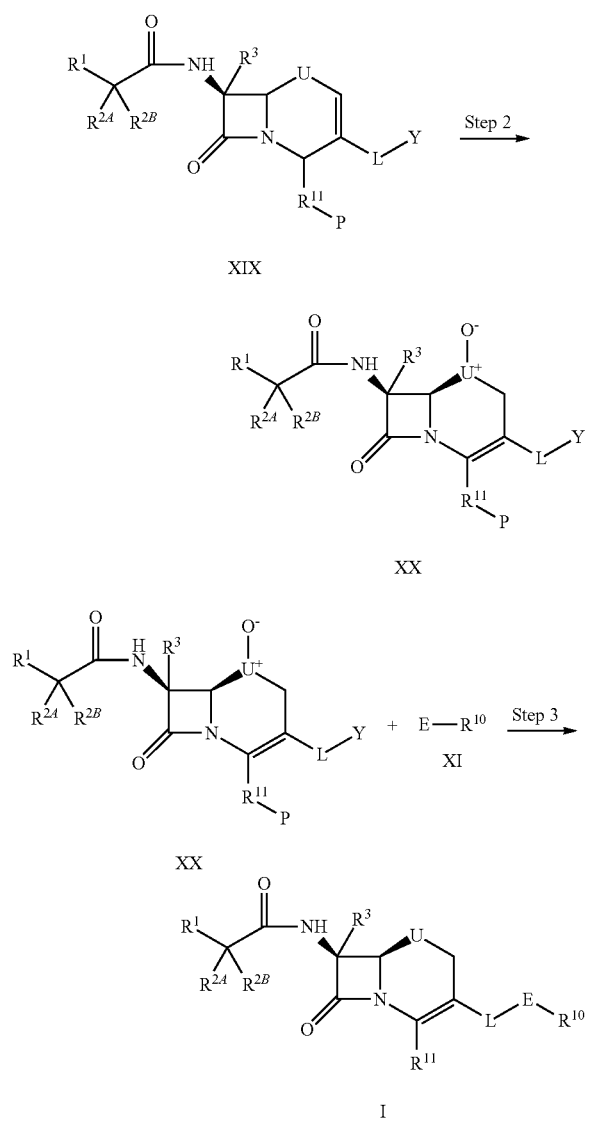

wherein $R^1$, $R^{2A}$, $R^{2B}$, $R^3$, $R^{10}$, $R^{11}$, L and E are as defined above, U is S, P is a protecting group, and Y is a leaving group (e.g., a halogen (Cl, Br, I, F), methanesulfonyloxy, p-toluenesulfonyloxy, trifluoromethanesulfonyloxy, etc.

1) Formation of 7-Side Chain: Synthesis of Compound (XIX)

Step 1

Compound (XIX) is obtained by subjecting Compound (XVIII) to a condensation reaction with Compound (IX). The reaction solvents include, for example, ethers (e.g., anisole, dioxane, tetrahydrofuran, diethyl ether, tert-butyl methyl ether, diisopropyl ether), esters (e.g., ethyl formate, ethyl acetate, n-butyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), nitros (e.g., nitromethane, nitorethane, nitrobenzene), dimethylsulfoxide, and water, or a mixed solvent selected from two or more of these solvents. The reaction temperature is usually in the range of from about −100° C. to 100° C., preferably in the range of from about −80° C. to 50° C., more preferably in the range of from about −60° C. to 0° C. The reaction time may vary according to the reagents, solvents or reaction temperature to be employed, but usually is 0.5 to 24 hours.

Step 2

Compound (XX) is obtained by subjecting Compound (XIX) to an oxidation reaction using an oxidation agent well-known to those skilled in the art (e.g., m-chloroperbenzoic acid)

The reaction solvents include, for example, ethers (e.g., anisole, dioxane, tetrahydrofuran, diethyl ether, tert-butyl methyl ether, diisopropyl ether), esters (e.g., ethyl formate, ethyl acetate, n-butyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), nitros (e.g., nitromethane, nitorethane, nitrobenzene), dimethylsulfoxide, and water, or a mixed solvent selected from two or more of these solvents. The reaction temperature is usually in the range of from about −100° C. to 100° C., preferably in the range of from about −80° C. to 50° C., more preferably in the range of from about −60° C. to −30° C. The reaction time may vary according to the reagents, solvents or reaction temperature to be employed, but usually is carried out for 0.5 to 24 hours.

2) Formation of 3-Side Chain: Synthesis of Compound (I)

Step 3

Compound (I) is obtained by subjecting Compound (XX) to a substitution reaction with Compound (XI) by a method well-known to those skilled in the art, followed by reducing it with a reduction agent well-known to those skilled in the art (e.g., phosphorus tribromide), and then subjecting it to a deprotection reaction. The reaction solvents include, for example, ethers (e.g., anisole, dioxane, tetrahydrofuran, diethyl ether, tert-butyl methyl ether, diisopropyl ether), esters (e.g., ethyl formate, ethyl acetate, n-butyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), nitros (e.g., nitromethane, nitorethane, nitrobenzene), dimethylsulfoxide, and water, or a mixed solvent selected from two or more of these solvents. The reaction temperature is usually in the range of from about −100° C. to 100° C., preferably in the range of from about −80° C. to 50° C., more preferably in the range of from about −40° C. to 0° C. The reaction time may vary according to the reagents, solvents or reaction temperature to be employed, but usually is 0.5 to 24 hours.

If Compound of Formula (I) has a tetrazole ring at 4-position, Compound (XVIII) used in the above Scheme 3 can be prepared according to Scheme 4.

Scheme 4

[Chemical Formula 98]

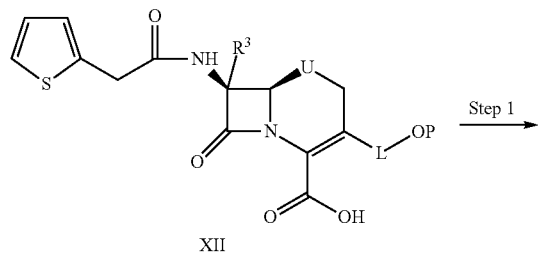

XII

Step 1 →

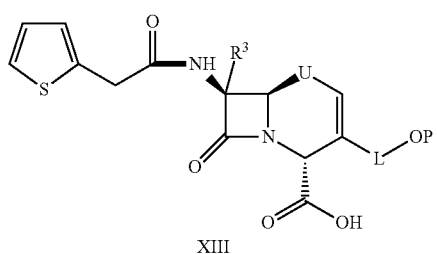

XIII

Step 2 →

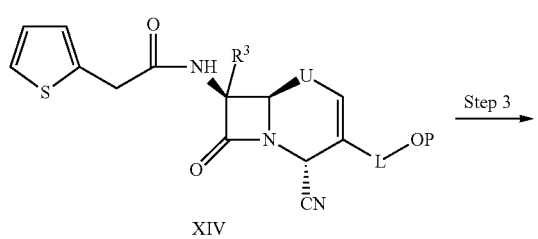

XIV

Step 3 →

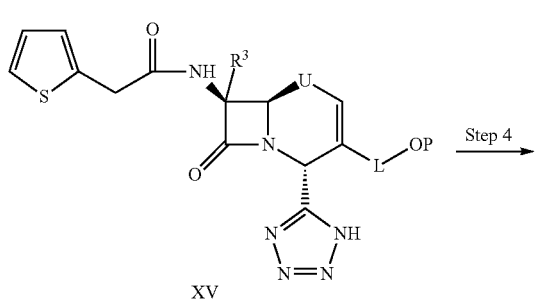

XV

Step 4 →

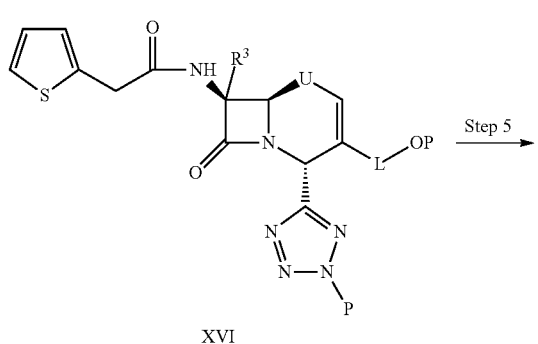

XVI

Step 5 →

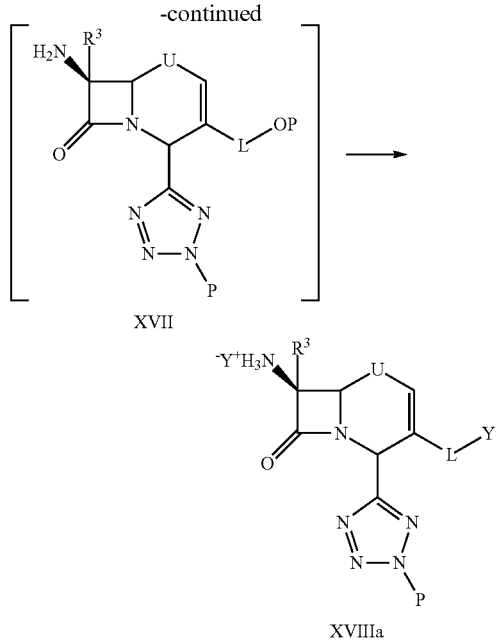

XVII

XVIIIa wherein $R^3$ and L are as defined above, U is S, P is a protecting group, and Y is a leaving group (e.g., a halogen (Cl, Br, I, F), methanesulfonyloxy, p-toluenesulfonyloxy, trifluoromethanesulfonyloxy, etc. In the above scheme 4, Compound (XII) has a thiophene ring, but which is not limited to and may be an alkyl group or a benzene ring.

Step 1

Compound (XIII) is obtained by isomerizing Compound (XII), followed by aminationg a carboxyl group at 4-position thereof by a method well-known to those skilled in the art. The reaction solvents include, for example, ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, and water, or a mixed solvent of these solvents.

The reaction temperature is usually in the range of from about −100° C. to 100° C., preferably in the range of from about −500° C. to 50° C., more preferably in the range of from about 10° C. to 40° C. The reaction time may vary according to the reagents, solvents or reaction temperature to be employed, but usually is 0.5 to 24 hours.

Step 2

Compound (XIV) is obtained by dehydrating Compound (XIII) by a method well-known to those skilled in the art, such as dehydration reaction using anhydrous trifluoroacetic acid (TFAA).

The reaction solvents include, for example, ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, and water, or a mixed solvent of these solvents.

The reaction temperature is usually in the range of from about −100° C. to 100° C., preferably in the range of from about −80° C. to 50° C., more preferably in the range of from about −60° C. to 0° C. The reaction time may vary according to the reagents, solvents or reaction temperature to be employed, but usually is 0.5 to 24 hours.

Step 3

Compound (XV) is obtained by reacting Compound (XIV) with, for example, hydrogen azide, trimethylsilyl azide (TMSN$_3$), or hydrazoates (e.g., sodium azide, tetra-n-butylammonium azide, and tetramethylguanidinium azide) to form a tetrazole ring. Trimethylsilyl azide is usually used in an amount of about 1 to 50 moles, preferably in an amount of 1 to 10 moles, for 1 mole of Compound (XIV). The reaction solvents include, for example, water, alcohols (e.g., methanol, ethanol), and carbonic acids (e.g., acetic acid).

The reaction temperature is usually in the range of from about 20° C. to 150° C., preferably in the range of from about 40° C. to 100° C., more preferably in the range of from about 60° C. to 90° C. The reaction time may vary according to the reagents, solvents or reaction temperature to be employed, but usually is 0.5 to 24 hours.

Step 4

Compound (XVI) is obtained by subjecting Compound (XV) to a protection reaction to protect nitrogen on the tetrazole ring.

Step 5

Compound (XVIIIa) is obtained by subjecting Compound (XVI) to a hydrolysis reaction to make amide on 7-side chain to an amino group, followed by treating the compound with hydrohalic acid such as hydrochloric acid. The reaction solvents include, for example, ethers (e.g., anisole, dioxane, tetrahydrofuran, diethyl ether, tert-butyl methyl ether, diisopropyl ether), esters (e.g., ethyl formate, ethyl acetate, n-butyl acetate, isopropyl acetate), halogenated hydrocarbons (e.g., dichloromethane, chloroform, carbon tetarachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), nitros (e.g., nitromethane, nitorethane, nitrobenzene), dimethylsulfoxide, and water, or a mixed solvent selected from two or more of these solvents. The reaction temperature is usually in the range of from about −100° C. to 100° C., preferably in the range of from about −50° C. to 50° C., more preferably in the range of from about −40° C. to 30° C. The reaction time may vary according to the reagents, solvents or reaction temperature to be employed, but usually is 0.5 to 24 hours.

The protecting group to be used in the above reaction such as amino-protecting groups, hydroxy-protecting groups, etc., includes, for example, protecting groups described in Protective Groups in Organic Synthesis, written by T. W. Greene, John Wiley & Sons Inc. (1991), etc. Methods for the introduction and removal of a protecting group are methods commonly used in synthetic organic chemistry (see, for example, methods described in Protective Groups in Organic Synthesis, written by T. W. Greene, John Wiley & Sons Inc. (1991)), etc., or can be obtained by a modified method thereof. Furthermore, a functional group included in each substituent can be converted by a known method (e.g., those described in Comprehensive Organic Transformations, written by R. C. Larock (1989), etc.) in addition to the above production methods. Some of the compounds of the present invention can be used as a synthetic intermediate, leading to a new derivative. Intermediates and desired compounds produced in each of the above production methods can be isolated and purified by a purification method commonly used in synthetic organic chemistry, for example, neutralization, filtration, extraction, washing, drying, concentration, recrystallization, any kind of chromatography, etc. Furthermore, intermediates can be subjected to a next reaction without any purification.

Examples of amino-protecting group include, for example, phthalimide, a lower alkoxycarbonyl(butoxycarbonyl (Boc) etc.), a lower alkenyloxycarbonyl(allyloxycarbonyl (Alloc), etc.), benzyloxycarbonyl, p-nitrobenzyloxycarbonyl, (substituted) aralkanoyl(p-nitrobenzoyl, etc.), an acyl (formyl, chloroacetyl, etc.), (substituted) aralkyl(trityl, etc.), benzhydryl (BH), etc.

Examples of hydroxy-protecting group include, for example, lower alkoxycarbonyl such as a C1-C4 alkoxycarbonyl (e.g., t-butyloxycarbonyl), a halogenated lower alkoxycarbonyl such as a halogenated (C1-C3) alkoxycarbonyl (e.g., 2-iodo ethyloxycarbonyl, 2,2,2-trichloroethyloxycarbonyl), an aryl-(lower)alkoxycarbonyl such as a phenyl-(C1-C4)alkoxycarbonyl having optionally a substituent(s) on the benzene ring (benzyloxycarbonyl, o-nitrobenzyloxycarbonyl, p-nitrobenzyloxycarbonyl, p-methoxybenzyloxycarbonyl), p-methoxybenzyl (PMB), a tri-lower alkylsilyl such as a tri-(C1-C4)alkylsilyl (e.g., trimethylsilyl, t-butyldimethylsilyi), a substituted methyl such as a C1-C4 alkoxymethyl (e.g., methoxymethyl), a C1-C4 alkoxy-(C1-C4)alkoxymethyl (e.g., 2-methoxyethoxymethyl), a C1-C4 alkylthiomethyl (e.g., methylthiomethyl), tetrahydropyranyl, etc.

The above-mentioned deprotecting reaction is carried out in a solvent such as tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, or a mixed solvent thereof, using a Lewis acid (e.g., AlCl$_3$, SnCl$_4$, TiCl$_4$), a protonic acid (e.g., HCl, NBr, H$_2$SO$_4$, HCOOH), etc.

The obtained compound is further chemically modified, and thereby an ester, or a compound of which an amino on the thiazole ring at the 7-position thereof is protected, or a pharmaceutically acceptable salt, or a solvate thereof can be synthesized.

Compound (I) is obtained by the reduction of Compound (XX) using a reduction agent well-known to those skilled in the art (e.g., phosphorus tribromide), followed by reaction with Compound (XI) and then subjecting it to a deprotection reaction.

The compounds of the present invention have a wide antimicrobial activity spectrum, and may be used for prevention or therapy against a variety of diseases caused by causative bacteria in a variety of mammals including humans, for example, airway infectious diseases, urinary system infectious diseases, respiratory system infectious diseases, sepsis, nephritis, cholecystitis, oral cavity infectious diseases, endocarditis, pneumonia, bone marrow membrane myelitis, otitis media, enteritis, empyema, wound infectious diseases, opportunistic infection, etc.

The compounds of the present invention exhibit high antimicrobial activity in particular against Gram negative bacteria, preferably, Gram negative bacteria of enterobacteria (E.

coli, Klebsiella, Serratia, Enterobacter, Citrobacter, Morganella, Providencia, Proteus, etc.), Gram negative bacteria colonized in respiratory system (Haemophilus, Moraxella, etc.), and Gram negative bacteria of glucose non fermentation (Pseudomonas aeruginosa, Pseudomonas other than P. aeruginosa, Stenotrophomonas, Burkholderia, Acinetobacter, etc.). The compounds are stable against beta-lactamase belonging to Classes A, B, C and D which is produced by these Gram negative bacteria, and have high antimicrobial activity against a variety of beta-lactam drug resistant Gram negative bacteria, such as ESBL producing bacteria, etc. These are extremely stable against metallo-beta-lactamase belonging to Class B including in particular IMP type, VIM type, L-1 type, etc. Thus, these are effective against a variety of beta-lactam drug resistant Gram negative bacteria including Cephem and Carbapenem. Moreover, the compounds of the present invention have antimicrobial activity against Gram positive bacteria including methicillin-resistant Staphylococcus aureus (MRSA), penicillin-resistant Streptococcus pneumoniae (PRSP), etc. Still more preferable compounds have features regarding kinetics in the body, such as high blood concentration, long duration of effects, and/or significant tissue migration. More preferable compounds are safe in terms of side effects, such as fever and nephrotoxty. More preferable compounds have high water solubility, and thus preferable as an injecting drug, in particular.

The compounds of the present invention can be administered either orally or parenterally. The compounds of the present invention, when administered orally, can be used in any dosage form of normal formulations, for example, solid drug such as tablet, powder, granule, capsule, etc.; solution drug; oleaginous suspension drug; or liquid drug such as syrup or elixir. The compounds of the present invention, when administered parenterally, can be used as an aqueous or oleaginous suspended injecting agent, or nasal drops. In preparation thereof, a conventional excipient, binder, lubricant, aqueous solvent, oleaginous solvent, emulsifier, suspending agent, preservative, stabilizer, etc. can be optionally used. A formulation of the present invention is produced by combining (for example, mixing) a therapeutically effective amount of a compound of the present invention with a pharmaceutically acceptable carrier or diluent.

The compounds of the present invention may be administered either parenterally or orally as an injecting agent, capsules, tablets, and granules, and preferably administered as an injecting agent. The dosage of the present compound may usually be, per 1 kg of body weight of a patient or animal, about 0.1 to 100 mg/day, preferably, about 0.5 to 50 mg/day, if desired, divided into 2-4 times per day. Carriers when used in an injecting agent are, for example, distilled water, brine, etc., and a base and the like may be used for pH adjustment. When used as capsules, granules, or tablets, carriers may be known excipients (e.g., starch, lactose, sucrose, calcium carbonate, calcium phosphate, etc.), binders (e.g., starch, acacia gum, carboxymethyl cellulose, hydroxypropyl cellulose, crystalline cellulose, etc.), lubricants (e.g., magnesium stearate, talc, etc.), etc.

EXAMPLES

Hereinafter, the present invention is described in more details with Examples, Reference Examples, Experiments and Formulation Examples. However, the present invention is not construed to be limited thereto.

The meaning of each abbreviation is as described below.
Ac: Acetyl
Allooc: Allyloxycarbonyl
BH: Benzhydryl
Boc: tert-Butoxycarbonyl
Bzh: Benzhydryl
DMF: N,N-dimethylformamide
EDC: 1-ethyl-3-(3-dimethylaminopropyl)carbodiimide
i-Pr: isopropyl
mCPBA: m-chloroperoxybenzoic acid
Me: methyl
ODS: Octadecylsilyl
PMB: para-Methoxybenzyl
t-Bu: tert-butyl
TFA: trifluoroacetic acid
WSCD: N-ethyl-N'-(3-dimethylaminopropyl)carbodiimide Example 1

Synthesis of Compound I-1

[Chemical Formula 99]

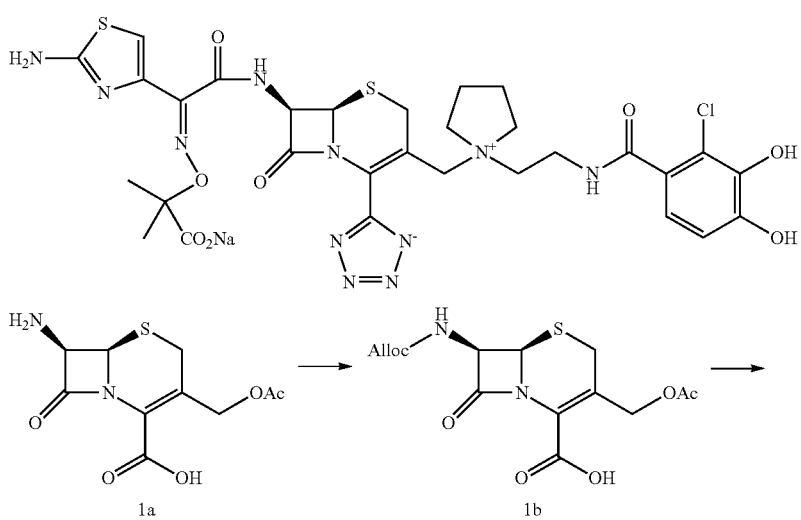

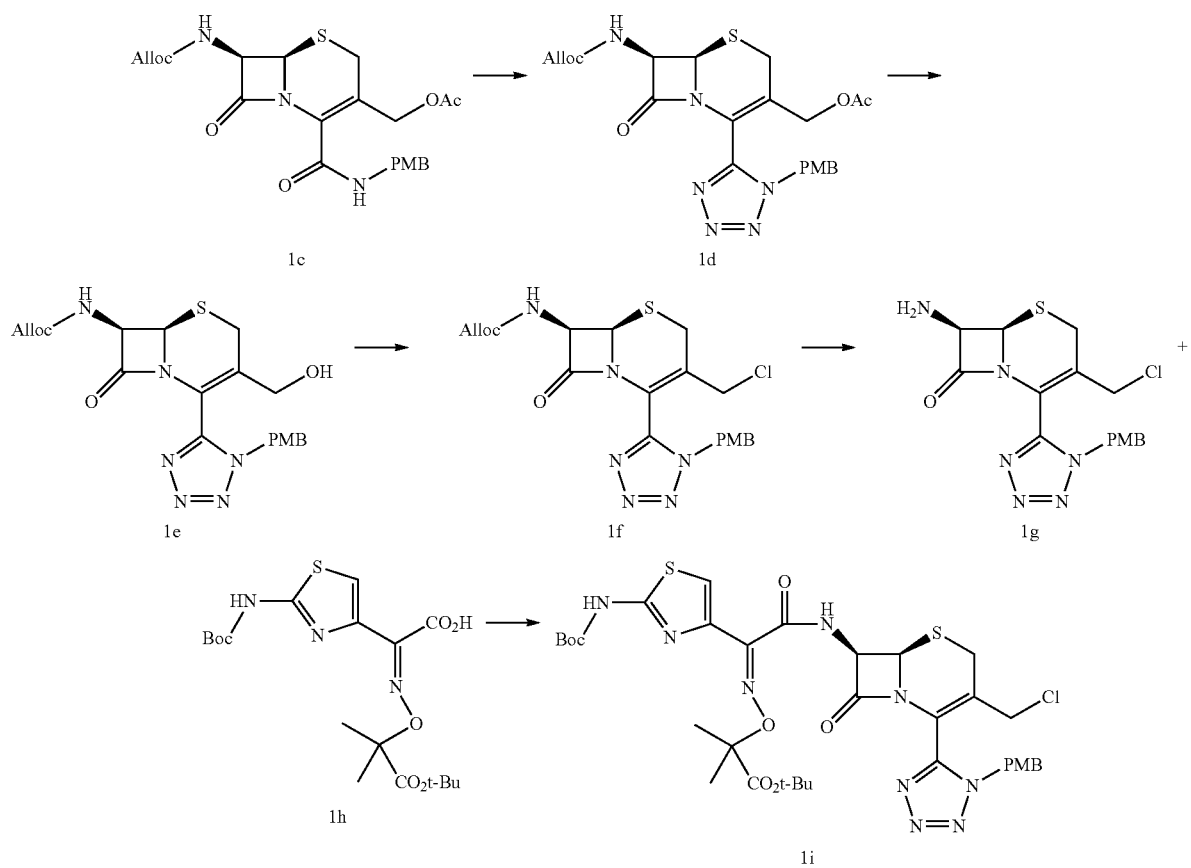
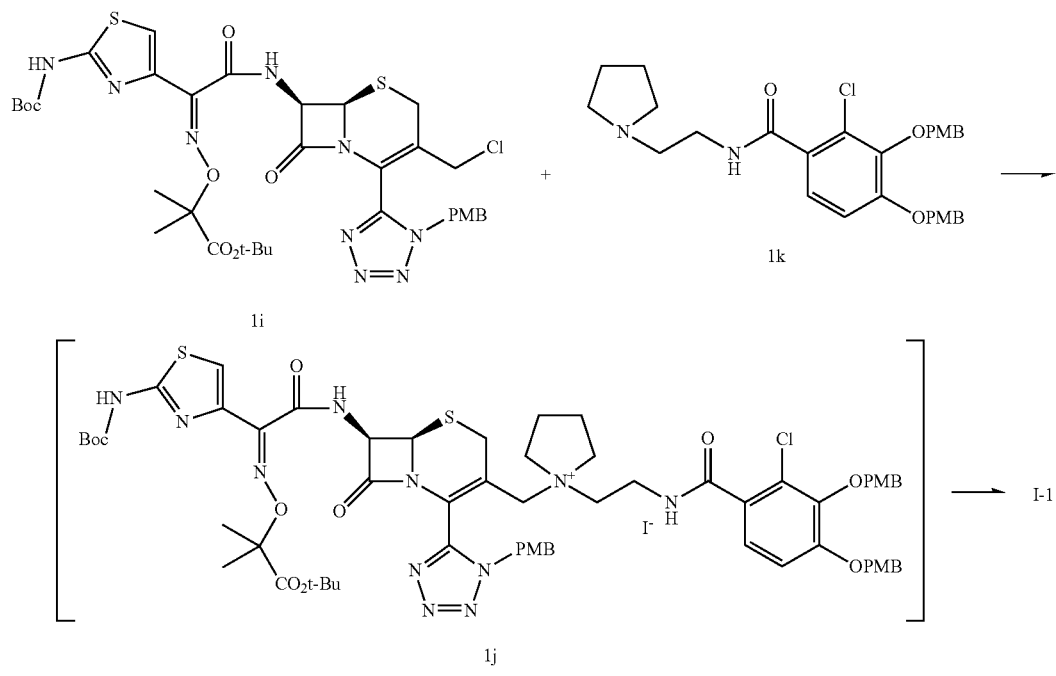

Step (1): Compound 1a→Compound 1b

Compound 1a (54.5 g, 200 mmol) and sodium hydrogen carbonate (42.0 g, 500 mmol) were dissolved in a mixture of water (1000 ml)/acetone (400 ml), and then allyl chloroformate (25.6 ml, 240 mmol) was added under ice-cooling. The mixture was stirred for 30 minutes under ice-cooling, and for 1 hour at room temperature. The reaction solution was concentrated in vacuo, and then diluted with ethyl acetate, and extracted with water. The aqueous layer was made acidic, extracted with ethyl acetate, washed with brine, and dried with magnesium sulfate. Magnesium sulfate was filtered off, and the liquid was concentrated in vacuo to yield the concentrated Compound 1b (66.39 g, 93%).

$^1$H-NMR (DMSO-$d_6$) δ: 8.42 (1H, d, J=8.73 Hz), 5.97-5.85 (1H, m), 5.54 (1H, dd, J=8.73, 4.84 Hz), 5.30 (1H, dd, J=17.23, 1.53 Hz), 5.20 (1H, dd, J=10.37, 1.53 Hz), 5.08 (1H, d, J=4.84 Hz), 4.98 (1H, d, J=12.73 Hz), 4.68 (1H, d, J=12.73 Hz), 4.53 (2H, d, J=5.19 Hz), 3.62 (1H, d, J=18.07 Hz), 3.48 (1H, d, J=18.07 Hz), 2.03 (3H, s).

Step (2): Compound 1b→Compound 1c

Compound 1b (65.0 g, 182 mmol) was suspended in methylene chloride (650 ml), and then 1-chloro-N,N,2-trimethyl-1-propenylamine (29.0 ml, 219 mmol) was added thereto, and the mixture was stirred for 30 minutes under ice-cooling. The reaction solution was cooled to −60° C., and then a solution of 4-methoxybenzylamine (59.6 ml, 456 mmol) in methylene chloride (60 ml) was added dropwise. Methylene chloride (200 ml) was added to the reaction solution, and then stirred for 10 minutes at −60° C. to −50° C. The reaction solution was diluted with methylene chloride/acetonitrile, and the organic layer was washed with hydrochloric acid, a saturated aqueous sodium bicarbonate and brine, and then dried with magnesium sulfate. Magnesium sulfate was filtered off, and the liquid was concentrated in vacuo, and methylene chloride/diisopropyl ether was added thereto, and then the precipitated crystals were collected by filtration to yield Compound 1c (73.94 g, 85%).

$^1$H-NMR (DMSO-$d_6$) δ: 8.76 (1H, t, J=5.68 Hz), 8.46 (1H, d, J=8.85 Hz), 7.23 (2H, d, J=8.39 Hz), 6.85 (2H, d, J=8.24 Hz), 5.96-5.85 (1H, m), 5.40 (1H, dd, J=8.85, 4.80 Hz), 5.30 (1H, d, J=17.23 Hz), 5.20 (1H, d, J=10.37 Hz), 5.02 (1H, d, J=4.80 Hz), 4.94 (1H, d, J=12.58 Hz), 4.71 (1H, d, J=12.58 Hz), 4.54 (2H, d, J=5.68 Hz), 4.36 (1H, dd, J=14.83, 5.76 Hz), 4.24 (1H, dd, J=14.83, 5.76 Hz), 3.72 (3H, s), 3.56 (1H, d, J=17.62 Hz), 3.43 (1H, d, J=17.62 Hz), 2.02 (3H, s).

Step (3): Compound 1c→Compound 1d

Compound 1c (39.0 g, 82 mmol) and pyridine (23.17 ml, 287 mmol) was suspended in methylene chloride (400 ml), and then, triphosgene (12.17 g, 41 mmol) was added thereto under ice-cooling, and the mixture was stirred for 30 minutes under ice-cooling. Under ice-cooling, trimethylsilylazide (12.17 g, 41 mmol) and methanol (8.32 ml, 205 mmol) were added thereto, and the mixture was allowed to stand overnight. The reaction solution was diluted with methylene chloride, and the organic layer was washed sequentially with hydrochloric acid, a saturated aqueous sodium bicarbonate and brine, and then dried with magnesium sulfate. Magnesium sulfate was filtered off, and the liquid was concentrated in vacuo and subjected to silica gel column chromatography, eluting with hexane/ethyl acetate. A fraction containing the desired compound was concentrated in vacuo to yield Compound 1d (21.29 g, 52%).

$^1$H-NMR (DMSO-$d_6$) δ: 8.47 (1H, d, J=8.85 Hz), 7.25 (2H, d, J=8.54 Hz), 6.92 (2H, d, J=8.54 Hz), 5.98-5.85 (1H, m), 5.61-5.56 (3H, m), 5.27-5.33 (2H, m), 5.20 (1H, d, J=9.30 Hz), 4.54 (2H, d, J=5.34 Hz), 4.31 (1H, d, J=12.73 Hz), 4.18 (1H, d, J=12.73 Hz), 3.74 (3H, s), 3.66 (1H, d, J=18.00 Hz), 3.57 (1H, d, J=18.00 Hz), 1.90 (3H, s).

Step (4): Compound 1d→Compound 1e

Compound 1d (21.29 g, 42.5 mmol) was dissolved in tetrahydrofuran (300 ml), and 3M sulfuric acid (284 ml, 851 mmol) was added and stirred for 3 hours at 45° C. The reaction solution was diluted with ethyl acetate. The organic layer was washed with water, a saturated aqueous sodium bicarbonate and brine, and dried with magnesium sulfate. Magnesium sulfate was filtered off, and the liquid was concentrated in vacuo to yield Compound 1e (19.63 g, 101%). The resulting Compound 1e was used in the next step without further purification.

$^1$H-NMR (DMSO-d) δ: 8.45 (1H, d, J=9.00 Hz), 7.24 (2H, d, J=8.62 Hz), 6.91 (2H, d, J=8.62 Hz), 5.98-5.85 (1H, m), 5.52-5.48 (3H, m), 5.33-5.18 (3H, m), 5.09 (1H, t, J=5.34 Hz), 4.53 (2H, d, J=5.19 Hz), 3.74 (3H, s), 3.55-3.60 (4H, m).

Step (5): Compound 1e→Compound 1f

Compound 1e (19.63 g, 42.8 mmol) and pyridine (5.18 ml, 64.2 mmol) was suspended in methylene chloride (200 ml), and added with triphosgene (5.08 g, 17.13 mmol) under ice-cooling and stirred for 2 hours under ice-cooling. The reaction solution was diluted with methylene chloride, and the organic layer was washed sequentially with hydrochloric acid, a saturated aqueous sodium bicarbonate and brine, and dried with magnesium sulfate. Magnesium sulfate was filtered off, and the liquid was concentrated in vacuo and subjected to silica gel column chromatography, eluting with hexane/ethyl acetate. A fraction containing the desired compound was concentrated in vacuo, the compound was crystallized from diisopropyl ether to yield Compound 1f (9.15 g, 45%).

$^1$H-NMR (DMSO-$d_6$) δ: 8.48 (1H, d, J=9.00 Hz), 7.24 (2H, d, J=8.39 Hz), 6.91 (2H, d, J=8.39 Hz), 5.97-5.85 (1H, m), 5.65-5.52 (3H, m), 5.32-5.27 (2H, m), 5.20 (1H, d, J=10.37 Hz), 4.53 (2H, d, J=4.88 Hz), 4.02 (1H, d, J=11.82 Hz), 3.97 (1H, d, J=11.82 Hz), 3.73-3.59 (5H, m).

Step (6): Compound 1f→Compound 1g

Compound 1f (9.15 g, 19.18 mmol) and dimedone (8.07 g, 57.6 mmol) was suspended in methylene chloride (90 ml), and palladium tetrakistriphenylphosphine (1.108 g, 0.959 mmol) was added and stirred for 1 hour at room temperature. The reaction solution was diluted with methylene chloride, and washed with a saturated aqueous sodium bicarbonate and brine, and dried with magnesium sulfate. Magnesium sulfate was filtered off, and the liquid was concentrated in vacuo and subjected to silica gel column chromatography, eluting with hexane/ethyl acetate. A fraction containing the desired compound was concentrated in vacuo, and ethyl acetate/diisopropyl ether was added, and the precipitated crystals were collected by filtration to yield Compound 1g (4.89 g, 65%).

$^1$H-NMR (DMSO-$d_6$) δ: 7.21 (2H, d, J=8.46 Hz), 6.90 (2H, d, J=8.46 Hz), 5.60 (1H, d, J=14.79 Hz), 5.49 (1H, d, J=14.79 Hz), 5.19 (1H, d, J=5.19 Hz), 4.82-4.74 (1H, m), 4.08 (1H, d, J=12.12 Hz), 4.03 (1H, d, J=12.12 Hz), 3.72 (3H, s), 3.67 (1H, d, J=17.92 Hz), 3.57 (1H, d, J=17.92 Hz), 2.38 (2H, d, J=9.46 Hz).

Step (7): Compound 1g+Compound 1h→
Compound 1i

Compound 1g (2.00 g, 5.09 mmol) and Compound 1h (2.30 g, 5.35 mmol) were dissolved in methylene chloride (20 ml), and the solution was cooled to −40° C. Dichlorophenyl phosphoric acid (1.14 ml, 7.64 mmol) was added, and N-methylmorpholine (1.68 ml, 15.27 mmol) was added dropwise at −40° C., and the mixture was stirred for 2 hours at −40° C. to −30° C. The reaction solution was diluted with methylene chloride, and washed sequentially with 0.2 N hydrochloric acid, a saturated aqueous sodium bicarbonate and brine, and dried with magnesium sulfate. Magnesium sulfate was filtered off, and the liquid was concentrated in vacuo and subjected to silica gel column chromatography, eluting with hexane/ethyl acetate. A fraction containing the desired compound was concentrated in vacuo to yield Compound 1i (3.54 g, 87%).

$^1$H-NMR (CDCl$_3$) δ: 8.38 (1H, d, J=8.66 Hz), 8.19 (1H, br s), 7.31 (1H, s), 7.15 (2H, d, J=8.69 Hz), 6.87 (2H, d, J=8.69 Hz), 5.91 (1H, dd, J=8.66, 4.99 Hz), 5.62 (1H, d, J=15.10 Hz), 5.44 (1H, d, J=15.10 Hz), 5.00 (1H, d, J=4.99 Hz), 3.96 (1H, d, J=12.20 Hz), 3.78 (3H, s), 3.73 (1H, d, J=12.20 Hz), 3.64 (1H, d, J=18.00 Hz), 3.39 (1H, d, J=18.00 Hz), 1.63 (3H, s), 1.55 (3H, s), 1.53 (9H, s), 1.39 (9H, s).

Step (8): Compound 1i+Compound 1k→
Compound I-1

To a solution of Compound 1i (1.61 g, 2.00 mmol) in dimethylformamide (4 mL) was added with sodium iodide (600 mg, 4.00 mmol), and the mixture was stirred for 5 minutes at room temperature. The mixture was cooled to 0° C., and Compound 1k (1.05 g, 2.00 mmol) was added thereto, and the mixture was stirred for 5 hours at 0 to 10° C. The reaction mixture was added slowly to 5% brine (40 ml) containing sodium thiosulfate (2 g) previously ice-cooled. The precipitated solid was collected by filtration, washed with water, and suspended in water. The suspension was freeze-dried to yield Compound 1j as a pale yellow solid. The resulting Compound 1j was used in the next step without further purification.

All amount of the resulting Compound 1j was dissolved in methylene chloride (20 ml), the solution was cooled to −40° C. Anisole (3.28 ml, 30.0 mmol) and 2M aluminum chloride in nitromethane (15.00 ml, 30.0 mmol) were added subsequently, and the solution was stirred for 1 hour at 0° C. The reaction solution was dissolved in water, an aqueous solution of 2N hydrochloric acid and acetonitril, and washed with diisopropyl ether. HP20-SS resin was added to the aqueous layer, and acetonitrile was removed in vacuo. The resulting mixture was subjected to ODS column chromatography, eluting with 20 mM hydrochloric acid/acetonitrile. To a fraction containing the desired compound, HP20-SS resin was added, and acetonitrile was removed in vacuo. The resulting mixture was subjected to HP20-SS column chromatography, eluting with water/acetonitrile. To a solution of the resulting desired compound, an aqueous 0.2 N sodium hydroxide solution was added to adjust pH to 6.0, and then a piece of dry ice was added. The resulting solution was concentrated in vacuo, and then freeze-dried to yield Compound I-1 as a white powder.

Yield: 627.7 mg, (35%)

$^1$H-NMR (D$_2$O) δ: 6.95 (1H, s), 6.92 (1H, s), 6.89 (1H, s), 5.91 (1H, d, J=4.96 Hz), 5.58 (1H, d, J=4.96 Hz), 4.13 (2H, t, J=16.78 Hz), 3.77 (1H, d, J=17.23 Hz), 3.58-3.34 (8H, m), 1.95-2.14 (3H, m), 1.51 (3H, s), 1.48 (3H, s).

Elemental analysis for: C30H33ClN11O8S2Na(H2O)4.8

Calcd.: C, 40.73; H, 4.85; Cl, 4.01; N, 17.42; S, 7.25; Na, 2.60(%).

Found: C, 40.72; H, 4.75; C, 3.79; N, 17.53; S, 6.99; Na, 2.70(%).

Example 2

Synthesis of Compound I-2

[Chemical Formula 101]

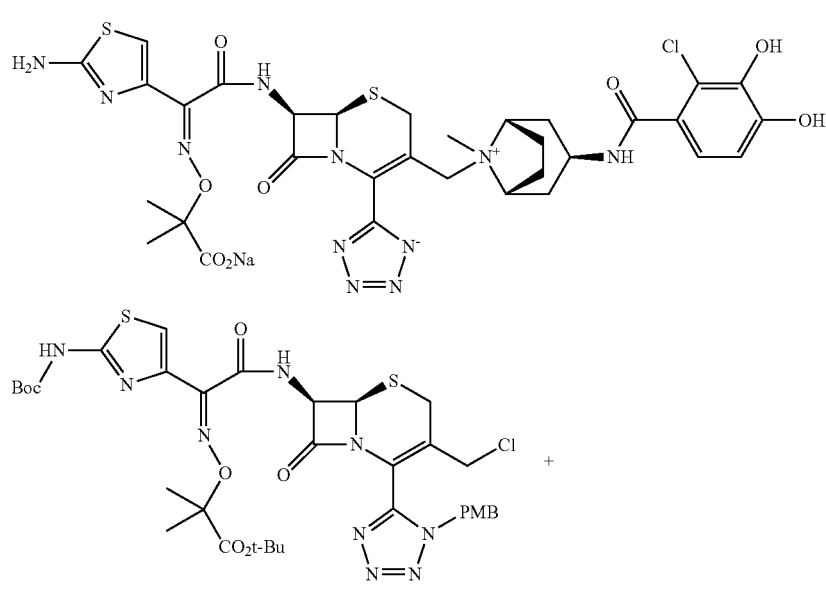

-continued

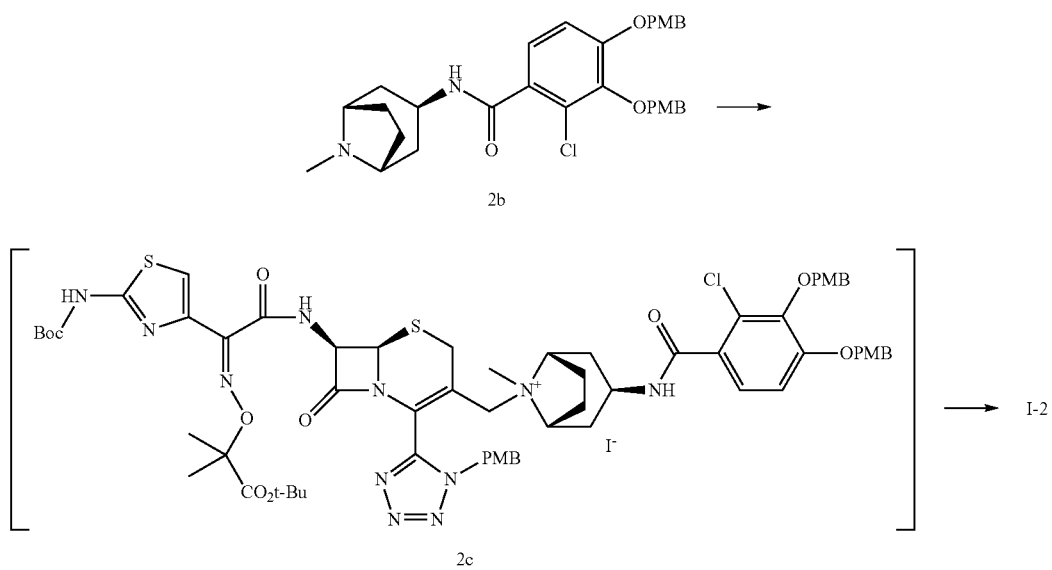

Step (1) Compound 2a+Compound 2b→ Compound I-2

The synthesis of Compound I-2 was carried out by treating Compound I-2 (804 mg, 1.00 mmol) and Compound 2b (551 mg, 1.00 mmol) similar to Step (8) of the synthesis of Compound I-1.

Yield: 371.5 mg, (38%)

$^1$H-NMR (D$_2$O) δ: 6.96 (1H, s), 6.85 (2H, s), 5.91 (1H, d, J=5.04 Hz), 5.59 (1H, d, J=5.04 Hz), 4.64 (1H, d, J=14.44 Hz), 4.19-4.01 (4H, m), 3.74 (1H, d, J=16.79 Hz), 3.65-3.63 (1H, m), 2.93 (3H, s), 2.79-2.55 (2H, m), 2.37-2.01 (5H, m), 1.52 (3H, s), 1.49 (3H, s).

Elemental analysis for: C32H35ClN11O8S2Na(H2O)5.1 (NaHCO3) 0.16

Calcd.: C, 41.55; H, 4.92; Cl, 3.81; N, 16.57; S, 6.90; Na, 2.87(%).

Found: C, 41.49; H, 5.00; Cl, 3.80; N, 16.74; S, 6.86; Na, 2.86(%).

Example 3

Synthesis of Compound I-3

[Chemical Formula 102]

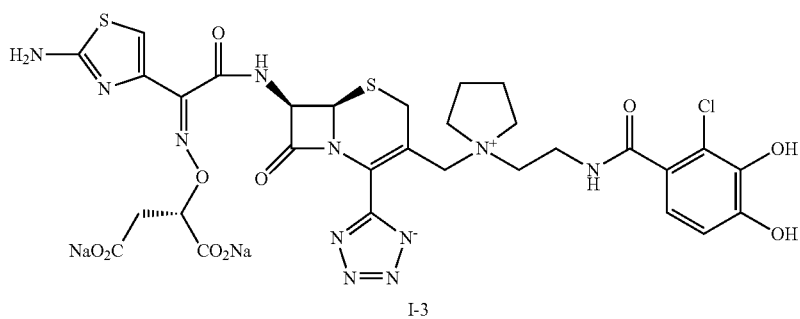

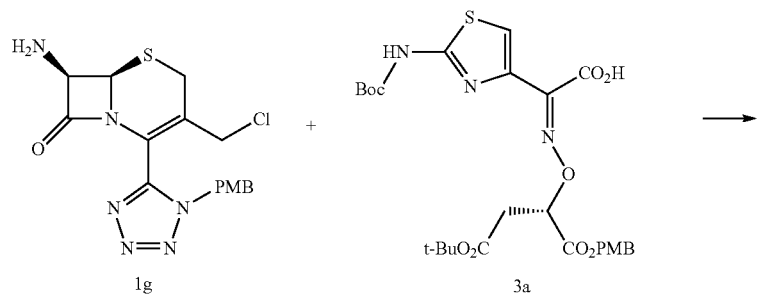

-continued

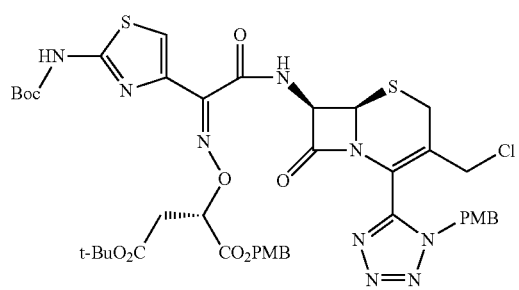

3b

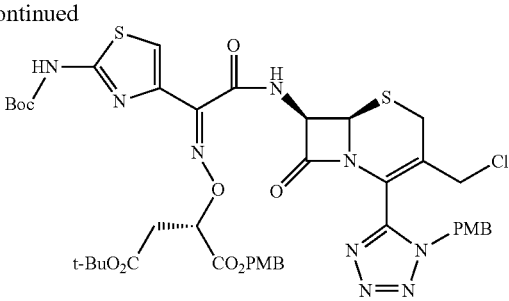

3b

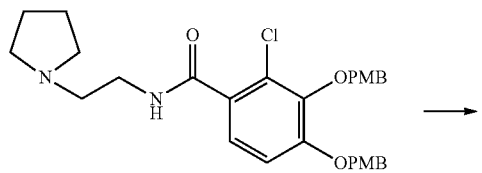

1k

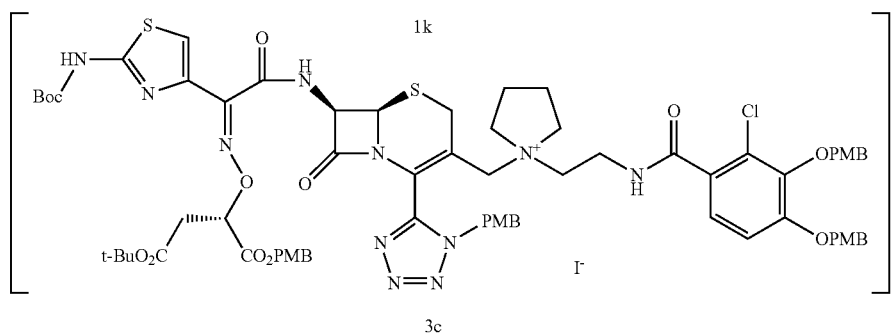

3c

Step (1): Compound 1g+Compound 3a→Compound 3b

Using Compound 1g (2.00 g, 5.09 mmol) and Compound 3a (3.10 g, 5.35 mmol), Compound 3b was synthesized according to a similar procedure as described in Step (7) of the synthesis of Compound I-1.

Yield: 3.25 g, (67%)

$^1$H-NMR (CDCl$_3$) δ: 8.37 (1H, d, J=8.08 Hz), 8.07 (1H, s), 7.35 (1H, s), 7.19-7.15 (4H, m), 6.88-6.80 (4H, m), 5.79 (1H, dd, J=8.08, 5.03 Hz), 5.63 (1H, d, J=15.02 Hz), 5.46 (1H, d, J=15.02 Hz), 5.37-5.32 (1H, m), 5.09-4.98 (3H, m), 3.92 (1H, d, J=12.20 Hz), 3.79 (3H, s), 3.78 (3H, s), 3.70-3.60 (2H, m), 3.36 (1H, d, J=17.84 Hz), 2.79-2.82 (2H, m), 1.54 (9H, s), 1.39 (9H, s).

Step (2): Compound 3b+Compound 1k→Compound I-3

Using Compound 3b (954 mg, 1.00 mmol) and Compound 1k (525 mg, 1.00 mmol), Compound I-3 was synthesized according to a similar procedure as described in Step (8) of the synthesis of Compound I-1.

Yield: 262.5 g, (26%)

$^1$H-NMR (D$_2$O) δ: 6.98 (1H, s), 6.94 (1H, d, J=8.62 Hz), 6.89 (1H, d, J=8.62 Hz), 5.85 (1H, d, J=5.03 Hz), 5.55 (1H, d, J=5.03 Hz), 4.99-4.88 (2H, m), 4.17 (1H, d, J=14.03 Hz), 4.06 (1H, d, J=16.93 Hz), 3.75 (1H, d, J=16.93 Hz), 3.59-3.36 (8H, m), 2.73-2.70 (2H, m), 2.17-1.95 (3H, m), 1.55-1.46 (1H, m).

Elemental analysis for: C30H30.2ClN11O10S2Na1.8 (H2O)6.8

Calcd.: C, 37.21; H, 4.56; Cl, 3.66; N, 15.91; S, 6.62; Na, 4.27(%).

Found: C, 37.26; H, 4.42; Cl, 3.66; N, 15.86; S, 6.49; Na, 4.34(%).

Example 4

Synthesis of Compound I-4

[Chemical Formula 103]

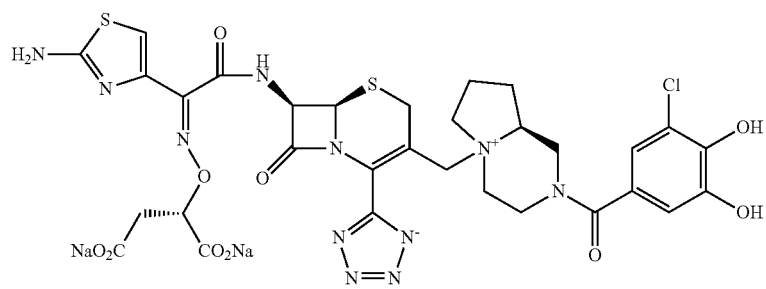

I-4

-continued

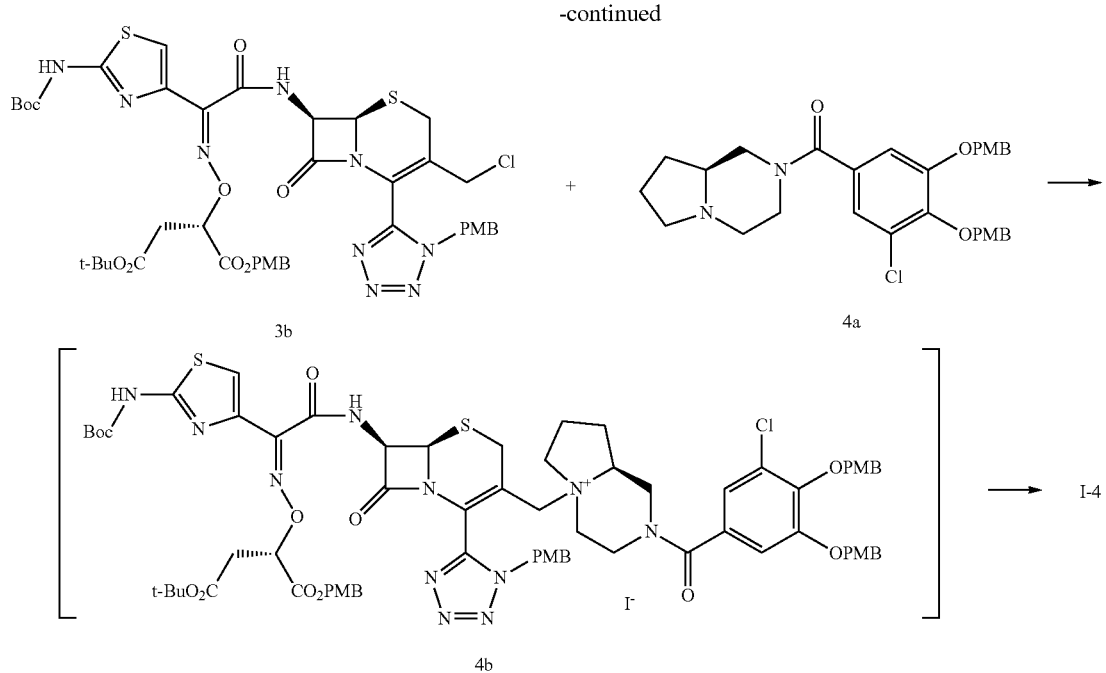

Step (1): Compound 3b+Compound 4a→Compound I-4

Using Compound 3b (954 mg, 1.00 mmol) and Compound 4a (537 mg, 1.00 mmol), Compound I-4 was synthesized according to a similar procedure as described in Step (8) of the synthesis of Compound I-1.

Yield: 381.7 g, (37%)

$^1$H-NMR (D$_2$O) δ: 7.05 (1H, br s), 6.98 (1H, s), 6.88 (1H, br s), 5.85 (1H, d, J=4.80 Hz), 5.54 (1H, d, J=4.80 Hz), 4.99-4.90 (2H, m), 4.31 (1H, d, J=14.34 Hz), 4.06-3.11 (11H, m), 2.77-2.65 (2H, m), 2.23-1.82 (3H, m), 1.39-1.56 (1H, m).

Elemental analysis for: C31H30.2ClN11O10S2Na1.8 (H2O)6.5

Calcd.: C, 38.19; H, 4.47; Cl, 3.64; N, 15.80; S, 6.58; Na, 4.24(%).

Found: C, 38.18; H, 4.34; Cl, 3.71; N, 15.84; S, 6.43; Na, 4.24(%).

Example 5

Synthesis of Compound I-5

[Chemical Formula 104]

I-5

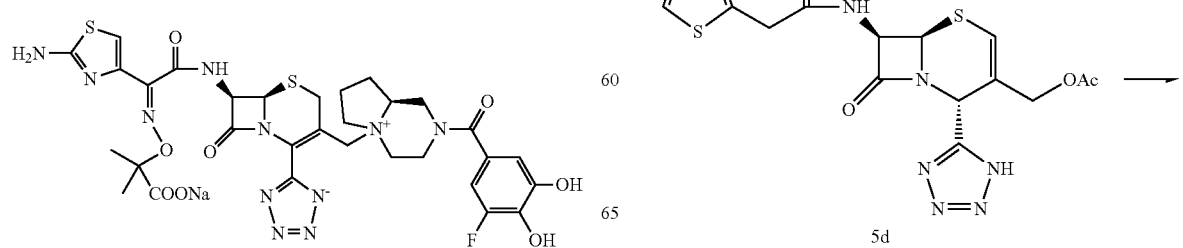

101
-continued
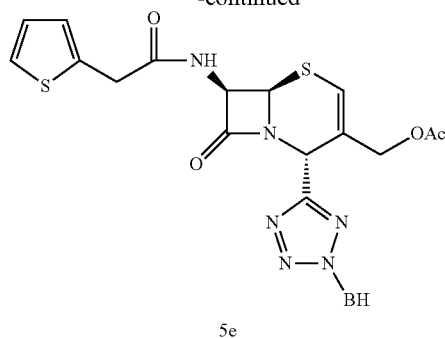
5e
+
102
-continued
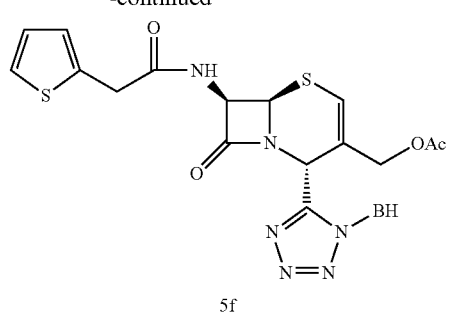
5f
[Chemical Formula 105]
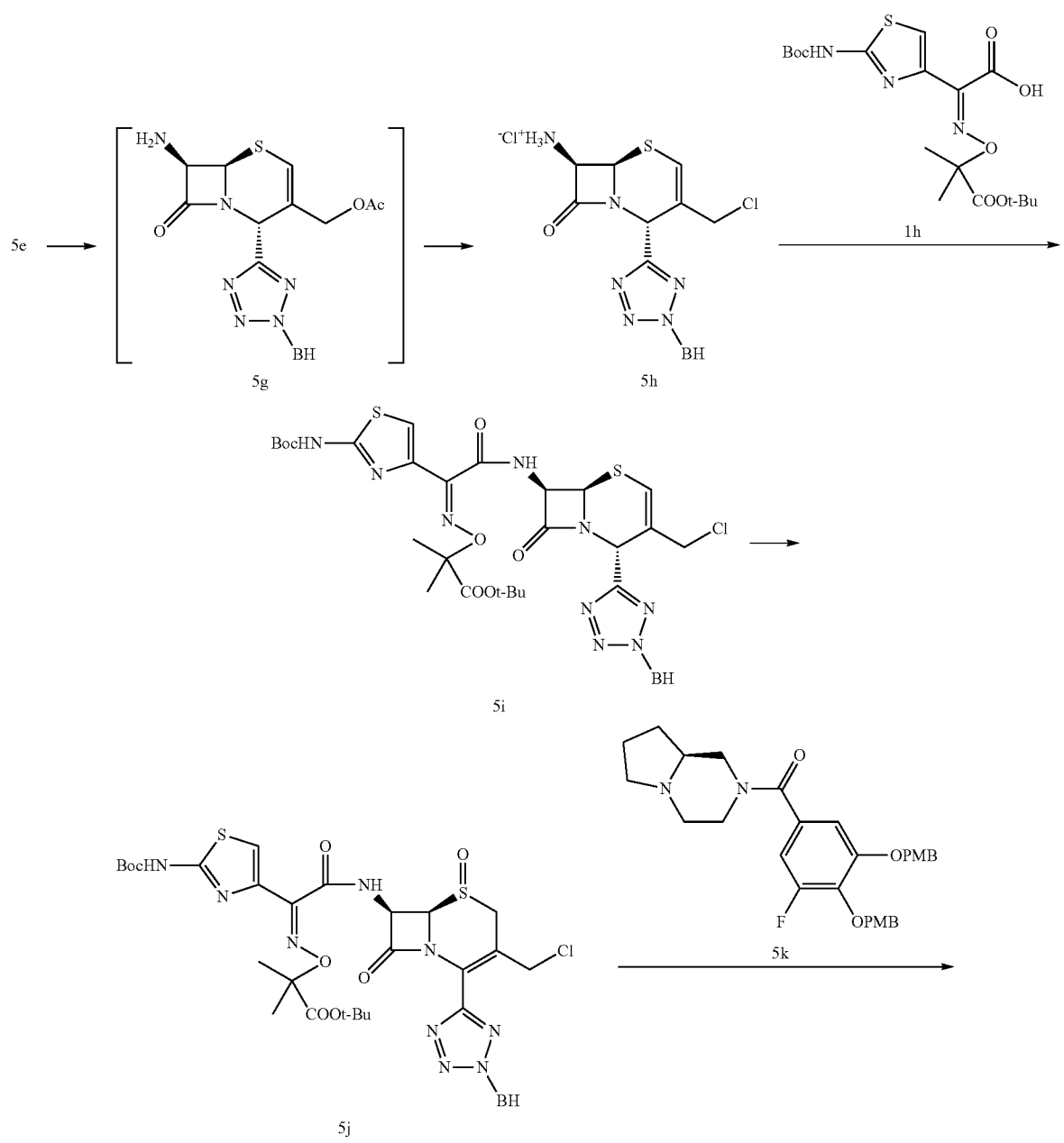

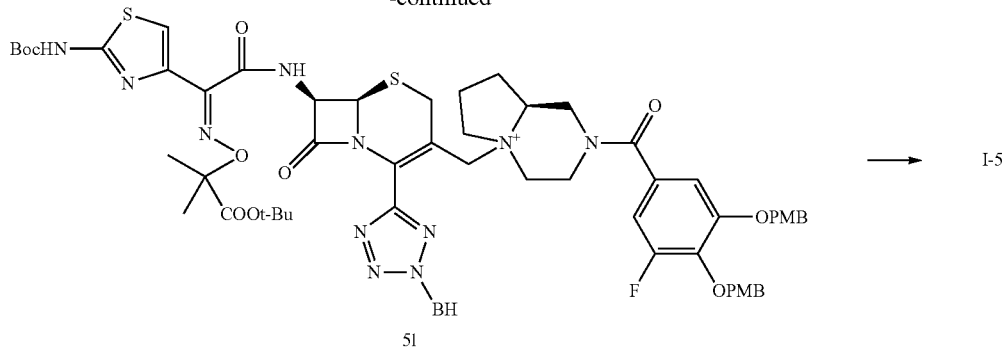

Step (1): Compound 5a→Compound 5b

A known Compound 5a (100 mg, 0.252 mmol) was dissolved in 1,4-dioxane (1 mL), and di-tert-butyl bicarbonate (0.076 mL, 0.328 mmol), ammonium carbonate (30.3 mg, 0.315 mmol), followed by pyridine (0.010 mL, 0.126 mmol) were added thereto, and the mixture was stirred overnight. Purified water was added to the reaction solution, and the aqueous layer was extracted with a mixture solution of methyl acetate-tetrahydrofuran. The organic layer was washed with purified water and brine, and dried over anhydrous magnesium sulfate. The magnesium sulfate was filtered off, and the solvent was removed in vacuo. The precipitated solid was collected by filtration, and washed with ethyl acetate to yield Compound 5b as a white solid. (Yield: 75 mg, 75%)

$^1$H-NMR (DMSO-$d_6$) δ: 9.20 (1H, d, J=7.5 Hz), 7.36 (1H, dt, j=5.0, 1.1 Hz), 6.97-6.89 (2H, m), 6.72 (1H, s), 5.43 (1H, dd, J=7.5, 3.7 Hz), 5.15 (1H, d, J=3.7 Hz), 4.90 (1H, s), 4.64 (2H, dd, J=18.1, 12.7 Hz), 3.76 (2H, s), 2.02 (3H, s).

Step (2): Compound 5b→Compound 5c

Compound 5b (13.2 g, 33.4 mmol) was suspended in tetrahydrofuran (135 mL), and cooled to −20° C. Pyridine (8.11 mL, 100 mmol) and anhydrous trifluoroacetic acid (7.06 mL, 50.1 mmol) was added to the solution, and the mixture was stirred for 30 minutes at −20° C. Purified water was added to the reaction solution, and the aqueous layer was extracted with ethyl acetate. The organic layer was washed with purified water and brine, and dried over anhydrous magnesium sulfate. The magnesium sulfate was filtered off, and the solvent was removed in vacuo. The resulting residue was subjected to silica gel chromatography to yield Compound 5c as orange foam. (Yield: 13.88 g, quantitative)

$^1$H-NMR (CDCl$_3$) δ: 7.29-7.25 (1H, m), 7.02-6.97 (2H, m), 6.53 (1H, d, J=1.1 Hz), 6.32 (1H, d, J=8.2 Hz), 5.72 (1H, dd, J=8.2, 4.1 Hz), 5.26 (1H, d, J=1.1 Hz), 5.11 (1H, d, J=4.1 Hz), 4.73 (1H, d, J=13.2 Hz), 4.61 (1H, d, J=13.2 Hz), 3.87 (2H, s), 2.09 (3H, s).

Step (3): Compound 5c→Compound 5d

Compound 5c (273 mg, 0.723 mmol) was dissolved in 1,4-dioxane, and trimethylsilylazide (0.192 mL, 1.447 mmol), followed by oxodibutylstannane (18.01 mg, 0.072 mmol) were added thereto, and the mixture was stirred for one hour at 90° C. The reaction solution was cooled to room temperature, and the solvent was removed. Purified water and ethyl acetate were added to the residue, and the mixture was extracted.

The organic layer was washed with purified water and brine, and dried over anhydrous magnesium sulfate. The magnesium sulfate was filtered off, and the solvent was removed in vacuo. The resulting residue was subjected to silica gel chromatography to yield Compound 5d. (Yield: 169.2 mg, 56%)

$^1$H-NMR (DMSO-$d_6$) δ: 9.25 (1H, d, J=7.8 Hz), 7.36 (1H, dd, J=4.9, 1.4 Hz), 6.97-6.85 (3H, m), 5.90 (1H, d, J=1.5 Hz), 5.44 (1H, dd, J=7.8, 4.0 Hz), 5.14 (1H, d, J=4.0 Hz), 4.60 (1H, d, J=12.7 Hz), 4.53 (1H, d, J=12.7 Hz), 3.77 (2H, s), 1.90 (3H, s).

Step (4): Compound 5d→Compound 5e

Compound 5d (85 mg, 0.243 mmol) was dissolved in tetrahydrofuran (1 mL), and diphenyldiazomethane (47.1 mg, 0.243 mmol) were added, and the mixture was stirred for 3.5 hours. Diphenyldiazomethane (11.8 mg, 0.606 mmol) was added, and the mixture was stirred for 35 minutes. The solvent was removed in vacuo, and the resulting residue was subjected to silica gel chromatography to yield Compound 5e (Yield: 72 mg, 61%) and Compound 5f. The position of diphenylmethyl group was determined by nuclear overhauser effect in 1H NMR.

Compound 5e: Less Polar One $^1$H-NMR (CDCl$_3$) δ: 7.41-7.12 (13H, m), 7.03-6.91 (2H, m), 6.41 (1H, s), 6.37 (1H, d, J=9.1 Hz), 5.80 (1H, s), 5.64 (1H, dd, J=9.1, 4.0 Hz), 5.26 (1H, d, J=4.0 Hz), 4.51 (1H, d, J=12.8 Hz), 4.39 (1H, d, J=12.8 Hz), 3.86 (2H, s), 1.89 (3H, s).

Compound 5f: More Polar One $^1$H-NMR (CDCl$_3$) δ: 7.42-7.33 (5H, m), 7.28-7.18 (4H, m), 7.13 (2H, dd, J=6.6, 3.0 Hz), 7.02-6.95 (2H, m), 6.90 (1H, s), 6.57 (1H, d, J=1.4 Hz), 6.30 (1H, d, J=9.1 Hz), 5.80 (1H, d, J=1.4 Hz), 5.01 (1H, dd, J=9.1, 4.0 Hz), 4.64 (1H, d, J=12.8 Hz), 4.58 (1H, d, J=4.0 Hz), 4.51 (1H, d, J=12.8 Hz), 3.82 (2H, s), 1.80 (3H, s).

Step (5): Compound 5e→Compound 5h

Phosphorous pentachloride (1.249 g, 6.00 mmol) was suspended in methylene chloride (15 mL), and the suspension was cooled to 0° C. Pyridine (0.53 mL, 6.60 mmol) and Compound 5e (1.689 g, 3.00 mmol) were added sequentially to the suspension. The suspension was stirred for 40 minutes at 0° C. and then warmed to room temperature and stirred for several minutes. The reaction solution was cooled to 0° C., and methanol (13.3 mL, 328 mmol) was added in one portion, and the mixture was warmed to room temperature. Purified water (130 mL) was added to the reaction solution, and the aqueous layer was extracted with methylene chloride.

The layer of methylene chloride was washed with sodium bicarbonate water and brine, and dried over anhydrous magnesium sulfate. The magnesium sulfate was filtered off, and a solution of 4 mol/L hydrochloric acid-ethyl acetate (2.25 mL, 9 mmol) was added to the organic layer, and the solution was stirred for 3 hours and 15 minutes. The solvent was removed in vacuo to yield jelly Compound 5h. (Yield: 2.02 g, 142%) Compound 5h was suspended in acetonitrile and scratched the wall surface with spatula to yield seed crystals of Compound 5h.

Separately, phosphorous pentachloride (9.12 g, 43.8 mmol) was suspended in methylene chloride (130 mL), and cooled to 0° C. Pyridine (3.90 mL, 48.2 mmol) and Compound 5e (12.8 g, 21.9 mmol) were added sequentially to the suspension, and the mixture was stirred for 45 minutes at room temperature. The reaction solution was cooled to −40° C., and methanol (13.3 mL, 328 mmol) was added in one portion, and the mixture was warmed to room temperature. Purified water (130 mL) was added to the reaction solution, and the aqueous layer was extracted with methylene chloride.

The layer of methylene chloride was washed with water and brine, and dried over anhydrous magnesium sulfate. The magnesium sulfate was filtered off, and a solution of 4 mol/L hydrochloric acid-dioxane (27.4 mL, 109 mmol) was added to the organic layer, and the mixture was stirred for 3 hours and 15 minutes at room temperature. 1,4-dioxane (150 mL) was added to the reaction solution, and the solvent was removed in vacuo to adjust the total amount about 30 mL. Acetonitrile (100 mL) was added to the resulting solution, and the above seed crystals of Compound 5h were added thereto, and the mixture was stirred at room temperature. The precipitated crystals were collected by filtration to yield Compound 5h. (Yield: 7.92 g, 73%)

$^1$H-NMR (DMSO-$d_6$) δ: 8.82 (2H, br s), 7.72 (1H, s), 7.45-7.26 (11H, m), 7.00 (1H, d, J=1.2 Hz), 5.94 (1H, d, J=1.2 Hz), 5.19 (1H, d, J=4.2 Hz), 4.94 (1H, d, J=4.2 Hz), 4.48 (1H, d, J=11.8 Hz), 4.16 (1H, d, J=11.8 Hz).

Step (6): Compound 5h→Compound 5i

Compound 5h was suspended in ethylene chloride (40 mL), and cooled to −40° C. Compound 1h (3.54 g, 8.24 mmol) was added to the suspension. Phenylphospate dichloride (1.85 mL, 12.36 mmol) was added and N-methylmorpholine (3.62 mL, 33.0 mmol) was added dropwise, and the solution was stirred for 30 minutes at −40° C. Purified water was added to the reaction solution, and the aqueous layer was extracted with ethyl acetate. The resulting organic layer was washed with purified water and brine, and dried over anhydrous magnesium sulfate. The magnesium sulfate was filtered off, and the solvent was removed in vacuo to yield Compound 5i. (Yield: 7.8 g, quantitative)

$^1$H-NMR (CDCl$_3$) δ: 8.32 (1H, d, J=8.5 Hz), 7.41-7.15 (16H, m), 6.46 (1H, s), 5.99 (1H, s), 5.79 (1H, dd, J=8.5, 4.0 Hz), 5.37 (1H, d, J=4.0 Hz), 5.29 (1H, s), 4.15-4.01 (2H, m), 1.63 (3H, s), 1.60 (3H, s), 1.52 (9H, s), 1.42 (9H, s).

Step (7): Compound 5i→Compound 5j

Compound 5i (2.30 g, 2.7 mmol) was dissolved in methylene chloride (25 mL) and cooled to −40° C. Meta-chloroperbenzoic acid (788 mg, 2.97 mmol) was added to the solution, and the solution was stirred for 1 hour and 15 minutes at −40° C. An aqueous solution of sodium hydrogen sulfite was added to the reaction solution, and methylene chloride was removed in vacuo. The concentrated solution was extracted with ethyl acetate, and the organic layer was washed with aqueous sodium bicarbonate, purified water and brine, and dried over anhydrous magnesium sulfate. The magnesium sulfate was filtered off, and the solvent was removed in vacuo. The resulting residue was subjected to silica gel chromatography to yield Compound 5j. (Yield: 1.41 g, 60%)

Compound 5j was suspended in ethanol, and the wall surface was scratched with spatula to yield chrystals.

$^1$H-NMR (CDCl$_3$) δ: 8.08 (1H, br s), 7.90 (1H, d, J=9.9 Hz), 7.39-7.18 (20H, m), 6.29 (1H, dd, J=9.7, 5.0 Hz), 5.13 (1H, d, J=12.4 Hz), 4.73 (1H, d, J=4.9 Hz), 4.29 (1H, d, J=12.1 Hz), 3.90 (1H, d, J=19.0 Hz), 3.50 (1H, d, J=19.0 Hz), 1.59 (6H, d, J=7.1 Hz), 1.56 (9H, s), 1.38 (10H, s).

Step (8): Compound 5j→Compound 5i→Compound I-5

Compound 5j (0.866 g, 1.00 mmol) was dissolved in N,N-dimethylformamide (3.0 mL), and the solution was cooled to 10° C. Sodium iodide (0.3 g, 2.00 mmol) and Compound 5k (521 mg, 1.00 mmol) were added thereto, and stirred for 3 hours and 35 minutes at the same temperature, and allowed to stand at 4° C. overnight. N,N-dimethylformamide (3.0 mL) was added to the reaction solution, and the solution was cooled to −40° C. Phosphorus tribromide was added thereto, and the solution was stirred at −40° C. for 30 minutes. The reaction solution was added to 5% brine, and the precipitated residue was collected by filtration, and dried in vacuo to yield Compound 5i as a powder.

Compound 5i was dissolved in dichloromethane (15 mL), and cooled to −40° C. Anisole (1.09 mL, 10 mol) and a solution of 2 mol/L aluminum chloride in nitromethane (5 mL, 10 mmol) were added thereto, and the solution was stirred for 50 minutes at 0° C. Purified water (30 mL) and diisopropyl ether (50 mL) were added to the reaction solution. Acetonitrile and 2N hydrochloric acid were added to the reaction solution, and the precipitation was dissolved, and the aqueous layer was separated. The organic layer was extracted with a mixture of water/acetonitrile/diluted hydrochloric acid. HP20SS was added to the combined aqueous layers, and the solution was concentrated. The concentrated suspension was subjected to HP20SS/ODS column chromatography, and eluted with water-acetonitrile. An aqueous 0.2 N sodium hydroxide solution was added dropwise to the fraction containing the desired substance to adjust pH to 5.3. The solution was concentrated in vacuo, and the concentrated solution was freeze-dried to yield Compound I-5 as a powder. (Yield: 378 mg, 48%)

$^1$H-NMR (D$_2$O) δ: 6.96 (1H, s), 6.90-6.74 (2H, m), 5.91 (1H, d, J=5.0 Hz), 5.58 (1H, d, J=5.0 Hz), 4.97-4.90 (1H, m), 4.26 (1H, t, J=12.7 Hz), 4.13-3.84 (2H, m), 3.82-3.42 (6H, m), 3.36-3.21 (1H, m), 2.25-1.79 (3H, br m), 1.52 (3H, s), 1.46 (3H, s).

Elemental analysis for: C31H33FN11O8S2Na(H2O)4.2

Calcd.: C, 42.66; H, 4.65; N, 17.96; S, 7.46; Na, 2.88; F, 2.09(%).

Found: C, 42.82; H, 4.80; N, 17.72; S, 7.38; Na, 2.64; F, 2.19(%).

Example 6

Synthesis of Compound I-6

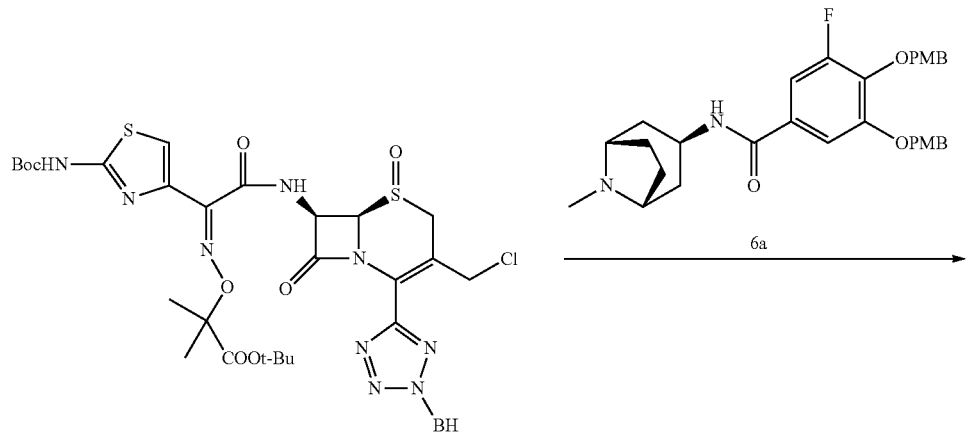

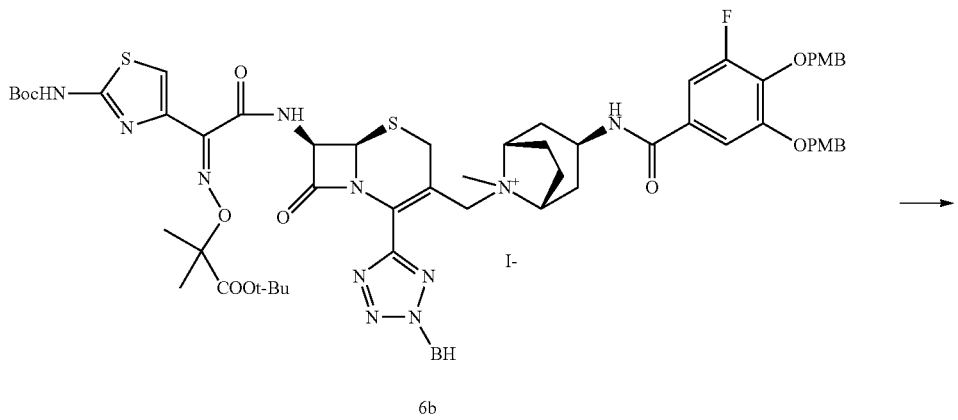

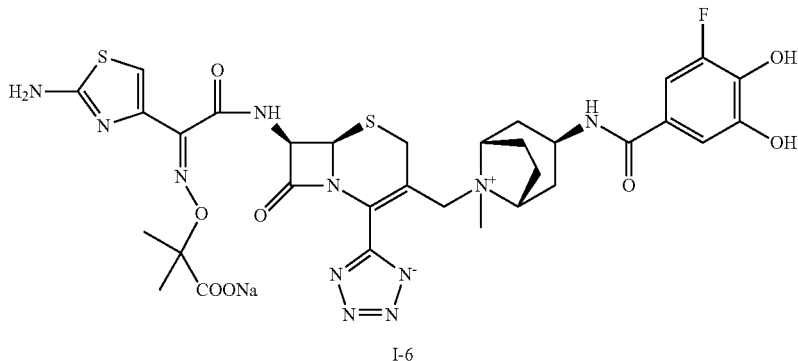

Step (1): Compound 5j→Compound 6b→Compound I-6

Using Compound 5j (0.866 mg, 1 mmol) and Compound 6a (535 mg, 1 mmol), Compound I-6 was synthesized according to a similar procedure as described in Step (8) of the synthesis of Compound I-5 (Yield: 237 mg, 29%).

$^1$H-NMR (D$_2$O) δ: 7.12-7.01 (2H, m), 6.96 (1H, d, J=0.8 Hz), 5.91 (1H, d, J=4.8 Hz), 5.59 (1H, d, J=4.8 Hz), 4.66-4.60 (1H, m), 4.22-3.98 (5H, m), 3.74 (1H, d, J=17.1 Hz), 3.63 (1H, br s), 2.94 (3H, s), 2.83-2.54 (3H, m), 2.38-2.33 (3H, m), 2.22-1.93 (3H, m), 1.52 (6H, s), 1.50 (6H, s).

Elemental analysis for: C32H35FN11O8S2Na(H2O)5.1

Calcd.: C, 42.66; H, 4.65; N, 17.96; S, 7.46; Na, 2.88; F, 2.09(%).

Found: C, 42.82; H, 4.80; N, 17.72; S, 7.38; Na, 2.64; F, 2.19(%).

Example 7

Synthesis of Compound I-7

[Chemical Formula 107]

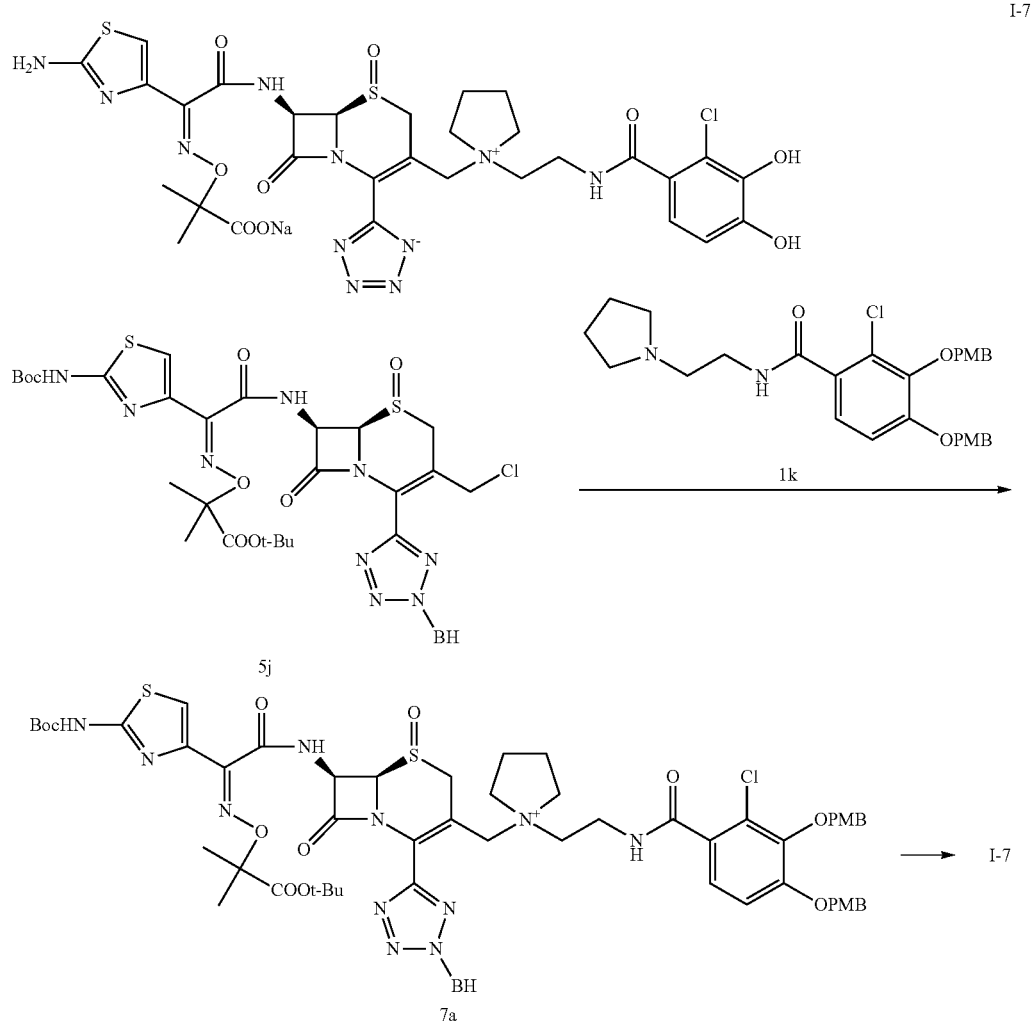

Compound 5j (0.866 g, 1.00 mmol) was dissolved in N,N-dimethylformamide (3.0 mL), and sodium iodide (0.3 g, 2.00 mmol) and Compound 1k (525 mg, 1.00 mmol) were added thereto. The solution was stirred overnight at 10° C. Purified water was added to the reaction solution, and the aqueous layer was extracted with ethyl acetate. The organic layer was washed with purified water and brine, and dried over anhydrous magnesium sulfate. The magnesium sulfate was filtered off, and the solvent was removed, in vacuo to yield Compound 7a.

Compound 7a was dissolved in dichloromethane (15 mL) and cooled to −40° C. Anisole (1.09 mL, 10 mol) and a solution of 2 mol/L aluminum chloride in nitromethane (5 mL, 10 mmol) were added thereto. The solution was stirred for 50 minutes at 0° C. Purified water (30 mL) and diisopropyl ether (50 mL) were added to the reaction solution. Acetonitrile and 2N hydrochloric acid were added to the reaction solution, and the precipitation was dissolved. The aqueous layer was separated, and the organic layer was extracted with a mixture of water/acetonitrile/diluted hydrochloric acid. HP20SS was added to the combined aqueous layers, and the solution was concentrated. The concentrated suspension was subjected to reverse phase column chromatography, and eluted with water-acetonitrile. An aqueous 0.2 N sodium hydroxide solution was applied to the fraction containing the desired substance to prepare a sodium salt, and the solution was concentrated in vacuo. The concentrated solution was freeze-dried to yield Compound I-7 as a powder.

(Yield: 177 mg, 22%)

$^1$H-NMR (D$_2$O) δ: 7.02-6.84 (3H, m), 6.19-6.16 (1H, m), 5.38-5.35 (1H, m), 5.17 (1H, d, J=12.4 Hz), 4.36 (1H, d, J=18.1 Hz), 4.08-4.03 (2H, m), 3.54-3.34 (6H, m), 2.11 (4H, br s), 1.53 (3H, s), 1.50 (3H, s).

Elemental analysis for: C30H33ClN11O9S2Na(H2O)5.9

Calcd.: C, 38.97; H, 4.75; N, 17.01; S, 7.05; Na, 2.70; Cl, 3.71(%).

Found: C, 39.14; H, 4.91; N, 16.74; S, 6.97; Na, 2.50; Cl, 3.85(%).

MS (M+H)=792.33

Example 8
Synthesis of Compound I-8
[Chemical Formula 108]
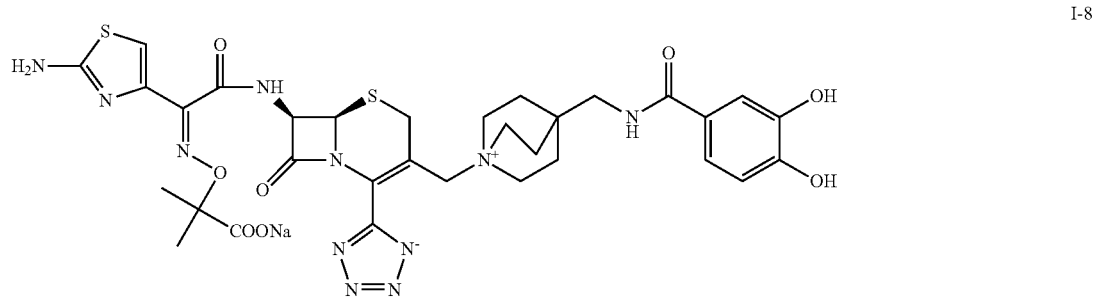
I-8
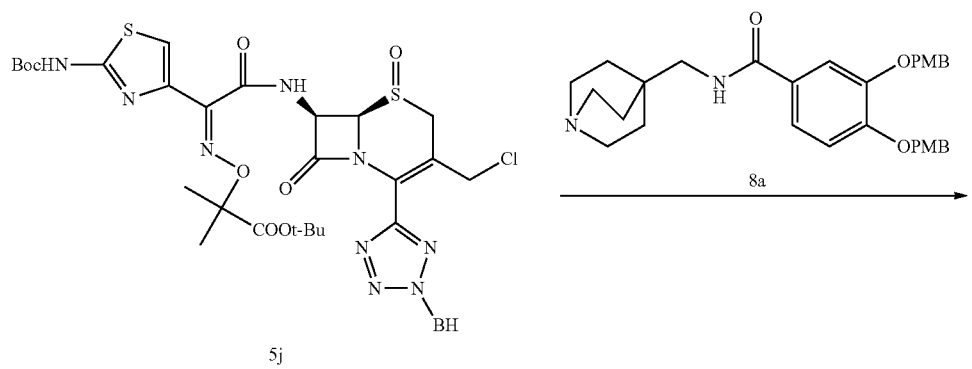
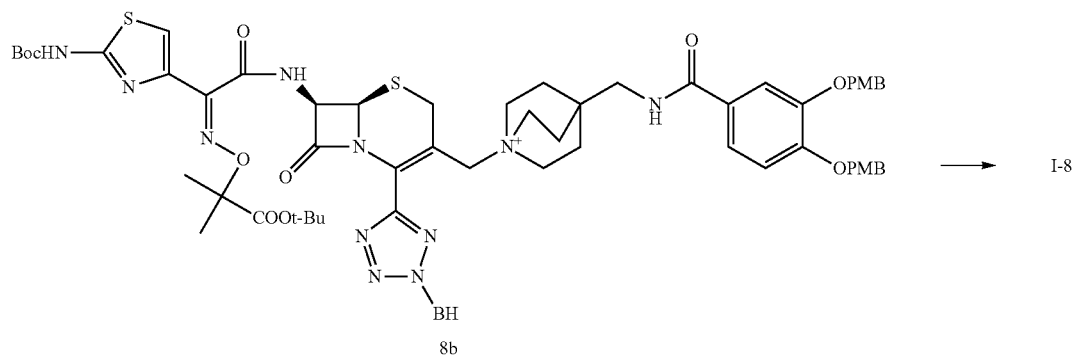
Using Compound 5j (0.693 mg, 0.8 mmol), Compound 8a (413 mg, 1 mmol) and sodium bromide (165 mg, 1.6 mmol), Compound I-8 was synthesized according to a similar procedure as described in Step (8) of the synthesis of Compound I-5. (Yield: 284 mg, 45)
$^1$H-NMR (D$_2$O) δ: 7.27-79.26 (1H, m), 7.25-7.21 (1H, m), 6.97 (1H, s), 6.94 (1H, s), 5.88 (1H, d, J=5.0 Hz), 5.55 (1H, d, J=5.0 Hz), 4.63 (1H, d, J=13.9 Hz), 4.00 (1H, d, J=17.2 Hz), 3.90 (1H, d, J=13.9 Hz), 3.63 (1H, d, J=17.2 Hz), 3.42-3.22 (5H, br m), 3.18-2.99 (3H, br m), 1.79 (6H, t, J=7.2 Hz), 1.51 (3H, s), 1.49 (3H, s).
MS (m+1)=768.36

Example 9

Synthesis of Compound I-9

[Chemical Formula 109]

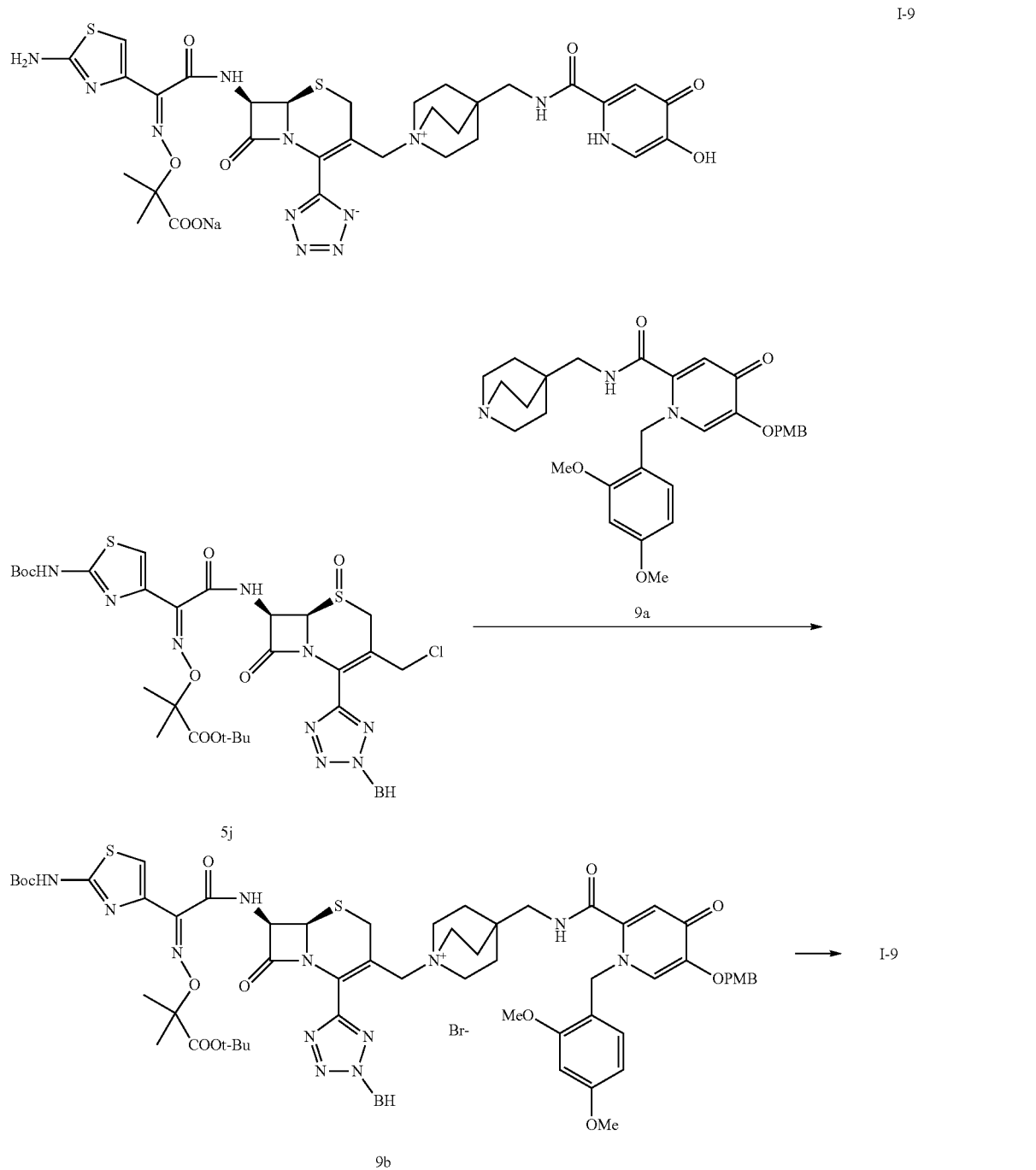

Using Compound 5j (0.693 mg, 0.8 mmol), Compound 9a (438 mg, 1 mmol) and sodium bromide (165 mg, 1.6 mmol), Compound I-9 was synthesized according to a similar procedure as described in Step (8) of the synthesis of Compound I-5. (Yield: 249 mg, 39%)

$^1$H-NMR (D$_2$O) δ: 7.76 (1H, s), 7.08 (1H, s), 6.96 (1H, s), 5.90 (1H, d, J=5.0 Hz), 5.57 (1H, d, J=5.0 Hz), 4.64 (1H, d, J=14.1 Hz), 4.03 (1H, d, J=17.0 Hz), 3.92 (1H, d, J=14.1 Hz), 3.65 (1H, d, J=17.0 Hz), 3.43-3.29 (5H, br m), 3.18-3.04 (3H, br m), 1.91-1.76 (6H, br m), 1.52 (3H, s), 1.49 (3H, s).

Elemental analysis for: C31H35N12O8S2Na(H2O)5.8
Calcd.: C, 41.59; H, 5.11; N, 18.75; S, 7.14; Na, 2.66(%).
Found: C, 41.59; H, 5.25; N, 18.77; S, 7.16; Na, 2.57(%).
MS (M+H)=769.35

Example 10

Synthesis of Compound I-10

[Chemical Formula 110]

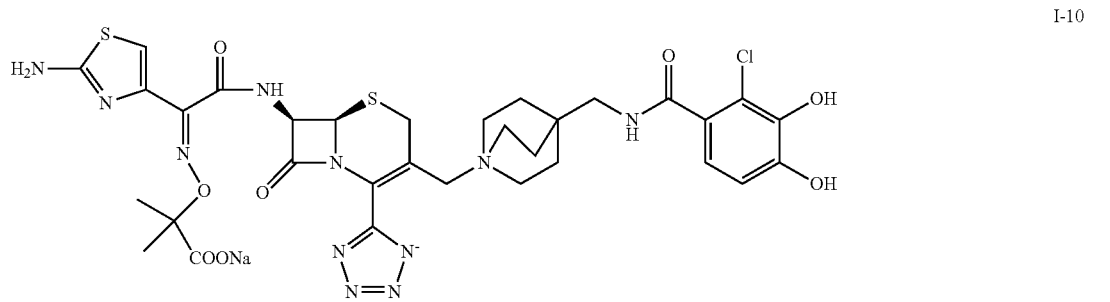

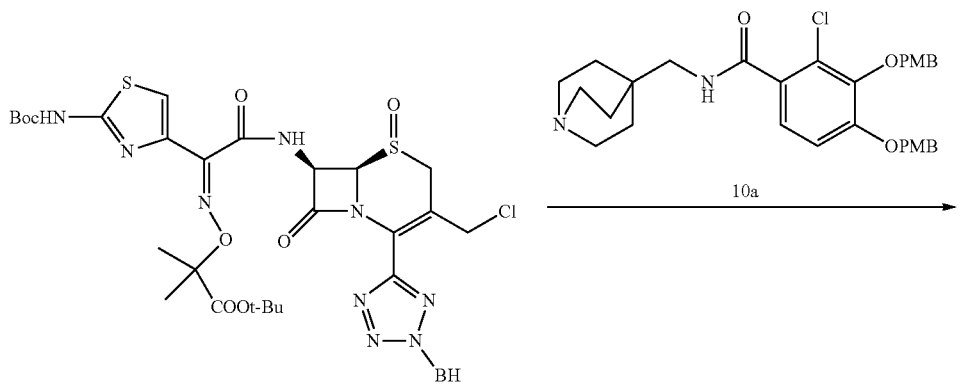

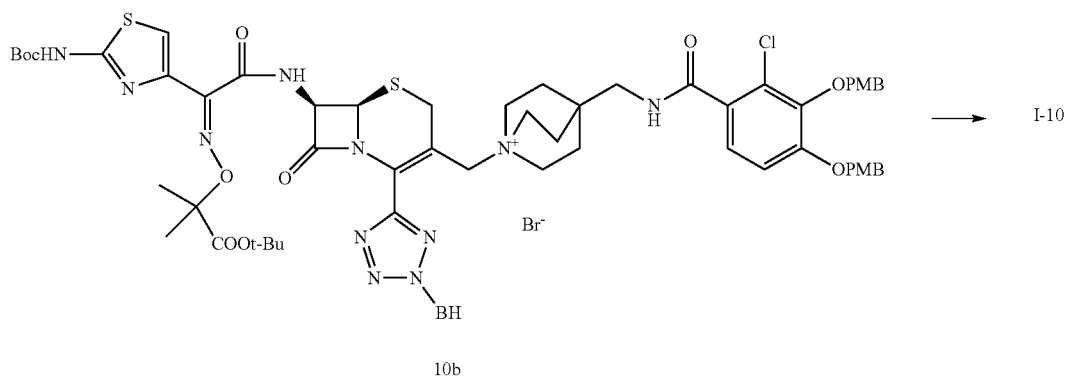

Using Compound 5j (0.693 mg, 0.8 mmol), Compound 10a (441 mg, 1 mmol) and sodium bromide (165 mg, 1.6 mmol), Compound I-10 was synthesized according to a similar procedure as described in Step (8) of the synthesis of Compound I-5. (Yield: 348 mg, 53%)

$^1$H-NMR (D$_2$O) δ: 6.95 (1H, s), 6.91 (1H, d, J=8.6 Hz), 6.87 (1H, d, J=8.6 Hz), 5.90 (1H, d, J=5.0 Hz), 5.56 (1H, d, J=5.0 Hz), 4.64 (H, c, J=14.2 Hz), 4.03 (1H, d, J=17.1 Hz), 3.92 (1H, d, J=14.2 Hz), 3.65 (1H, d, J=17.1 Hz), 3.43-3.30 (3H, br m), 3.28 (2H, s), 3.20-3.02 (3H, br m), 1.90-1.76 (6H, br m), 1.52 (3H, s), 1.49 (3H, s).

Elemental analysis for: C32H35ClN11O8S2Na(H2O)5.7

Calcd.: C, 41.42; H, 4.91; N, 16.56; S, 6.96; Na, 2.54; Cl, 4.19(%).

Found: C, 41.46; H, 5.05; N, 16.62; S, 6.92; Na, 2.48; Cl, 3.82(%).

Example 11

Synthesis of Compound I-11

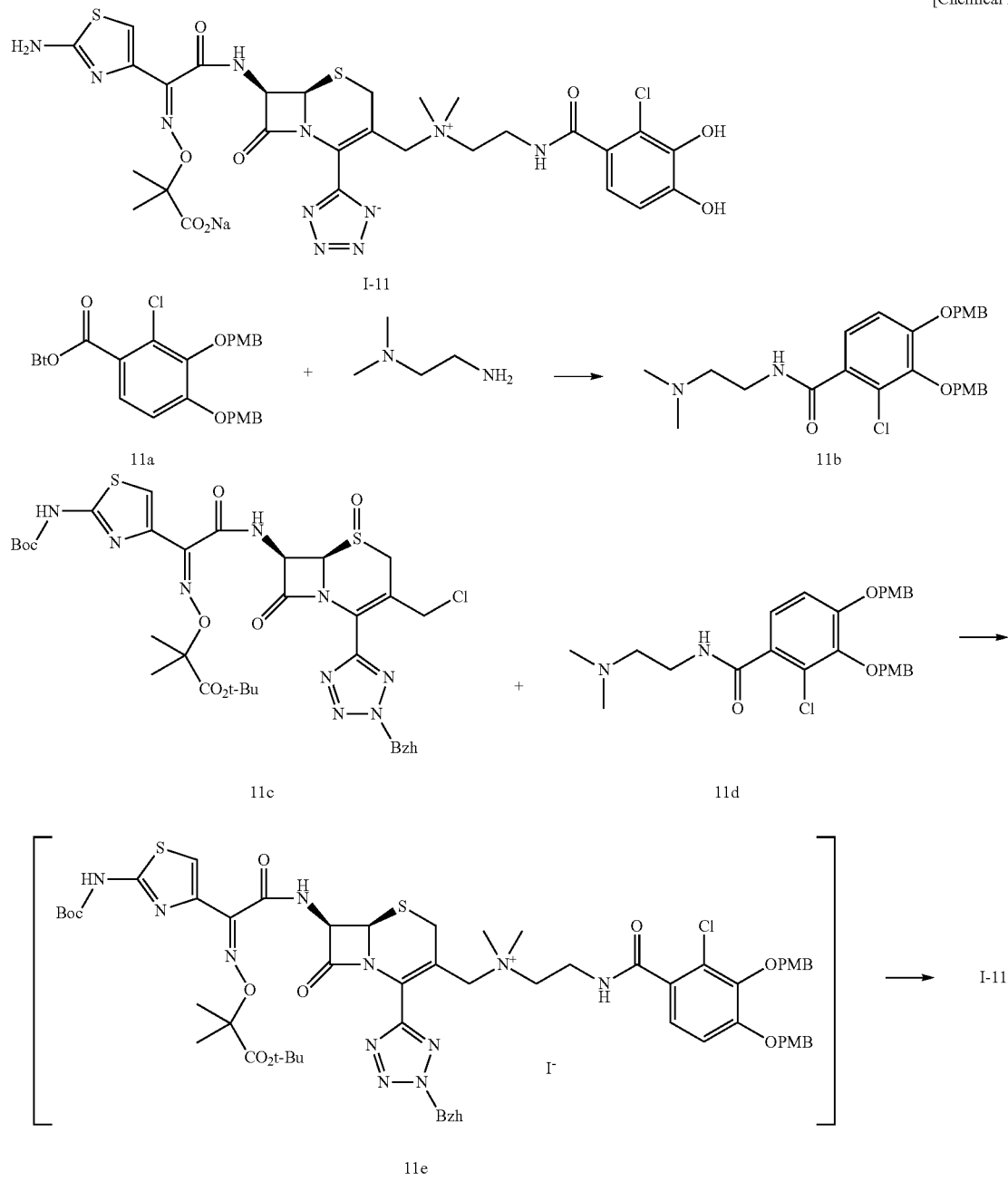

Step (1): Compound 11a→Compound 11b

Compound 11a (2.73 g 5.00 mmol) was dissolved in methylene chloride (300 ml), and N,N-ethylenediamine (655 µL, 6.00 mmol) was added thereto under ice-cooling. The solution was stirred overnight at room temperature. The reaction solution was diluted with methylene chloride, and washed sequentially with an aqueous 0.2 N sodium hydroxide solution, water and brine. The organic layer was dried with magnesium sulfate. Magnesium sulfate was filtered off, and the liquid was concentrated in vacuo. Diisopropyl ether was added thereto, and the precipitated crystals were collected by filtration to yield Compound 11b (2.25 g, 90%).

$^1$H-NMR (CDCl$_3$) δ: 7.41 (1H, d, J=8.56 Hz), 7.36-7.33 (4H, m), 6.94-6.90 (3H, m), 6.86-6.81 (3H, m), 5.07 (2H, s), 4.95 (2H, s), 3.83 (3H, s), 3.80 (3H, s), 3.49-3.54 (2H, m), 2.51 (2H, t, J=5.96 Hz), 2.25 (6H, s).

Step (2): Compound 11c+Compound 11d→Compound I-11

To a solution of Compound 11c (693 mg, 0.80 mmol) in dimethylformamide (1.5 mL) was added sodium iodide (240 mg, 1.60 mmol). The solution was stirred for 5 minutes at room temperature. The solution was cooled to 0° C., and Compound 11d (439 mg, 0.88 mmol) was added thereto. The solution was stirred for 6 hours at 0 to 10° C. Dimethylformamide (4.5 mL) was added thereto, and cooled to −40° C. Phosphate tribromide (15 µL, 1.60 mmol) was added, and the solution was stirred for 30 minutes at −40° C. The reaction mixture was added slowly to a previously ice-cooled 5% brine containing sodium thiosulfate (1 g). The precipitated solid was collected by filtration, and washed with water. The solid was suspended in water, and freeze-dried to yield Compound 11e as a white solid. The resulting Compound 11e was used in the next step without further purification.

All amount of the resulting Compound 11e was dissolved in methylene chloride (10 ml), and the solution was cooled to −40° C. Anisole (1.97 ml, 18.0 mmol) and a solution of 2M aluminum chloride in nitromethane (6.00 ml, 12.0 mmol) were added subsequently, and the solution was stirred for 1 hour at 0° C. The reaction solution was dissolved in water, a 2N hydrochloric acid and acetonitrile, and washed with diisopropyl ether. HP20-SS resin was added to the aqueous layer, and acetonitrile was removed in vacuo. The resulting mixture was purified by ODS column chromatography. To the solution of resulting desired compound, an aqueous 0.2 N sodium hydroxide was added to adjust pH to 6.0, and a piece of dry ice was then added. The resulting solution was concentrated in vacuo, and freeze-dried to yield Compound I-11 as a white powder.

Yield: 440.2 mg, (61%)

$^1$H-NMR (D$_2$O) δ: 6.95-6.90 (3H, m), 5.91 (1H, d, J=5.03 Hz), 5.59 (1H, d, J=5.03 Hz), 4.92 (1H, d, J=14.49 Hz), 4.17 (1H, d, J=13.42 Hz), 4.09 (1H, d, J=17.08 Hz), 3.57-3.77 (3H, m), 3.50-3.42 (1H, m), 3.22-3.14 (1H, m), 3.07 (3H, s), 2.91 (3H, s), 1.52 (3H, s), 1.49 (3H, s).

Elemental analysis for: C28H31.1ClN11O8S2Na0.9 (H2O)5.2

Calcd.: C, 385.94; H, 4.84; Cl, 4.10; N, 1.84; S, 7.43; Na, 2.40(%).

Found: C, 39.03; H, 4.80; Cl, 4.36; N, 17.65; S, 7.33; Na, 2.35(%).

Example 12

Synthesis of Compound I-12

[Chemical Formula 112]

I-12

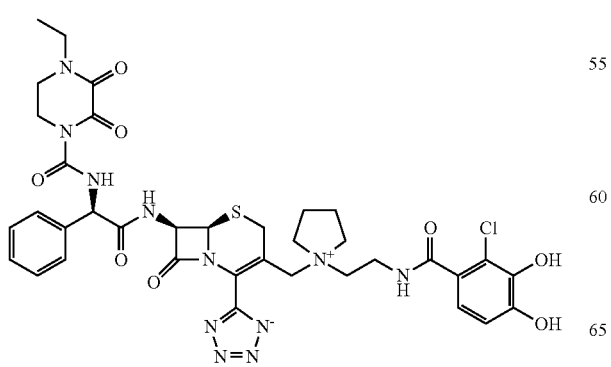

-continued

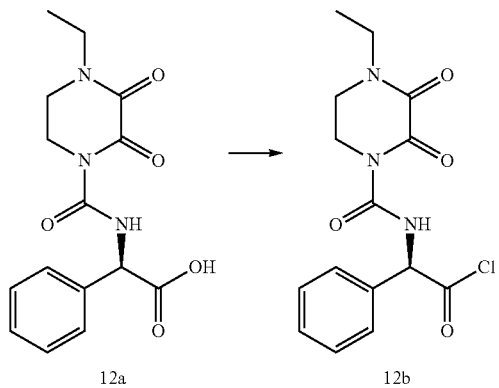

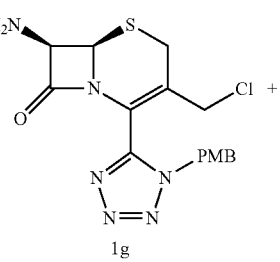

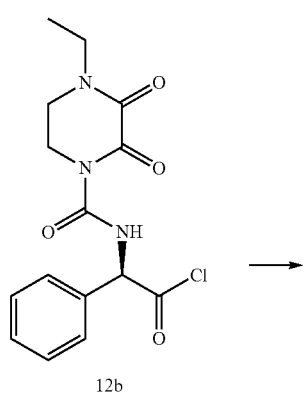

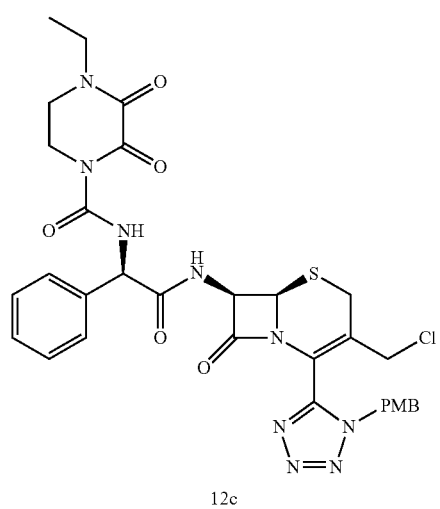

[Chemical Formula 113]

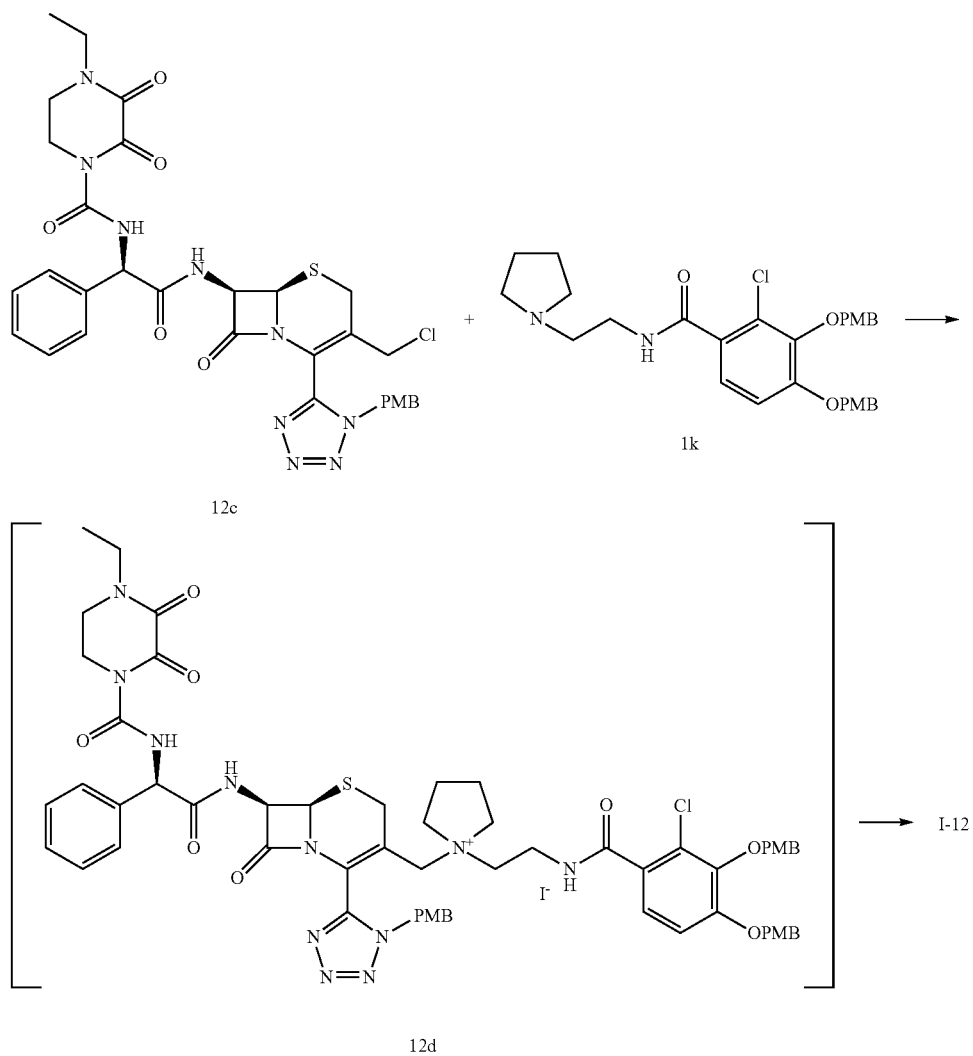

Step (1): Compound 12a→Compound 12b+Compound 1g→Compound 12c

Compound 12a (2.24 g, 7.00 mmol) was suspended in methylene chloride (20 ml), and oxalyl dichloride (735 µL, 8.40 mmol) and a drop of dimethylformamide were added thereto under ice-cooling. The suspension was stirred for 3 hours at room temperature. Further, oxalyl dichloride (184 µL, 2.10 mmol) was added thereto, and the mixture was stirred for 2 hours at room temperature. Toluene was added to the reaction solution, and the solution was concentrated in vacuo. Additional toluene was added thereto, and the solution was concentrated to yield Compound 12b (2.55 g, 108%). The resulting Compound 12b was used in the next step without further purification.

All amount of the resulting Compound 12b was dissolved in methylene chloride (20 ml), and a solution of Compound 1g (2.00 g, 5.09 mmol) and pyridine (616 µL, 7.64 mmol) in methylene chloride (20 ml) was added thereto at –40° C. The reaction solution was stirred for 1 hour at a temperature between –40° C. and –30° C. The reaction solution was diluted with methylene chloride, the solution was washed sequentially with hydrochloric acid, a saturated aqueous sodium bicarbonate and brine, and the organic layer was dried with magnesium sulfate. Magnesium sulfate was filtered off, and the liquid was concentrated in vacuo, subjected to silica gel column chromatography, eluting with chloroform/methanol. A fraction containing the desired compound was concentrated in vacuo, and ethyl acetate/diisopropyl ether was added thereto, and the precipitated solid was collected by filtration to yield Compound 12c (2.86 g, 81%).

$^1$H-NMR (CDCl$_3$) δ: 9.81 (1H, d, J=5.95 Hz), 7.44-7.27 (3H, m), 7.19-7.17 (2H, m), 7.08 (2H, d, J=8.62 Hz), 6.84 (2H, d, J=8.62 Hz), 5.85-5.80 (2H, m), 5.72 (1H, d, J=15.86 Hz), 5.41 (1H, d, J=6.25 Hz), 5.29 (1H, d, J=15.25 Hz), 4.77 (1H, d, J=4.88 Hz), 4.24-4.07 (3H, m), 3.94-3.80 (2H, m), 3.78 (3H, s), 3.71-3.43 (5H, m), 1.27 (3H, t, J=7.17 Hz).

Step (2): Compound 12c+Compound 1k→Compound I-12

Using Compound 12c (694 mg, 1.00 mmol) and Compound 1k (578 mg, 1.10 mmol), Compound I-12 was synthesized according to a similar procedure as described in Step (8) of the synthesis of Compound I-1.

Yield: 207.2 g, (18%)

—H-NMR (DMSO-$d_6$) δ: 9.85 (1H, d, J=7.24 Hz), 9.47 (1H, d, J=8.27 Hz), 8.29 (1H, s), 7.45-7.30 (5H, m), 6.74 (2H, s), 5.73 (1H, dd, J=8.27, 5.07 Hz), 5.63 (1H, d, J=7.24 Hz), 5.26 (1H, d, J=5.07 Hz), 5.13 (1H, d, J=14.18 Hz), 4.04-3.84 (4H, m), 3.62-3.53 (4H, m), 1.95-1.67 (3H, m), 1.08 (3H, t, J=7.09 Hz).

Elemental analysis for: C36H40ClN11O8S(H2O)3.1
Calcd.: C, 49.24; H, 5.30; Cl, 4.04; N, 17.55; S, 3.65(%).
Found: C, 49.24; H, 5.26; Cl, 4.05; N, 17.42; S, 3.61(%).

Example 13

Synthesis of Compound I-13

[Chemical Formula 114]

Step (1): Compound 5j→Compound 13b→Compound I-13

Using Compound 5j (0.866 mg, 1 mmol) and Compound 13a (537 mg, 1 mmol), Compound I-13 was synthesized according to a similar procedure as described in Step (8) of the synthesis of Compound I-5. (Yield: 398 mg, 49%).

$^1$H-NMR (D$_2$O) δ: 7.04 (1H, s), 6.96 (1H, s), 6.88 (1H, s), 5.91 (1H, d, J=5.1 Hz), 5.58 (1H, d, J=5.1 Hz), 4.94 (1H, d, J=14.1 Hz), 4.27 (1H, d, J=14.1 Hz), 4.17-3.85 (2H, m), 3.84-3.40 (7H, m), 3.37-3.00 (3H, m), 2.25-1.75 (3H, m), 1.52 (3H, s), 1.37 (3H, dd, J=41.8, 29.5 Hz).

Elemental analysis for: C31H33ClN11O8S2Na(H2O)5.4 (NaHCO3) 0.1
Calcd.: C, 40.61; H, 4.76; N, 16.99; S, 7.02; Na, 2.98; Cl, 4.27(%).

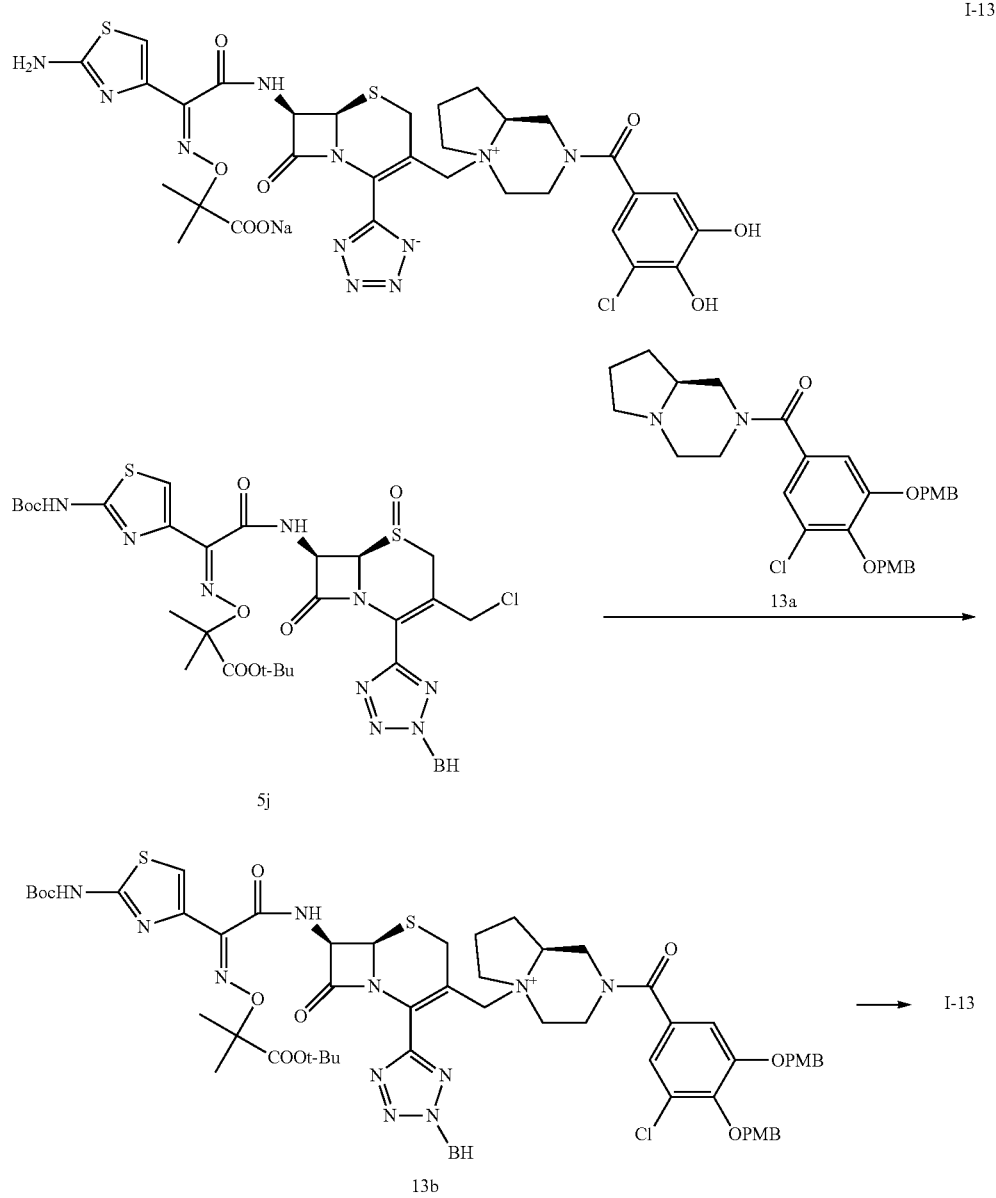

Found: C, 40.78; H, 4.83; N, 16.82; S, 7.00; Na, 2.76; Cl, 3.87(%).

MS (M+H)=788.34

Example 14

Synthesis of Compound I-14

[Chemical Formula 115]

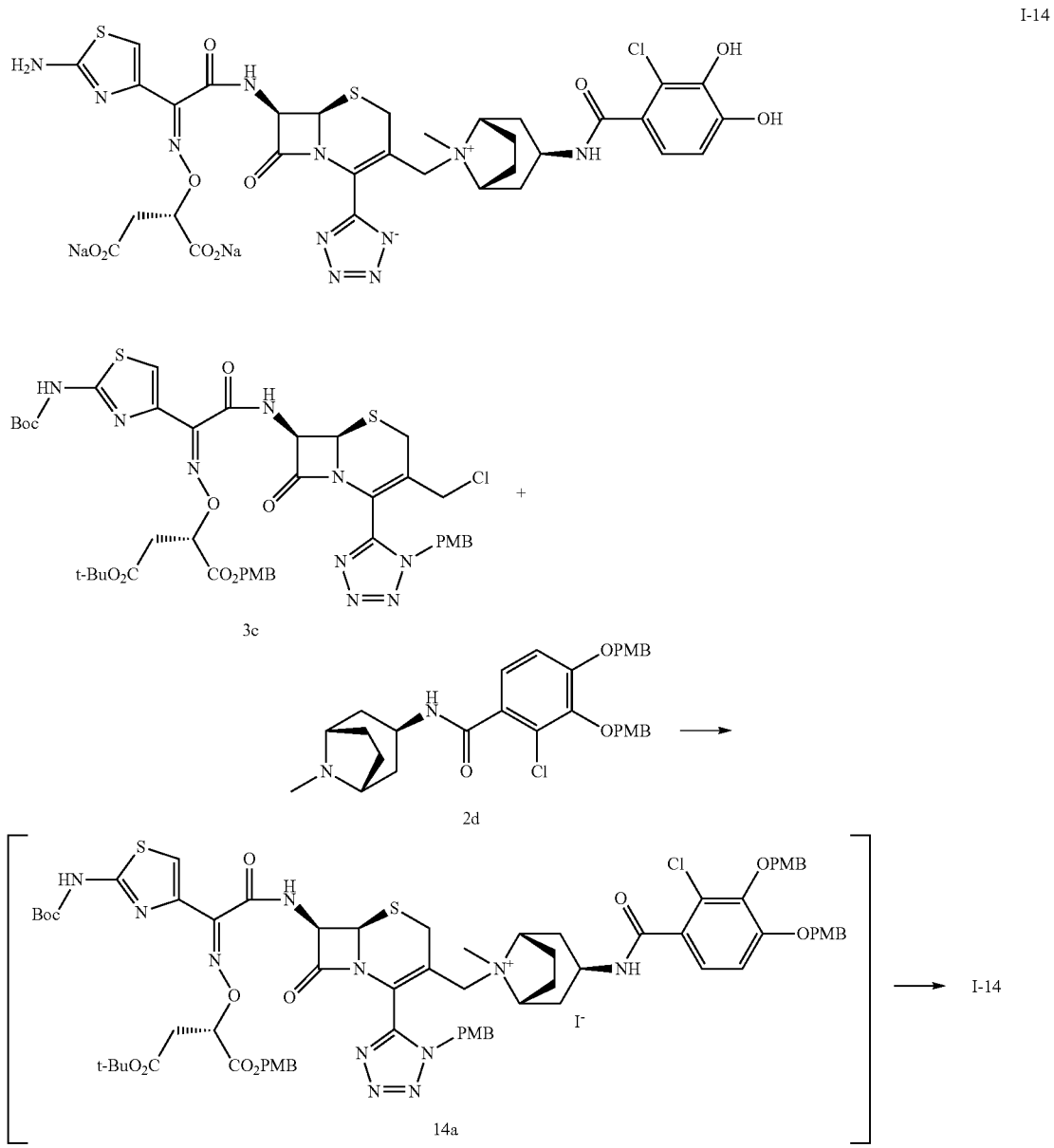

Step (1): Compound 3c+Compound 2d→Compound I-14

Using Compound 3c (954 mg, 1.00 mmol) and Compound 2d (551 mg, 1.00 mmol), Compound I-14 was synthesized according to a similar procedure as described in Step (8) of the synthesis of Compound I-1.

Yield: 324.6 g, (31%)

$^1$H-NMR (D$_2$O) δ: 6.98 (1H, s), 6.87 (2H, s), 5.85 (1H, d, J=4.96 Hz), 5.55 (1H, d, J=4.96 Hz), 4.99-4.95 (1H, m) 4.62 (1H, d, J=14.18 Hz), 4.19-4.02 (4H, m), 3.74 (1H, d, J=16.01 Hz), 3.66-3.62 (1H, m), 2.94 (3H, br s), 2.79-2.55 (5H, m), 2.37-2.30 (2H, m), 2.02-2.15 (2H, m).

Elemental analysis for: C32H32.1ClN11O10S2Na1.9 (H2O)7.3

Calcd. C, 38.22; H, 4.68; Cl, 3.53; N, 15.32; S, 6.38; Na, 4.34(%)

Found: C, 38.21; H, 4.60; Cl, 3.55; N, 15.26; S, 6.25; Na, 4.30 (%)

Example 15

Synthesis of Compound I-15

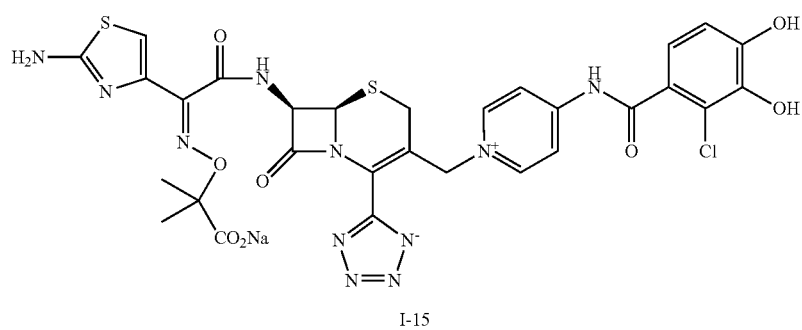

[Chemical Formula 116]

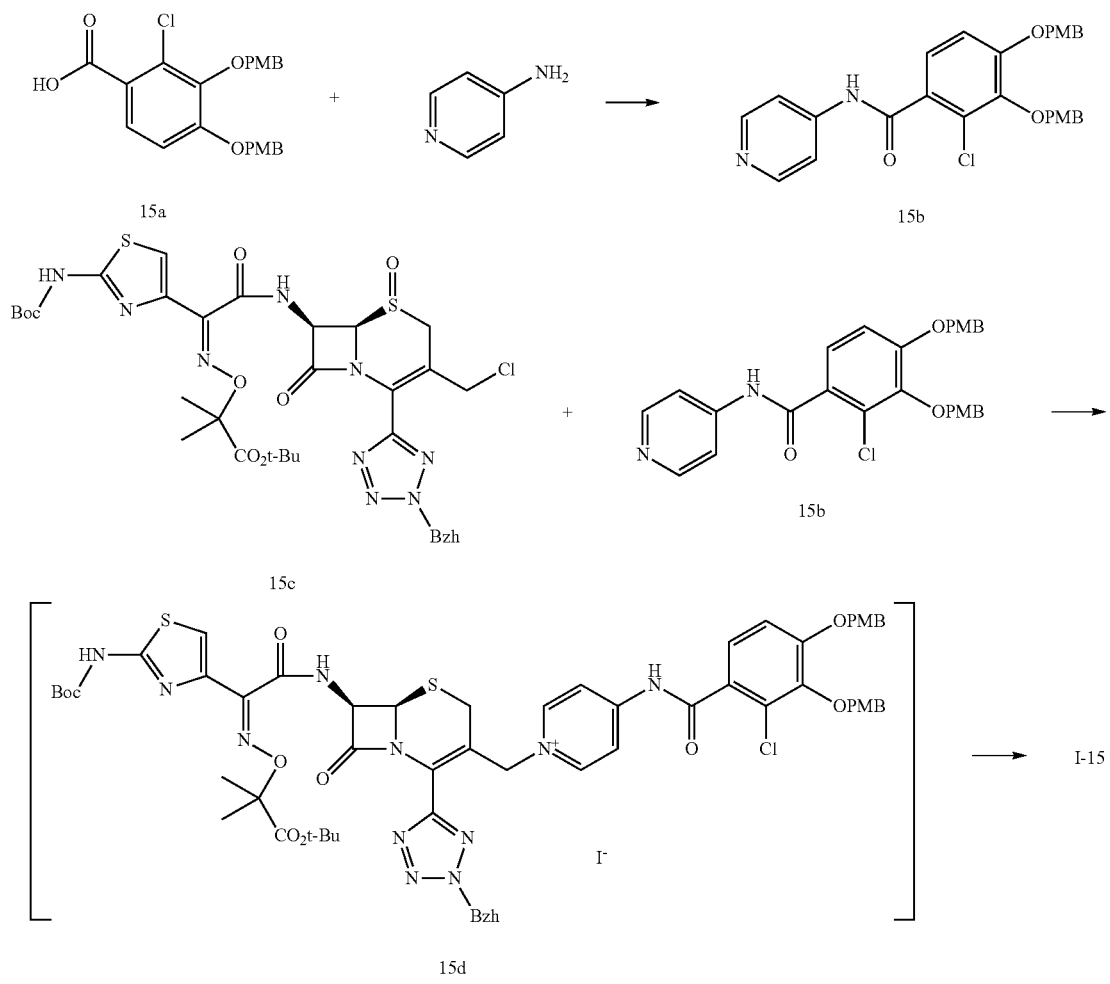

Step (1): Compound 15a→Compound 15b

Compound 15a (5.00 g, 11.66 mmol) was suspended in methylene chloride (50 ml), and then 1-chloro-N,N,2-trimethyl-1-propenylamine (1.70 ml, 12.82 mmol) was added thereto under ice-cooling, and the solution was stirred for 30 minutes at room temperature. 4-Aminopyridine (1.32 g, 13.99 mmol) was added thereto under ice-cooling, and then the solution was stirred overnight at room temperature. The reaction solution was diluted with methylene chloride, and washed sequentially with a saturated sodium hydrogen carbonate water solution and brine, and then the organic layer was dried with magnesium sulfate. Magnesium sulfate was filtered off, and the liquid was concentrated in vacuo, and methylene chloride was added to the residue, and the precipitated solid was collected by filtration to yield Compound 15b (2.23 g, 38%).

$^1$H-NMR (CDCl$_3$) δ: 8.53 (2H, dd, J=4.87, 1.51 Hz), 8.23 (1H, br s), 7.58-7.55 (3H, n), 7.31-7.38 (4H, m), 7.00 (1H, d, J=8.73 Hz), 6.93 (2H, d, J=8.73 Hz), 6.83 (2H, d, J=8.73 Hz), 5.12 (2H, s), 4.98 (2H, s), 3.83 (3H, s), 3.80 (3H, s).

Step (2): Compound 15c+Compound 15b→Compound I-15

To a solution of Compound 15c (693 mg, 0.80 mmol) in dimethylformamide (1.5 mL), sodium iodide (240 mg, 1.60 mmol) was added, and the mixture was stirred for 5 minutes at room temperature. After cooling the solution to 0° C., Compound 15b (444 mg, 0.88 mmol) was added and the solution was stirred for 6 hours at room temperature. Dimethylformamide (4.5 mL) was added, and the solution was cooled to −40° C. Phosphorus tribromide (151 μL, 1.60 mmol) was added thereto, and the solution was stirred for 30 minutes at −40° C. The reaction mixture was added slowly to ice-cooled 5% brine containing sodium thiosulfate (1 g). The precipitated solid was collected by filtration, and washed with water, and then suspended in water. The suspension was freeze-dried to yield Compound 15d as a pale yellow solid. The resulting Compound 15d was used in the next step without further purification.

All amount of the resulting Compound 15d was dissolved in methylene chloride (10 ml), and the solution was cooled to −40° C. Anisole (1.97 ml, 18.0 mmol) and a solution of 2M aluminum chloride in nitromethane (6.00 ml, 12.0 mmol) were added subsequently, and the solution was stirred for 1 hour at 0° C. The reaction solution was dissolved in water, an aqueous 2N hydrochloric acid solution and acetonitrile, and the solution was washed with diisopropyl ether. HP20-SS resin was added to the aqueous layer, and acetonitrile was removed in vacuo. The resulting mixture was purified by ODS column chromatography. To a solution of the resulting desired compound, an aqueous 0.2 N sodium hydroxide solution was added to adjust pH to 6.0, and a piece of dry ice was added. The resulting solution was concentrated in vacuo, and then freeze-dried to yield Compound I-15 as a yellow powder.

Yield: 445.3 mg, (47%)

$^1$H-NMR (D$_2$O) δ: 8.62 (2H, d, J=7.02 Hz), 8.12 (2H, d, J=7.02 Hz), 7.14 (1H, d, J=8.16 Hz), 6.95 (1H, s), 6.90 (1H, d, J=8.16 Hz), 5.93 (1H, d, J=4.80 Hz), 5.51 (1H, d, J=4.80 Hz), 5.35 (1H, d, J=14.72 Hz), 5.25 (1H, d, J=14.72 Hz), 3.75 (1H, d, J=17.16 Hz), 3.47 (1H, d, J=17.16 Hz), 1.50 (3H, s), 1.47 (3H, s)

Elemental analysis for: C29H25ClN11O8S2Na(H2O)5.1

Calcd.: C, 40.03; H, 4.08; Cl, 4.07; N, 17.71; S, 7.37; Na, 2.64(%).

Found: C, 40.06; H, 4.04; Cl, 4.11; N, 17.70; S, 7.32; Na, 2.50(%).

Example 16

Synthesis of Compound I-16

[Chemical Formula 117]

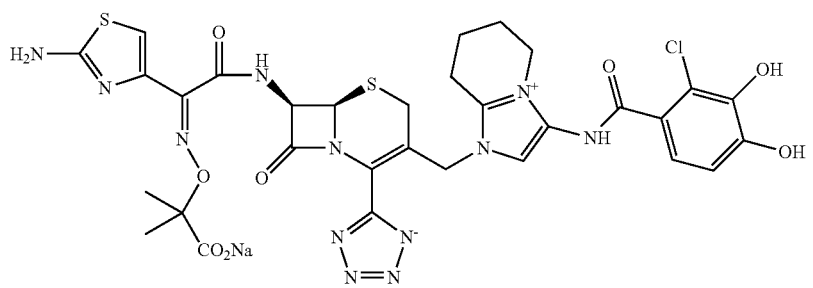

I-16

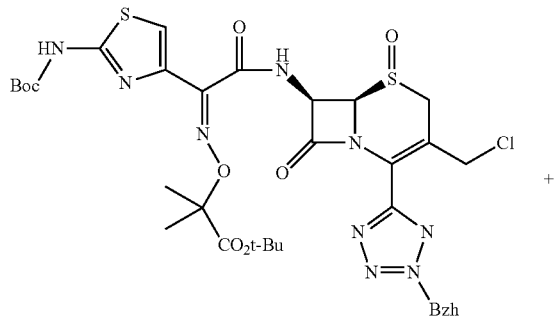

11c

+

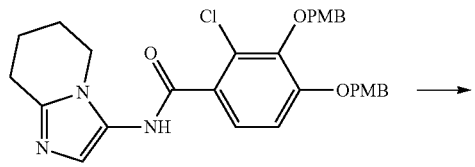

16a

-continued

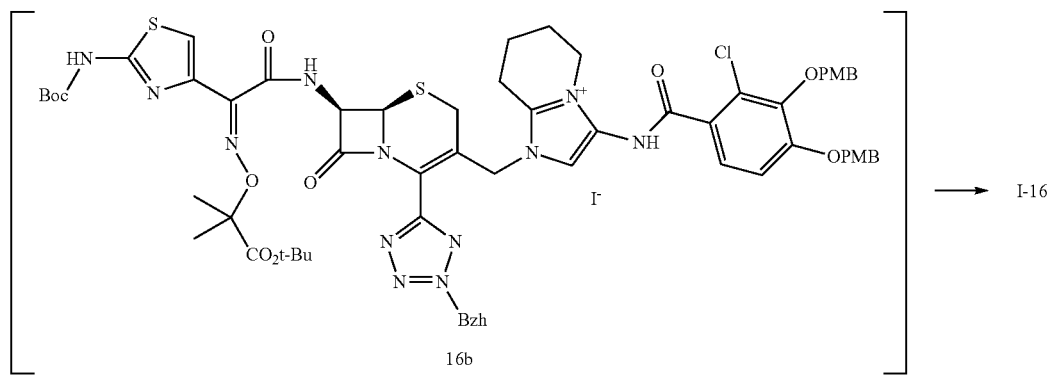

16b

Step (1): Compound 11c+Compound 16a→Compound I-16

Using Compound 11c (693 mg, 0.80 mmol) and Compound 16a (482 mg, 0.88 mmol), Compound I-16 was synthesized according to a similar procedure as described in Step (2) of the synthesis of Compound I-15.

Yield: 239.7 mg, (32%)

$^1$H-NMR (D$_2$O) δ: 7.54 (1H, s), 7.14 (1H, d, J=8.77 Hz), 6.96 (1H, s), 6.93 (1H, d, J=8.77 Hz), 5.89 (1H, d, J=4.19 Hz), 5.48 (1H, d, J=4.19 Hz), 5.10 (1H, d, J=15.40 Hz), 3.99 (2H, br s), 3.74 (1H, d, J=18.23 Hz), 3.52 (1H, d, J=18.23 Hz), 2.79-2.62 (2H, m), 1.91-2.06 (4H, m), 1.51 (3H, s), 1.48 (3H, s).

Elemental analysis for: C31H30.1ClN12O8S2Na0.9 (H2O)5.6

Calcd.: C, 40.47; H, 4.53; Cl, 3.85; N, 18.27; S, 6.97; Na, 2.25(%).

Found: C, 40.56; H, 4.57; Cl, 3.93; N, 18.17; S, 6.82; Na, 2.16(%).

Example 17

Synthesis of Compound I-17

[Chemical Formula 118]

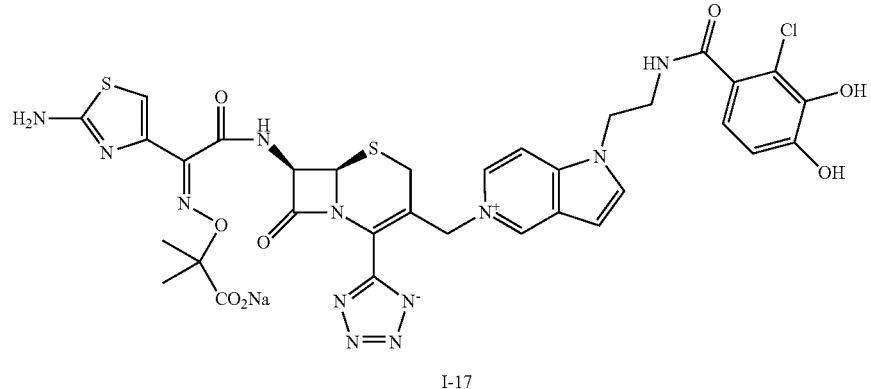

I-17

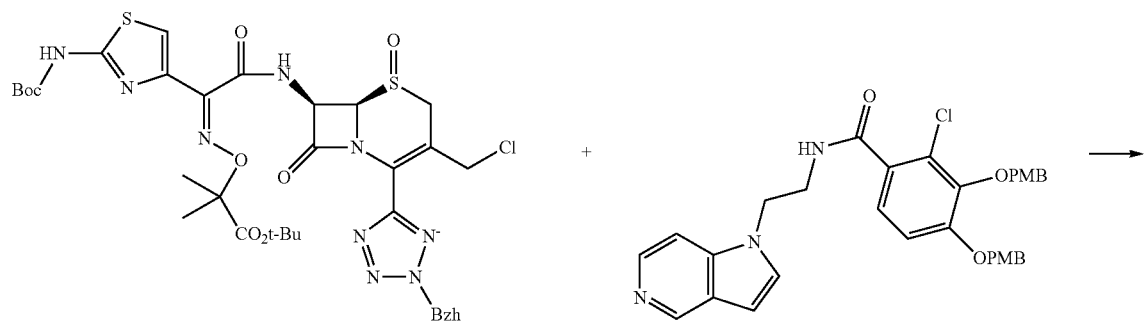

11c
17a

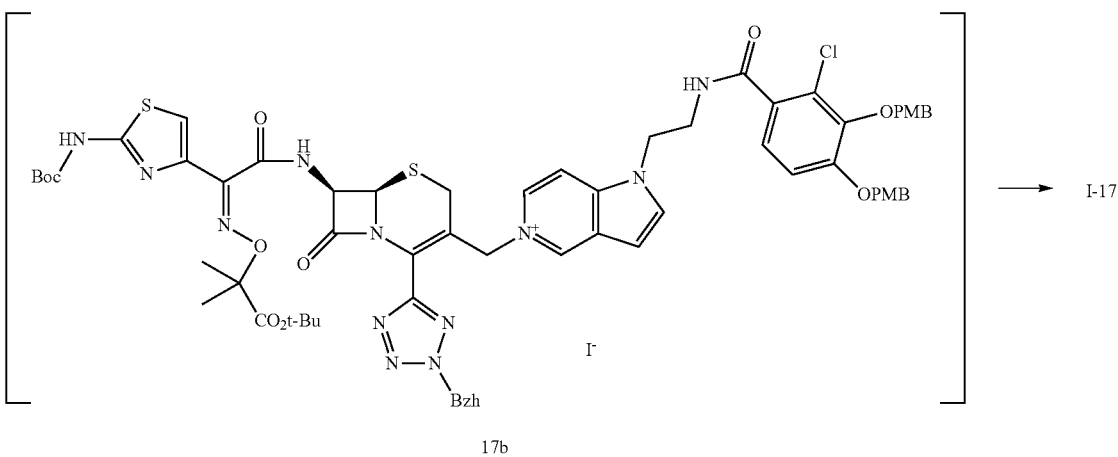

Step (1): Compound 11c+Compound 17a→Compound I-17

Compound I-17 was synthesized according to a similar procedure as described in Step (2) of the synthesis of Compound I-15 using Compound 11c (693 mg, 0.80 mmol) and Compound 17a (503 mg, 0.88 mmol).

Yield: 485.9 mg, (62%)

$^1$H-NMR (D$_2$O) δ: 9.00 (1H, s), 8.18 (1H, d, J=7.22 Hz), 7.93 (1H, d, J=7.22 Hz), 7.86 (1H, d, J=3.36 Hz), 7.07 (1H, d, J=3.36 Hz), 6.95 (1H, s), 6.77 (1H, d, J=8.39 Hz), 6.60 (1H, d, J=8.39 Hz), 5.91 (1H, d, J=4.95 Hz), 5.46 (1H, d, J=14.94 Hz), 5.37 (1H, d, J=4.95 Hz), 5.28 (1H, d, J=14.94 Hz), 4.61 (2H, t, J=5.04 Hz), 3.84 (2H, t, J=5.04 Hz), 3.39 (1H, d, J=18.13 Hz), 3.30 (1H, d, J=18.13 Hz), 1.45 (6H, s).

Elemental analysis for: C33H30.2ClN12O8S2Na0.8 (H2O)4.6

Calcd.: C, 42.91; H, 4.30; Cl, 3.84; N, 18.20; S, 6.94; Na, 1.99(%).

Found: C, 43.15; H, 4.32; Cl, 3.99; N, 17.92; S, 6.66; Na, 2.08(%).

Example 18 and Example 19

Synthesis of Compound I-18 and Compound I-19

[Chemical Formula 119]

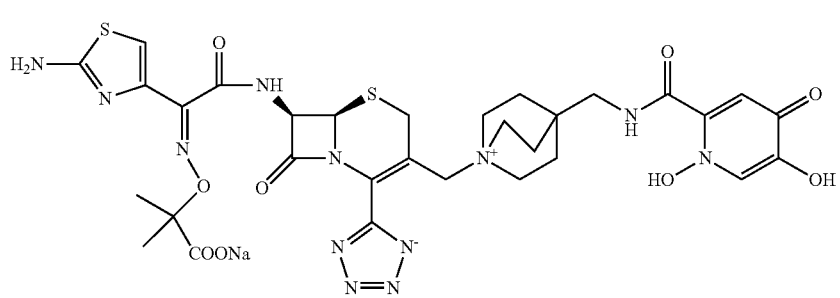

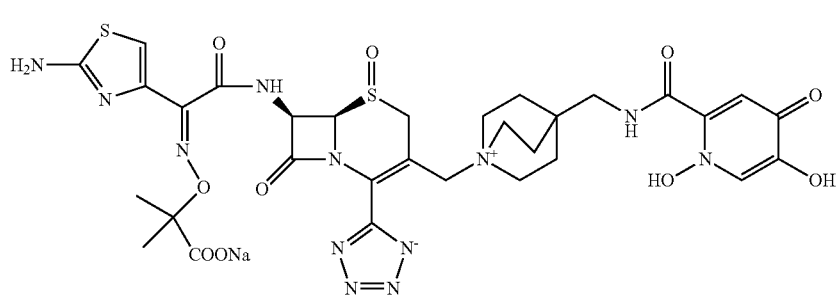

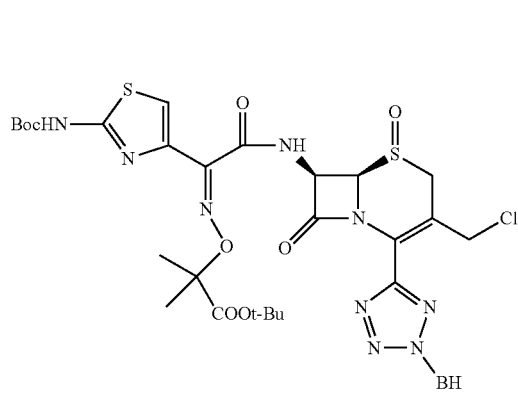
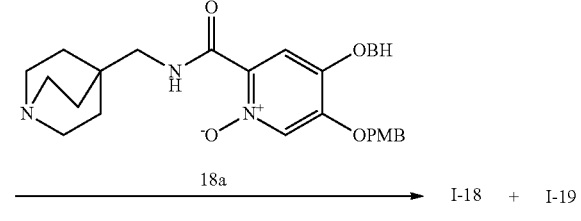

Compound 5j (0.866 g, 1.00 mmol) was dissolved in N,N-dimethylformamide (3.0 mL), and the solution was cooled to 10° C. Sodium bromide (0.3 g, 2.00 mmol) and Compound 18a (525 mg, 1.00 mmol) were added thereto, and the solution was stirred overnight at the same temperature. To the reaction solution, N,N-dimethylformamide (3.0 mL) was added, and the solution was cooled to −30° C. Potassium iodide (930 mg, 5.6 mmol) and acetyl chloride (0.228 mL, 3.20 mmol) were added sequentially, and the mixture was stirred for 7 hours at 0° C. The reaction solution was added to an aqueous 5% sodium hydrogen sulfite (30 mL). The precipitated solid was collected by filtration, and washed with purified water, and dried in vacuo. The resulting powder was dissolved in dichloromethane (15 mL), and the solution was cooled to −40° C. Anisole (1.09 mL, 10 mol) and a solution of 2 mol/L aluminum chloride in nitromethane (5 mL, 10 mmol) were added thereto, and the solution was stirred for 50 minutes at 0° C. To the reaction solution, purified water (30 mL) and diisopropyl ether (50 mL) were added. To the reaction solution, acetonitrile and 2N hydrochloric acid were added to dissolve the precipitated substance, and the aqueous layer was then separated. The organic layer was extracted with a mixture of water/acetonitrile/diluted hydrochloric acid, and HP20SS was added to the combined aqueous layers, and the mixture was concentrated. The concentrated suspension was subjected to reverse phase column chromatography, eluting with water-acetonitrile to collect fractions containing Compound I-18 or Compound I-19. To each fraction, 0.2 N aqueous sodium hydroxide was added dropwise, and pH was adjusted to 5.3, and the solution was concentrated in vacuo. The each concentrated solution was freeze-dried to yield Compound I-18 and Compound I-19 as a powder.

(Compound I-18; Yield: 172 mg, 27%, Compound I-19; Yield: 122 mg, 19%)

Compound I-18

$^1$H-NMR (D$_2$O) δ: 7.68 (1H, s), 7.39 (1H, s), 6.97 (1H, s), 5.90 (1H, d, J=4.8 Hz), 5.57 (1H, d, J=4.8 Hz), 4.64 (1H, d, J=14.4 Hz), 4.04 (1H, d, J=17.2 Hz), 3.92 (1H, d, J=14.4 Hz), 3.65 (1H, d, J=17.2 Hz), 3.44-3.31 (5H, m), 3.19-3.04 (3H, m), 1.90-1.76 (6H, m), 1.51 (3H, s), 1.49 (3H, s).

MS (m+1)=785.38

Compound I-19

$^1$H-NMR (D$_2$O) δ: 7.68 (1H, s), 7.39 (1H, s), 6.98 (1H, s), 6.15 (1H, d, J=4.9 Hz), 5.35 (1H, d, J=4.9 Hz), 4.96 (1H, d, J=14.4 Hz), 4.23 (1H, d, J=17.6 Hz), 3.96-3.80 (2H, m), 3.48-3.27 (5H, m), 3.21-3.05 (4H, m), 1.89-1.75 (3H, m), 1.83 (6H, s), 1.53 (3H, s), 1.50 (3H, s).

MS (m+1)=801.14

Example 22

Synthesis of Compound I-22

[Chemical Formula 120]

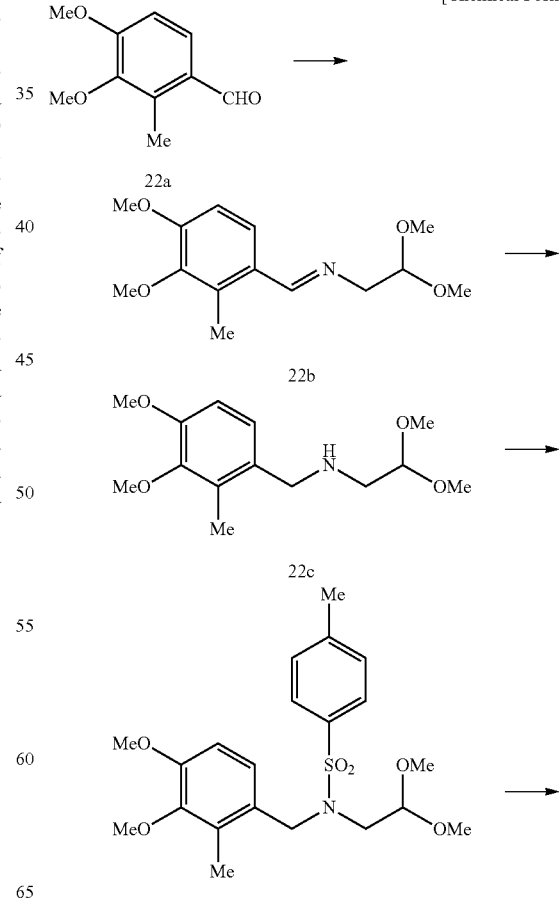

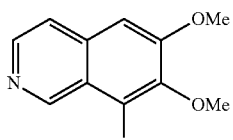

22e

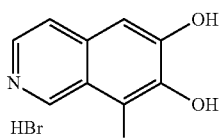

22f

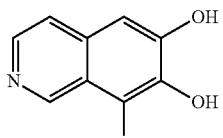

22g

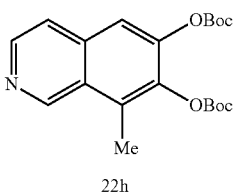

22h

Compound 22d

To a solution of Compound 22a (29.6 g) in toluene (300 mL), 2,2-dimethoxyethylamine (25.9 g) was added. A Dean-Stark trap was attached, and the mixture was heated to reflux for 2.5 hours. The solvent was removed, and the residue was dissolved in ethyl acetate. The solution was washed with water and brine. This solution was dried with anhydrous magnesium sulfate, filtered and concentrated to yield a crude product 22b.

The crude product 22b obtained above was dissolved in ethanol (150 mL), sodium boron hydride (13.5 g, 92 wt %) was added thereto. The mixture was stirred for 2 hours at room temperature, and then allowed to stand overnight. Water was added carefully to the reaction solution, and then the solution was eluted with dichloromethane three times. The organic layer was dried with anhydrous magnesium sulfate, filtered, and concentrated to yield crude product 22c.

The crude product 22c obtained above was dissolved in dichloromethane (300 mL), and pyridine (16.9 g) and p-toluenesulfonyl chloride (37.5 q) were added to the solution under ice-cooling. The reaction solution was stirred for 2 hours at room temperature, and water was added thereto. The organic layer was washed with aqueous sodium bicarbonate and brine, and dried with anhydrous magnesium sulfate, filtered, and concentrated. The residue was purified by silica gel column chromatography to yield Compound 22d (53.6 g, 3 steps 77%).

$^1$H-NMR (CDCl3) δ: 2.21 (3H, s), 2.44 (3H, s), 3.15 (1H, d, J=5.40 Hz), 3.18 (6H, s), 3.75 (3H, s), 3.83 (3H, s), 4.21 (1H, t, J=5.40 Hz), 4.33 (2H, s), 6.67 (1H, d, J=8.40 Hz), 6.88 (1H, d, J=8.40 Hz), 7.30 (2H, dd, J=1.80, 6.60 Hz), 7.71 (1H, dd, 1.80, 6.60 Hz).

Compound 22e

To a solution of Compound 22d (52.6 g) in 1,4-dioxane (500 mL), 6N hydrochloric acid (93 mL) was added, and the solution was heated to reflux for 3 hours. The solution was cooled to room temperature, and the solvent was removed. The residue was diluted diethyl ether and hexane. This solution was eluted with water three times. The aqueous layer was neutralized with 5N an aqueous sodium hydroxide solution, and eluted with dichloromethane. The organic layer was dried with anhydrous magnesium sulfate, filtered, and concentrated. The residue was purified by silica gel column chromatography to yield Compound 22e (20.8 g, 82%).

$^1$H-NMR (CDCl3) δ: 2.67 (3H, s), 3.86 (3H, s), 4.00 (3H, s), 6.97 (1H, s), 7.49 (1H, d, J=5.70 Hz), 8.42 (1H, d, J=5.70 Hz), 9.25 (1H, s).

Compound 22f

To a solution of Compound 22e (6.0 g) in dichloromethane (60 mL), boron tribromide (18.5 g) was added dropwise under ice-cooling. The reaction solution was stirred for 1 hour at room temperature, and cooled to −50° C. Methanol was added carefully to degrade excess boron tribromide, and the solvent was removed. Ethyl acetate was added to the residue, and the precipitated solid was collected by filtration. Dryness in vacuo yields Compound 22f (6.6 g, 87%).

$^1$H-NMR (DMSO-d6) δ: 2.57 (3H, s), 7.36 (1H, s), 8.14 (H1, d, J=6.30 Hz), 8.32 (1H, d, J=6.30 Hz), 9.37 (1H, s).

Compound 22g

Compound 22f (6.6 g) was heated to dissolve in water (150 mL), and activated carbon was added to the solution. The solution was filtered through celite, and 28% ammonia water was added to the resulting filtrate to adjust pH to 8. The precipitated solid was collected by filtration, and dried in vacuo to yield Compound 22g (4.9 g, 109%).

$^1$H-NMR (DMSO-d6) δ: 2.49 (3H, s), 6.93 (1H, s), 7.44 (1H, d, J=5.70 Hz), 8.14 (1H, d, J=5.70 Hz), 9.01 (1H, s).

Compound 22h

To a solution of Compound 22g (1.0 g) in dichloromethane (10 mL), di-t-butyl dicarbonate (2.87 g) and N,N-diaminopyridine (35 mg) were added, and the solution was stirred for 1 hour at room temperature. Further, di-t-butyl dicarbonate (872 mg) was added, and the solution was stirred for 1 hour. The reaction solution was concentrated, and the resulting residue was purified by silica gel column chromatography to yield Compound 22h (1.76 g, 82%).

$^1$H-NMR (CDCl$_3$) δ: 1.58 (9H, s), 1.58 (9H, s), 2.67 (3H, s), 7.59 (2H, m), 8.54 (1H, d, J=5.70 Hz), 9.40 (1H, s)

[Chemical Formula 121]

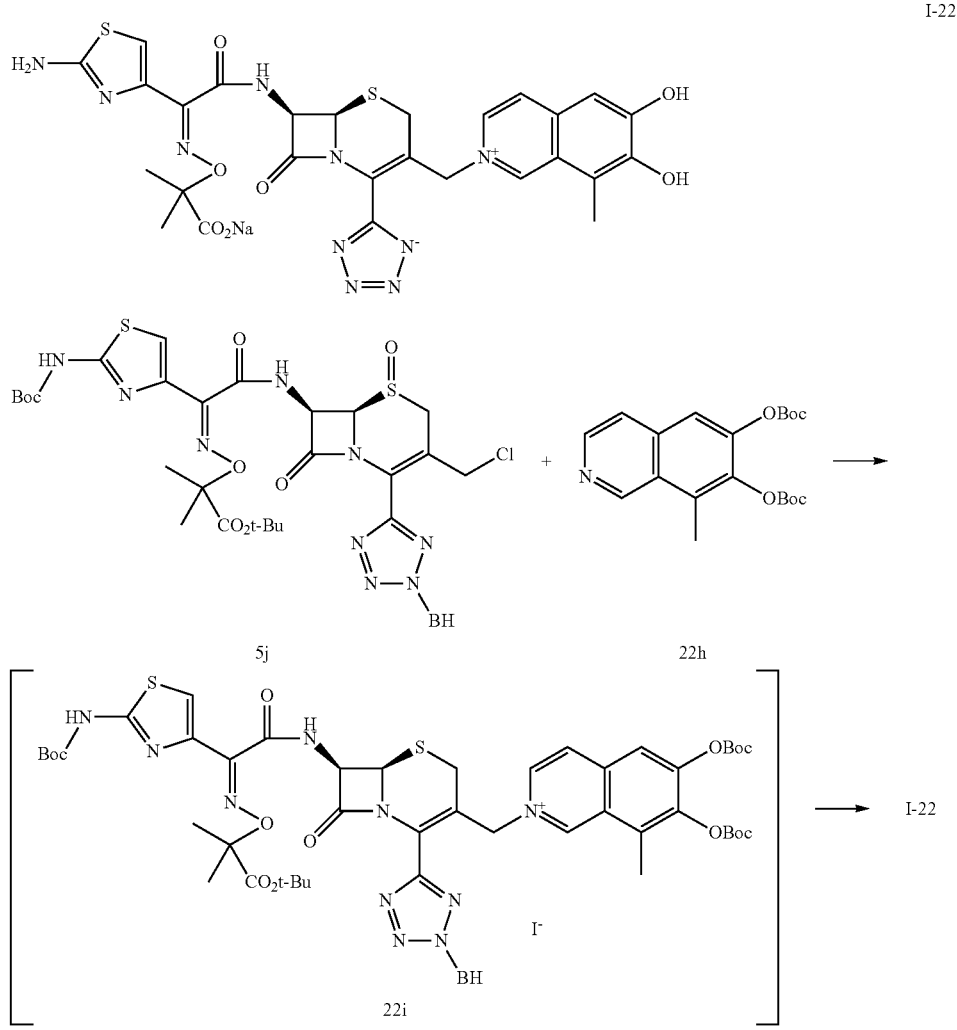

Compound 5j+Compound 22h→Compound I-22

To a solution of Compound 5j (693 mg, 0.80 mmol) in dimethylformamide (1.5 mL), sodium iodide (240 mg, 1.60 mmol) was added, and the mixture was stirred for 5 minutes at room temperature. After cooling the solution to 0° C., Compound 22h (240 mg, 0.64 mmol) was added, and the mixture was stirred for 6 hours at room temperature. Dimethylformamide (4.5 mL) was added, and the solution was cooled to −40° C. Phosphorus tribromide (151 μL, 1.60 mmol) was added thereto, and the solution was stirred for 30 minutes at −40° C. The reaction mixture was added slowly to ice-cooled 5% brine containing sodium thiosulfate (1 g). The precipitated solid was collected by filtration, and washed with water, and suspended in water. The suspension was freeze-dried to yield Compound 22i as a yellow solid. The resulting Compound 22i was used in the next step without further purification.

All amount of the resulting Compound 22i was dissolved in methylene chloride (10 ml), and the solution was cooled to −40° C. Anisole (1.97 ml, 18.0 mmol) and a solution of 2M aluminum chloride in nitromethane (6.00 ml, 12.0 mmol) were added subsequently, and the solution was stirred for 1 hour at 0° C. The reaction solution was dissolved in water, an aqueous 2N hydrochloric acid solution and acetonitrile, and then the solution was washed with diisopropyl ether. HP20-SS resin was added to the aqueous layer, and acetonitrile was removed in vacuo. The resulting mixture was purified by ODS column chromatography. To a solution of the resulting desired compound, an aqueous 0.2 N sodium hydroxide was added to adjust pH to 6.0, and a piece of dry ice was added. The resulting solution was concentrated in vacuo, and freeze-dried to yield Compound I-22 as a yellow powder.

Yield: 47 mg, (6%)

$^1$H-NMR (D$_2$O) δ: 8.68 (1H, s), 7.80 (1H, d, J=6.29 Hz), 7.58 (1H, d, J=6.29 Hz), 6.93 (1H, s), 6.83 (1H, s), 5.89 (1H, d, J=4.70 Hz), 5.47 (1H, d, J=4.70 Hz), 5.32 (1H, d, J=14.60 Hz), 5.15 (1H, d, J=14.60 Hz), 3.70 (1H, d, J=17.88 Hz), 3.48 (1H, d, J=17.88 Hz), 2.39 (3H, s), 1.48 (3H, s), 1.46 (3H, s).

Elemental analysis for: C27H25N10O7S2Na(H2O)5 (NaHCO3)0.6

Calcd.: C, 39.98; H, 4.33; N, 18.89; S, 7.73; Na, 4.44(%).

Found: C, 39.98; H, 4.53; N, 18.99; S, 7.83; Na, 4.41(%).

Example 23

Synthesis of Compound I-23

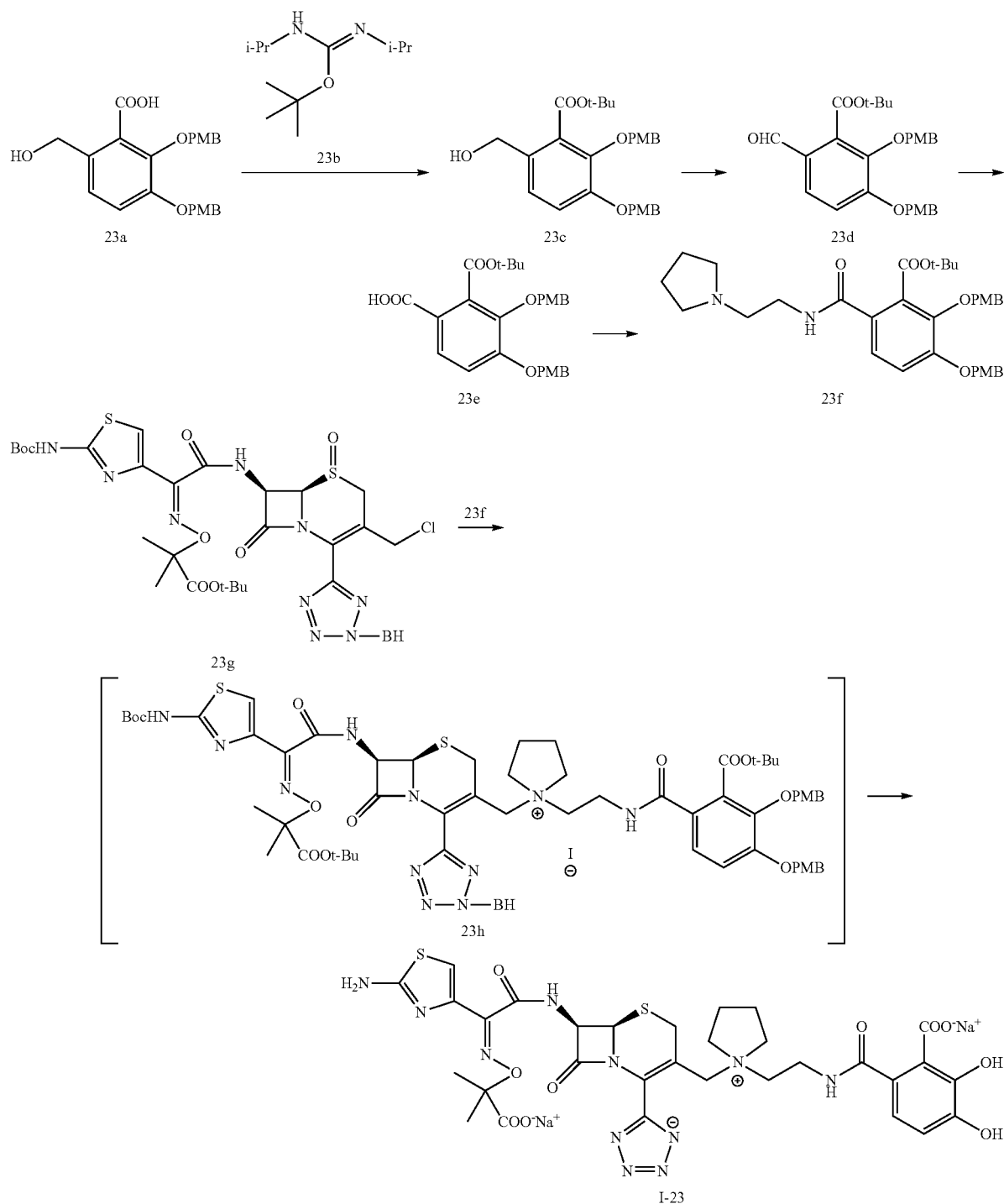

[Chemical Formula 122]

Step (1): Synthesis of Compound 23c

Compound 23a (10.19 g, 24.0 mmol) in dichloromethane (100 mL) was added with Compound 23b (9.62 g, 48.0 mmol) and stirred overnight at room temperature. The solvent was removed under reduced pressure, and the residue was added with water and extracted with ethyl acetate. The organic layer was washed sequentially with water and brine, and dried over anhydrous magnesium sulfate. Inorganic substances were filtered off, and the filtrate was dried under reduced pressure. The crude product thus obtained was purified by silica gel column chromatography (hexane-ethyl acetate) to yield Compound 23c (4.45 g, 39%) as an orange oil.

¹H-NMR (CDCl₃) δ: 1.55 (9H, s), 2.54 (1H, t, J=6.65 Hz), 3.80 (3H, s), 3.83 (3H, s), 4.52 (2H, d, J=6.65 Hz), 5.00 (2H, s), 5.05 (2H, s), 6.81 (2H, d, J=8.66 Hz), 6.90 (2H, d, J=8.66 Hz), 7.00 (1H, d, J=8.28 Hz), 7.08 (1H, d, J=8.28 Hz), 7.29 (2H, d, J=8.53 Hz), 7.35 (2H, d, J=8.53 Hz).

Step (2): Synthesis of Compound 23d

After cooling a solution of Compound 23c (4.45 g, 9.26 mmol) in dichloromethane (45 mL) to 0° C., Dess-Martin Periodinane (4.32 g, 10.19 mmol) was added and stirred overnight at room temperature. Water was added to the reaction mixture, and dichloromethane was removed under reduced pressure. The residue was extracted with ethyl acetate. The organic layer was washed sequentially with water and brine, and dried over anhydrous magnesium sulfate. Inorganic substances were filtered off, and the filtrate was dried under reduced pressure. The crude product thus obtained was purified by silica gel column chromatography (hexane-ethyl acetate) to yield Compound 23d (2.91 g, 66%) as a white solid.

¹H-NMR (CDCl₃) δ: 1.56 (9H, s), 3.80 (3H, s), 3.84 (3H, s), 4.97 (2H, s), 5.14 (2H, s), 6.80 (2H, d, J=8.08 Hz), 6.93 (2H, d, J=8.34 Hz), 7.10 (1H, d, J=8.34 Hz), 7.26-7.28 (2H, m), 7.37 (2H, d, C=8.34 Hz), 7.60 (1H, d, J=8.34 Hz), 9.88 (1H, s).

Step (3): Synthesis of Compound 23e

Compound 23d (2.91 g, 6.08 mmol) was dissolved in a mixture of 1,4-doxane (30 mL) water (10 mL) and cooled to 0° C. Amidosulfuric acid (1.18 g, 12.16 mmol) and sodium chlorite (1.38 g, 12.16 mmol) were added sequentially, and the mixture was stirred at 0° C. for 30 minutes. The reaction mixture was added slowly with aqueous sodium bisulfite (2.53 g, 24.32 mmol) and extracted with ethyl acetate. The organic layer was washed sequentially with water and brine, and dried over anhydrous magnesium sulfate. Inorganic substances were filtered off, and the filtrate was dried under reduced pressure. The residue thus obtained was added with diisopropyl ether, and the obtained solid was filtered to yield Compound 23e (2.79 g, 93%) as a white solid.

¹H-NMR (DMSO-D₆) δ: 1.45 (9H, s), 3.74 (3H, s), 3.78 (3H, s), 4.84 (2H, s), 5.19 (2H, s), 6.83 (2H, d, J=8.66 Hz), 6.98 (2H, d, J=8.78 Hz), 7.20 (2H, d, J=8.66 Hz), 7.31 (1H, d, J=8.78 Hz), 7.46 (2H, d, J=8.66 Hz), 7.69 (1H, d, J=8.66 Hz).

Step (4): Synthesis of Compound 23f

After cooling a solution of Compound 23e (989 mg, 2.0 mmol) in dimethylformamide (3 mL) to 0° C., 1-hydroxybenzotriazole (324 mg, 2.4 mmol), 1-(2-aminoethyl)pyrrolidine (301 µL, 2.4 mmol), EDC.HCl (460 mg, 2.4 mmol) were added sequentially, and the solution was stirred at room temperature for 4.5 hours. Ice water was added to the reaction mixture and extracted with ethyl acetate. The organic layer was washed sequentially with 1 mol/L aqueous sodium hydroxide, water and brine, and dried over anhydrous magnesium sulfate. Inorganic substances were filtered off, and the filtrate was concentrated at 25° C. under reduced pressure. The residue was dried under reduced pressure to yield Compound 23f (1.16 g, 98%) as a yellow oil.

¹H-NMR (CDCl₃) δ: 1.53 (9H, s), 1.79 (4H, br s), 2.58 (4H, br s), 2.70 (2H, c, J=5.81 Hz), 3.52 (2H, q, J=5.56 Hz), 3.79 (3H, s), 3.83 (3H, s), 4.97 (2H, s), 5.07 (2H, s), 6.80 (2, d, J=8.34 Hz), 6.91 (2H, d, J=8.34 Hz), 6.96 (1H, d, J=8.59 Hz), 7.29 (2H, d, J=8.34 Hz), 7.33-7.36 (3H, m).

Step (5): Synthesis of Compound I-23

After cooling a solution of Compound 23f (473 mg, 0.80 mmol) in DMA (1.5 mL) to 10° C., Compound 23g (693 mg, 0.80 mmol) was added, and the solution was degassed under reduced pressure. Sodium iodide (240 mg, 1.6 mmol) was added and stirred at 15° C. for 6 hours. After addition of DMF (4.5 mL), the solution was cooled to −40° C. Phosphorus tribromide (151 µL, 1.6 mmol) was added and stirred at −40° C. for 30 minutes. The reaction mixture was added slowly to 5% sodium chloride solution. The precipitated solid was filtered and washed with water and suspended in water. The suspension was freeze-dried to yield Compound 23h as a brown solid. The obtained Compound 23h was used directly in the next step without purification.

After the whole amount of Compound 23h was dissolved in dichloromethane (10 mL) and the solution was cooled to −40° C., anisole (1.05 mL, 9.6 mmol) and 2 mol/L L-aluminum chloride/nitromethane solution (4.80 mL, 9.6 mmol) were sequentially, and the solution was stirred at 0° C. for 30 minutes. The reaction mixture was added with diisopropyl ether and small amount of water and stirred to result precipitates. The supernatant was removed by decantation. The insoluble material retained in the container was added with acetonitrile and stirred to make it completely dissolved. Diisopropyl ether was added to separate aqueous layer. The organic layer was re-extracted with water, and the aqueous layers were combined. HP20-SS resin was added and acetonitrile was removed under reduced pressure. The obtained mixed solution was purified by ODS column chromatography (water-acetonitrile). 0.2 mol/L aqueous sodium hydroxide solution was added to the desired fraction to adjust pH=6.0, small amount of dry ice was added. The obtained solution was concentrated under reduced pressure and freeze-dried to yield Compound I-23 (279 mg, 42%) as a yellow powder.

¹H-NMR (D₂O) δ: 1.29 (1H, br s), 1.49 (3H, s), 1.51 (3H, s), 1.94-2.05 (2H, br m), 2.09-2.19 (1H, br m), 3.31-3.61 (9H, m), 3.79 (1H, d, J=17.19 Hz), 4.12-4.16 (2H, m), 5.61 (1H, d, J=5.02 Hz), 5.93 (1H, d, J=5.02 Hz), 6.71 (1H, d, J=8.16 Hz), 6.97-6.99 (2H, m).

MS (m+1)=786.07

Elemental analysis for: C31H33N11O10S2Na2.6.2H2O

Calcd.: C, 39.55; H, 4.86; N, 16.37; Na, 4.88; S, 6.81(%).

Found: C, 39.55; H, 4.99; N, 16.46; Na, 4.92; S, 6.61(%).

Example 24

Synthesis of Compound I-24

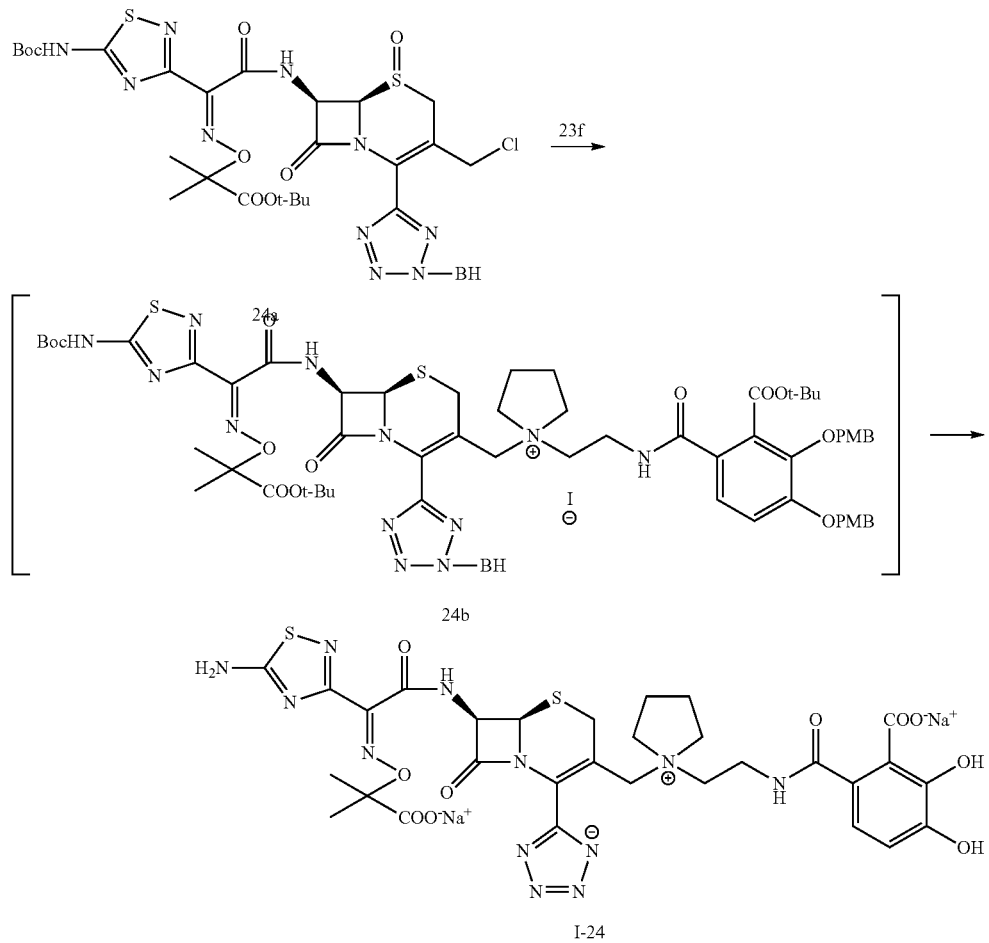

According to a similar procedure as described in Step (5) in Example 23 using Compound 24a (694 mg, 0.80 mmol) and Compound 23f (473 mg, 0.80 mmol), Compound I-24 (158 mg, 24%) was obtained as a yellow powder.

$^1$H-NMR (D$_2$O) δ: 1.29 (1H, br s), 1.53 (3H, s), 1.55 (3H, s), 1.94-2.05 (2H, br m), 2.10-2.18 (1H, br m), 3.33-3.61 (9H, m), 3.79 (1H, d, J=17.19 Hz), 4.14 (2H, d, J=16.06 Hz), 5.61 (1H, d, J=5.02 Hz), 5.96 (1H, d, J=5.02 Hz), 6.71 (1H, d, J=8.16 Hz), 6.98 (1H, d, J=8.16 Hz).
MS (m+1)=787.08

Elemental analysis for: C30H32N12O10S2Na2.6.5H2O
Calcd.: C, 38.01; H, 4.79; N, 17.73; Na, 4.85; S, 6.77(%).
Found: C, 37.93; H, 4.79; N, 17.90; Na, 4.96; S, 6.69(%).

The compounds described in the following Examples were synthesized according to similar procedures as described above.

Example 25

Compound I-25

[Chemical Formula 124]

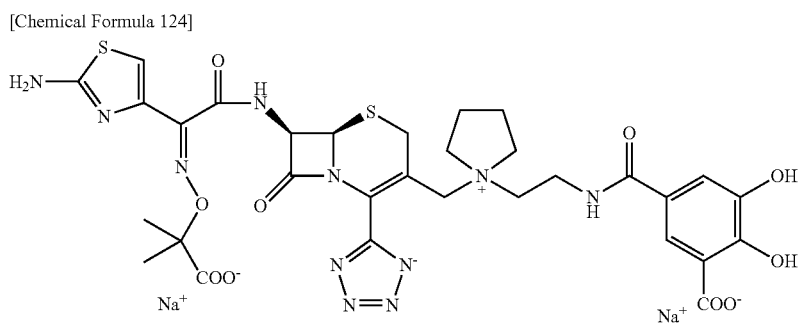

I-25

¹H-NMR (D₂O) δ: 7.79 (1H, br s), 7.38 (1H, br s), 6.97 (1H, d, J=3.64 Hz), 5.94 (1H, br s), 5.60 (1H, br s), 4.15-4.12 (2H, m), 3.78 (1H, d, J=16.81 Hz), 3.58-3.37 (5H, m), 2.12-1.98 (3H, m), 1.51 (3H, s), 1.49 (3H, s), 1.35 (1H, br s).
Elemental analysis for C31H33N11O10S2Na2(H2O)6.6
Calcd.: C, 39.25; H, 4.91; N, 16.24; S, 6.76; Na, 4.85(%).
Found: C, 39.18; H, 4.81; N, 16.48; S, 6.48; Na, 4.60(%).

Example 26

Compound I-26

[Chemical Formula 125]

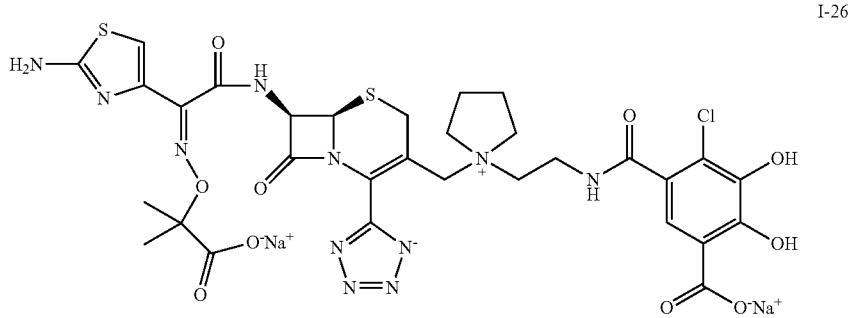

I-26

¹H-NMR (D₂O) δ: 7.45 (1H, s), 6.96 (1H, s), 5.93 (1H, d, J=4.96 Hz), 5.60 (1H, d, J=4.96 Hz), 4.18 (1H, d, J=14.81 Hz), 4.12 (1H, d, J=17.32 Hz), 3.79 (1H, d, J=17.32 Hz), 3.64-3.36 (5H, m), 2.17-1.93 (3H, m), 1.51 (3H, s), 1.48 (3H, s), 1.32 (1H, s). Elemental analysis for C31H32ClN11O10S2Na2(H2O)4.1
Calcd.: C, 39.69; H, 4.32; Cl, 3.78; N, 16.42; S, 6.84; Na, 4.90(%).
Found: C, 39.43; H, 4.30; Cl, 3.86; N, 16.72; S, 6.89; Na, 4.79(%).

Example 27

Compound I-27

[Chemical Formula 126]

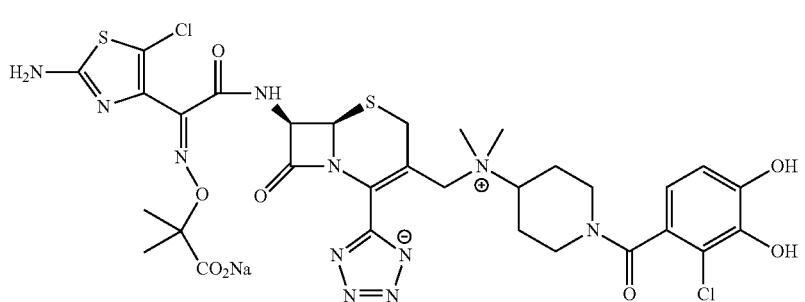

I-27

¹H-NMR (D₂O) δ: 6.95-6.90 (1H, m), 6.83-6.65 (1H, m), 5.89-5.77 (1H, m), 5.59-5.56 (1H, m), 5.09-4.90 (1H, m), 4.71-4.47 (1H, m), 4.09-4.00 (2H, m), 3.73-3.44 (3H, m), 3.08-2.80 (5H, m), 2.69-2.58 (3H, m), 2.27-1.82 (1H, m), 1.75-1.66 (1H, m), 1.53-1.27 (6H, m), 1.53 (3H, s), 1.51 (3H, s).
MS (m+1)=824.02

Example 28
Compound I-28
[Chemical Formula 127]
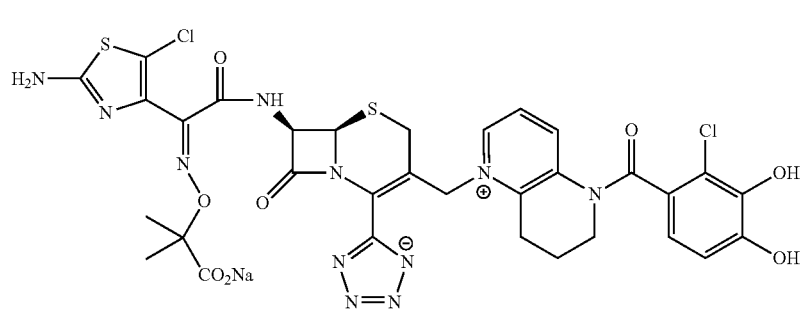
I-28
$^1$H-NMR (D$_2$O) δ: 8.65-8.60 (1H, m), 7.63 (1H, s), 7.01-6.95 (2H, m), 5.95 (1H, d, J=4.6 Hz), 5.61 (1H, t, J=16.0 Hz), 5.48 (1H, d, J=4.6 Hz), 5.31 (1H, d, J=16.0 Hz), 4.06 (1H, s), 3.62-3.46 (3H, m), 3.04-2.99 (1H, m), 2.89-2.77 (1H, m), 2.12-2.03 (2H, m), 1.52-1.26 (7H, m).
MS (m+1)=830.06
Example 29
Compound I-29
[Chemical Formula 128]
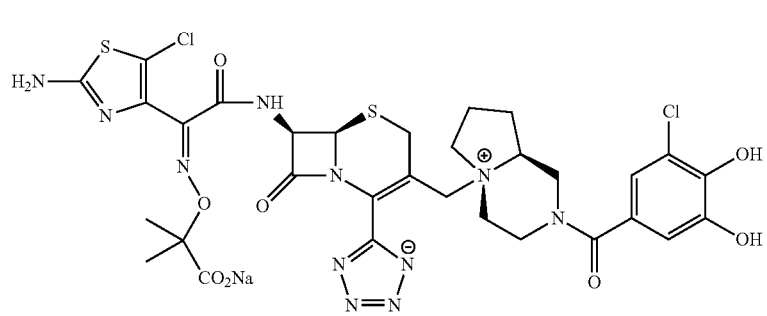
I-29
$^1$H-NMR (D$_2$O) δ: 6.96-6.93 (1H, m), 6.90-6.87 (1H, m), 5.91-5.88 (1H, m), 5.59-5.56 (1H, m), 4.20 (1H, d, J=12.9 Hz), 4.09 (1H, d, J=14.7 Hz), 3.74 (1H, d, J=14.7 Hz), 3.57-3.55 (2H, m), 3.38-3.29 (5H, m), 3.09-3.03 (2H, m), 1.78-1.35 (11H, m).
MS (m+1)=822.18

Example 30
Compound I-30
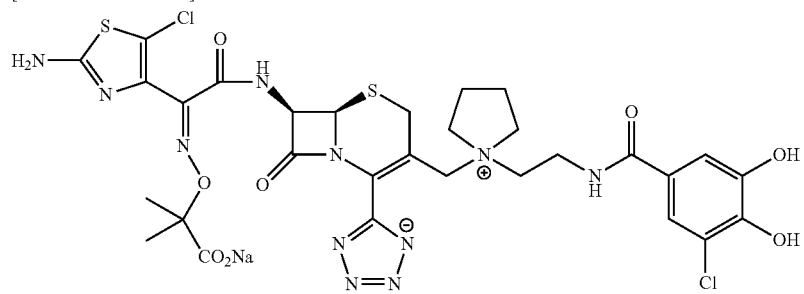
I-30
$^1$H-NMR (D$_2$O) δ: 7.28 (1H, s), 7.15 (1H, s), 5.89 (1H, d, J=4.7 Hz), 5.55 (1H, d, J=4.7 Hz), 4.09 (2H, t, J=17.3 Hz), 3.73 (1H, d, J=17.3 Hz), 3.55-3.27 (9H, m), 2.07-1.93 (3H, m), 1.52 (3H, s), 1.50 (3H, s), 1.35-1.34 (1H, m).
MS (m+1)=810.08
Example 31
Compound I-31
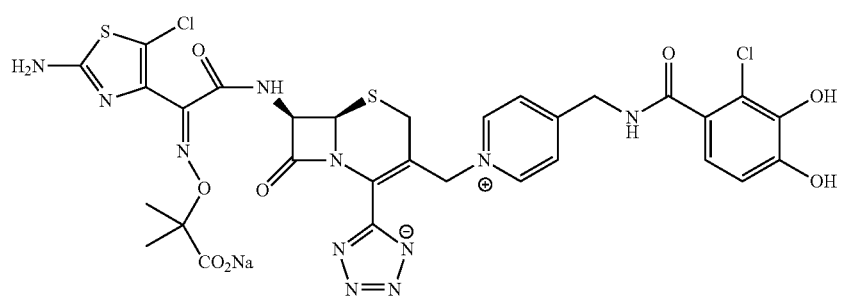
I-31
$^1$H-NMR (D$_2$O) δ: 8.82 (2H, d, J=5.9 Hz), 7.99 (2H, d, J=5.9 Hz), 7.03 (1H, d, J=8.2 Hz), 6.88 (1H, d, J=8.2 Hz), 5.92 (1H, d, J=4.8 Hz), 5.48-5.37 (2H, m), 5.47 (1H, d, J=4.8 Hz), 4.82-4.78 (2H, m), 3.71 (1H, d, J=18.1 Hz), 3.41 (1H, d, J=18.1 Hz), 1.48 (3H, s), 1.47 (3H, s).
MS (m+1)=803.86
Example 32
Compound I-32
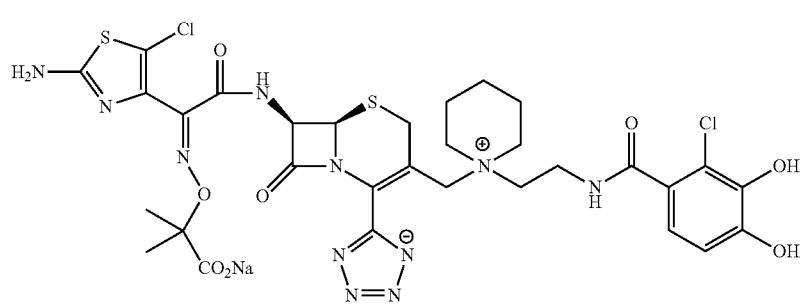
I-32

$^1$H-NMR (D$_2$O) δ: 6.94 (1H, d, J=8.2 Hz), 6.88 (1H, d, J=8.2 Hz), 5.90 (1H, d, J=5.0 Hz), 5.57 (1H, d, J=5.0 Hz), 4.95 (1H, d, J=14.2 Hz), 4.20 (1H, d, J=14.2 Hz), 4.08 (1H, d, J=16.8 Hz), 3.74 (1H, d, J=16.8 Hz), 3.58-3.53 (2H, m), 3.42-3.25 (4H, m), 3.11-3.02 (2H, m), 1.86-1.35 (6H, m), 1.52 (3H, s), 1.50 (3H, s).
MS (m+1)=824.02
Example 33
Compound I-33
[Chemical Formula 132]
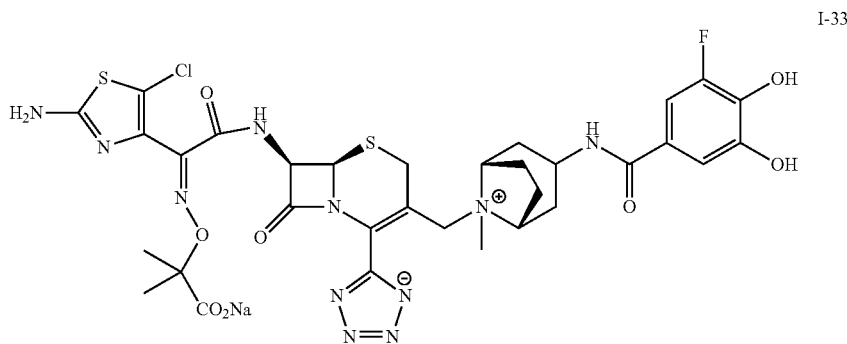
I-33
$^1$H-NMR (D$_2$O) δ: 7.10-7.03 (2H, m), 5, 92 (1H, d, J=5.10 Hz), 5.58 (1H, d, J=5.0 Hz), 4.65 (1H, d, J=13.8 Hz), 4.17-3.63 (5H, m), 3.74 (1H, d, J=16.7 Hz), 2.93 (3H, s), 2.80-2.02 (8H, m), 1.53 (3H, s), 1.51 (3H, s),
MS (m+1)=820.13
Example 34
Compound I-34
[Chemical Formula 133]
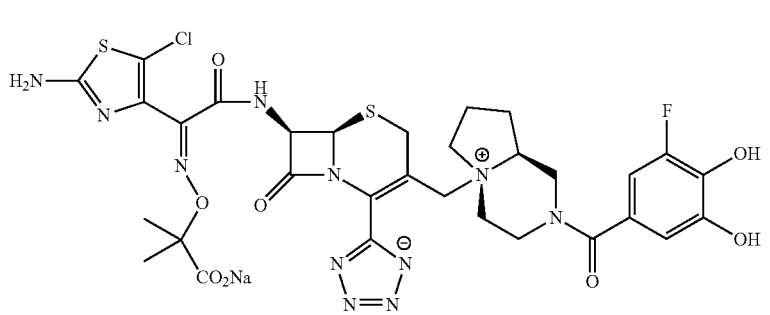
I-34
$^1$H-NMR (D$_2$O) δ: 6.87-6.15 (2H, m), 5.89 (1H, d, J=4.4 Hz), 5.56 (1H, d, J=4.4 Hz), 4.99 (1H, d, J=13.9 Hz), 4.26 (1H, d, J=13.9 Hz), 4.06-3.08 (11H, m), 2.21-1.78 (4H, m), 1.53 (3H, s), 1.50 (3H, s).
MS (m+1)=806.38

Example 35
Compound I-35
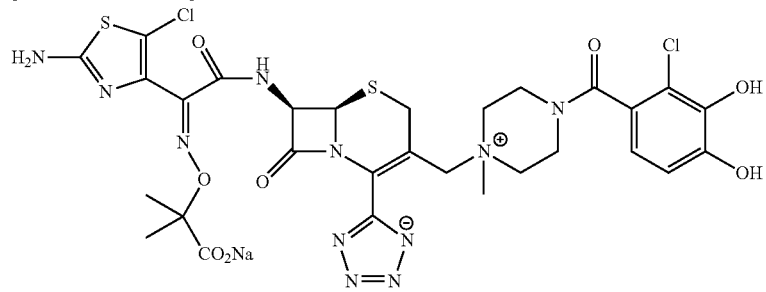
¹H-NMR (D₂O) δ: 6.97-6.91 (1H, m), 6.81-6.71 (1H, m), 5.94-5.91 (1H, m), 5.57 (1H, d, J=5.0 Hz), 5.04-4.91 (2H, m), 4.26-2.82 (13H, m), 1.53 (3H, s), 1.50 (3H, s).
MS (m+1)=796.04
Example 36
Compound I-36
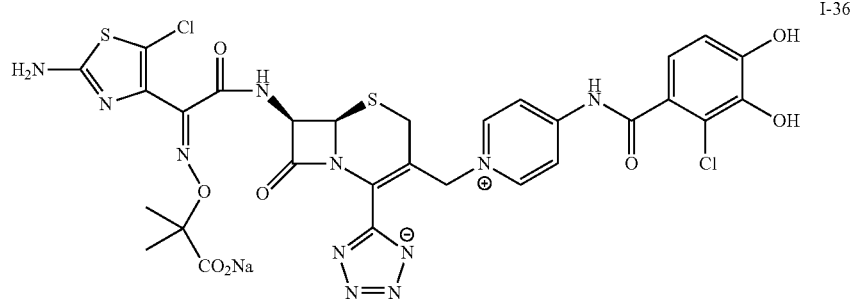
¹H-NMR (D₂O) δ: 8.59-8.56 (2H, m), 8.00-7.98 (2H, m), 7.05-7.02 (1H, m), 6.77-6.75 (1H, m), 5.89-5.86 (1H, m), 5.42-5.23 (3H, m), 3.67-3.64 (1H, m), 3.40-3.37 (1H, m), 1.44-1.42 (6H, m).
MS (m+1)=789.96
Example 37
Compound I-37
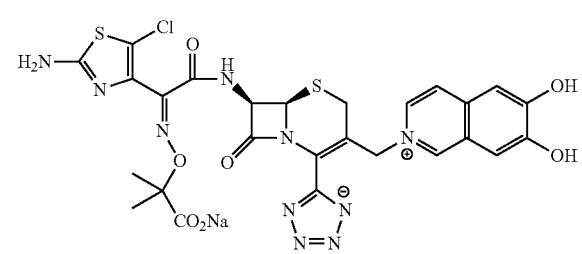
¹H-NMR (D₂O) δ: 8.71 (1H, s), 7.85 (1H, d, J=6.9 Hz), 7.60 (1H, d, J=6.9 Hz), 7.22 (1H, s), 6.94 (1H, s), 5.90 (1H, d, J=5.0 Hz), 5.44 (1H, d, J=5.0 Hz), 5.28 (1H, d, J=14.9 Hz), 5.16 (1H, d, J=14.9 Hz), 3.62 (1H, d, J=18.0 Hz), 3.40 (1H, d, J=18.0 Hz), 1.48 (3H, s), 1.46 (3H, s).
MS (m+1)=686.96
Example 38
Compound I-38
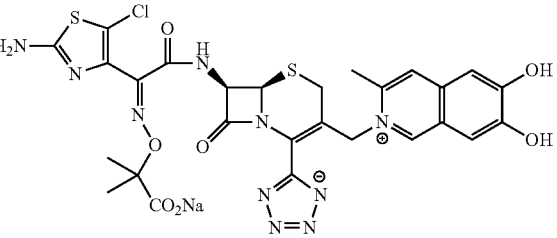
¹H-NMR (D₂O) δ: 8.73 (1H, s), 7.43 (1H, s), 7.21 (1H, s), 6.87 (1H, s), 5.90 (1H, d, J=4.8 Hz), 5.45-5.41 (2H, m), 5.13 (1H, d, J=15.7 Hz), 3.45 (2H, s), 2.33 (3H, s), 1.50 (3H, s), 1.47 (3H, s).
MS (m+1)=701.00

Example 41
Compound I-41
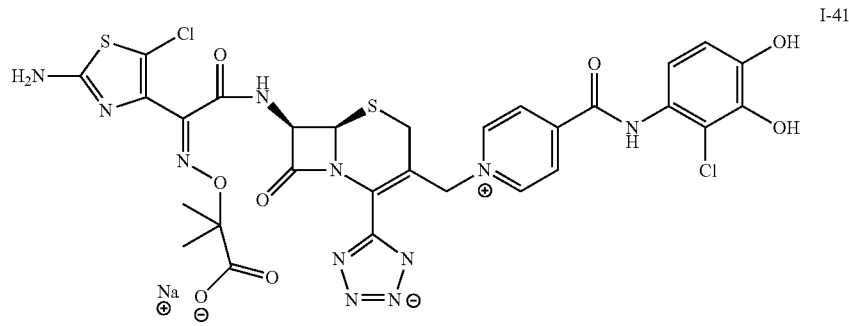
¹H-NMR (DMSO-d₆) δ: 1.27-1.52 (m, 6H), 3.38-3.68 (m, 4H), 4.98-6.39 (m, 4H), 6.72-6.83 (m, 3H), 7.18 (s, 2H), 8.56 (d, J=6.6 Hz, 2H), 9.61 (d, J=6.6 Hz, 2H), 11.50 (br s, 1H)
MS (m+1) 756.42
¹H-NMR (DMSO-d₆) δ: 1.37 (s, 3H), 1.52 (s, 3H), 2.97 (d, J=17.1 Hz, 1H), 3.61 (d, J=17.1 Hz, 1H), 4.94 (d, J=13.5 Hz, 1H), 5.37 (s, 1H), 5.41 (d, J=135 Hz, 1H), 6.02 (t, J=6.0 Hz, 1H), 6.70 (t, J=7.8 Hz, 2H), 6.90 (s, 1H), 7.19 (s, 1H), 7.92 (br s, 1H), 9.05 (br s, 4H), 10.31 (br s, 1H), 11.22 (br s, 1H), 12.37 (br s, 1H).
MS (m+1) 771.38
Example 42
Compound I-42
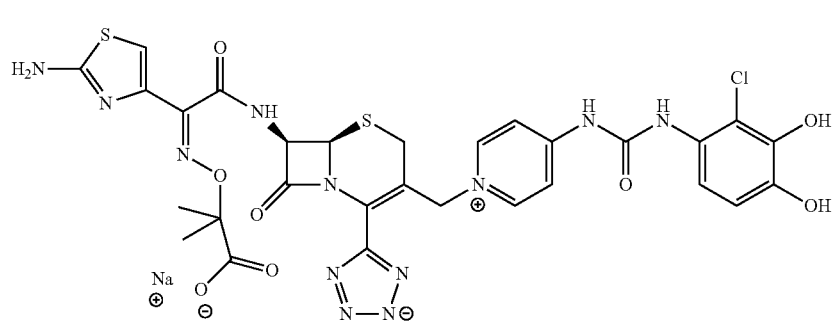
Example 43
Compound I-43
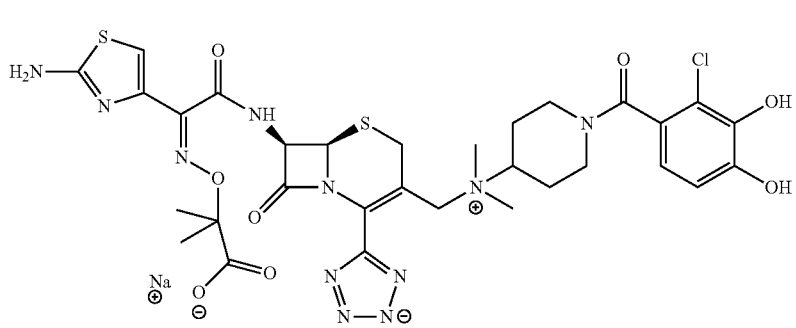

¹H-NMR (DMSO-d₆) δ: 1.15-2.04 (m, 4H), 1.32 (s, 3H), 1.45 (s, 3H), 2.27-3.36 (m, 9H), 3.61 (d, J=11.4 Hz, 1H), 3.90 (d, J=11.4 Hz), 3.93-4.00 (m, 1H), 4.39 (d, J=12.0 Hz, 1H), 4.59 (d, J=12.0 Hz, 1H), 5.23-5.38 (m, 1H), 5.39 (d, J=5.4 Hz, 1H), 5.82-5.87 (m, 1H), 6.49-6.67 (m, 1H), 6.73 (s, 1H), 6.73-6.78 (m, 1H), 7.18 (s, 2H), 11.40 (br s, 2H).
MS (m+1) 790.52
Example 44
Compound I-44
[Chemical Formula 141]
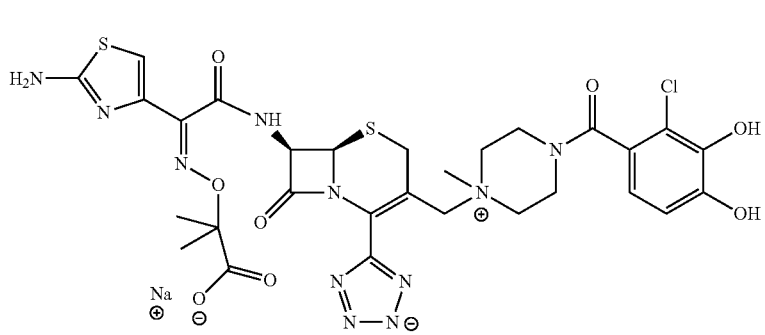
I-44
¹H-NMR (DMSO-d₆) δ: 1.33 (s, 1H), 1.48 (s, 1 h) 2.70-3.90 (m, 11H), 41.0-4.30 (m, 2H), 5.00-5.10 (m, 1H), 5.35 (d, J=5.1 Hz, 1H), 5.84-5.94 (1H, 1, 6.52-6.80 (m, 4H), 7.19 (s, 2H), 11.30 (hr s, 2H).
MS (m+1) 762.47
Example 45
Compound I-4.5
[Chemical Formula 142]
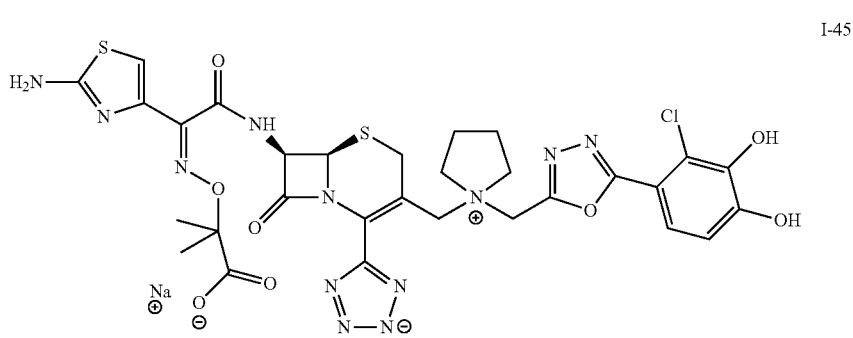
I-45
¹H-NMR (DMSO-d₆) δ: 0.82 (hr s, 1H), 1.36 (s, 3H), 1.46 (s, 3H), 1.71-1.76 (m, 2H), 1.91-1.99 (m, 1H), 2.58 (s, 1H), 3.38-4.20 (m, 6M), 4.92 (d, J=15.0 Hz, 1H), 5.13 (d, J=15.0 Hz, 1H), 5.30 (d, J=13.5 Hz, 1H), 5.40 (d, J=5.1 Hz, 1H), 5.79 (br s, 1H), 6.74 (s, 1H), 6.90 (d, J=8.1 Hz, 1H), 7.18-7.21 (m, 3M), 7.34 (d, J=8.1 Hz), 10.88 (br s, 1H)
MS (m+1) 787.49

Example 46
Compound I-46
[Chemical Formula 143]
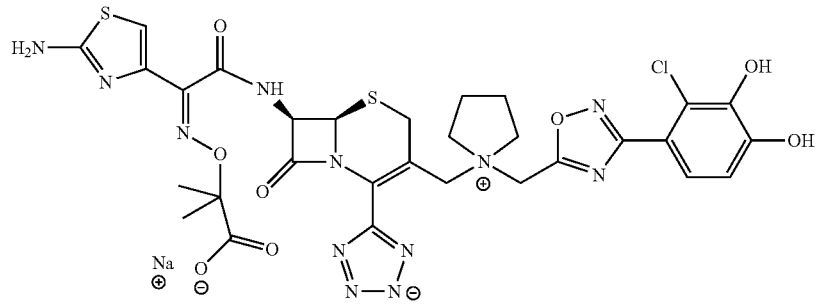
I-46
$^1$H-NMR (DMSO-$d_6$): δ: 0.90 (br s, 1H), 1.35 (s, 3H), 1.45 (s, 3H), 1.71-1.77 (m, 2H), 1.90-1.93 (m, 1H), 2.61 (s, 1H), 3.39-4.04 (m, 5H), 4.30 (d, J=14.1 Hz, 1H), 5.00 (d, J=15.3 Hz, 1H), 5.22 (d, J=15.1 Hz, 1H), 5.33-5.40 (m, 2H), 5.87 (t, J=6.3 Hz, 1H), 6.73 (s, 1H), 6.89 (d, J=8.7 Hz), 7.19-7.22 (m, 3H), 7.36 (d, J=8.7 Hz, 1H), 11.0 (br s, 1H).
MS (m+1) 787.44
Example 47
Compound I-47
[Chemical Formula 144]
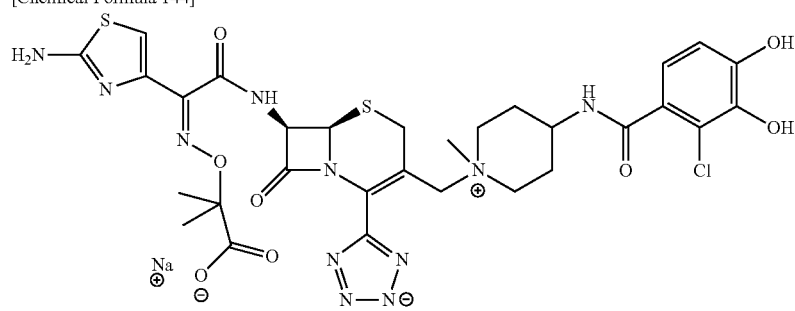
I-47
$^1$H-NMR (DMSO-d) δ: 1.38 (s, 3H), 1.50 (s, 3H), 1.81 (br s, 2H), 1.94 (br s, 2H), 2.69-4.22 (m, 11H), 5.11-5.34 (m, 1H), 5.41 (d, J=5.1 Hz, 1H), 5.88-5.92 (m, 1H), 6.61-6.97 (m, 3H), 7.23 (br s, 2H), 8.05-8.21 (m, 1H), 11.43 (br s, 1H).
MS (m+1) 776.46
Example 48
Compound I-48
[Chemical Formula 145]
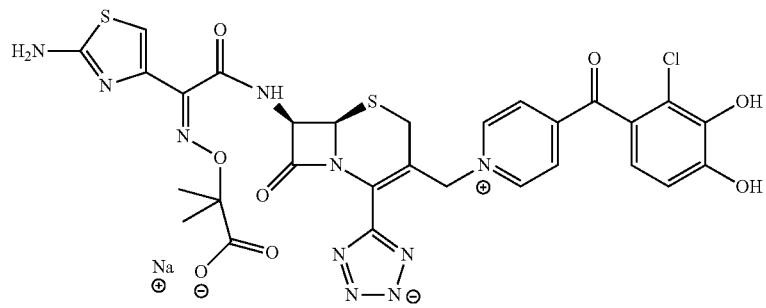
I-48

¹H-NMR (DMSO-d₆) δ: 1.43 (s, 3H), 1.47 (s, 3H), 3.45 (d, J=17.7 Hz, 1H), 3.71 (d, J=17.7 Hz, 1H), 5.41-5.49 (m, 2H), 5.55 (d, J=13.6 Hz, 1H), 5.92 (br s, 1H), 6.46 (d, J=8.4 Hz, 1H), 6.76 (s, 1H), 9.51 (d, 8.4 Hz, 2H), 10.19 (br s,
MS (m+1) 741.35
Example 49
Compound I-49
[Chemical Formula 146]
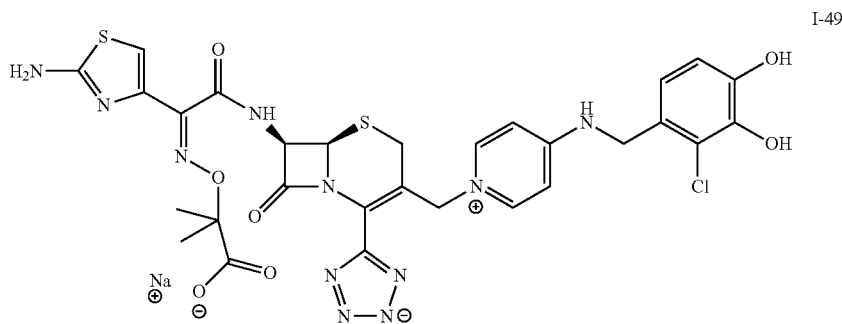
I-49
¹H-NMR (DMSO-d₆) δ: 1.33 (s, 3H), 1.43 (s, 3H), 3.06 (d, J=17.7 Hz, 3.56 (d, J=17.7 Hz), 4.44 (s, 2H), 4.74 (d, J=13.8 Hz, 1H), 5.08 (d, J=13.8 Hz, 1H), 5.30 (d, J=4.8 Hz, 1H), 5.85-5.90 (m, 11H), 6.65-6.74 (m, 2H), 6.71 (s, 1H), 6.99 (d, 7.2 Hz, 2H), 7.18 (s, 2H), 8.45 (d, J=7.2 Hz, 1H), 8.3 (d, J=7.2 Hz, 1H), 9.02 (br s, 1H), 11.20 (br s, 1H).
MS (m+1) 742.44
Example 50
Compound I-50
[Chemical Formula 147]
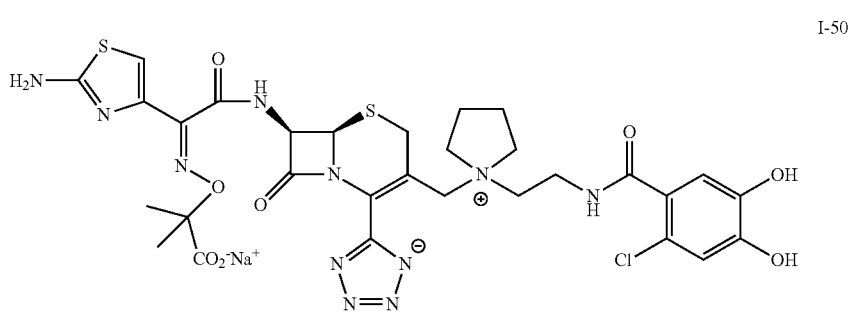
I-50
¹H-NMR (D₂O) δ: 1.48 (3H, s), 1.51 (3H, s), 1.80-2.35 (4H, m), 3.20-3.80 (10H, m), 4.00-4.20 (2H, m), 5.56 (1H, d, J=4.8 Hz), 5.89 (1H, d, J=4.8 Hz), 6.80-7.10 (3H, m).
MS (m+1) 776.54

Example 51
Compound I-51
[Chemical Formula 148]
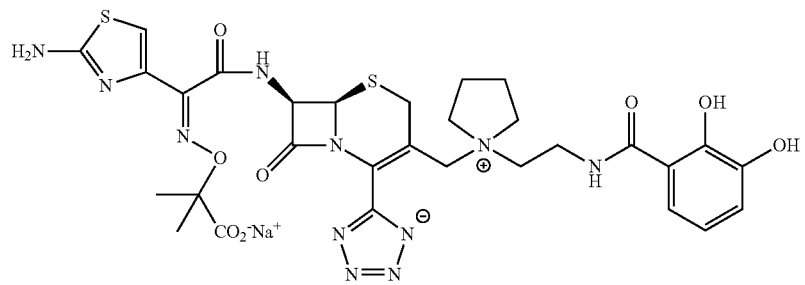
I-51
$^1$H-NMR (D2O) δ: 1.49 (3H, s), 1.51 (3H, s), 3.20-3.80 (8H, m), 4.00-4.20 (2H, m), 5.56 (1H, d, J=5.1 Hz), 5.90 (1H, d, J=5.1 Hz), 6.83 (1H, m), 7.19 (1H, d, J=1.5 Hz), 7.21 (1H, d, J=1.5 Hz).
MS (m+1) 742.57
Example 52
Compound I-52
[Chemical Formula 149]
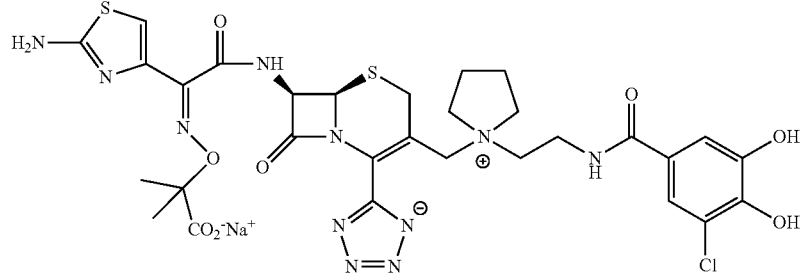
I-52
$^1$H-NMR (D2O) δ: 1.48 (3H, s), 1.50 (3H, s), 3.20-3.80 (10H, m), 4.00-4.20 (2H, m), 5.55 (1H, d, J=4.8 Hz), 5.88 (1H, d, J=4.8 Hz), 7.15 (1H, s), 7.28 (1H, s), 7.29 (1H, s).
MS (m+1)=776.56
Example 53
Compound I-53
[Chemical Formula 150]
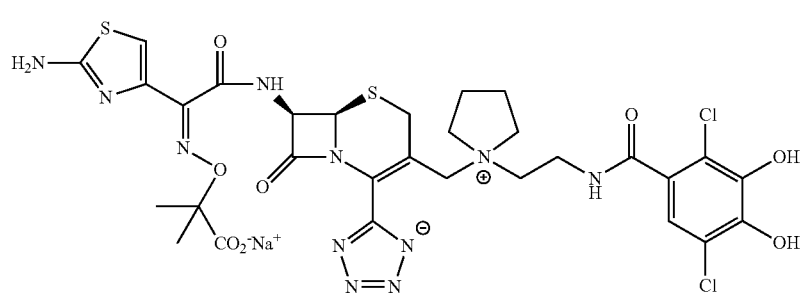
I-53

$^1$H-NMR (D2O) δ: 1.48 (3H, s), 1.51 (3H, s), 1.90-2.20 (4H, m), 3.20-3.82 (10H, m), 4.10-4.25 (2H, m), 5.90 (1H, d, J=5.1 Hz), 5.90 (1H, d, J=5.2 Hz), 6.95 (1H, s), 7.03 (1H, s).
Elemental analysis for C30H32Cl2N11O8S2Na(H$_2$O)5.8 (NaHCO3)0.3
Calcd.: C, 37.82; H, 4.60; N, 16.01; S, 6.66; Na, 3.11(%).
Found: C, 37.69; H, 4.59; N, 16.25; S, 6.62; Na, 3.34(%).
Example 54
Compound I-54
[Chemical Formula 151]
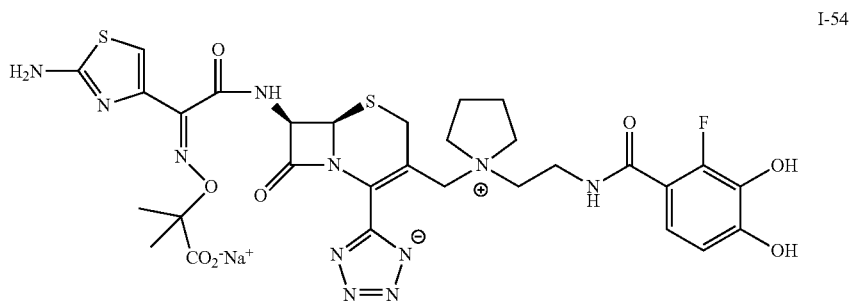
I-54
$^1$H-NMR (D2O) δ: 1.48 (3H, s), 1.51 (3H, s), 1.90-2.20 (4H, m), 3.10-3.85 (10H, m), 4.00-4.20 (2H, m), 5.58 (1H, d, J=4.8 Hz), 5.90 (1H, d, J=4.8 Hz), 6.84 (1H, d, J=8.7 Hz), 6.94 (1H, s), 7.00-7.20 (1H, m).
MS (m+1)=760.60
Example 55
Compound I-55
[Chemical Formula 152]
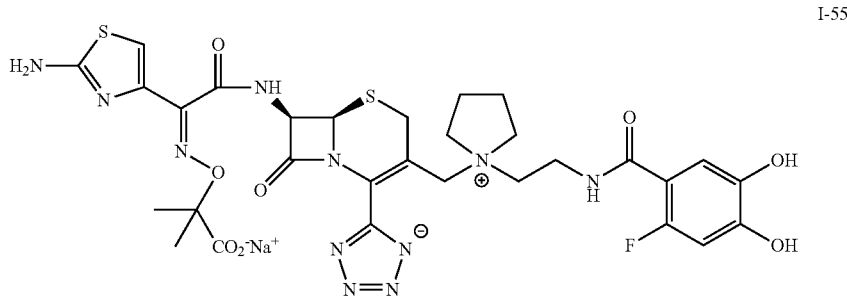
I-55
$^1$H-NMR (D2O) δ: 1.48 (3H, s), 1.51 (3H, s), 1.80-2.20 (4H, m), 3.15-3.80 (10H, m), 4.00-4.20 (2H, m), 5.57 (1H, d, J=5.1 Hz), 5.90 (1H, d, J=5.1 Hz), 6.83 (1H, d, J=12.3 Hz), 6.93 (1H, s), 7.17 (1H, d, J=7.2 Hz).
MS (m+1)=760.63

Example 56
Compound I-56
[Chemical Formula 153]
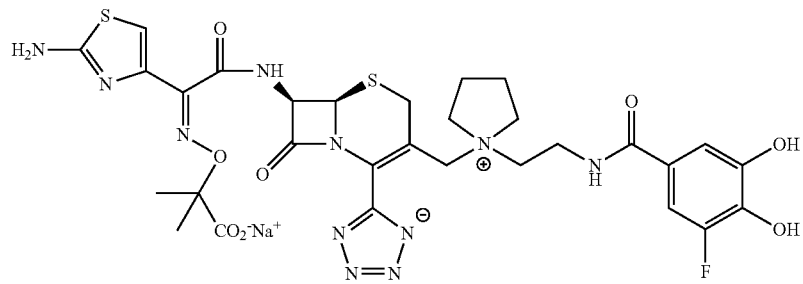
I-56
$^1$H-NMR (D2O) δ: 1.48 (3H, s), 1.51 (3H, s), 1.80-2.20 (4H, m), 3.20-3.80 (10H, m), 4.00-4.20 (2H, m), 5.56 (1H, d, J=5.1 Hz), 5.89 (1H, d, J=5.1 Hz), 6.92 (1H, s), 7.00-7.20 (2H, m).
Elemental analysis for C30H33FN11O8S2Na(H2O)5.3
Calcd.: C, 41.10; H, 4.93; F, 2.23; N, 17.62; S, 7.24; Na, 2.70(%).
Found: C, 41.07; H, 5.01; F, 2.17; N, 17.56; S, 7.31; Na, 2.62(%).
Example 57
Compound I-57
[Chemical Formula 154]
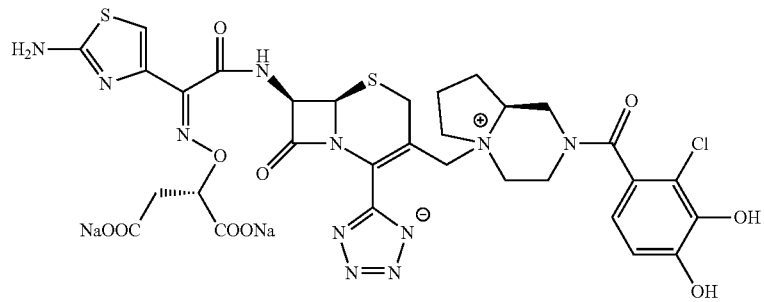
I-57
$^1$H-NMR (D$_2$O) δ: 7.00-6.90 (2H, m), 6.84-6.76 (1H, m), 5.88-5.83 (1H, m), 5.57-5.50 (1H, m), 5.01-4.88 (1H, m), 4.19-3.95 (4H, m), 3.83-3.08 (9H, m), 2.72-2.70 (2H, m), 2.23-1.96 (3H, m).
MS (m+1)=818.33

Example 58
Compound I-58
[Chemical Formula 155]
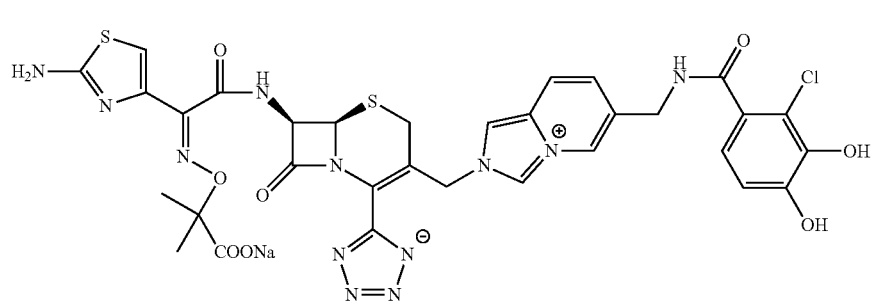
I-58
$^1$H-NMR (D$_2$O) δ: 9.42 (1H, s), 8.23 (1H, s), 7.95 (1H, s), 7.67 (1H, d, J=9.9 Hz), 7.21-7.18 (1H, m), 6.90 (2H, d, J=8.6 Hz), 6.79 (1H, d, J=8.2 Hz), 5.88 (1H, d, J=5.0 Hz), 5.47 (1H, d, J=5.0 Hz), 5.27 (1H, d, J=15.3 Hz), 5.20 (1H, d, J=15.3 Hz), 4.51 (2H, s), 3.75 (1H, d, J=18.1 Hz), 3.44 (1H, d, J=18.1 Hz), 1.51-1.47 (6H, m).
MS (m+1)=809.36
Example 59
Compound I-59
[Chemical Formula 156]
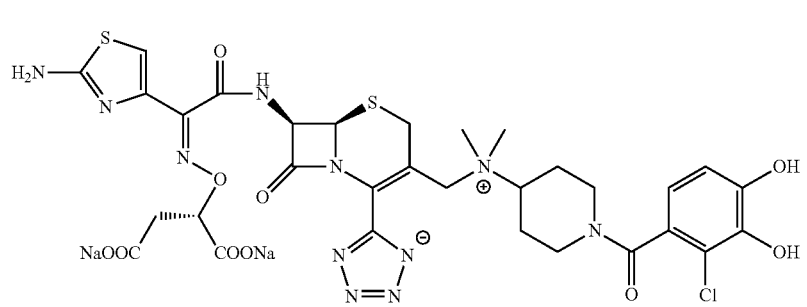
I-59
$^1$H-NMR (D$_2$O) δ: 7.03-6.89 (2H, m), 6.85-6.71 (1H, m), 5.90-5.82 (1H, m), 5.60-5.51 (1H, m), 4.56-4.52 (1H, m), 4.06 (2H, d, J=13.3 Hz), 3.71 (1H, d, J=17.1 Hz), 3.49 (2H, s), 3.12-2.93 (5H, m), 2.77-2.72 (6H, m), 2.28-2.04 (1H, m), 1.86-1.19 (3H, m).
MS (m+1)=820.02

Example 60
Compound 160
[Chemical Formula 157]
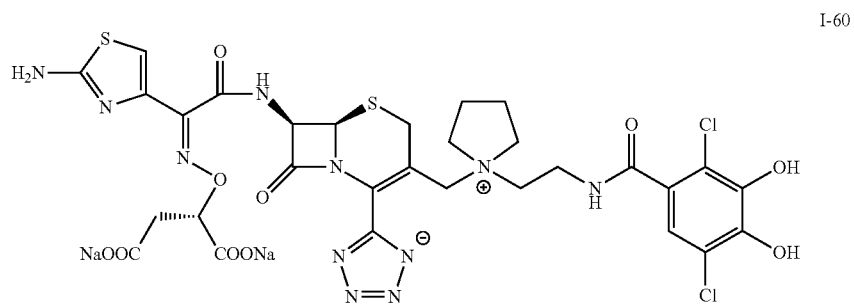
I-60
$^1$H-NMR (D$_2$O) δ: 7.34 (1H, s), 7.20 (1H, s), 6.98 (1H, s), 5.85 (1H, d, J=4.9 Hz), 5.55 (1H, d, J=4.9 Hz), 4.98 (2H, dd, J=8.6, 4.6 Hz), 4.89-4.84 (1H, m), 4.15 (1H, d, J=14.2 Hz), 4.06 (1H, d, J=17.1 Hz), 3.75 (1H, d, J=17.1 Hz), 3.54-3.35 (9H, m), 2.79-2.69 (2H, m), 2.19-1.88 (3H, m), 1.57-1.39 (1H, m).
MS (m+1)=806.02
Example 61
Compound I-61
[Chemical Formula 158]
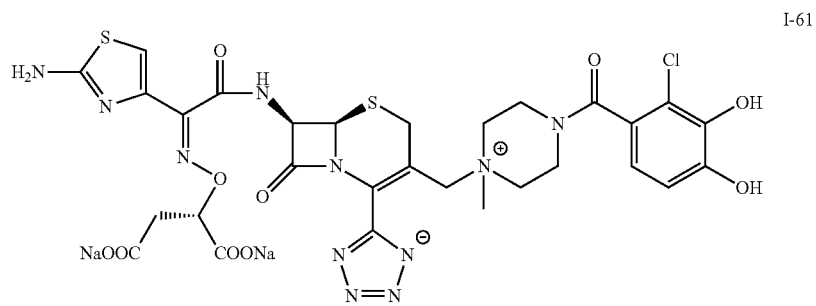
I-61
$^1$H-NMR (D$_2$O) δ: 7.01-6.90 (2H, m), 6.83-6.73 (1H, m), 5.91-5.82 (1H, m), 5.58-5.52 (1H, m), 4.98 (1H, dd, J=5.9, 9.4 Hz), 4.25-4.22 (2H, m), 4.05-4.01 (1H, m), 3.86 (1H, br s), 3.70-3.52 (5H, m), 3.36-3.18 (2H, m), 3.12-2.89 (4H, m), 2.77-2.64 (2H, m).
MS (m+1)=791.98

Example 62
Compound I-62
[Chemical Formula 159]
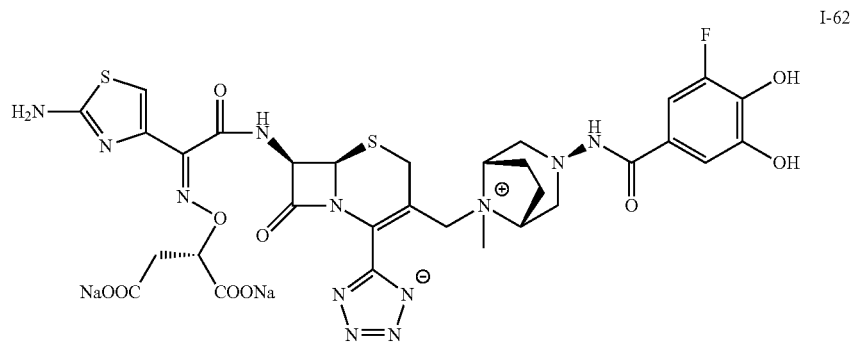
$^1$H-NMR (D$_2$O) δ: 7.11-6.99 (3H, m), 5.86 (1H, d, J=5.0 Hz), 5.56 (1H, d, J=5.0 Hz), 4.98 (1H, dd, J=8.1, 5.1 Hz), 4.63 (1H, d, J=14.4 Hz), 4.16-3.96 (4H, m), 3.80-3.60 (2H, m), 2.94 (3H, s), 2.81-2.64 (4H, m), 2.62-2.49 (1H, m), 2.44-2.31 (2H, m), 2.26-2.03 (3H, m), 1.41 (1H, s).
MS (m+1)=816.16
Example 63
Compound I-63
[Chemical Formula 160]
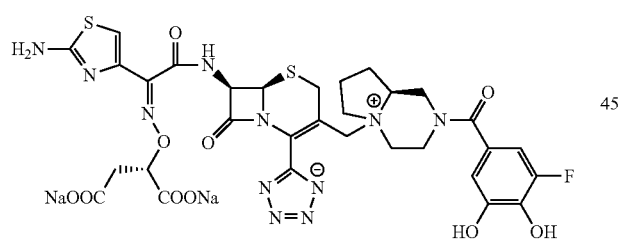
$^1$H-NMR (D$_2$O) δ: 6.98 (1H, s), 6.92-6.71 (2H, br m), 5.85 (1H, d, J=5.0 Hz), 5.60-5.51 (1H, m), 4.99-4.95 (1H, m), 4.30 (1H, d, J=13.6 Hz), 4.16-3.04 (1H, m), 2.76-2.67 (2H, m), 2.05-1.90 (3H, m), 1.46-1.43 (1H, m).
MS (m+1)=802.02
Example 64
Compound I-64
[Chemical Formula 161]
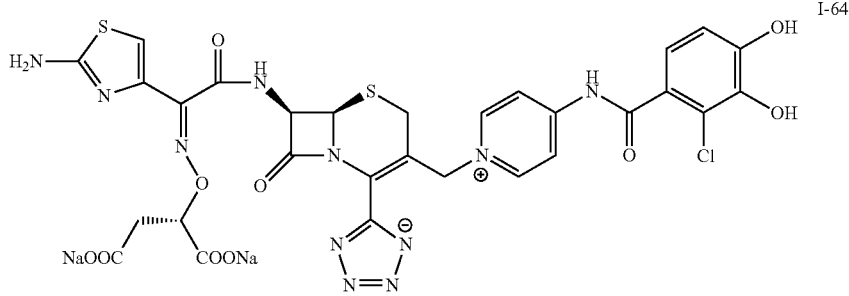

¹H-NMR (D₂O) δ: 8.63 (2H, d, J=7.2 Hz), 8.13 (2H, d, J=7.2 Hz), 7.19 (1H, d, J=8.5 Hz), 6.99 (1H, s), 6.94 (1H, d, J=8.5 Hz), 5.89 (1H, d, J=4.9 Hz), 5.48 (1H, d, J=4.9 Hz), 5.31 (2H, dd, J=34.6, 14.9 Hz), 4.96 (1H, dd, J=9.0, 4.3 Hz), 3.72 (1H, d, J=18.1 Hz), 3.48 (1H, d, J=18.1 Hz), 2.74-2.65 (2H, m).

MS (m+1)=802.02

¹H-NMR (D₂O) δ: 8.96 (1H, s), 8.01 (1H, d, J=6.6 Hz), 7.81 (1H, d, J=6.6 Hz), 7.39 (1H, s), 7.20 (1H, s), 6.88 (1H, s), 5.84 (1H, d, J=5.0 Hz), 5.45 (1H, d, J=5.0 Hz), 5.31 (2H, dd, J=28.0, 14.9 Hz), 4.96 (1H, dd, J=9.9, 3.5 Hz), 3.69 (1H, d, J=16.9 Hz), 3.42 (1H, d, J=18.2 Hz), 2.81-2.64 (2H, m).

MS (m+1)=682.97

Example 65

Compound I-65

[Chemical Formula 162]

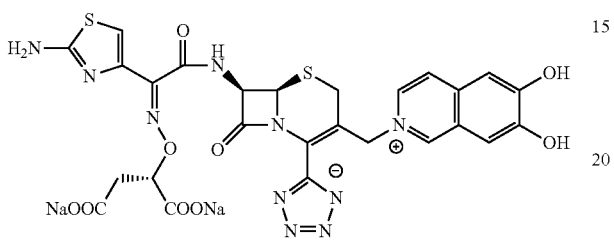

I-65

Example 66

Compound I-66

[Chemical Formula 163]

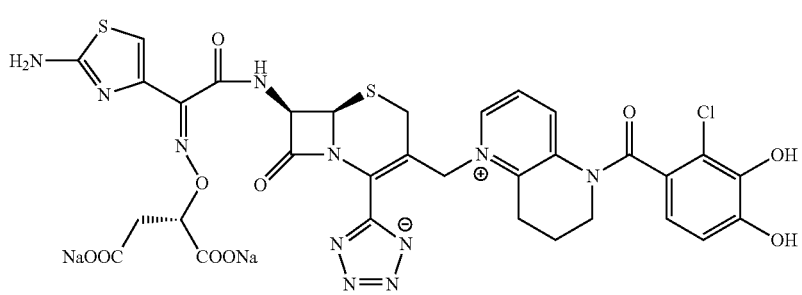

I-66

¹H-NMR (D₂O) δ: 8.66-8.63 (1H, m), 7.66 (1H, br s), 7.06-6.95 (3H, m), 5.90 (1H, d, J=4.8 Hz), 5.70-5.53 (1H, m), 5.47 (1H, d, J=4.8 Hz), 5.33 (1H, d, J=15.2 Hz), 5.03-4.96 (1H, m), 4.06 (1H, s), 3.71-3.45 (3H, m), 3.14-2.67 (4H, m), 2.29-1.95 (2H, br m).

MS (m+1)=825.96

Example 67

Compound I-67

[Chemical Formula 164]

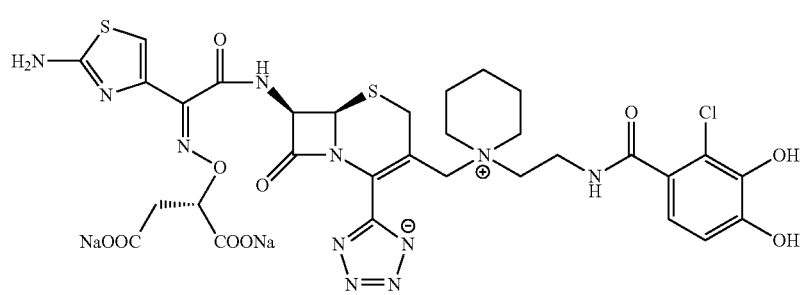

I-67

¹H-NMR (D₂O) δ: 6.98 (1H, s), 6.96 (1H, d, J=8.3 Hz), 6.90 (1H, d, J=8.3 Hz), 5.84 (1H, d, J=5.0 Hz), 5.55 (1H, d, J=5.0 Hz), 4.99-4.93 (3H, m), 4.22 (1H, d, J=14.2 Hz), 4.05 (1H, d, J=16.9 Hz), 3.73 (1H, d, J=16.9 Hz), 3.56-3.29 (7H, m), 3.37-3.05 (2H, m), 2.81-2.69 (2H, m), 1.96-1.52 (6H, m).
MS (m+1)=820.02
Example 68
Compound I-68
[Chemical Formula 165]
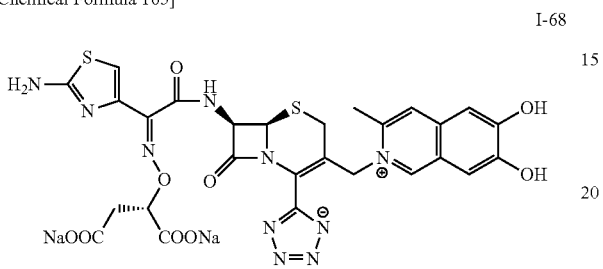
I-68
¹H-NMR (D₂O) δ: 8.80 (1H, s), 7.48 (1H, s), 7.20 (1H, s), 6.91 (2H, s), 5.84 (1H, d, J=4.7 Hz), 5.44 (1H, d, J=15.8 Hz), 5.40 (1H, d, J=4.7 Hz), 5.16 (1H, d, J=15.8 Hz), 4.98 (1H, dd, J=9.9, 3.6 Hz), 3.46 (2H, s), 2.82-2.66 (2H, m), 2.37 (3H, s).
MS (m+1)=697.01
Example 69
Compound I-69
[Chemical Formula 166]
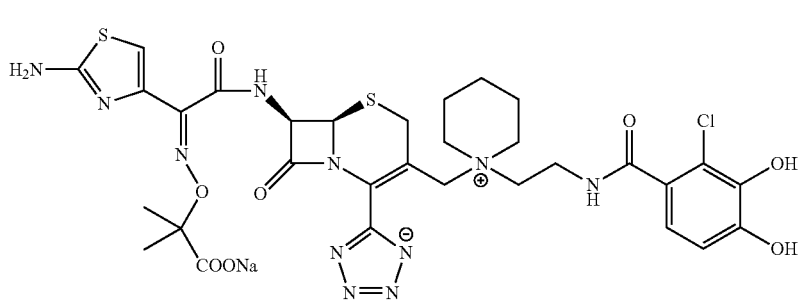
I-69
¹H-NMR (D₂O) δ: 6.98-6.86 (3H, m), 5.90 (1H, d, J=5.0 Hz), 5.58 (1H, d, J=5.0 Hz), 4.92 (1H, d, J=14.2 Hz), 4.21 (1H, d, J=14.2 Hz), 4.09 (1H, d, J=16.8 Hz), 3.75 (1H, d, J=16.8 Hz), 3.57-3.07 (9H, m), 1.75 (5H, t, J=41.0 Hz), 1.48-1.36 (9H, m).
MS (m+1)=790.03
Example 70
Compound I-70
[Chemical Formula 167]
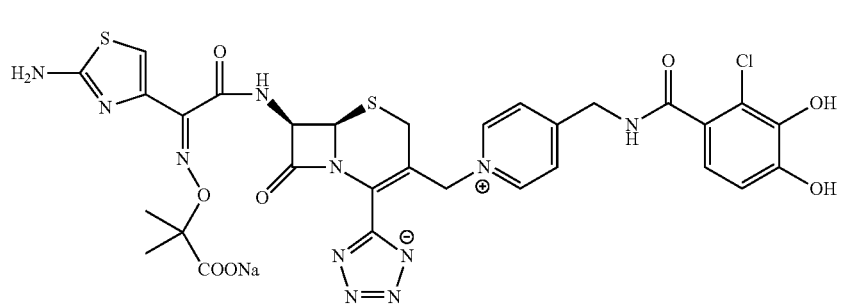
I-70

$^1$H-NMR (D$_2$O) δ: 9.01 (2N, d, J=6.8 Hz), 8.08 (2H, d, J=6.8 Hz), 7.18 (1H, s), 7.05 (1H, d, J=8.7 Hz), 6.88 (1H, d, J=8.7 Hz), 5.90 (1H, d, J=4.9 Hz), 5.70 (1H, d, J=15.1 Hz), 5.55 (1H, d, J=4.9 Hz), 5.48 (1H, d, J=15.1 Hz), 5.23 (1H, dd, J=7.0, 4.9 Hz), 4.85 (2H, s), 3.83 (1H, d, J=18.3 Hz), 3.43 (1H, d, J=18.3 Hz), 3.10-3.03 (2H, m).
MS (m+1)=799.93

Example 71

Compound I-71

[Chemical Formula 168]

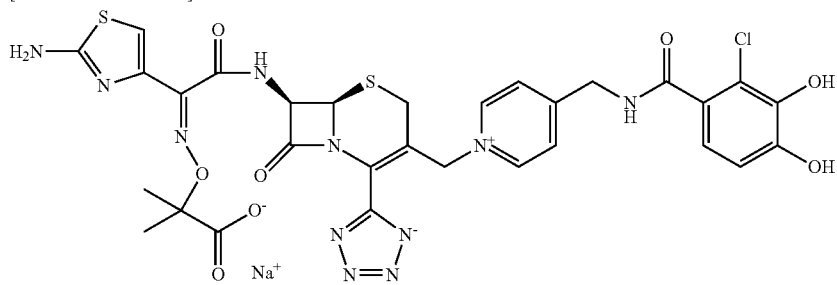

I-71

$^1$H-NMR (D$_2$O) δ: 8.83 (2H, d, J=6.6 Hz), 8.03 (3H, d, J=6.6 Hz), 7.07 (1H, d, J=8.2 Hz), 6.96 (1H, s), 6.92 (1H, d, J=8.2 Hz), 5.93 (1H, d, J=4.9 Hz), 5.51 (1H, d, J=4.9 Hz), 5.44 (2H, d, J=9.3 Hz), 3.75 (1H, d, J=18.1 Hz), 3.44 (1H, d, J=18.1 Hz), 1.49 (3H, s), 1.47 (3H, s).
MS (m+1)=769.91

Example 72

Compound I-72

[Chemical Formula 169]

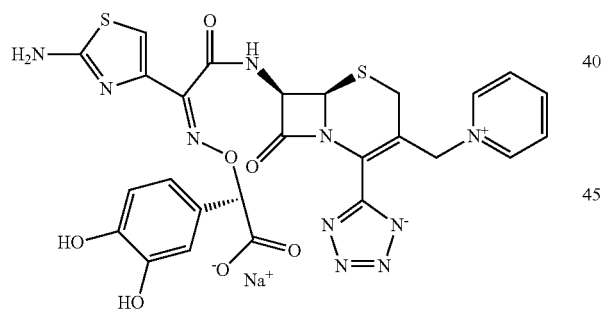

I-72

$^1$H-NMR (D$_2$O) δ: 8.89-8.83 (2H, m), 8.64-8.56 (1H, m), 8.14-8.06 (2H, m), 7.01-6.97 (2H, m), 6.92-6.87 (1H, m), 6.80-6.76 (1H, m), 5.81 (1H, d, J=5.2 Hz), 5.44-5.38 (3H, m), 5.37-5.29 (1H, m), 4.89-4.86 (1H, m), 3.61-3.53 (1H, m), 3.07-2.99 (1H, m).
MS (m+1)=650.93

Example 73

Compound I-73

[Chemical Formula 170]

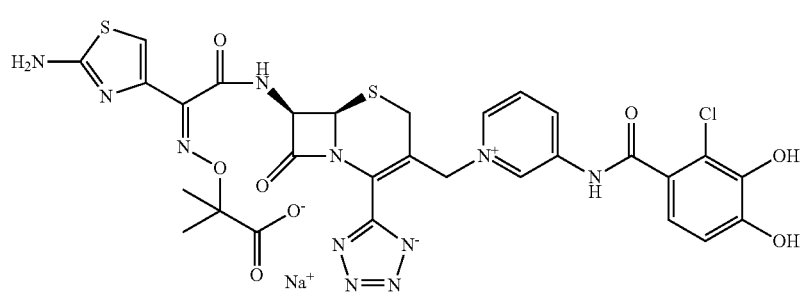

I-73

¹H-NMR (D₂O) δ: 9.46 (1H, s), 8.65-8.62 (1H, m), 8.47-8.42 (1H, m), 8.00-7.93 (1H, m), 7.05 (1H, d, J=8.6 Hz), 6.92-6.81 (2H, m), 5.90 (1H, d, J=4.9 Hz), 5.50 (1H, d, J=4.9 Hz), 5.43 (2H, s), 3.76 (1H, d, J=18.0 Hz), 3.43 (1H, d, J=18.0 Hz), 1.43 (6H, s).
MS (m+1)=755.90

¹H-NMR (D₂O) δ: 8.54 (18H, br s), 8.12 (18H, br s), 7.55 (1H, br s), 6.94-6.84 (3H, m), 5.85 (1H, d, J=4.9 Hz), 5.51 (1H, br s), 5.40 (1H, d, J=4.9 Hz), 5.22 (1H, d, J=15.3 Hz), 3.96 (18H, br s), 3.55-3.35 (3H, m), 2.97-2.90 (1H, m), 2.76 (1H, br s), 2.04 (2H, br s), 1.42 (3H, s), 1.39 (3H, s).

Elemental analysis for C32H29ClN11O8S2Na(H2O)8.2 (NaCl)0.1

Example 74

Compound I-74

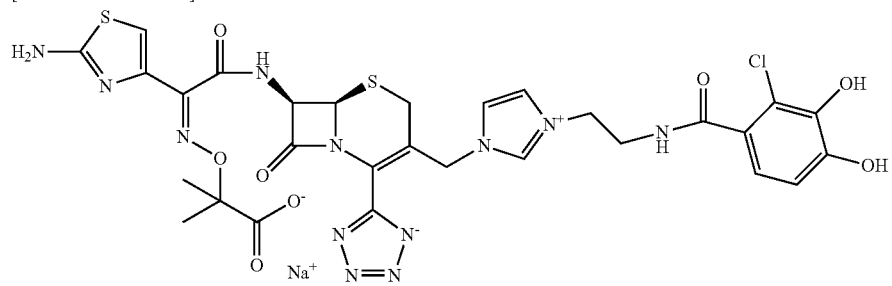

I-74

¹H-NMR (D₂O) δ: 8.97 (1H, s), 7.63 (1H, s), 7.56 (1H, s), 6.93 (1H, s), 6.89 (1H, d, J=8.2 Hz), 6.84 (1H, d, J=8.2 Hz), 5.85 (1H, d, J=5.2 Hz), 5.22 (1H, d, J=5.2 Hz), 5.12-4.89 (2H, m), 4.47-4.44 (2H, m), 3.88-3.82 (2H, m), 3.54 (1H, d, J=18.4 Hz), 3.32 (1H, d, J=18.4 Hz), 1.46 (6H, br s).
MS (m+1)=772.90

Calcd.: C, 39.55; H, 4.71; Cl, 4.01; N, 15.85; S, 6.60; Na, 2.60(%).

Found: C, 39.80; H, 4.64; Cl, 4.17; N, 15.20; S, 6.43; Na, 2.30(%).

Example 75

Compound I-75

Example 76

Compound I-76

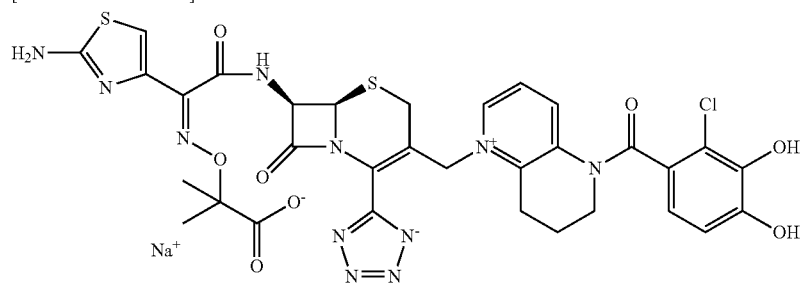

I-75

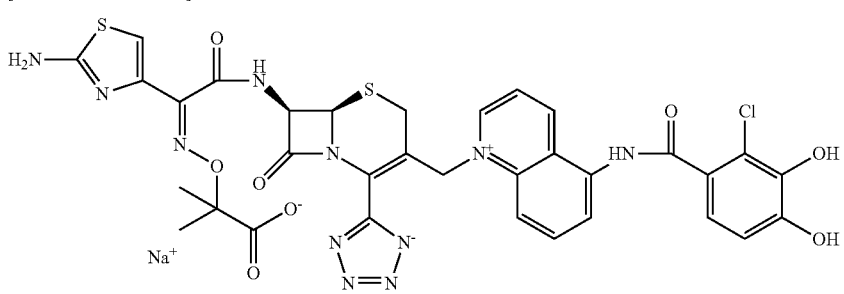

I-76

$^1$H-NMR (D$_2$O) δ: 9.39-9.24 (2H, m), 8.24-8.08 (3H, m), 7.91 (1H, br s), 7.28 (1H, br s), 6.97 (2H, br s), 6.10-5.76 (5H, m), 3.55 (1H, br s), 1.51 (3H, s), 1.46 (3H, s).

Elemental analysis for C33H27ClN11O8S2Na(H2O)8.7
Calcd.: C, 40.24; H, 4.54; Cl, 3.60; N, 15.64; S, 6.51; Na, 2.33(%).

Found: C, 40.28; H, 4.30; Cl, 3.83; N, 15.37; S, 6.57; Na, 2.30(%).

Example 77

Compound I-77

[Chemical Formula 174]

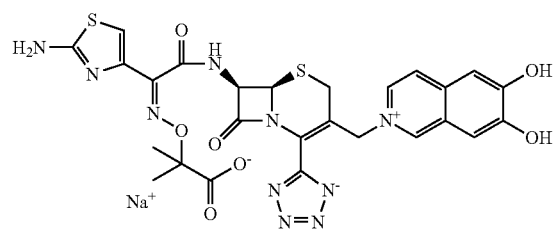

$^1$H-NMR (D$_2$O) δ: 8.61 (1H, s), 7.77 (1H, d, J=6.9 Hz), 7.50 (1H, d, J=6.9 Hz), 7.11 (1H, s), 6.85 (1H, s), 6.83 (1H, s), 5.88 (1H, d, J=4.9 Hz), 5.42 (1H, d, J=4.9 Hz), 5.23 (1H, d, J=14.9 Hz), 5.12 (1H, d, J=14.9 Hz), 3.61 (1H, d, J=18.0 Hz), 3.38 (1H, d, J=18.0 Hz), 1.47 (3H, s), 1.45 (3H, s).
MS (m+1)=652.94

Example 78

Compound I-78

[Chemical Formula 175]

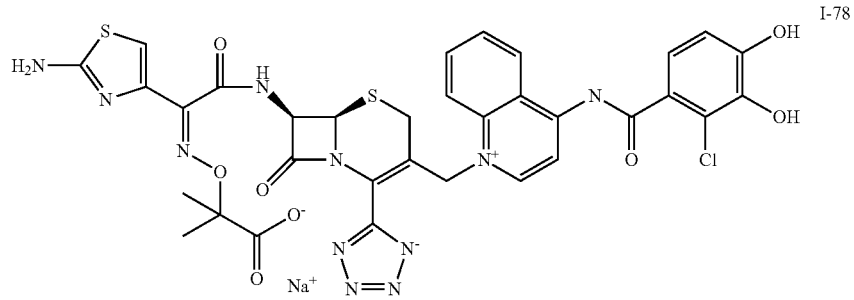

$^1$H-NMR (D$_2$O) δ: 8.90 (1H, br s), 8.41 (1H, br s), 8.22 (1H, br s), 7.87 (1H, br s), 7.68 (1H, br s), 7.56 (1H, br s), 6.90 (1H, br s), 6.72 (1H, br s), 6.56 (1H, br s), 5.76-5.72 (2H, br m), 5.46-5.38 (1H, m), 5.21 (1H, br s), 3.35 (2H, br s), 1.37 (3H, s), 1.34 (3H, s).

Elemental analysis for C33H27ClN11O8S2Na(H2O)9.3 (NaHCO3)0.1
Calcd.: C, 39.59; H, 4.59; Cl, 3.53; N, 15.34; S, 6.39; Na, 2.52(%).

Found: C, 39.72; H, 4.49; Cl, 3.71; N, 15.46; S, 6.40; Na, 2.59(%).

Example 79

Compound I-79

[Chemical Formula 176]

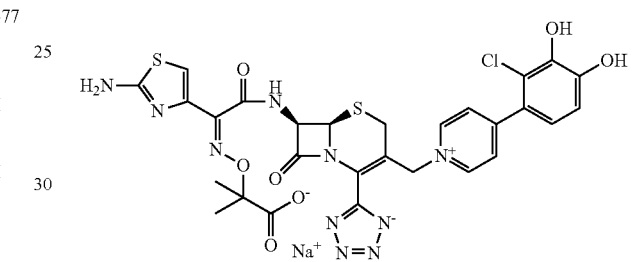

$^1$H-NMR (D$_2$O) δ: 8.76 (2H, br s), 8.07 (2H, br s), 6.95-6.92 (3H, m), 5.93 (1H, d, J=4.2 Hz), 5.51-5.40 (2H, m), 3.77 (1H, d, J=18.0 Hz), 3.49 (1H, d, J=18.0 Hz), 1.49 (3H, s), 1.47 (3H, s).

Elemental analysis for C28H24.2ClN10O7S2Na0.8(H2O)6.2
Calcd.: C, 39.92; H, 4.38; Cl, 4.21; N, 16.63; S, 7.61; Na, 2.18(%).

Found: C, 40.14; H, 4.25; Cl, 4.99; N, 15.40; S, 6.80; Na, 2.28 (8).

Example 80
Compound I-80
[Chemical Formula 177]
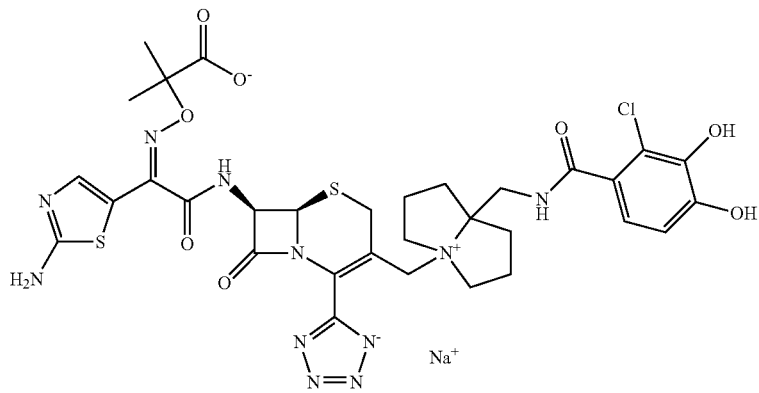
I-80
¹H-NMR (D₂O) δ: 6.97-6.89 (3H, m), 5.92 (1H, d, J=5.0 Hz), 5.59 (1H, d, J=5.0 Hz), 4.19 (1H, d, J=14.4 Hz), 4.04 (1H, d, J=17.1 Hz), 3.95 (1H, d, J=14.4 Hz), 3.84-3.80 (1H, m), 3.72-3.64 (3H, m), 3.40-3.32 (1H, m), 3.26-3.17 (1H, m), 2.38-2.03 (6H, m), 1.93-1.78 (2H, m), 1.52 (3H, s), 1.49 (3H, s).
MS (m+1)=801.95
¹H-NMR (D₂O) δ: 6.93 (1H, d, J=0.7 Hz), 6.78 (1H, s), 6.36 (1H, s), 5.89 (1H, d, J=5.0 Hz), 5.49 (1H, d, J=5.0 Hz), 5.01 (1H, d, J=13.6 Hz), 4.59 (2H, s), 4.43 (2H, s), 4.14 (1H, d, J=13.6 Hz), 4.05 (1H, d, J=17.1 Hz), 3.71 (1H, d, J=17.1 Hz), 3.25 (3H, s), 1.51 (3H, s), 1.49 (3H, s).
MS (m+1)=656.98
Example 81
Compound I-81
[Chemical Formula 178]
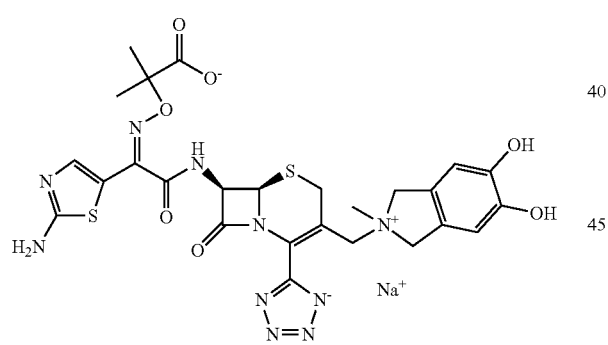
I-81
Example 82
Compound I-82
[Chemical Formula 179]
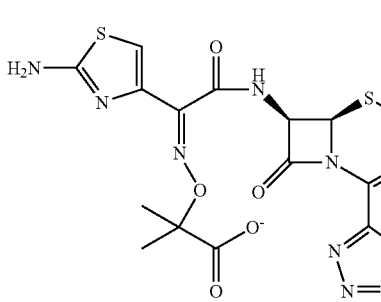
I-82

¹H-NMR (D₂O) δ: 6.93 (1H, d, J=8.4 Hz), 6.88 (1H, d, J=8.4 Hz), 5.95 (1H, d, J=5.0 Hz), 5.59 (1H, d, J=5.0 Hz), 4.13 (2H, t, J=15.8 Hz), 3.77 (1H, d, J=17.3 Hz), 3.59-3.33 (9H, m), 2.11-1.92 (3H, m), 1.55 (3H, s), 1.52 (3H, s), 1.49-1.35 (1H, m).
MS (m+1)=777.31
Example 83
Compound I-83
[Chemical Formula 180]
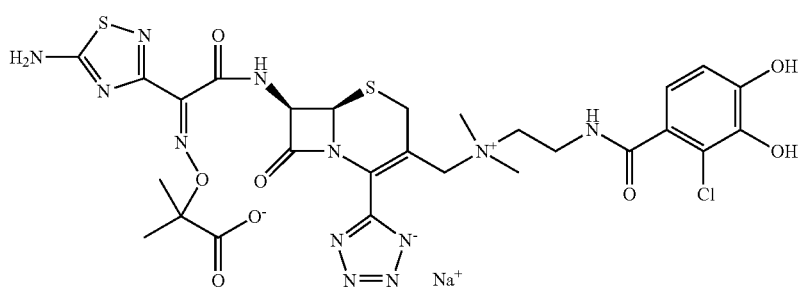
I-83
¹H-NMR (D₂O) δ: 6.92 (1H, d, J=8.4 Hz), 6.87 (1H, d, J=8.4 Hz), 5.93 (1H, d, J=5.0 Hz), 5.59 (1H, d, J=5.0 Hz), 4.92 (1H, d, J=13.8 Hz), 4.16 (1H, d, J=13.8 Hz), 4.08 (1H, d, J=17.1 Hz), 3.78-3.56 (3H, m), 3.52-3.38 (1H, m), 3.23-3.14 (1H, m), 3.05 (3H, s), 2.89 (3H, s), 1.55 (3H, s), 1.53 (3H, s).
MS (m+1)=751.12
Example 84
Compound I-84
[Chemical Formula 181]
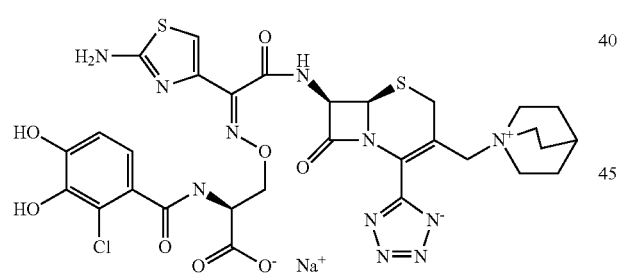
I-81
¹H-NMR (D₂O) δ: 7.13 (1H, d, J=8.6 Hz), 6.98 (1H, s), 6.88 (1H, d, J=8.6 Hz), 5.85 (1H, d, J=5.0 Hz), 5.38 (1H, d, J=5.0 Hz), 4.72-4.64 (3H, m), 4.55 (1H, d, J=13.9 Hz), 3.65 (1H, d, J=17.1 Hz), 3.55 (1H, d, J=13.9 Hz), 3.32-2.91 (8H, m), 1.88-1.82 (6H, m).
MS (m+1)=774.24
Example 85
Compound I-85
[Chemical Formula 182]
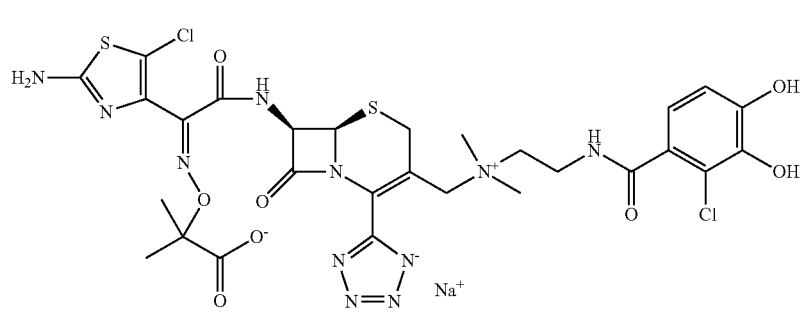
I-85

$^1$H-NMR (D$_2$O) δ: 6.91 (1H, d, J=8.4 Hz), 6.87 (1H, d, J=8.4 Hz), 5.90 (1H, d, J=5.0 Hz), 5.56 (1H, d, J=5.0 Hz), 4.93 (1H, d, J=13.9 Hz), 4.16 (1H, d, J=13.9 Hz), 4.06 (1H, d, J=17.0 Hz), 3.73-3.37 (4H, m), 3.23-3.14 (1H, m), 3.04 (3H, s), 2.88 (3H, s), 1.53 (3H, s), 1.50 (3H, s).
MS (m+1)=784.11
Example 86
Compound I-86
[Chemical Formula 183]
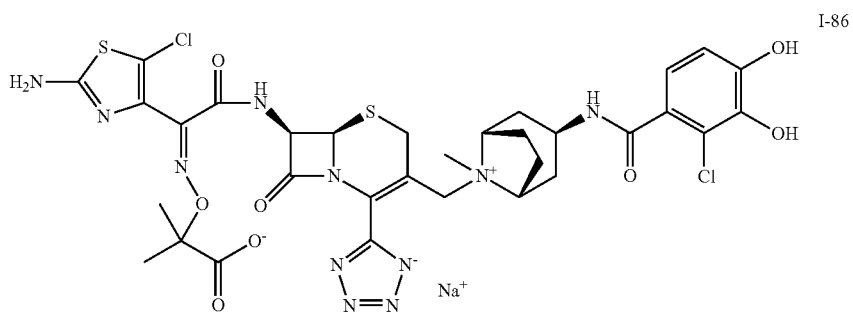
$^1$H-NMR (D$_2$O) δ: 6.87 (2H, s), 5.91 (1H, d, J=5.0 Hz), 5.57 (1H, d, J=5.0 Hz), 4.72-4.62 (1H, m), 4.17-3.98 (4H, m), 3.73 (1H, d, J=17.1 Hz), 3.62 (1H, br s), 2.92 (3H, s), 2.78-1.93 (8H, m), 1.53 (3H, s), 1.51 (3H, s).
MS (m+1)=836.15
Example 87
Compound I-87
[Chemical Formula 184]
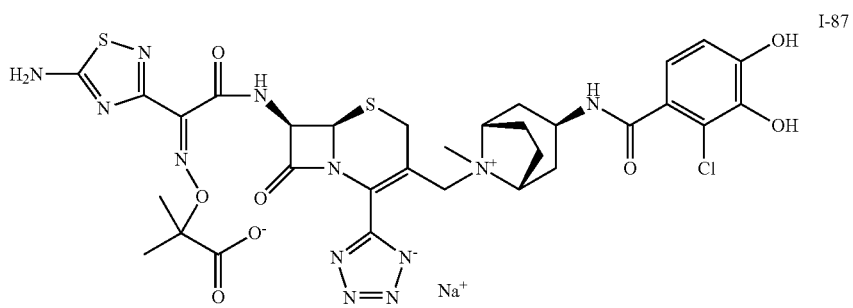
$^1$H-NMR (D$_2$O) δ: 6.85 (2H), 5.93 (1H, d, J=5.0 Hz), 5.59 (1H, d, J=5.0 Hz), 4.63 (1H, d, J=14.8 Hz), 4.19-3.90 (4H, m), 3.77-3.61 (2H, m), 2.91 (3H, s), 2.79-1.99 (8H, m), 1.56 (3H, s), 1.53 (3H, s).
MS (m+1)=803.20

Example 88
Compound I-88
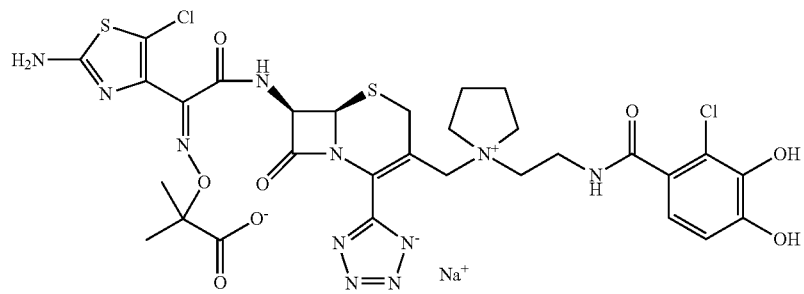
¹H-NMR (D₂O) δ: 6.94 (1H, d, J=8.4 Hz), 6.88 (1H, d, J=8.4 Hz), 5.92 (1H, d, J=5.0 Hz), 5.58 (1H, d, J=5.0 Hz), 4.16 (1H, d, J=14.8 Hz), 4.10 (1H, d, J=17.1 Hz), 3.77 (1H, d, J=17.1 Hz), 3.57-3.34 (9H, m), 2.16-1.96 (3H, m), 1.52 (3H, s), 1.50 (3H, s), 1.46-1.38 (1H, m).
MS (m+1)=810.15
Example 89
Compound I-89
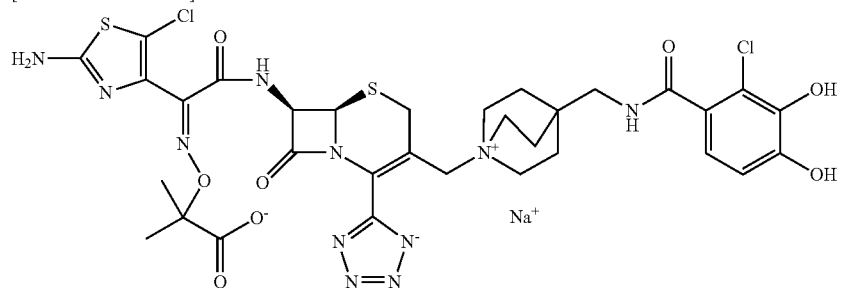
¹H-NMR (D₂O) δ: 6.89 (2H, br s), 5.91 (1H, d, J=5.0 Hz), 5.57 (1H, d, J=5.0 Hz), 4.65 (1H, d, J=13.8 Hz), 4.04 (1H, d, J=17.5 Hz), 3.92 (1H, d, J=13.8 Hz), 3.65 (1H, d, J=17.5 Hz), 3.41-3.27 (5H, m), 3.17-3.06 (3 n, m), 1.87-1.80 (6H, m), 1.53 (3H, s), 1.50 (3H, s).
MS (m+1)=836.19
Example 90
Compound I-90
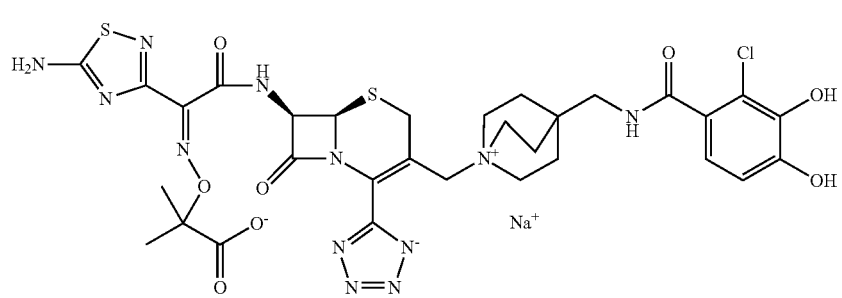

¹H-NMR (D₂O) δ: 6.89 (1H, s), 6.88 (1H, s), 5.93 (1H, d, J=5.0 Hz), 5.57 (1H, d, J=5.0 Hz), 4.65 (1H, d, J=14.3 Hz), 4.03 (1H, d, J=17.3 Hz), 3.91 (1H, d, J=14.3 Hz), 3.64 (1H, d, J=17.3 Hz), 3.40-3.31 (3H, m), 3.29-3.26 (2H, m), 3.17-3.05 (3H, m), 1.87-1.79 (6H, m), 1.55 (3H, s), 1.53 (3H, s).
MS (m+1)=803.24

Example 91

Compound I-91

[Chemical Formula 188]

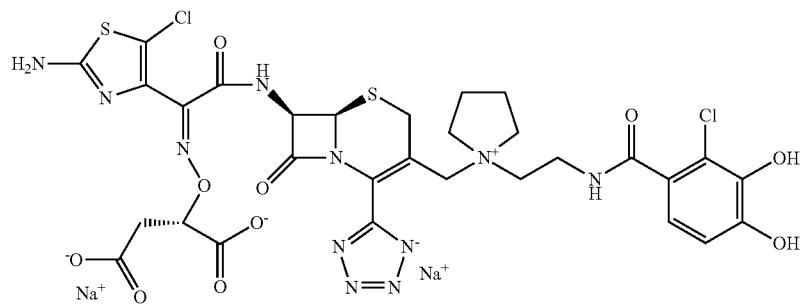

I-91

¹H-NMR (D₂O) δ: 6.93 (1H, d, J=8.4 Hz), 6.87 (1H, d, J=8.4 Hz), 5.85 (1H, d, J=5.2 Hz), 5.52 (1H, d, J=5.2 Hz), 4.98 (1H, t, J=6.9 Hz), 4.87 (1H, d, J=14.6 Hz), 4.14 (1H, d, J=14.6 Hz), 4.04 (1H, d, J=16.9 Hz), 3.73 (1H, d, J=16.9 Hz), 3.57-3.30 (8H, m), 2.77 (2H, d, J=6.9 Hz), 2.14-1.96 (3H, m), 1.49-1.44 (1H, m).
MS (m+1)=839.86

Example 92

Compound I-92

[Chemical Formula 189]

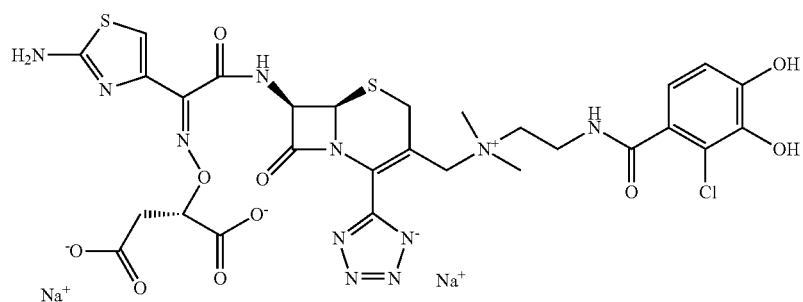

I-92

¹H-NMR (D₂O) δ: 6.98 (1H, s), 6.92 (1H, d, J=8.4 Hz), 6.88 (1H, d, J=8.4 Hz), 5.84 (1H, d, J=4.9 Hz), 5.55 (1H, d, J=4.9 Hz), 4.99-4.89 (2H, m), 4.19 (1H, d, J=13.9 Hz), 4.04 (1H, d, J=16.9 Hz), 3.73-3.61 (2H, m), 3.52-3.44 (1H, m), 3.23-3.16 (1H, m), 3.07 (3H, s), 2.92 (3H, s), 2.73-2.70 (2H, m).
Elemental analysis for C28H28ClN11O10S2Na2(H2O)6
Calcd.: C, 36.07; H, 4.32; Cl, 3.80; N, 16.53; S, 6.88; Na, 4.93(%).
Found: C, 36.04; H, 4.32; Cl, 3.87; N, 16.70; S, 6.92; Na, 4.64(%).

Example 93
Compound I-93
[Chemical Formula 190]
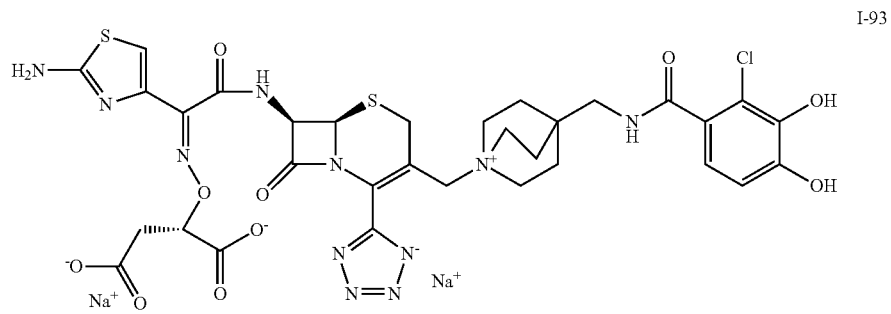
I-93
¹H-NMR (D₂O) δ: 7.00 (1H, s), 6.91 (1H, d, J=8.3 Hz), 6.88 (1H, d, J=8.3 Hz), 5.85 (1H, d, J=5.0 Hz), 5.54 (1H, d, J=5.0 Hz), 4.99-4.96 (1H, m), 4.65 (1H, d, J=13.9 Hz), 3.98 (2H, t, J=15.1 Hz), 3.65 (1H, d, J=17.6 Hz), 3.39-3.30 (5H, m), 3.15-3.10 (3H, m), 2.71 (2H, d, J=6.7 Hz), 1.90-1.81 (6H, m).
MS (m+1)=832.19
Example 94
Compound I-94
[Chemical Formula 191]
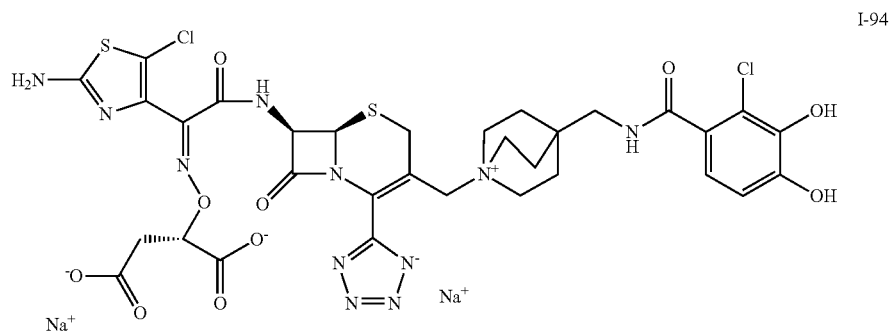
I-94
¹H-NMR (D₂O) δ: 6.92 (1H, d, J=8.3 Hz), 6.89 (1H, d, J=8.3 Hz), 5.85 (1H, d, J=5.0 Hz), 5.53 (1H, d, J=5.0 Hz), 5.00 (1H, t, J=6.7 Hz), 4.65 (1H, d, J=13.9 Hz), 3.98 (2H, t, J=15.1 Hz), 3.65 (1H, d, J=17.6 Hz), 3.41-3.29 (5H, m), 3.17-3.10 (3H, m), 2.73 (2H, d, J=6.7 Hz), 1.90-1.81 (6H, m).
MS (m+1)=866.15

Example 95
Compound I-95
[Chemical Formula 192]
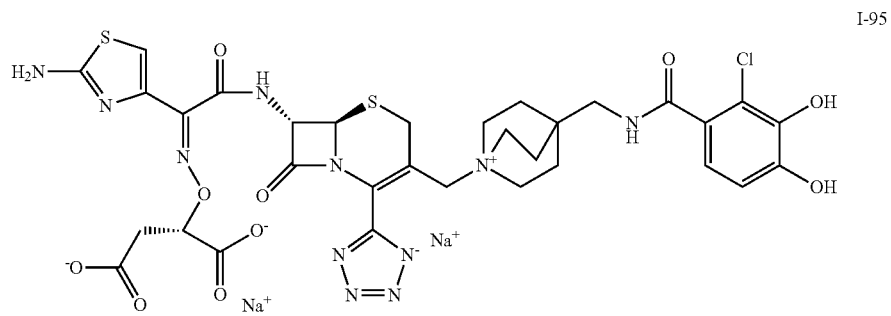
I-95
$^1$H-NMR (D$_2$O) δ: 6.97 (1H, s), 6.89 (2H, dd, J=12.2, 8.5 Hz), 5.42 (1H, d, J=2.5 Hz), 5.11 (1H, d, J=2.5 Hz), 4.91 (1H, dd, J=11.3, 2.9 Hz), 4.26 (1H, d, J=13.8 Hz), 4.11 (1H, d, J=17.1 Hz), 3.93 (1H, d, J=13.9 Hz), 3.62 (1H, d, J=17.3 Hz), 3.45-3.33 (3H, m), 3.30 (2H, s), 3.20-3.07 (3H, m), 2.76 (1H, dd, J=15.6, 3.1 Hz), 2.57 (1H, dd, J=15.6, 11.2 Hz), 1.91-1.81 (6H, m).
MS (m+1)=832.19
Example 96
Compound I-96
[Chemical Formula 193]
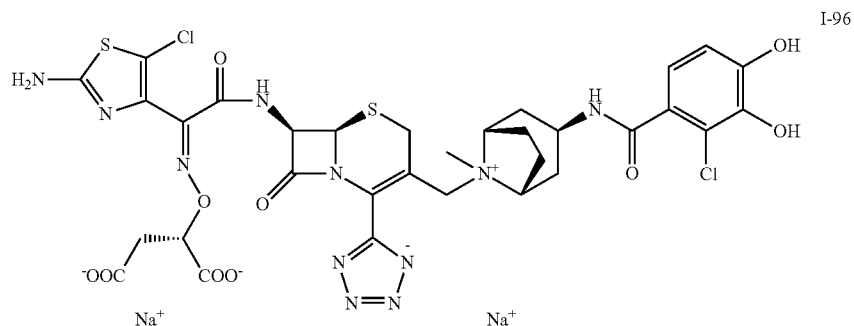
I-96
$^1$H-NMR (D$_2$O) δ: 6.89 (2H, s), 5.85 (1H, d, J=5.1 Hz), 5.54 (1H, d, J=5.1 Hz), 5.00 (1H, t, J=6.6 Hz), 4.63 (1H, d, J=14.1 Hz), 4.14-4.05 (4H, m), 3.73 (1H, d, J=16.9 Hz), 3.63 (1H, br s), 2.93 (3H, s), 2.74-2.72 (4H, m), 2.62-2.58 (1H, m), 2.32-2.30 (2H, m), 2.11-2.04 (3H, m).
MS (m+1)=865.99

Example 97
Compound I-97
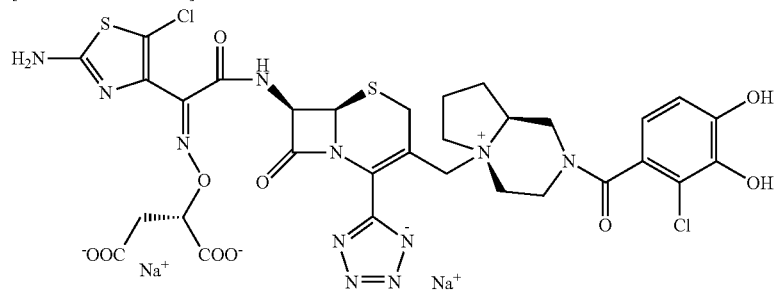
$^1$H-NMR (D$_2$O) δ: 6.96-6.93 (1H, m), 6.82-6.78 (1H, m), 5.86 (1H, d, J=4.8 Hz), 5.56-5.50 (1H, m), 5.00-4.98 (1H, m), 4.26-4.05 (3H, m), 3.78-2.96 (9H, n), 2.75-2.75 (2H, m), 2.24-1.60 (5H, m).
MS (m+1)=851.99
Example 98
Compound I-98
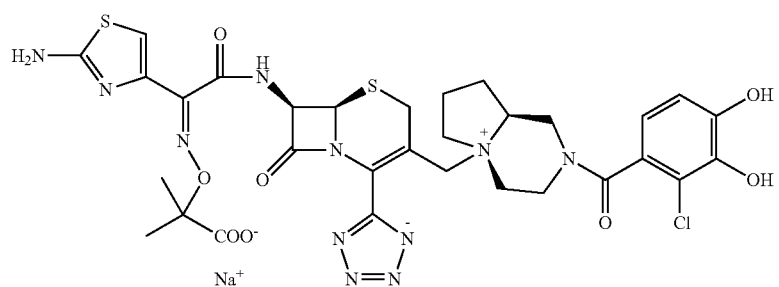
$^1$H-NMR (D$_2$O) δ: 6.93-6.90 (2H, m), 6.78-6.68 (1H, n), 5.90-5.90 (1H, m), 5.60-5.54 (1H, m), 4.32-3.95 (3H, m), 3.57-3.15 (10H, m), 2.36-1.61 (4H, m), 1.51 (6H, d, J=11.0 Hz).
MS (m+1)=788.02
Example 99
Compound I-99
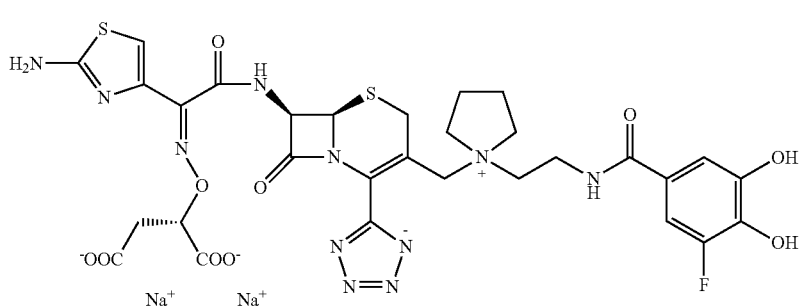

¹H-NMR (D₂O) δ: 7.19-7.09 (2.1H, m), 6.99 (0.9H, s), 5.86 (1.1H, d, J=5.0 Hz), 5.56 (1.00H, d, J=5.0 Hz), 4.98 (1.0H, dd, J=8.7, 4.6 Hz), 4.86 (2.2H, d, J=14.4 Hz), 4.16 (1.0H, d, J=14.4 Hz), 4.06 (1.0, d, J=17.0 Hz), 3.76 (1.2H, d, J=17.0 Hz), 3.62-3.26 (8.6H, m), 2.74-2.69 (2.0H, m), 2.05-1.98 (3.4H, m), 1.51-1.49 (0.9H, m).
MS (m+1)=790.03
Example 100
Compound I-100
[Chemical Formula 197]
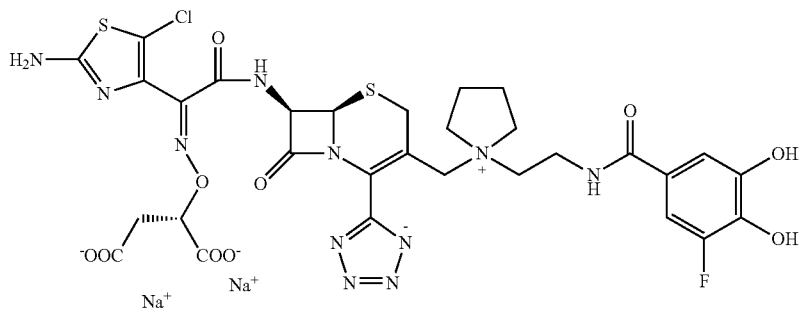
I-100
¹H-NMR (D₂O) δ: 7.16-7.13 (2H, m), 5.87 (1H, d, J=5.0 Hz), 5.55 (1H, d, J=5.0 Hz), 5.00 (1H, t, J=6.5 Hz), 4.87 (2H, d, J=14.4 Hz), 4.16 (1H, t, J=14.4 Hz), 4.06 (1H, d, J=16.9 Hz), 3.76 (1H, d, J=16.9 Hz), 3.62-3.26 (9H, m), 2.74 (2H, d, J=6.8 Hz), 2.18-1.93 (3H, m), 1.51-1.49 (1H, m).
MS (m+1)=824.02
Example 101
Compound I-101
[Chemical Formula 198]
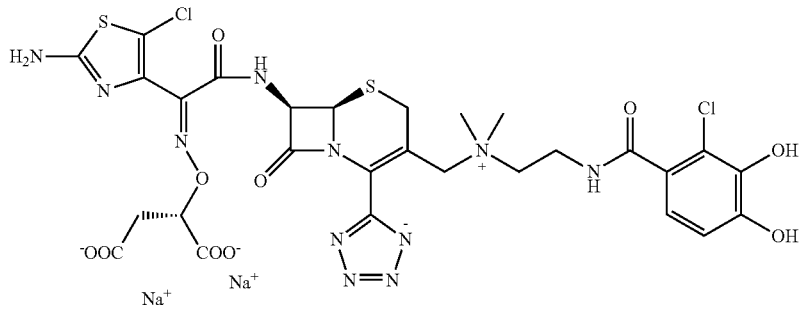
I-101
¹H-NMR (D₂O) δ: 6.94 (2H, d, J=8.4 Hz), 6.90 (2H, d, J=8.4 Hz), 5.86 (1H, d, J=5.0 Hz), 5.55 (1H, d, J=5.0 Hz), 4.99 (1H, t, J=6.6 Hz), 4.92 (1H, d, J=13.9 Hz), 4.19 (1H, d, J=13.9 Hz), 4.05 (1H, d, J=17.1 Hz), 3.76-3.59 (3H, m), 3.55-3.42 (1H, m), 3.22-3.15 (1H, m), 3.08 (3H, s), 2.92 (3H, s), 2.75 (2H, d, J=6.6 Hz).
MS (m+1)=813.90

Example 102
Compound I-102
[Chemical Formula 199]
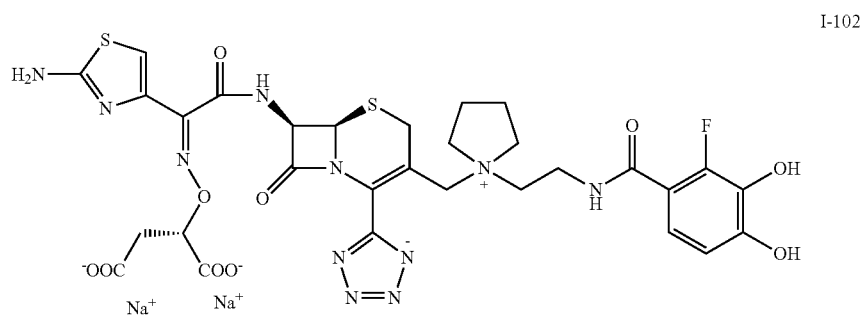
I-102
$^1$H-NMR (D$_2$O) δ: 7.14 (1H, t, J=8.7 Hz), 6.98 (1H, s), 6.78 (1H, d, J=8.7 Hz), 5.87 (1H, d, J=5.0 Hz), 5.56 (1H, d, J=5.0 Hz), 4.98 (1H, dd, J=8.9, 4.8 Hz), 4.87 (1H, d, J=14.4 Hz), 4.15 (1H, d, J=14.4 Hz), 4.07 (1H, d, J=16.9 Hz), 3.76 (1H, d, J=16.9 Hz), 3.62-3.23 (8H, m), 2.71 (2H, t, J=4.8 Hz), 2.09-2.03 (3H, m), 1.53-1.51 (1H, m).
MS (m+1)=790.00
Example 103
Compound I-103
[Chemical Formula 200]
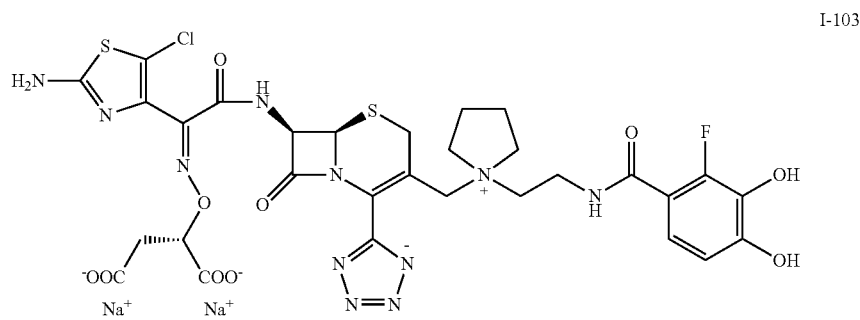
I-103
$^1$H-NMR (D$_2$O) δ: 7.15 (1H, t, J=8.8 Hz), 6.79 (1H, d, J=8.8 Hz), 5.87 (1H, d, J=5.0 Hz), 5.55 (1H, d, J=5.0 Hz), 5.00 (1H, t, J=6.7 Hz), 4.86 (2H, d, J=14.3 Hz), 4.15 (1H, d, J=14.3 Hz), 4.06 (1H, d, J=17.1 Hz), 3.75 (1H, d, J=17.1 Hz), 3.62-3.20 (8H, m), 2.75 (2H, d, J=6.7 Hz), 2.15-1.92 (3H, m), 1.51-1.49 (1H, m).
MS (m+1)=823.98

Example 104
Compound I-104
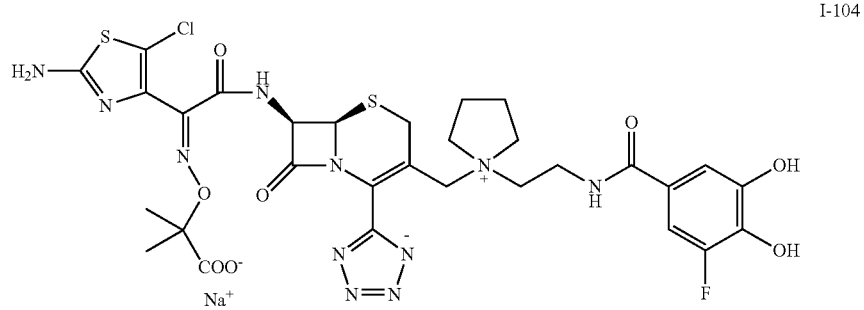
$^1$H-NMR (D$_2$O) δ: 7.13-7.11 (2H, m), 5.92 (1H, d, J=5.0 Hz), 5.58 (1H, d, J=5.0 Hz), 4.88 (1H, d, J=14.4 Hz), 4.11 (2H, t, J=15.2 Hz), 3.75 (1H, d, J=17.1 Hz), 3.56-3.24 (8H, m), 2.13-1.93 (3H, m), 1.53 (3H, s), 1.50 (3H, s), 1.42-1.25 (1H, m).
MS (m+1)=794.03
Example 105
Compound I-105
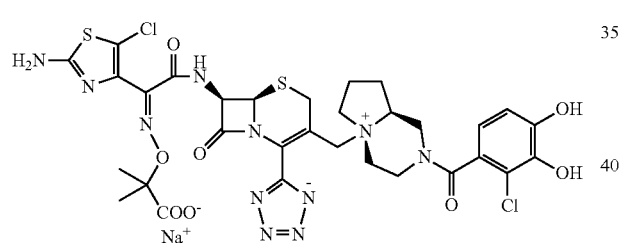
$^1$H-NMR (D$_2$O) δ: 7.00-6.87 (1H, m), 6.94-6.92 (1H, m), 6.85-6.72 (1H, m), 5.59-5.52 (1H, m), 5.04-4.97 (1H, m), 4.30-4.22 (1H, m), 4.17-3.92 (2H, m), 3.76-2.98 (9H, m), 2.44-1.57 (4H, m), 1.53 (3H, s), 1.50 (3H, s), 1.43-1.21 (1H, m).
MS (m+1)=821.93
Example 106
Compound I-106
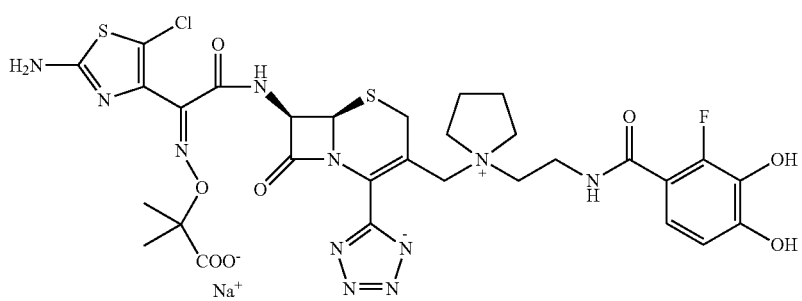
$^1$H-NMR (D$_2$O) δ: 7.15 (1H, t, J=8.7 Hz), 6.78 (1H, d, J=8.7 Hz), 5.93 (1H, d, J=5.0 Hz), 5.58 (1H, d, J=5.0 Hz), 4.14 (1H, d, J=13.8 Hz), 4.10 (1H, d, J=17.1 Hz), 3.76 (1H, d, J=17.1 Hz), 3.59-3.25 (8H, m), 2.18-1.90 (3H, m), 1.52 (3H, s), 1.50 (3H, s), 1.47-1.39 (1H, m).
MS (m+1)=793.92

Example 107
Compound I-107
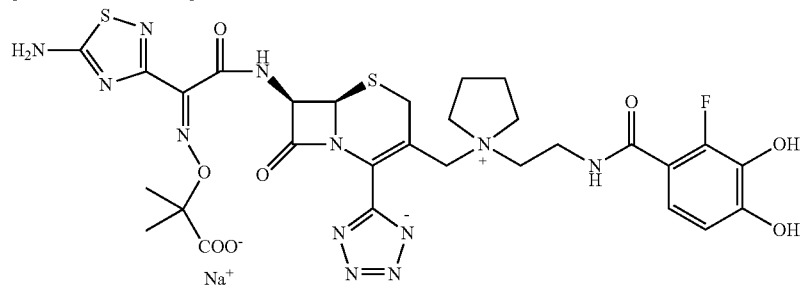
¹H-NMR (D₂O) δ: 7.15-7.10 (1H, br m), 6.76 (1H, d, J=8.6 Hz), 5.94 (1H, d, J=5.1 Hz), 5.59 (1H, d, J=5.1 Hz), 4.87 (1H, d, J=14.7 Hz), 4.15-4.08 (2H, m), 3.75 (1H, d, J=16.9 Hz), 3.59-3.24 (8H, m), 2.11-1.92 (3H, m), 1.55 (3H, s), 1.53 (3H, s), 1.46-1.36 (1H, m).
MS (m+1)=761.05
Example 108
Compound I-108
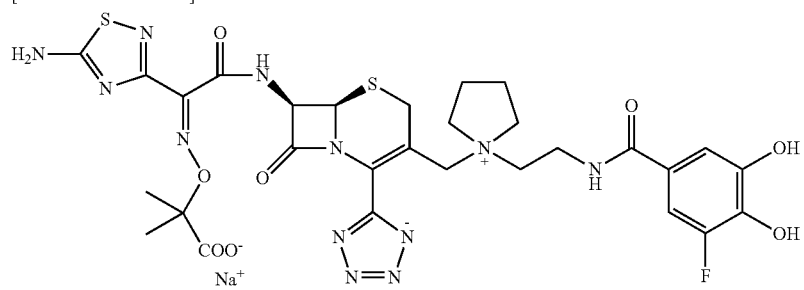
¹H-NMR (D₂O) δ: 7.15-7.08 (2H, m), 5.94 (1H, d, J=5.1 Hz), 5.59 (1H, d, J=5.1 Hz), 4.87 (1H, d, J=14.4 Hz), 4.16-4.07 (2H, m), 3.76 (1H, d, J=16.9 Hz), 3.56-3.30 (8H, m), 2.16-1.89 (3H, m), 1.55 (3H, s), 1.53 (3H, s), 1.45-1.36 (1H, m).
MS (m+1)=760.98
Example 109
Compound I-109
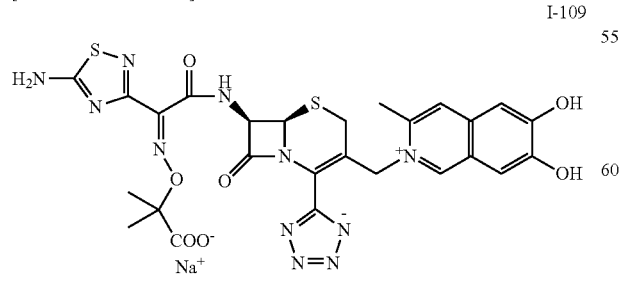
¹H-NMR (D₂O) δ: 8.63 (1H, s), 7.37 (1H, s), 7.21 (1H, s), 6.81 (1H, s), 5.93 (1H, d, J=4.8 Hz), 5.45 (1H, d, J=4.8 Hz), 5.41 (1H, d, J=16.6 Hz), 5.10 (1H, d, J=16.6 Hz), 3.48 (2H, d, J=18.2 Hz), 3.42 (2H, d, J=18.2 Hz), 2.29 (3H, s), 1.53 (3H, s), 1.50 (3H, s).
MS (m+1)=668.03
Example 110
Compound I-110
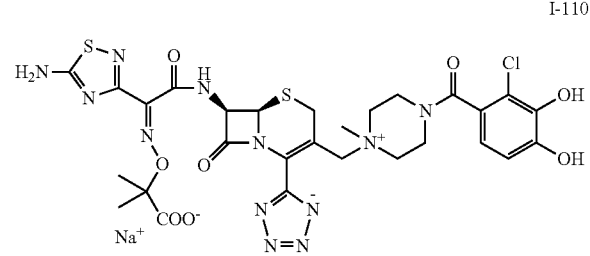
¹H-NMR (D₂O) δ: 6.96-6.89 (1H, m), 6.77-6.68 (1H, m), 5.96-5.93 (1H, m), 5.60-5.56 (1H, m), 5.08-4.88 (1H, m), 4.28-4.14 (1H, m), 4.07 (1H, t, J=16.1 Hz), 3.92-3.78 (1H, m), 3.76-3.39 (5H, m), 3.31-2.81 (7H, m), 1.55 (3H, s), 1.53 (3H, s).

MS (m+1)=763.00

Example 111

Compound I-111

[Chemical Formula 208]

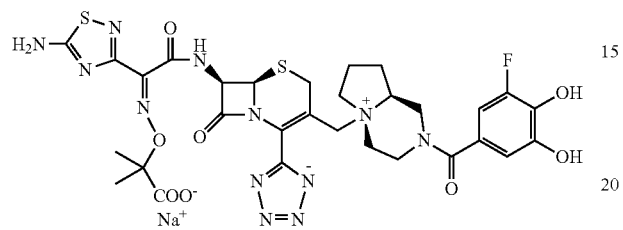

I-111

$^1$H-NMR (D$_2$O) δ: 6.87-6.73 (2H, m), 5.92 (1H, d, J=5.0 Hz), 5.58 (1H, d, J=5.0 Hz), 4.97 (1H, d, J=14.3 Hz), 4.26 (1H, d, J=14.3 Hz), 4.08-3.07 (11H, m), 1.96 (3H, dd, J=70.3, 49.0 Hz), 1.55 (3H, s), 1.53 (3H, s), 1.38 (1H, d, J=15.7 Hz).

MS (m+1)=773.08

Example 112

Compound I-112

[Chemical Formula 209]

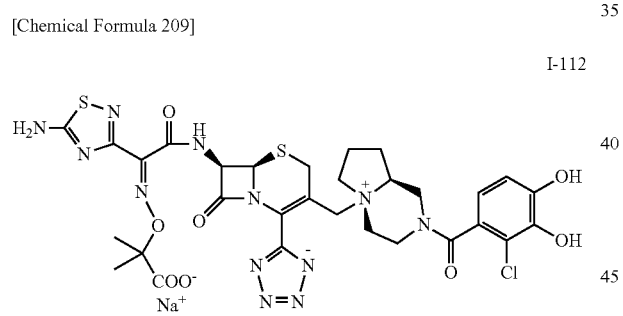

I-112

$^1$H-NMR (D$_2$O) δ: 6.98-6.88 (1H, m), 6.83-6.72 (1H, m), 5.98-5.90 (1H, m), 5.61-5.53 (1H, m), 4.35-2.93 (13H, m), 2.44-1.78 (3H, m), 1.55 (3H, s), 1.53 (3H, s), 1.43-1.28 (1H, m).

MS (m+1)=789.02

Example 113

Compound I-113

[Chemical Formula 210]

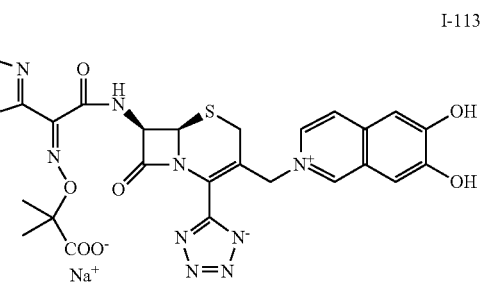

I-113

$^1$H-NMR (D$_2$O) δ: 8.60 (1H, s), 7.75 (1H, d, J=6.9 Hz), 7.55 (1H, d, J=6.9 Hz), 7.21 (1H, s), 6.89 (1H, s), 5.94 (1H, d, J=4.9 Hz), 5.47 (1H, d, J=4.9 Hz), 5.26 (1H, d, j=15.1 Hz), 5.12 (1H, d, J=15.1 Hz), 3.62 (1H, d, J=17.9 Hz), 3.42 (1H, d, J=17.9 Hz), 1.51 (3H, s), 1.49 (3H, s).

MS (m+1)=653.99

Example 114

Compound I-114

[Chemical Formula 211]

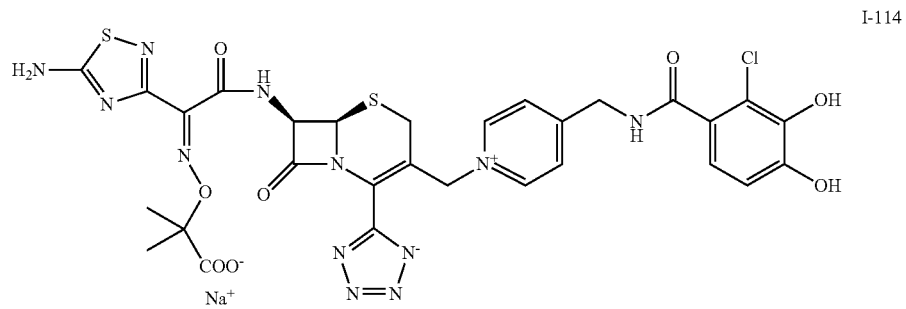

I-114

¹H-NMR (D₂O) δ: 8.82 (2H, d, J=6.1 Hz), 8.00 (2H, d, J=6.1 Hz), 7.03 (1H, d, J=8.4 Hz), 6.88 (1H, d, J=8.4 Hz), 5.94 (1H, d, J=5.0 Hz), 5.50 (1H, 6, J=5.0 Hz), 5.46 (1H, d, J=15.3 Hz), 5.39 (1H, d, J=15.3 Hz), 3.73 (1H, d, J=18.1 Hz), 3.43 (1H, d, J=18.1 Hz), 1.51 (3H, s), 1.50 (3H, s).
MS (m+1)=770.99
Example 115
Compound I-115
[Chemical Formula 212]
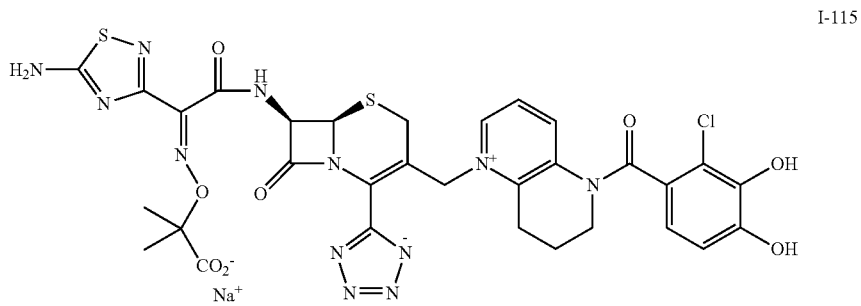
I-115
¹H-NMR (D₂O) δ: 8.63 (1H, br s), 8.19 (1H, br s), 7.63 (1H, br s), 6.99-6.91 (2H, m), 5.98 (1H, d, J=4.6 Hz), 5.66-5.54 (1H, m), 5.49 (1H, d, J=4.6 Hz), 5.31 (1H, d, J=15.7 Hz), 4.04 (1H, br s), 3.66-3.43 (3H, m), 3.09-2.95 (1H, m), 2.89-2.74 (1H, br m), 2.22-1.95 (2H, br m), 1.54 (3H, s), 1.52 (3H, s).
MS (m+1)=797.02
Example 116
Compound I-116
[Chemical Formula 213]
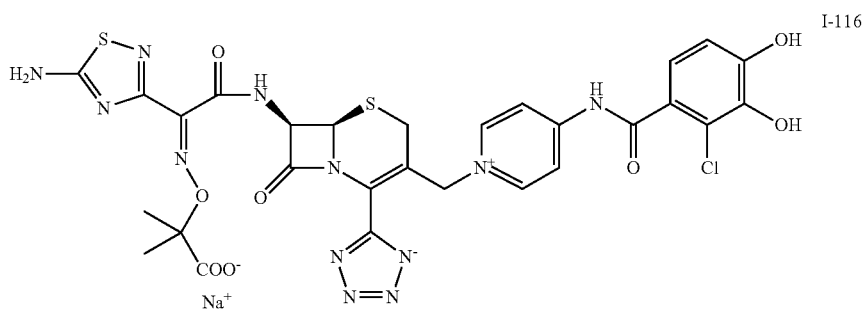
I-116
¹H-NMR (D₂O) δ: 8.59 (2H, br s), 8.02 (2H, br s), 7.07 (1H, d, J=8.2 Hz), 6.80 (1H, d, J=8.2 Hz), 5.93 (1H, d, J=4.4 Hz), 5.48 (1H, d, J=4.4 Hz), 5.25 (2H, s), 3.70 (1H, d, J=17.7 Hz), 3.41 (1H, d, J=17.7 Hz), 1.48 (3H, s), 1.47 (3H, s).
MS (m+1)=756.98

Example 117
Compound I-117
[Chemical Formula 214]
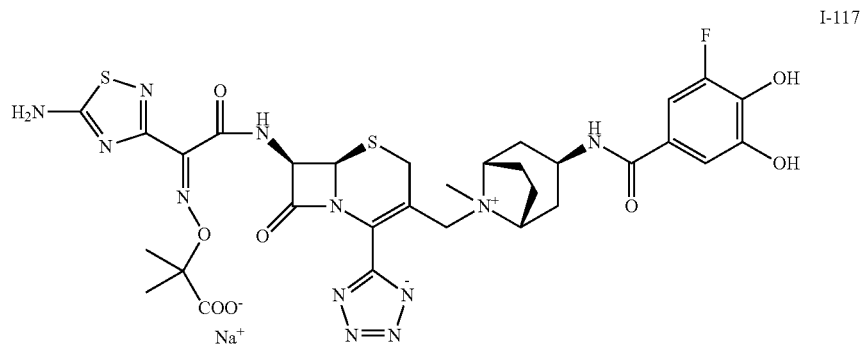
I-117
$^1$H-NMR (D$_2$O) δ: 7.07-7.00 (2H, m), 5.94 (1H, d, J=5.0 Hz), 5.59 (1H, d, J=5.0 Hz), 4.65 (1H, d, J=13.9 Hz), 4.16-3.93 (4H, m), 3.75 (1H, d, J=17.4 Hz), 3.64 (1H, br s), 2.93 (3H, s), 2.82-2.00 (8H, m), 1.56 (3H, s), 1.54 (3H, s).
MS (m+1)=787.04
Example 118
Compound I-118
[Chemical Formula 215]
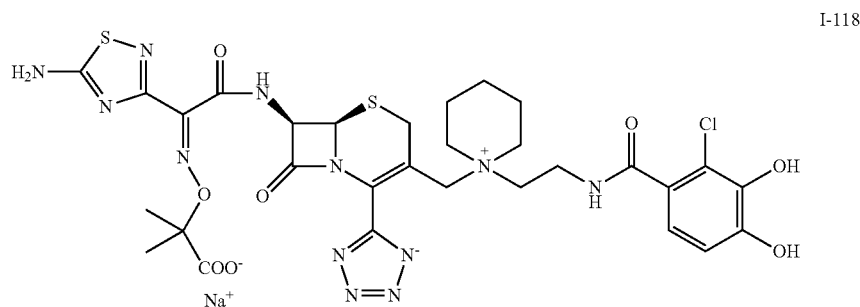
I-118
$^1$H-NMR (D$_2$O) δ: 6.93 (1H, d, J=8.3 Hz), 6.87 (1H, d, J=8.3 Hz), 5.93 (1H, d, J=5.0 Hz), 5.59 (1H, d, J=5.0 Hz), 4.93 (1H, d, J=14.4 Hz), 4.20 (1H, d, J=14.4 Hz), 4.10 (1H, d, J=17.2 Hz), 3.74 (1H, d, J=17.2 Hz), 3.61-3.51 (2H, m), 3.46-3.24 (4H, m), 3.14-3.02 (2H, m), 1.94-1.43 (12H, m).
MS (m+1)=791.29

Example 119
Compound I-119
[Chemical Formula 216]
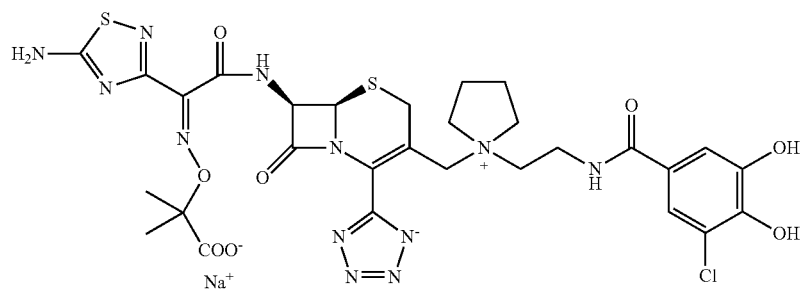
I-119
$^1$H-NMR (D$_2$O) δ: 7.29 (1H, br s), 7.14 (1H, br s), 5.93 (1H, d, J=5.1 Hz), 5.58 (1H, t, J=5.1 Hz), 4.16-4.02 (2H, m), 3.82-3.16 (10H, m), 2.14-1.87 (3H, m), 1.54 (3H, s), 1.52 (3H, s), 1.41-1.34 (1H, m).
MS (m+1)=777.04
Example 120
Compound I-120
[Chemical Formula 217]
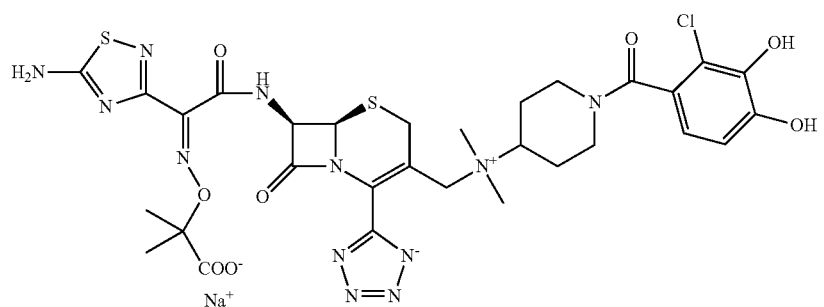
I-120
$^1$H-NMR (D$_2$O) δ: 6.97-6.89 (1H, m), 6.82-6.71 (1H, m), 5.95-5.90 (1H, m), 5.61-5.57 (1H, m), 5.01-4.86 (1H, m), 4.75-4.47 (1H, m), 4.12-3.98 (2H, m), 3.74-3.60 (2H, m), 3.52-3.43 (3H, m), 3.24-2.58 (9H, m), 2.32-1.65 (2H, m), 1.55 (3H, s), 1.53 (3H, s), 1.46-1.21 (1H, m).
MS (m+1)=791.04
Example 121
Compound I-121
[Chemical Formula 218]
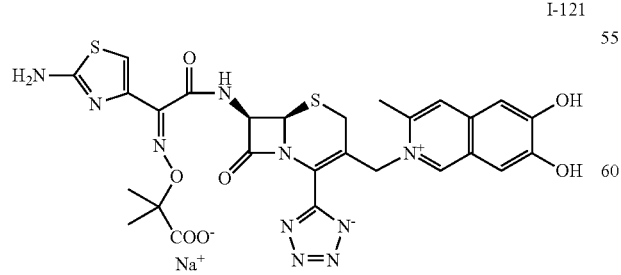
I-121
$^1$H-NMR (D$_2$O) δ: 8.56 (1H, s), 7.24 (1H, s), 7.06 (1H, s), 6.89 (1H, s), 6.70 (1H, s), 5.89 (1H, d, J=4.8 Hz), 5.39-5.33 (2H, m), 5.05 (1H, d, J=15.8 Hz), 3.42 (1H, d, J=18.2 Hz), 3.36 (1H, d, J=18.2 Hz), 2.26 (3H, s), 1.49 (3H, s), 1.45 (3H, s). MS (m+1)=667.02

Example 122
Compound I-122
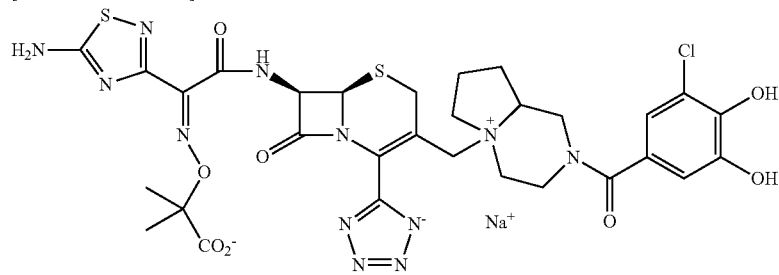
I-122
$^1$H-NMR (D$_2$O) δ: 6.87-6.77 (2H, m), 5.94 (1H, d, J=5.1 Hz), 5.59 (1H, d, J=5.1 Hz), 4.92 (1H, d, j=14.4 Hz), 4.20 (1H, d, J=14.4 Hz), 4.11 (1H, d, J=17.2 Hz), 3.79-3.72 (1H, m), 3.65-3.50 (2H, n), 3.41-3.28 (4H, m), 3.14-3.05 (2H, m), 1.89-1.61 (4H, m), 1.55 (3H, s), 1.53 (3H, s), 1.37 (1H, d, J=14.9 Hz).
Elemental analysis for C30H32ClN12O8S2Na1.5(H2O) 6.6
Calcd.: C, 38.27; H, 4.84; Cl, 3.77; N, 17.85; S, 6.81; Na, 3.66(%).
Found: C, 38.36; H, 4.96; Cl, 3.94; N, 17.75; S, 6.75; Na, 3.60 (%).
Example 123
Synthesis of Compound II-1
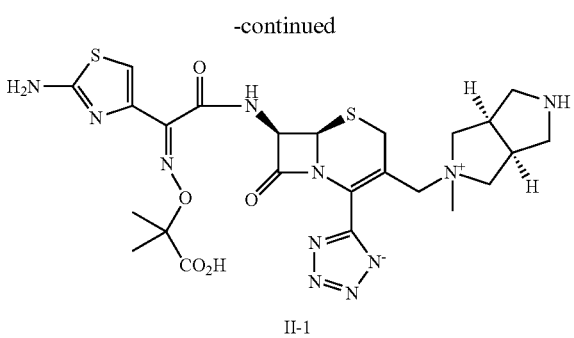
II-1
Synthesis of Compound 1k
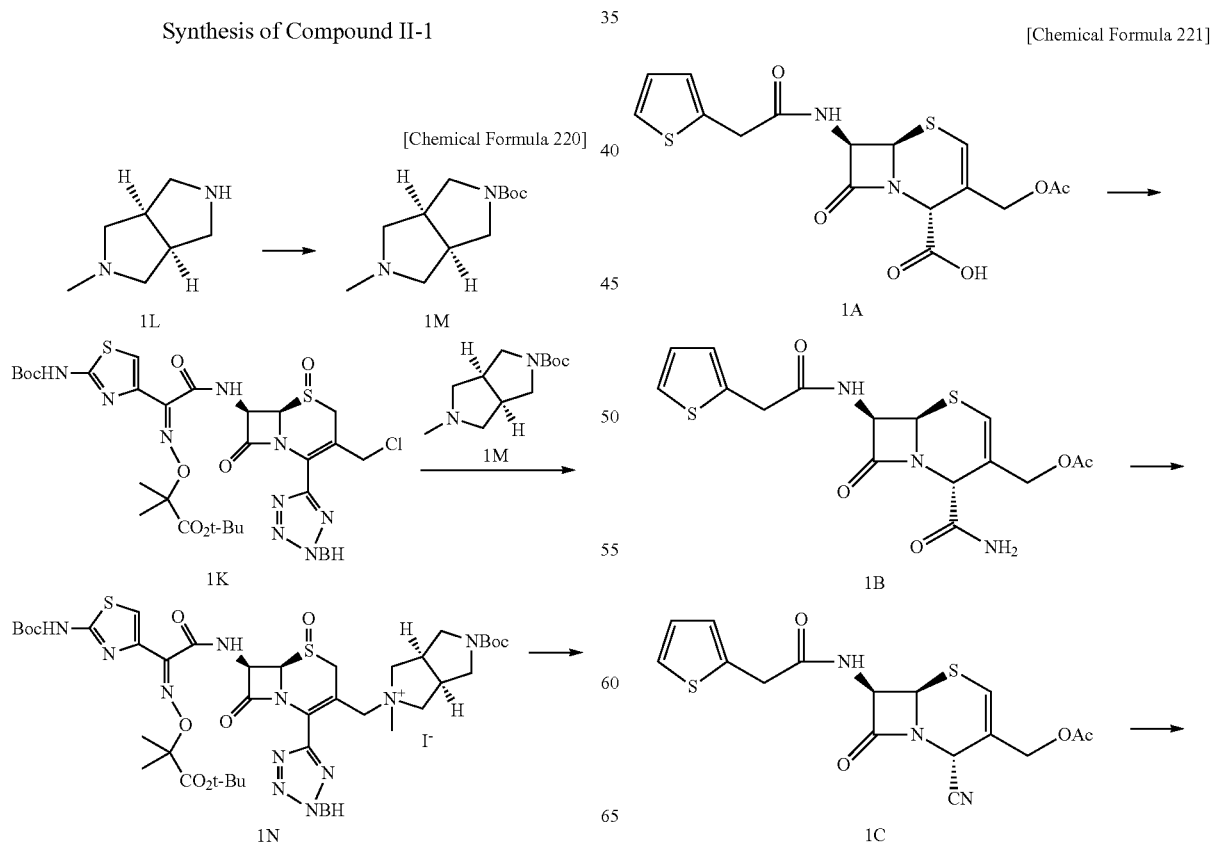

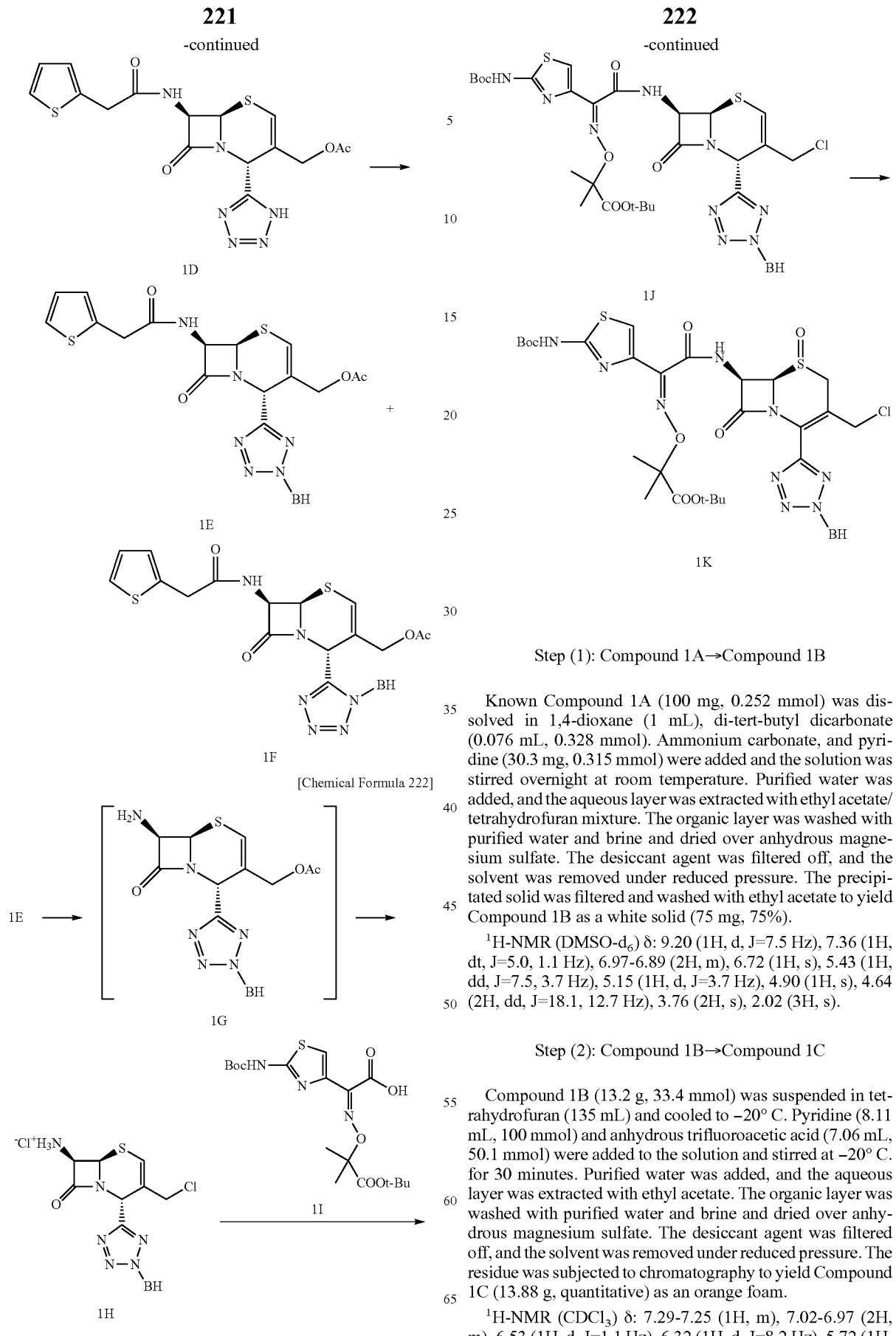

Step (1): Compound 1A→Compound 1B

Known Compound 1A (100 mg, 0.252 mmol) was dissolved in 1,4-dioxane (1 mL), di-tert-butyl dicarbonate (0.076 mL, 0.328 mmol). Ammonium carbonate, and pyridine (30.3 mg, 0.315 mmol) were added and the solution was stirred overnight at room temperature. Purified water was added, and the aqueous layer was extracted with ethyl acetate/tetrahydrofuran mixture. The organic layer was washed with purified water and brine and dried over anhydrous magnesium sulfate. The desiccant agent was filtered off, and the solvent was removed under reduced pressure. The precipitated solid was filtered and washed with ethyl acetate to yield Compound 1B as a white solid (75 mg, 75%).

$^1$H-NMR (DMSO-$d_6$) δ: 9.20 (1H, d, J=7.5 Hz), 7.36 (1H, dt, J=5.0, 1.1 Hz), 6.97-6.89 (2H, m), 6.72 (1H, s), 5.43 (1H, dd, J=7.5, 3.7 Hz), 5.15 (1H, d, J=3.7 Hz), 4.90 (1H, s), 4.64 (2H, dd, J=18.1, 12.7 Hz), 3.76 (2H, s), 2.02 (3H, s).

Step (2): Compound 1B→Compound 1C

Compound 1B (13.2 g, 33.4 mmol) was suspended in tetrahydrofuran (135 mL) and cooled to −20° C. Pyridine (8.11 mL, 100 mmol) and anhydrous trifluoroacetic acid (7.06 mL, 50.1 mmol) were added to the solution and stirred at −20° C. for 30 minutes. Purified water was added, and the aqueous layer was extracted with ethyl acetate. The organic layer was washed with purified water and brine and dried over anhydrous magnesium sulfate. The desiccant agent was filtered off, and the solvent was removed under reduced pressure. The residue was subjected to chromatography to yield Compound 1C (13.88 g, quantitative) as an orange foam.

$^1$H-NMR (CDCl$_3$) δ: 7.29-7.25 (1H, m), 7.02-6.97 (2H, m), 6.53 (1H, d, J=1.1 Hz), 6.32 (1H, d, J=8.2 Hz), 5.72 (1H, dd, J=8.2, 4.1 Hz), 5.26 (1H, d, J=1.1 Hz), 5.11 (1H, d, J=4.1 Hz), 4.73 (1H, d, J=13.2 Hz), 4.61 (1H, d, J=13.2 Hz), 3.87 (2H, s), 2.09 (3H, s).

Step (3): Compound 1C→Compound 1D

Compound 1C (273 mg, 0.723 mmol) was dissolved in 1,4-dioxane. Trimethylsilylazide (0.192 mL, 1.447 mmol) and dibutyltin oxide (18.01 mg, 0.072 mmol) were added, and the mixture was stirred at 90° C. for 1.5 hours. The mixture was cooled to room temperature, and the solvent was removed under reduced pressure. To the residue, purified water and ethyl acetate were added extracted with ethyl acetate. The organic layer was washed with purified water and brine and dried over anhydrous magnesium sulfate. The desiccant agent was filtered off, and the solvent was removed under reduced pressure. The residue was subjected to silica gel chromatography to yield Compound 1D (169.2 g, 56%).
$^1$H-NMR (DMSO-$d_6$) δ: 9.25 (1H, d, J=7.8 Hz), 7.36 (1H, dd, J=4.9, 1.4 Hz), 6.97-6.85 (3H, m), 5.90 (1H, d, J=1.5 Hz), 5.44 (1H, dd, J=7.8, 4.0 Hz), 5.14 (1H, d, J=4.0 Hz), 4.60 (1H, d, J=12.7 Hz), 4.53 (1H, d, J=12.7 Hz), 3.77 (2H, s), 1.90 (3H, s).

Step (4): Compound 1D→Compound 1E, Compound 1F

Compound 1D (85 mg, 0.243 mmol) was dissolved in tetrahydrofuran (1 mL). Diphenyldiazomethane (47.1 mg, 0.243 mmol) was added and stirred for 3.5 hours. Additional Diphenyldiazomethane (11.8 mg, 0.606 mmol) was added and stirred for 35 minutes. The solvent was removed under reduced pressure, obtained residue was subjected to silica gel chromatography to yielded Compound 1E (72 mg, 61%) and Compound 1F. The position of diphenylmethyl group was determined by Nuclear Overhauser Effect in 1H NMR.

Compound 1E: Less Polar One $^1$H-NMR (CDCl$_3$) δ: 7.41-7.12 (13H, m), 7.03-6.91 (2H, m), 6.41 (1H, s), 6.37 (1H, d, J=9.1 Hz), 5.80 (1H, s), 5.64 (1H, dd, J=9.1, 4.0 Hz), 5.26 (1H, d, J=4.0 Hz), 4.51 (1H, d, J=12.8 Hz), 4.39 (1H, J=12.8 Hz), 3.86 (2H, s), 1.89 (3H, s)

Compound 1E: More Polar One $^1$H-NMR (CDCl$_3$) δ: 7.42-7.33 (5H, m), 7.28-7.18 (4H, m), 7.13 (2H, dd, J=6.6, 3.0 Hz), 7.02-6.95 (2H, m), 6.90 (1H, s), 6.57 (1H, d, J=1.4 Hz), 6.30 (1H, d, J=9.1 Hz), 5.80 (1H, d, J=1.4 Hz), 5.01 (1H, dd, J=9.1, 4.0 Hz), 4.64 (1H, d, J=12.8 Hz), 4.58 (1H, d, J=4.0 Hz), 4.51 (1H, d, J=12.8 Hz), 3.82 (2H, s), 1.80 (3H, s).

Step (5): Compound 1E→Compound 1H

Phosphorous pentachloride (1.249 g, 6.00 mmol) was suspended in methylene chloride (15 mL), and the suspension was cooled to 0° C. Pyridine (0.53 mL, 6.60 mmol) and Compound 1E (1.689 g, 3.00 mmol) were added sequentially to the suspension. The suspension was stirred for 40 minutes at 0° C. and then warmed to room temperature and stirred for several minutes. The reaction solution was cooled to 0° C., and methanol (13.3 mL, 328 mmol) was added in one portion, and the mixture was warmed to room temperature. Purified water (130 mL) was added to the reaction solution, and the aqueous layer was extracted with methylene chloride.

The layer of methylene chloride was washed with sodium bicarbonate water and brine, and dried over anhydrous magnesium sulfate. The desiccant was filtered off, and a solution of 4 mol/L hydrochloric acid-ethyl acetate (2.25 mL, 9 mmol) was added to the organic layer, and the solution was stirred for 3 hours and 15 minutes. The solvent was removed in vacuo to yield jelly Compound 1H. (Yield: 2.02 g, 142%) Compound 1H was suspended in acetonitrile and scratched the wall surface with spatula to yield seed crystals of Compound 1H.

Separately, phosphorous pentachloride (9.12 g, 43.8 mmol) was suspended in methylene chloride (130 mL), and cooled to 0° C. Pyridine (3.90 mL, 48.2 mmol) and Compound 1E (12.8 g, 21.9 mmol) were added sequentially to the suspension, and the mixture was stirred for 45 minutes at room temperature. The reaction solution was cooled to −40° C., and methanol (13.3 mL, 328 mmol) was added in one portion, and the mixture was warmed to room temperature. Purified water (130 mL) was added to the reaction solution, and the aqueous layer was extracted with methylene chloride.

The layer of methylene chloride was washed with water and brine, and dried over anhydrous magnesium sulfate. The desiccant agent was filtered off, and a solution of 4 mol/L hydrochloric acid-dioxane (27.4 mL, 109 mmol) was added to the organic layer, and the mixture was stirred for 3 hours and 15 minutes at room temperature. 1,4-dioxane (150 mL) was added to the reaction solution, and the solvent was removed in vacuo to adjust the total amount about 30 mL. Acetonitrile (100 mL) was added to the resulting solution, and the above seed crystals of Compound 1H were added thereto, and the mixture was stirred at room temperature. The precipitated crystals were collected by filtration to yield Compound 1H (Yield: 7.92 g, 73%).
$^1$H-NMR (DMSO-$d_6$) δ: 8.82 (2H, br s), 7.72 (1H, s), 7.45-7.26 (11H, m), 7.00 (1H, d, J=1.2 Hz), 5.94 (1H, d, J=1.2 Hz), 5.19 (1H, d, J=4.2 Hz), 4.94 (1H, d, J=4.2 Hz), 4.48 (1H, d, J=11.8 Hz), 4.16 (1H, d, J=11.8 Hz).

Step (6): Compound 1H→Compound 1J

Compound 1H was suspended in ethylene chloride (40 mL), and cooled to −40° C. Compound II (3.54 g, 8.24 mmol) was added to the suspension. Phenylphosphoricdichloride (1.85 mL, 12.36 mmol) was added and N-methylmorpholine (3.62 mL, 33.0 mmol) was added dropwise, and the solution was stirred for 30 minutes at −40° C. Purified water was added to the reaction solution, and the aqueous layer was extracted with ethyl acetate. The resulting organic layer was washed with purified water and brine, and dried over anhydrous magnesium sulfate. The magnesium sulfate was filtered off, and the solvent was removed in vacuo to yield Compound 1J. (Yield: 7.8 g, quantitative)
$^1$H-NMR (CDCl$_3$) δ: 8.32 (1H, d, J=8.5 Hz), 7.41-7.15 (16H, m), 6.46 (1H, s), 5.99 (1H, s), 5.79 (1H, dd, J=8.5, 4.0 Hz), 5.37 (1H, d, J=4.0 Hz), 5.29 (1H, s), 4.15-4.01 (2H, m), 1.63 (3H, s), 1.60 (3H, s), 1.52 (9H, s), 1.42 (9H, s).

Step (7): Compound 1J→Compound 1K

Compound 1J (2.30 g, 2.7 mmol) was dissolved in methylene chloride (25 mL) and cooled to −40° C. Meta-chlorobenzoic acid (788 mg, 2.97 mmol) was added to the solution, and the solution was stirred for 1 hour and 15 minutes at −40° C. An aqueous solution of sodium hydrogen sulfite was added to the reaction solution, and methylene chloride was removed in vacuo. The concentrated solution was extracted with ethyl acetate, and the organic layer was washed with aqueous sodium bicarbonate, purified water and brine, and dried over anhydrous magnesium sulfate. The desiccant agent was filtered off, and the solvent was removed in vacuo. The resulting residue was subjected to silica gel chromatography to yield Compound 1K (Yield: 1.41 g, 60%).

Compound 1K was suspended in ethanol, and the wall surface was scratched with spatula to yield crystals.

$^1$H-NMR (CDCl$_3$) δ: 8.08 (1H, br s), 7.90 (1H, d, J=9.9 Hz), 7.39-7.18 (20H, m), 6.29 (1H, dd, J=9.7, 5.0 Hz), 5.13 (1H, d, J=12.4 Hz), 4.73 (1H, d, J=4.9 Hz), 4.29 (1H, d, J=12.1 Hz), 3.90 (1H, d, J=19.0 Hz), 3.50 (11H, d, J=19.0 Hz), 1.59 (6H, d, J=7.1 Hz), 1.56 (9H, s), 1.38 (10H, s).

Preparation of Compound 1M

A solution of 4 mol/L hydrochloric acid-ethyl acetate was added to the pentaacetate of Compound 1L (14.4 g, 33.7 mmol). The solution was stirred at room temperature for 30 minutes, and then concentrated and azeotropically dried with toluene. Tetrahydrofuran (45 mL) and ethanol (90 mL) were added, and di-tert-butyl dicarbonate (24.2 mL, 104 mmol) was added under ice-cooling and stirred at room temperature for 2.5 hours. To this solution, a solution of 5.3 mol/L sodium methoxide (45.9 mL, 243 mmol) was added and stirred at room temperature for 30 minutes. The solution was then added with silica gel, concentrated and subjected to chromatography. The fraction containing the desired compound was concentrated and dried under reduced pressure to yield Compound 1M (3.16 g, 40%).

$^1$H-NMR (CDCl$_3$) δ: 3.54-3.53 (3H, m), 3.25-3.22 (2H, m), 2.83-2.80 (2H, m), 2.66-2.62 (2H, m), 2.38-2.35 (2H, m), 2.32 (3H, s). 1.45 (9H, s).

Compound 1K+Compound 1M→Compound 1N

To a solution of Compound 1K (0.560 g, 0.646 mmol) in dimethylformamide (1.5 mL), sodium iodide (0.194 g, 1.29 mmol) was added. After stirring at 15° C. for 10 minutes, Compound 1M (0.146 g, 0.646 mmol) was added and stirred at 15° C. for two hours. To this solution, 0.2 mol/L hydrochloric aced was added, extracted with ethyl acetate, washed with water and brine, and dried over magnesium sulfate. The magnesium sulfate was removed and concentrated under reduced pressure to yielded Compound 1N (0.739 g). The obtained Compound 1N was used in the next step without purification.

Compound 1N→Compound II-1

The whole amount of the obtained Compound 1N was dissolved in methylene chloride (7.5 ml) and cooled to −40° C. Phosphorus tribromide (0.177 mL, 1.87 mmol) was added and stirred at −40° C. for one hour. To the reaction solution, anisole (0.682 mL, 6.24 mmol), 2 mol/L aluminum chloride/ nitromethane solution (3.12 mL, 6.24 mmol) were added and stirred at a temperature between −20° C. and 0° C. for 1.5 hours. After addition of 0.2 mol/L hydrochloric acid and acetonitrile to make insoluble materials dissolved, the solution was washed with diisopropylether. The aqueous layer was added with HP-20SS resin and concentrated and subjected to ODS column chromatography eluting with water-acetonitrile. The fraction containing desired compound was concentrated under reduced pressure and freeze-dried to yield Compound II-1 (0.140 g, 0.227 mmol) as white powder.

MS: 618.34 (M+H)

$^1$H-NMR (DMSO-d6) δ: 10.07-10.03 (1H, m), 7.27 (2H, br s), 6.76 (1H, s), 5.87 (1H, dd, J=8.5, 5.1 Hz), 5.61 (1H, d, J=5.1 Hz), 5.13-5.09 (1H, m), 4.15-2.70 (18H, m), 1.47 (3H, s), 1.40 (3H, s).

Example 124

Synthesis of Compound II-2

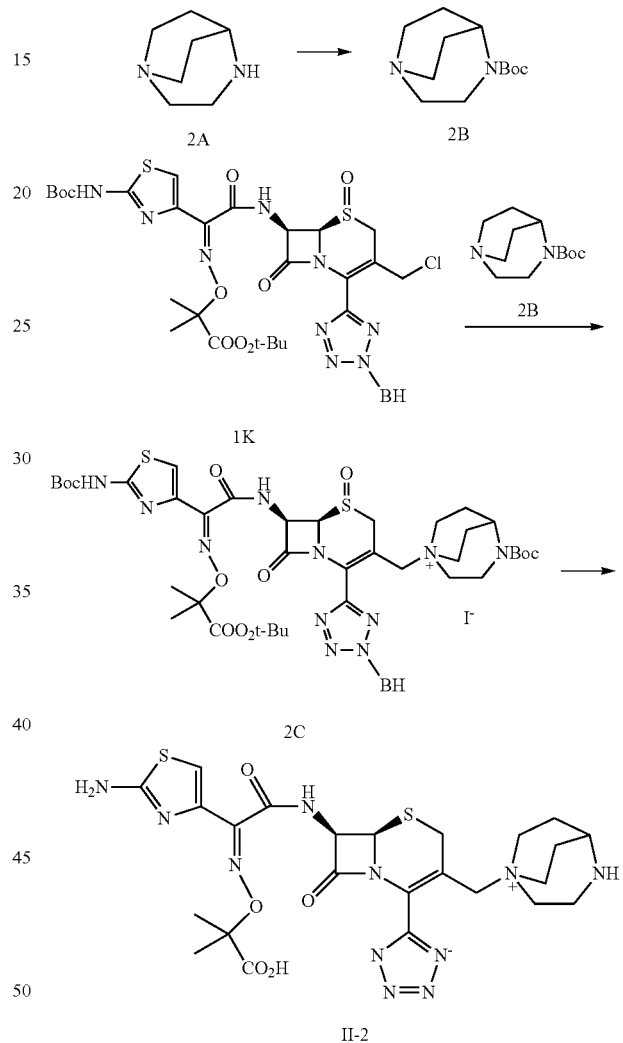

[Chemical Formula 223]

Preparation of Compound 2B

To a solution of Compound 2A (0.300 g, 2.38 mmol) in tetrahydrofuran (6 mL), di-tert-butyl dicarbonate (0.828 mL, 3.57 mmol) was added and stirred at room temperature for two hours. The suspension was filtered, washed with methanol, added with silica gel, concentrated and then subjected to silica gel chromatography. The fraction containing desired compound was concentrated and freeze-dried to yield Compound 2B (0.262 g, 49%).

$^1$H-NMR (DMSO-d$_6$) δ: 4.07-4.01 (1H, m), 3.49 (2H, t, J=5.8 Hz), 2.89-2.77 (6H, m, m), 1.88-1.79 (2H, m), 1.62-1.51 (2H, m), 1.39 (9H, s).

Compound 1K+Compound 2B→Compound 2C→Compound II-2

Compound 2C (0.141 g, 35%) was obtained from Compound 1K (0.560 g, 0.646 mmol) according to the procedure as described in the synthesis of Compound II-1.
MS: 618.31 (M+H)
$^1$H-NMR (DMSO-d$_6$) δ: 9.96 (1H, br s), 7.27 (2H, br s), 6.75 (1H, s), 5.86 (1H, dd, J=8.1, 5.2 Hz), 5.43 (1H, d, J=5.2 Hz), 5.15 (1H, d, j=12.6 Hz), 4.12-1.96 (18H, m), 1.46 (3H, s), 1.41 (3H, s).

Example 125

Synthesis of Compound II-3

[Chemical Formula 224]

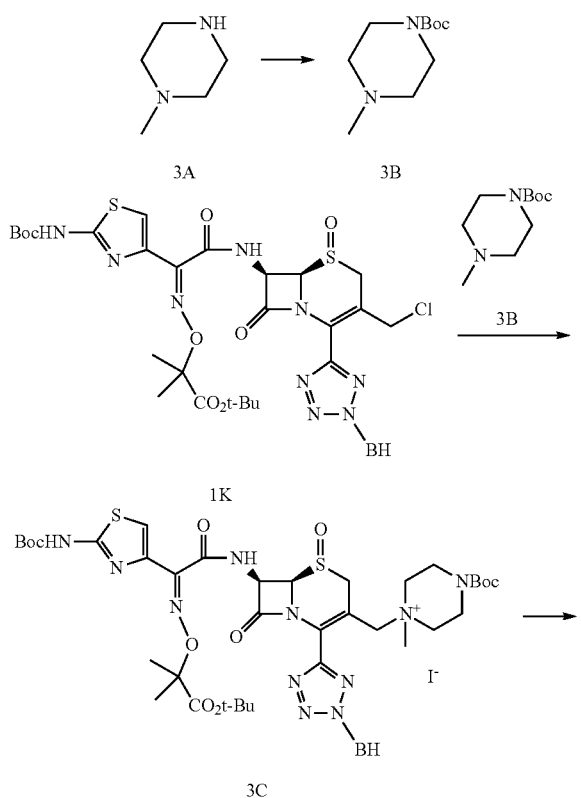

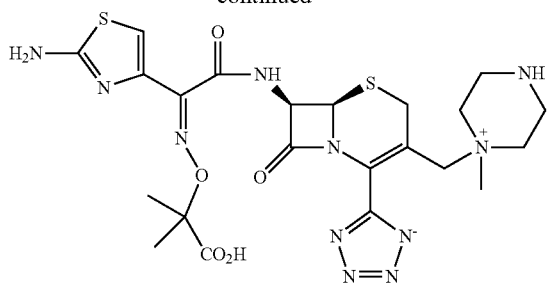

II-3

Preparation of Compound 3B

To a solution of Compound 3A (1.00 g, 10.0 mmol) in tetrahydrofuran (10 mL), di-tert-butyl dicarbonate (3.48 mL, 15.0 mmol) was added under ice-cooling and stirred at room temperature for 2 hours. The solution was concentrated and subjected to silica gel column chromatography. The fraction containing the desired compound was concentrated and dried under reduced pressure to yield Compound 3B (2.15 g, quantitative).
$^1$H-NMR (CDCl3) δ: 3.44 (4H, t, J=5.0 Hz), 2.34 (4H, t, J=5.0 Hz), 2.29 (3H, s), 1.46 (9H, s).

Compound 1K+Compound 3B→Compound 3C→Compound II-3

Compound II-3 (0.172 g, 36%) was obtained from Compound 1K (0.693 g, 0.800 mol) and Compound 3C according to the procedure as described in the synthesis of Compound II-1.
MS: 592.27 (M+H)
$^1$H-NMR (DMSO-d$_6$) δ: 9.50 (1H, d, J=7.5 Hz), 7.29-7.19 (3H, m), 6.73 (1H, s), 5.83 (1H, dd, J=8.3, 5.1 Hz), 5.42 (1H, d, J=5.1 Hz), 5.25-5.21 (1H, m), 4.07-3.04 (12H, m), 2.22 (3H, s), 1.46-1.43 (6H, m).

Example 126

Synthesis of Compound II-4

[Chemical Formula 225]

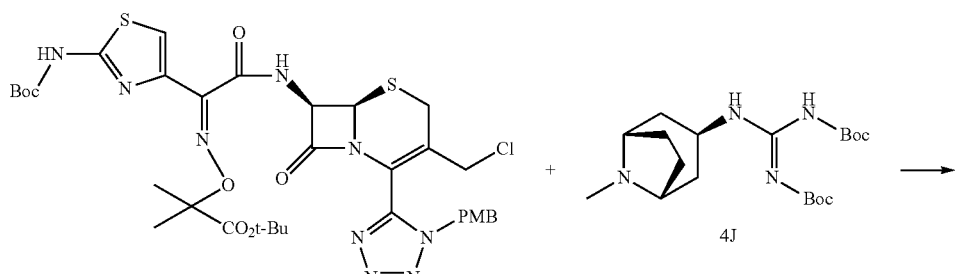

-continued
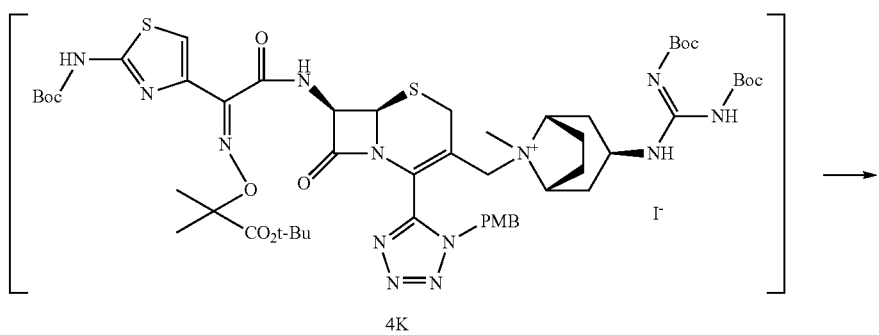
4K
II-4
Preparation of Compound 4I
[Chemical Formula 226]
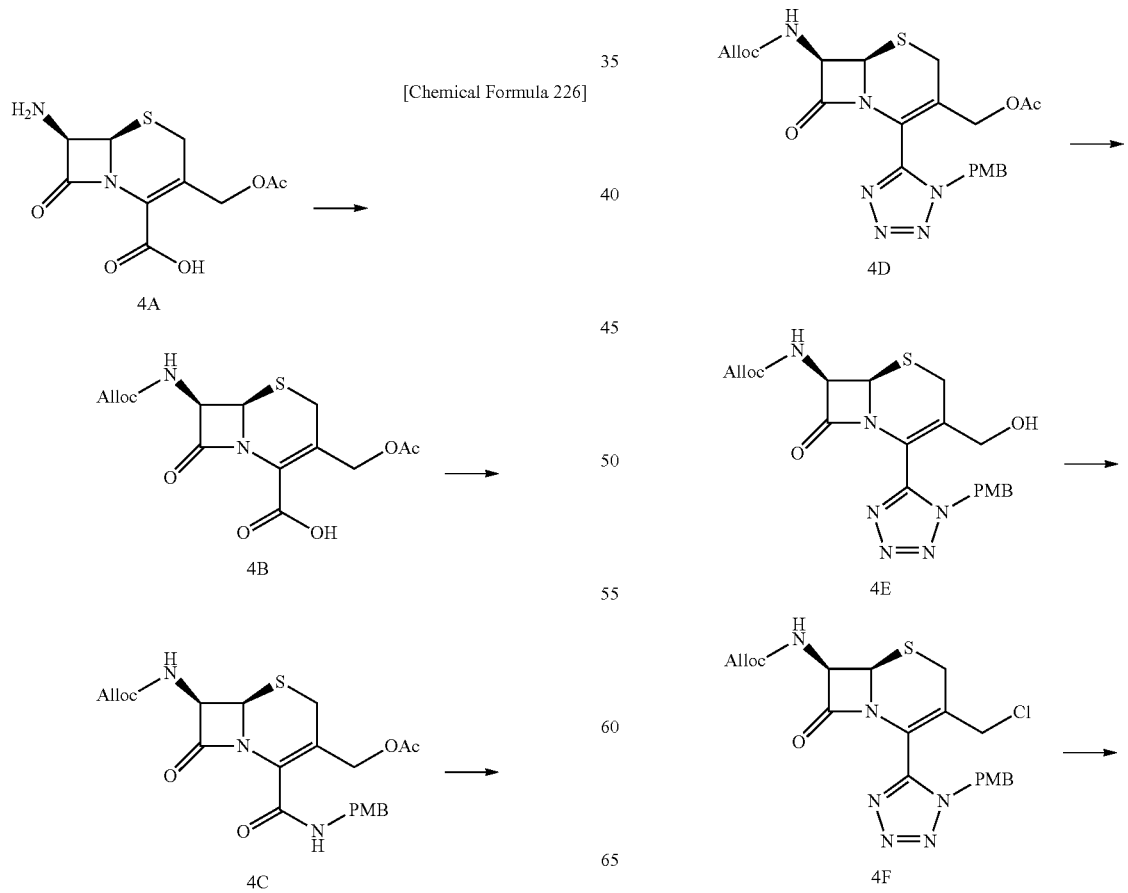

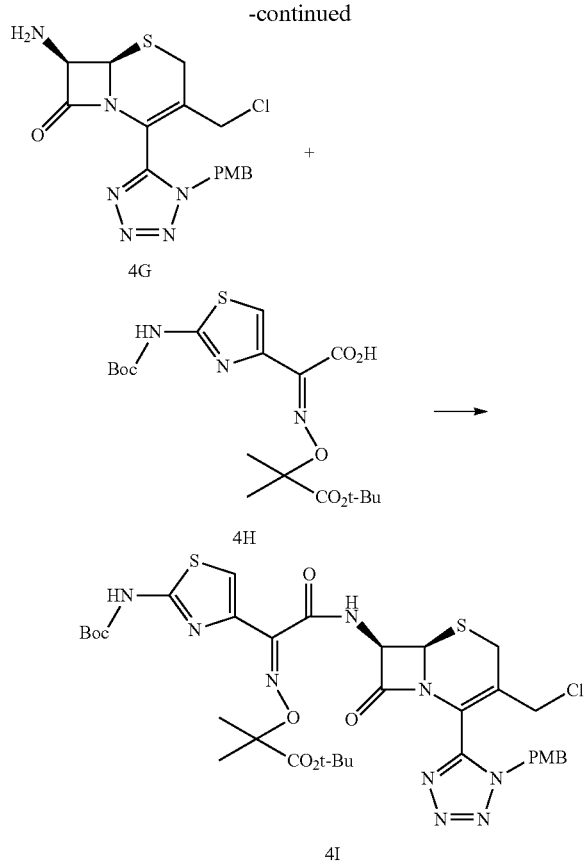

Step (1): Compound 4A→Compound 4B

Compound 4A (54.5 g, 200 mmol) and sodium bicarbonate (42.0 g, 500 mmol) were dissolved in water (1000 mL)/acetone (400 mL) mixture, and allyl chloroformate (25.6 mL, 240 mmol) was added under ice-cooling. The solution was stirred under ice-cooling for 30 minutes and at room temperature for one hour. The reaction solution was concentrated under reduced pressure, diluted with ethyl acetate and extracted with water. The aqueous layer was acidified, extracted with ethyl acetate, washed with brine, and dried magnesium sulfate. The magnesium sulfate was filtered off, and the filtrate was concentrated under reduced pressure to yield Compound 4B (66.39 g, 93%).

$^1$H-NMR (DMSO-$d_6$) δ: 8.42 (1H, d, J=8.73 Hz), 5.97-5.85 (1H, m), 5.54 (1H, dd, J=8.73, 4.84 Hz), 5.30 (1H, dd, J=17.23, 1.53 Hz), 5.20 (1H, dd, J=10.37, 1.53 Hz), 5.08 (1H, d, J=4.84 Hz), 4.98 (1H, d, J=12.73 Hz), 4.68 (1H, d, J=12.73 Hz), 4.53 (2H, d, J=5.19 Hz), 3.62 (1H, d, J=18.07 Hz), 3.48 (1H, d, J=18.07 Hz), 2.03 (3H, s).

Step (2): Compound 4B→Compound 4C

Compound 4B (65.0 g, 182 mmol) was suspended in methylene chloride (650 mL), and 1-chloro-N,N,2-trymethyl-1-propenylamine (29.0 mL, 219 mmol) was added under ice-cooling and stirred for 30 minutes under ice-cooling. After cooling the reaction mixture to −60° C., a solution of 4-methoxybenzylamine (59.6 mL, 456 mmol) in methylene chloride (60 mL) was added dropwise. Methylene chloride (200 mL) was added to the reaction mixture and stirred at a temperature between −60° C. and −50° C. for 10 minutes. The reaction mixture was diluted with methylene chloride/acetonitrile, and the organic layer was washed with hydrochloric acid, saturated aqueous sodium bicarbonate and brine, and dried over magnesium sulfate. The magnesium sulfate was filtered off, and the filtrate was concentrated under reduced pressure. Methylene chloride/diisopropyl ether was added, and precipitated crystals were flitted to yield Compound 4C (73.94 g, 85%).

$^1$H-NMR (DMSO-$d_6$) δ: 8.76 (1H, t, J=5.68 Hz), 8.46 (1H, d, J=8.85 Hz), 7.23 (2H, d, J=8.39 Hz), 6.85 (2H, d, J=8.24 Hz), 5.96-5.85 (1H, m), 5.40 (1H, dd, J=8.85, 4.80 Hz), 5.30 (1H, d, J=17.23 Hz), 5.20 (1H, d, J=10.37 Hz), 5.02 (1H, d, J=4.80 Hz), 4.94 (1H, d, J=12.58 Hz), 4.71 (1H, d, J=12.58 Hz), 4.54 (2H, d, J=5.68 Hz), 4.36 (1H, dd, J=14.83, 5.76 Hz), 4.24 (1H, dd, J=14.83, 5.76 Hz), 3.72 (3H, s), 3.56 (1H, d, J=17.62 Hz), 3.43 (1H, d, J=17.62 Hz), 2.02 (3H, s).

Step (3): Compound 4C→Compound 4D

Compound 4C (39.0 g, 82 mmol) and pyridine (23.17 mL, 287 mmol) were suspended in methylene chloride (400 mL). To this suspension, triphosgene (12.17 g, 41 mmol) was added and stirred for 30 min under ice-cooling. Trimethylsilylazide (12.17 g, 41 mmol) and methanol (8.32 mL, 205 mmol) were added under ice-cooling, and the reaction mixture was let stand overnight at room temperature. The reaction mixture was diluted with methylene chloride, and the organic layer was washed sequentially with hydrochloric acid, saturated aqueous sodium bicarbonate and brine, and dried over magnesium sulfate. The magnesium sulfate was filtered off, and the filtrate was concentrated under reduced pressure, and then subjected to silica gel column chromatography eluting with hexanes/ethyl acetate. The fraction containing the desired compound was concentrated under reduced pressure to yield Compound 40 (21.29 g, 52%).

$^1$H-NMR (DMSO-d) δ: 8.47 (1H, d, J=8.85 Hz), 7.25 (2H, d, J=8.54 Hz), 6.92 (2H, d, J=8.54 Hz), 5.98-5.85 (1H, m), 5.61-5.56 (3H, m), 5.27-5.33 (2H, m), 5.20 (1H, d, J=9.30 Hz), 4.54 (2H, d, J=5.34 Hz), 4.31 (1H, d, J=12.73 Hz), 4.18 (1H, d, J=12.73 Hz), 3.74 (3H, s), 3.66 (1H, d, J=18.00 Hz), 3.57 (1H, d, J=18.00 Hz), 1.90 (3H, s).

Step (4): Compound 4D→Compound 4E

Compound 4D (21.29 g, 42.5 mmol) was dissolved in tetrahydrofuran (300 mL), and 3 mol/L sulfuric acid (284 mL, 851 mmol) was added and stirred at 45° C. for 3 hours. The reaction mixture was diluted with ethyl acetate, and the organic layer was washed with water, saturated aqueous sodium bicarbonate and brine, and dried over magnesium sulfate. The magnesium sulfate was filtered off, and the filtrate was concentrated under reduced pressure to yield Compound 4E (19.63 g, 101%). The obtained Compound 4E was used directly in the next step without purification.

$^1$H-NMR (DMSO-$d_6$) δ: 8.45 (1H, d, J=9.00 Hz), 7.24 (2H, d, J=8.62 Hz), 6.91 (2H, d, J=8.62 Hz), 5.98-5.85 (1H, m), 5.52-5.48 (3H, m), 5.33-5.18 (3H, m), 5.09 (1H, t, J=5.34 Hz), 4.53 (2H, d, J=5.19 Hz), 3.74 (3H, s), 3.55-3.60 (4H, m).

Step (5): Compound 4E→Compound 4F

Compound 4E (19.63 g, 42.8 mmol) and pyridine (5.18 mL, 64.2 mmol) were suspended in methylene chloride (200 mL), and triphosgene (5.08 g, 17.13 mmol) was added and stirred for 2 hours under ice-cooling. The reaction mixture was diluted with methylene chloride, and the organic layer was washed sequentially with hydrochloric acid, saturated aqueous sodium bicarbonate and brine, and dried over magnesium sulfate. The magnesium sulfate was filtered off, and the filtrate was concentrated under reduced pressure, and then subjected to silica gel column chromatography, eluting with hexanes/ethyl acetate. The fraction containing the desired compound was concentrated under reduced pressure, and crystallized from diisopropyl ether to yield Compound 4F (9.15 g, 45%).

$^1$H-NMR (DMSO-d) δ: 8.48 (1H, d, J=9.00 Hz), 7.24 (2H, d, J=8.39 Hz), 6.91 (2H, d, J=8.39 Hz), 5.97-5.85 (1H, m), 5.65-5.52 (3H, m), 5.32-5.27 (2H, m), 5.20 (1H, d, J=10.37 Hz), 4.53 (2H, d, J=4.88 Hz), 4.02 (1H, d, J=11.82 Hz), 3.97 (1H, d, J=11.82 Hz), 3.73-3.59 (5H, m).

Step (6): Compound 4F→Compound 4G

Compound 4F (9.15 g, 19.18 mmol) and dimedone (8.07 g, 57.6 mmol) were suspended in methylene chloride (90 mL) and added with tetrakis triphenylphosphine palladium (1.108 g, 0.959 mmol) and stirred at room temperature for 1 hour. The reaction mixture was diluted with methylene chloride, washed with saturated aqueous sodium bicarbonate and brine, and dried over magnesium sulfate. The magnesium sulfate was filtered off, and the filtrate was concentrated under reduced pressure, and then subjected to silica gel column chromatography eluting with hexanes/ethyl acetate. The fraction containing the desired compound was concentrated under reduced pressure, and ethyl acetate/diisopropyl ether was added, and filtered and the precipitated crystals were corrected to yield Compound 4G (4.89 g, 65%).

$^1$H-NMR (DMSO-d$_5$) δ: 7.21 (2H, d, J=8.46 Hz), 6.90 (2H, d, J=8.46 Hz), 5.60 (1H, d, J=14.79 Hz), 5.49 (1H, d, J=14.79 Hz), 5.19 (1H, d, J=5.19 Hz), 4.82-4.74 (1H, m), 4.08 (1H, d, J=12.12 Hz), 4.03 (1H, d, J=12.12 Hz), 3.72 (3H, s), 3.67 (1H, d, J=17.92 Hz), 3.57 (1H, d, J=17.92 Hz), 2.38 (2H, d, J=9.46 Hz).

Step (7): Compound 4G+Compound 4H→Compound 4I

Compound 4G (2.00 g, 5.09 mmol) and Compound 4H (2.30 g, 5.35 mmol) were dissolved in methylene chloride (20 mL), and the solution was cooled to −40° C. Dichlorophenylphosphoric acid (1.14 mL, 7.64 mmol) was added. N-methylmorpholine (1.68 mL, 15.27 mmol) was added dropwise at −40° C., and the solution was stirred at −40° C. to −30° C. for 2 hours. The reaction mixture was diluted with methylene chloride, washed sequentially with 0.2 mol/L hydrochloric acid, saturated aqueous sodium bicarbonate and brine, and dried over magnesium sulfate. The magnesium sulfate was filtered off, and the filtrate was concentrated under reduced pressure, and then subjected to silica gel column chromatography eluting with hexanes/ethyl acetate. The fraction containing the desired compound was concentrated under reduced pressure to yield Compound 4I (3.54 g, 87%).

$^1$H-NMR (CDCl$_3$) δ: 8.38 (1H, d, J=8.66 Hz), 8.19 (1H, br s), 7.31 (1H, s), 7.15 (2H, d, J=8.69 Hz), 6.87 (2H, d, J=8.69 Hz), 5.91 (1H, dd, J=8.66, 4.99 Hz), 5.62 (1H, d, J=15.10 Hz), 5.44 (1H, d, J=15.10 Hz), 5.00 (1H, d, J=4.99 Hz), 3.96 (1H, d, J=12.20 Hz), 3.78 (3H, s), 3.73 (1H, d, J=12.20 Hz), 3.64 (1H, d, J=18.00 Hz), 3.39 (1H, d, J=18.00 Hz), 1.63 (3H, s), 1.55 (3H, s), 1.53 (9H, s), 1.39 (9H, s).

Compound 4I+Compound 4J→Compound II-4

To a solution of Compound 4I (804 mg, 1.00 mmol) in dimethylformamide (2 mL), sodium iodide (300 mg, 2.00 mmol) was added, and the solution was stirred at room temperature for 5 min. The solution was cooled to 0° C., and Compound 4J (382 mg, 1.00 mmol) was added and stirred at 0-10° C. for 5 hours. The reaction mixture was poured into ice-cooled solution of 5% sodium chloride (20 mL) containing sodium thiosulfate (1 g). The precipitated solid was collected by filtration, washed with water and then suspended in water. The suspension was freeze-dried to yield Compound 4K as a pale yellow solid. The obtained Compound 4K was used directly in the next step without purification.

The whole amount of the obtained Compound 4K was dissolved in methylene chloride (10 mL), and the solution was cooled to −40° C. To this solution, anisole (2.49 mL, 22.5 mmol) and 2 mol/L aluminum chloride/nitromethane solution (7.50 mL, 15.0 mmol) were added sequentially, and the solution was stirred at 0° C. for 1 hour. The reaction mixture was dissolved in water, 2 mol/L hydrochloric acid and acetonitrile, and the solution was washed with diisopropyl ether. The aqueous layer was added with HP20-SS resin, and acetonitrile was removed under reduced pressure. The obtained mixture was subjected to ODS column chromatography eluting with water/acetonitrile. A solution of the desired compound was concentrated under reduced pressure and freeze-dried to yield Compound II-4 as a while powder.

Yield: 183.0 mg (22%)

$^1$H-NMR (D$_2$O) δ: 6.95 (1H, s), 5.90 (1H, d, J=4.80 Hz), 5.57 (1H, d, J=4.80 Hz), 4.63 (1H, d, J=14.95 Hz), 4.12-3.99 (3H, m), 3.87-3.82 (1H, m), 3.72 (1H, d, J=16.47 Hz), 3.64-3.61 (1H, m), 2.89 (3H, br s), 2.78-2.51 (2H, m), 2.31-2.21 (2H, m), 2.10-1.94 (3H, m), 1.52 (3H, s), 1.49 (3H, s).

Elemental analysis for C26H35N13O5S2(H2O)5.2

Calcd: C, 40.69; H, 5.96; N, 23.73; S, 8.36(%)

Found: C, 40.53; H, 5.71; N, 23.78; S, 8.60(%)

Example 127

Synthesis of Compound II-5

[Chemical Formula 227]

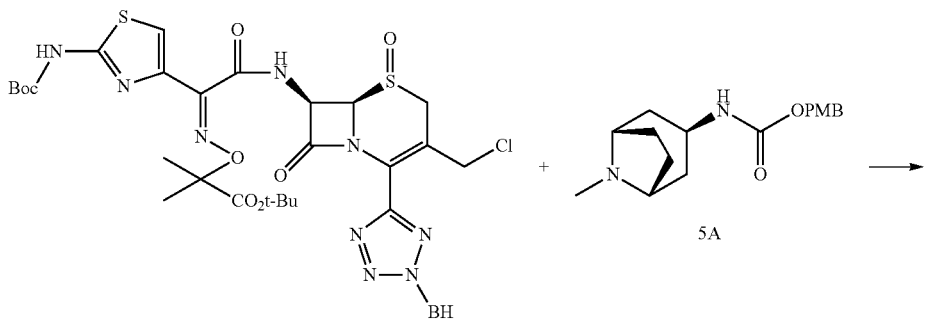

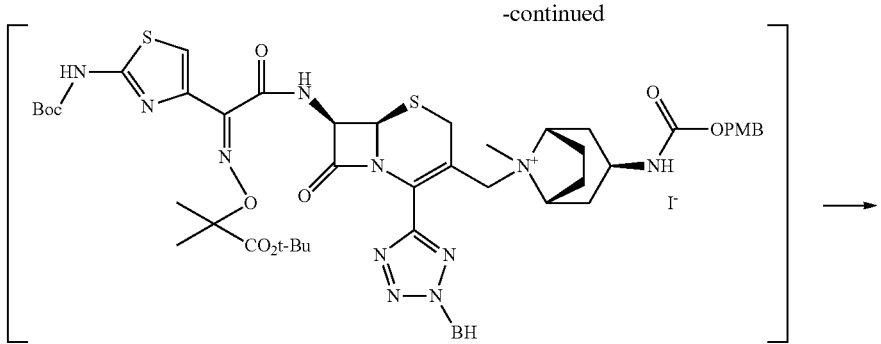

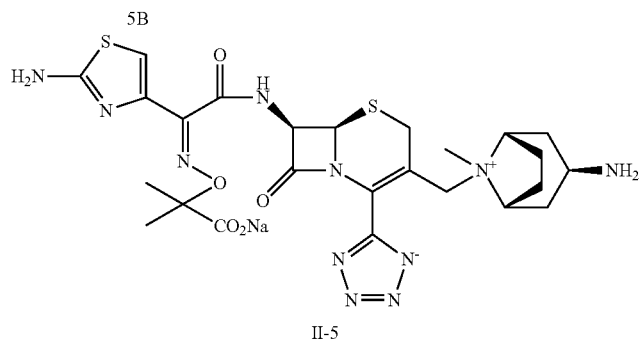

Compound 4I+Compound 5A→Compound II-5

A solution of Compound 41 (693 mg, 0.80 mmol) and Compound 5A (268 mg, 0.88 mmol) in dimethylformamide (1.5 mL) was cooled to 0° C., and the solution was added with sodium iodide (240 mg, 1.60 mmol) and stirred at 0-10° C. for 6 hours. Dimethylformamide (4.5 mL) was added, and the solution was cooled to −40° C. Phosphorus tribromide (151 μL, 1.60 mmol) was added and the solution was stirred at −40° C. for 30 min. The reaction mixture was poured into ice-cooled solution of 5% sodium chloride (20 mL) containing sodium thiosulfate (1 g). The precipitated solid was collected by filtration, washed with water and then suspended in water. The suspension was freeze-dried to yield Compound 5B as a pale yellow solid. The obtained Compound 5B was used directly in the next step without purification.

The whole amount of the obtained Compound 5B was dissolved in methylene chloride (10 mL), and the solution was cooled to −40° C. To this solution, anisole (1.57 mL, 14.4 mmol) and 2 mol/L aluminum chloride/nitromethane solution (4.80 mL, 9.6 mmol) were added sequentially, and the solution was stirred at 0° C. for 1 hour. The reaction mixture was dissolved in water, 2 mol/L hydrochloric acid and acetonitrile, and the solution was washed with diisopropyl ether. The aqueous layer was added with HP20-SS resin, and acetonitrile was removed under reduced pressure. The obtained mixture was subjected to ODS column chromatography eluting with water/acetonitrile. A solution of the desired compound was concentrated under reduced pressure and freeze-dried to yield Compound II-5 as a pale yellow powder.

Yield: 259.6 mg, (43%)

$^1$H-NMR (D$_2$O) δ: 6.95 (1H, s), 5.91 (1H, d, J=4.88 Hz), 5.58 (1H, d, J=4.8 Hz), 4.66 (1H, d, J=14.64 Hz), 4.12-4.04 (3H, m), 3.81-3.66 (3H, m), 2.91 (3H, br s), 2.80-2.65 (2H, m), 2.43-1.88 (5H, m), 1.52 (3H, s), 1.49 (3H, s).

Elemental analysis for C25H33N11O5S2(H2O)5.6

Calcd: C, 40.99; H, 6.08; N, 21.03; S, 8.75(%)

Found: C, 40.99; H, 5.87; N, 21.01; S, 8.91(%)

Example 128 and Example 129

Synthesis of Compound II-6 and compound II-7

[Chemical Formula 228]

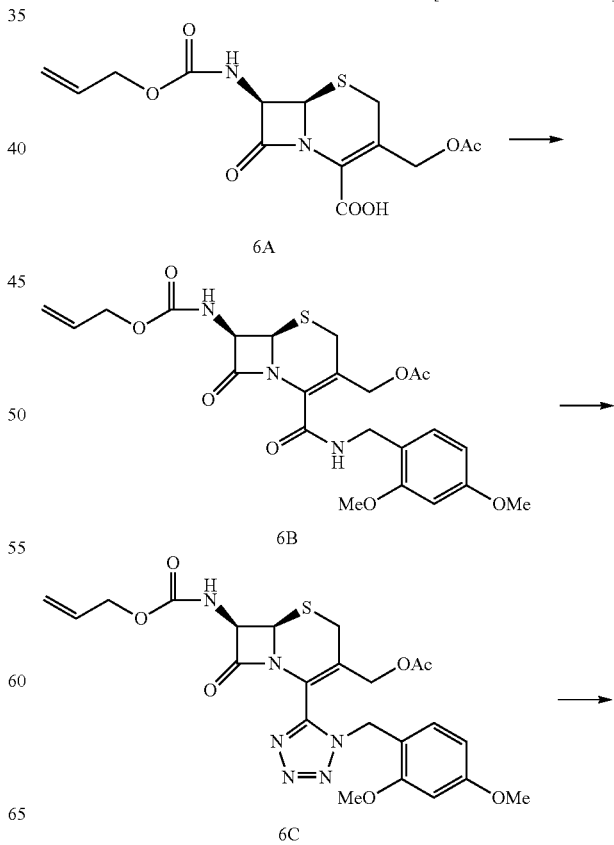

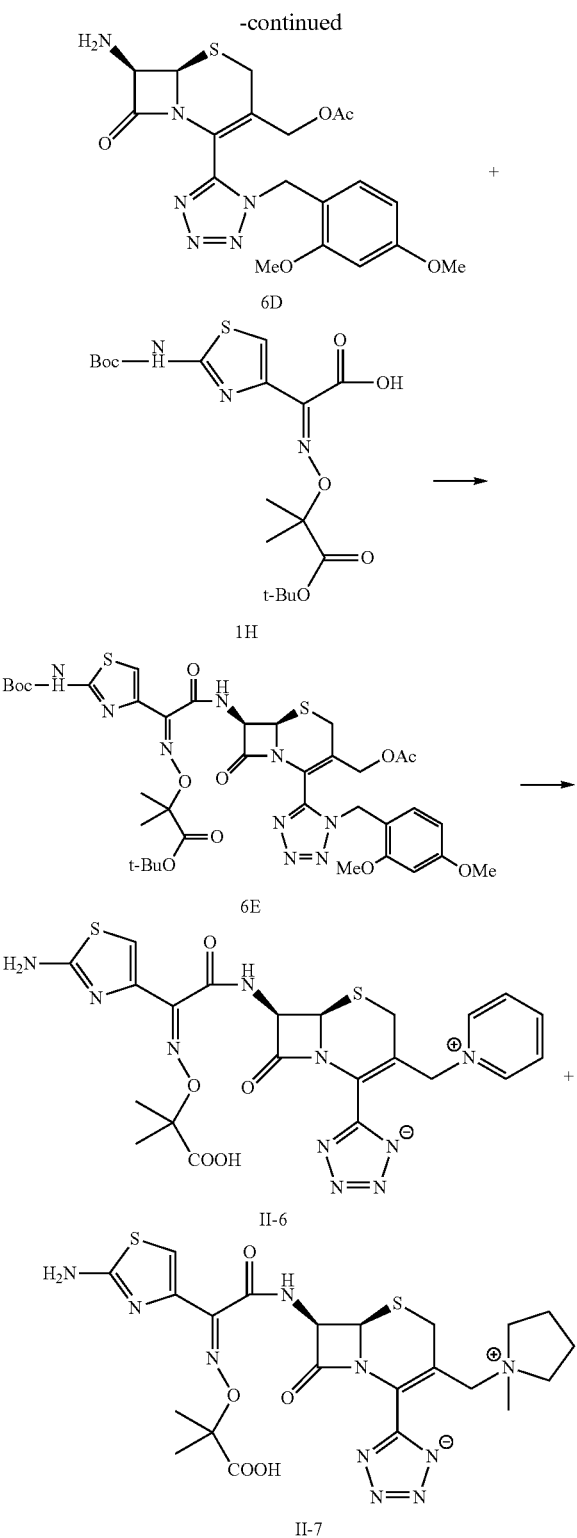

Step (1): Compound 6A→Compound 6B

To a solution of Compound 6A (26.5 g), dimethoxybenzy-lamine (14.85 g) in methylene chloride (120 mL), WSCD (18.4 g) was added under ice-cooling. After stirring at room temperature for 3 hours, the solution was diluted with ethyl acetate, and washed with diluted hydrochloric acid and water.

The residue was crystallized from methylene chloride/ether to yield Compound 6B (26.4 g).

$^1$H-NMR (CDCl3) δ: 2.01 (3H, s), 3.41, 3.55 (2H, AB-q), 3.73 (3H, s), 3.76 (3H, s), 4.48-4.52 (2H, m), 4.70, 4.91 (2H, AB-q, J=12.6 Hz), 5.00 (1H, d, J=4.8 Hz), 5.14-5.33 (2H, m), 5.39 (1H, dd, J=4.8, 9.0 Hz), 5.86-5.93 (1H, m), 6.4-6.52 (2H, m), 7.17 (1H, d, J=8.4 Hz), 8.42 (1H, d, J=8.7 Hz), 8.50-8.53 (1H, m)

MS (ESI): 506.5$^+$ (M+H)$^+$

Step (2): Compound 6B→Compound 6C

Compound 6B (6.5 g) was dissolved in methylene chloride (100 mL), and pyridine (2.06 mL) and then PCl$_5$ (3.48 mL) were added under ice-cooling, and the solution was stirred for 80 min. MeSiN$_3$ (8.53 mL), pyridine (6.68 mL) and methanol (2.6 mL) were added sequentially, and the solution was stirred at room temperature for 1.5 hours and at 40° C. for 4 hours. The solution was washed with diluted hydrochloric acid and then brine, and concentrated. The residue was purified on silica gel chromatography to yield Compound 6C (4.02 g).

$^1$H-NMR (CDCl3) δ: 2.01 (3H, s), 3.36, 3.50 (2H, AB-q), 3.75 (3H, s), 3.81 (3H, s), 4.33, 4.41 (28, AB-q, J=12.9 Hz), 4.56-4.63 (2H, m), 4.90 (1H, d, J=4.8 Hz), 5.23-5.58 (3H, m), 5.57 (1H, dd, J=4.8, 12.0 Hz), 5.86-5.59 (1H, m), 6.43-6.50 (3H, m), 7.07 (1H, d, J=8.1 Hz)

MS (ESI): 531.4$^+$ (M+H)$^+$

Step (3): Compound 6C→Compound 6D

To a solution of Compound 6C (4.00 g) and dimedone (3.17 g) in methylene chloride (40 mL), Ph$_3$P (250 mg) and then (Ph$_3$P)$_4$Pd (250 mg) were added at room temperature, and the solution was stirred for 2.5 hours. The solution was concentrated to 20 mL and washed with aqueous NaHCO$_3$ solution and water, and concentrated to yield Compound 6D (3.31 g).

$^1$H-NMR (CDCl3) δ: 2.00 (3H, s), 3.73 (3H, s), 3.79 (3H, s), 4.25, 4.33 (2H, AB-q, J=10.5 Hz), 4.92 (1H, d, J=5.1 Hz), 5.51 (1H, d, J=5.1 Hz), 6.41-6.48 (2H, m), 7.08 (2H, m), 7.62-7.70 (1H, m)

MS (ESI): 448$^+$ (M+H)$^+$

Step (4): Compound 6D→Compound 6E

WSCD (1.88 g) was added to a solution of Compound 6D (3.31 g) and Compound 1H (3.24 g) in methylene chloride (50 mL), and the solution was stirred for 30 min under ice-cooling. The solution was diluted with ethyl acetate, washed with water, aqueous NaHCO$_3$ solution and brine, and concentrated. The residue was purified on silica gel chromatography to yield Compound 6E (3.10 g).

$^1$H-NMR (CDCl3) δ: 1.40 (9H, s), 1.41 (9H, s), 1.61 (3H, s), 1.63 (3H, s), 3.13, 3.47 (2H, AB-q, J=18.0 Hz), 3.75 (3H, s), 3.80 (3H, s), 4.23, 4.37 (2H, AB-q, J=10 Hz), 4.98 (1H, m), 7.70-3.31 (3H, m), 8.28 (1H, d, J=8.1 Hz),

MS (ESI): 859.8$^+$ (M+H)$^+$

Step (5): Compound 6E→Compound II-6

Compound 6E (257 mg) was dissolved in methylene chloride (2 mL), and the solution was cooled to −60° C. and Me$_3$Si—I (0.7 mL) was added. The solution was stirred for 20 min at room temperature and concentrated under reduced pressure. The residue was dissolved in DMF (2 mL). Pyridine (0.15 mL) was added to the solution and the solution was stirred at room temperature for 1 hour. Isopropyl ether (20 mL) was added, and the precipitated gummy material was collected and dissolved in methylene chloride (0.5 mL). Anisole (0.20 mL) and then TFA (4 mL) were added, and the solution was stirred for 40 min. Solvent was concentrated, and isopropyl ether (20 mL) was added. Precipitation was corrected by filtration, which was then purified on HP-20 column chromatography. The eluted solution was freeze-dried to yield Compound II-6 (49 mg).

¹H-NMR (d-DMSO) δ: 1.48 (3H, s), 1.50 (3H, s), 3.28, 3.66 (2H, AB-q, J=17.7 Hz), 5.35, 5.43 (2H, AB-q, J=13.8 Hz), 5.33 (1H, d, J=5.1 Hz), 5.83 (1H, dd, J=5.1, 8.7 Hz), 7.12 (2H, s), 7.59 (1H, s), 8.20-8.24 (2H, m), 8.61-8.66 (2H, m), 9.32-9.44 (3H, m).

MS (ESI): 571.3⁺ (M+H)⁺

Step (6): Compound 6E→Compound II-7

Compound 6E (215 mg) was dissolved in methylene chloride (2 mL) and the solution was cooled to −60° C. Me₃Si—I (0.21 mL) was added to the solution, and the solution was stirred at room temperature for 20 min and concentrated under reduced pressure. The residue was dissolved in DMF (2 mL), and methylpyrrolidine (0.07 mL) was added. The solution was stirred at room temperature for 1.5 hours and let stand at −20° C. for two days. Isopropyl ether (20 mL) was added, and precipitated gummy material was collected and dissolved in methylene chloride (0.5 mL). Anisole (0.20 mL) and then TFA (4 mL) were added, and the solution was stirred for 40 min. Solvent was concentrated, and isopropyl ether (20 mL) was added, and precipitation was collected by filtration and purified on HP-20 column chromatography. The eluted solution was freeze-dried to yield Compound II-7 (31 mg).

¹H-NMR (d6-DMSO) δ: 1.80-2.16 (4H, m), 2.77 (3H, s), 3.05-3.75 (4H, m), 3.70, 3.91 (2H, AB-q, J=17.0 Hz), 4.10, 4.89 (2H, AB-q, J=13.8 Hz), 5.43 (1H, d, J=4.8 Hz), 5.85 (1H, bb, J=4.8, 7.2 Hz), 6.72 (1H, s), 7.20 (2H, bs), 7.30 (1H, bs), 7.60 (1H, s), 9.43 (1H, d, J=8.7 Hz)

MS (ESI): 577.3+ (M+H)⁺

Example 130

Synthesis of Compound II-8

[Chemical Formula 229]

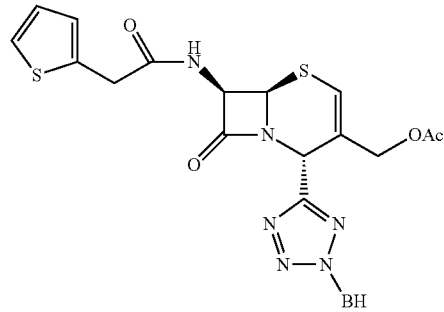

8A

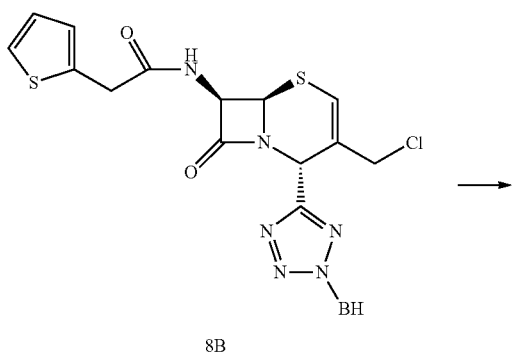

8B

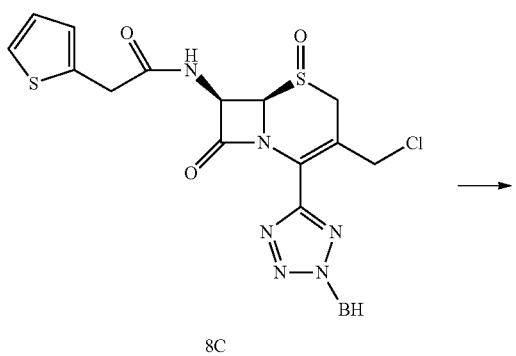

8C

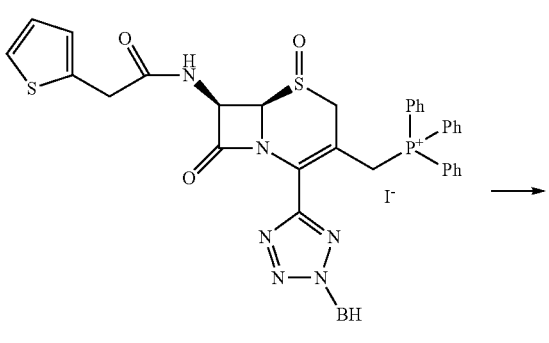

8D

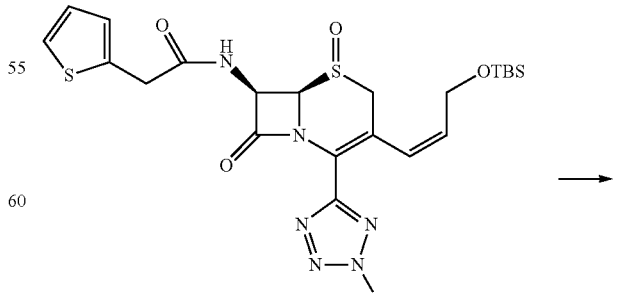

8E

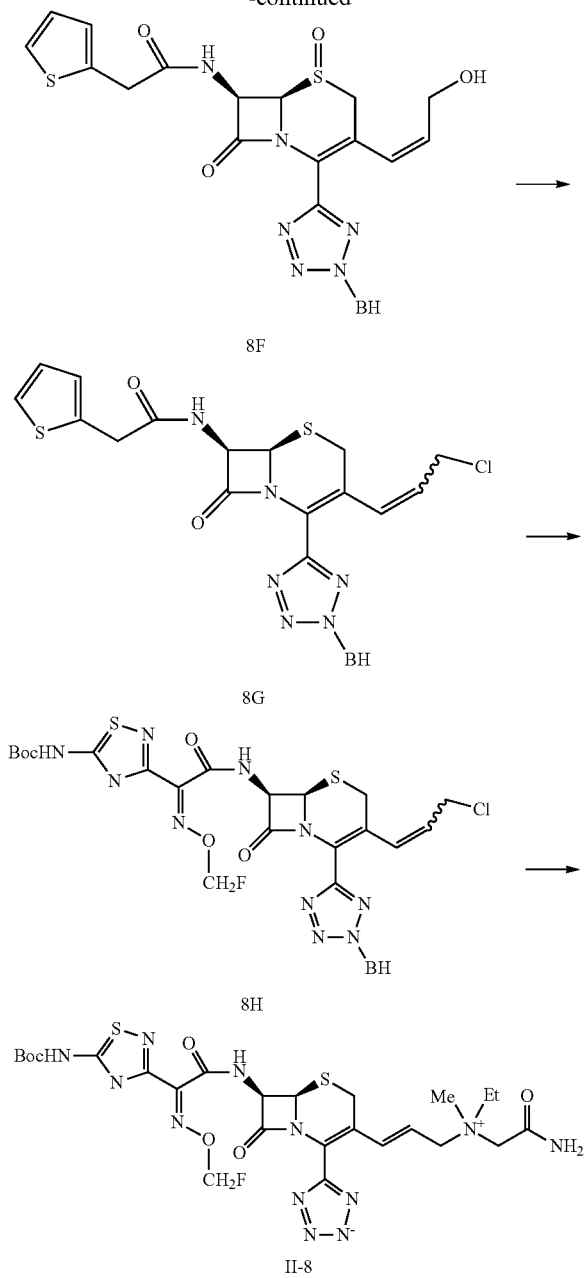

Step (2): Synthesis of Compound 8C

Compound 8B was dissolved in methylene chloride (50 mL) and cooled to −50° C., and a solution of mCPBA (3.43 g, 12.9 mmol) in methylene chloride (30 mL) was added dropwise over 10 min. The reaction solution was stirred at −50° C. for additional 30 ml, and then sodium thiosulfate (1.36 g, 8.61 mmol) in water (50 mL) was added. To this mixture, ethyl acetate was added and concentrated under reduced pressure. The precipitated solid was collected by filtration to yield Compound 8C (2.5 g, 50%).

$^1$H-NMR (DMSO-$d_6$) δ: 3.81, 3.90 (ABq, J=15.5 Hz, 2H), 3.76, 4.02 (ABq, J=17.9 Hz, 2H), 4.50, 4.68 (ABq, J=11.6 Hz, 2H), 5.10 (d, J=40.5 Hz, 1H), 5.92 (dd, J=4.8, 8.4 Hz, 1H), 6.95-6.97 (m, 2H), 7.30-7.44 (m, 11H), 7.82 (s, 1H), 8.49 (d, J=7.8 Hz, 1H).

Step (3): Synthesis of Compound 8D

Compound 8C (4.92 g, 8.5 mmol) was dissolved in DMF (20 mL), sodium iodide (2.55 g, 17 mmol) and triphenylphosphine (2.67 g, 10.2 mmol) were added. The solution was stirred at room temperature for 30 min. The reaction solution was poured into stirring diisopropyl ether (70 mL) and water (100 mL). The precipitated solid was collected by filtration. The solid was air-dried to yield Compound 80 (8.19 g, 100%).

$^1$H-NMR (DMSO-$d_6$) δ: 3.54-3.92 (m, 4H), 5.01-5.36 (m, 2H), 5.18 (d, J=4.5 Hz, 2H), 5.84-5.88 (m, 1H), 6.93-6.96 (m, 2H), 7.18-7.79 (m, 27H), 8.58 (d, J=7.8 Hz, 1H)

Step (4): Synthesis of Compound 8E

Compound 8D (25.54 g, 26.6 mmol) and 2-(tert-butylsilyl oxy)acetaldehyde were dissolved in methylene chloride (250 mL). 8.4% aqueous sodium bicarbonate (260 mL) was added, and the solution was stirred at room temperature for 20 hours. The methylene chloride layer was separated and dried over anhydrous magnesium sulfate. The solvent was removed under reduced pressure. The residue was purified on silica gel chromatography (hexanes-ethyl acetate) to yield Compound 8E (2.85 g, 26%).

$^1$H-NMR (CDCl$_3$) δ: −0.07 (s, 6H), 0.81 (s, 9H), 3.59-3.61 (m, 1H), 3.62 (ABq, J=18.0 Hz, 2H), 4.00-4.02 (m, 1H), 4.60 (d, j=3.3 Hz, 1H), 5.61 (m, 1H), 6.11 (dd, J=4.5, 9.9 Hz, 1H), 6.18 (d, J=11.7 Hz, 1H), 6.89 (d, J=9.6 Hz, 1H), 6.97-7.00 (m, 2H), 7.22-7.36 (m, 12H).

Step (5): Synthesis of Compound 8F

Compound 8E (4.65 g, 6.63 mmol) was dissolved in tetrahydrofuran (50 mL), and acetic acid (0.95 mL, 16.58 mmol) and 1 mol/L tetrabutylammonium fluoride/tetrahydrofuran (9.95 mL, 9.95 mmol) were added. The reaction solution was stirred at room temperature for 4 hours, and water and ethyl acetate were added. The organic layer was separated. The organic layer was washed sequentially with aqueous sodium bicarbonate, brine and water, and dried over anhydrous magnesium sulfate. The solvent was removed, and diisopropyl ether was added to the residue. The precipitated solid was collected by filtration to yield Compound 8F (3.14 g, 81%).

$^1$H-NMR (CDCl$_3$) δ: 3.58 (ABq, J=19.2 Hz, 2H), 3.71-3.77 (m, 1H), 3.85 (s, 1H), 4.07-4.14 (m, 1H), 4.61 (d, J=4.8 Hz, 1H), 5.69-5.77 (m, 1H), 6.06-6.12 (m, 1H), 6.94-7.00 (m, 2H), 7.23-7.40 (m, 12H).

Step (1): Synthesis of Compound 8B

Compound 8A (5.87 g, 10 mmol) was dissolved in methylene chloride (50 mL), and 4 mol/L hydrochloric acid/ethyl acetate solution (10 mL, 40 mmol) was added. The reaction solution was stirred at room temperature for 2.5 hours, and the solvent was removed under reduced pressure. Diisopropyl ether was added to the obtained residue, and the precipitated solid was collected by filtration to yield Compound 8B (5.5 g, 98%).

$^1$H-NMR (CDCl$_3$) δ: 3.86 (s, 2H), 4.03, 4.07 (ABq, J=12.3 Hz, 2H), 3.76 (d, J=3.9 Hz, 1H), 5.62 (dd, J=4.2, 8.7 Hz, 1H), 5.95 (s, 1H), 6.42 (s, 1H), 6.52 (d, J=8.7 Hz, 1H), 6.97-7.02 (m, 2H), 7.23-7.39 (m, 12H).

Step (6): Synthesis of Compound 8G

Compound 8F (3.07 g, 5.23 g) was dissolved in DMF (30 mL), and the solution was cooled to −50° C. Phosphorus trichloride (1.37 mL, 15.7 mL) was added, and the temperature of the solution was gradually elevated to 0° C. with stirring. To the resultant solution, ethyl acetate and water were added, and the organic layer was separated. The organic layer was washed with water and brine, and dried over anhydrous magnesium sulfate. The solvent was removed under reduced pressure to yield Compound 8G (2.25 g, 73%, Z:E=4:6).

$^1$H-NMR (CDCl$_3$) δ: 3.36-4.06 (m, 6H), 5.11-5.16 (m, 1H), 5.53-5.62 (m, 0.4H), 5.84-5.98 (m, 1.6H), 6.15 (d, J=11.1 Hz, 0.4H), 6.36-6.41 (m, 1H), 6.79 (d, J=15.9 Hz, 0.6H), 6.96-7.01 (m, 2H), 7.21-7.41 (m, 12H).

Step (7): Synthesis of Compound 8H

Phosphorus pentachloride (0.75 g, 3.50 mmol) was suspended in methylene chloride (10 mL), and pyridine (0.32 mL, 3.96 mmol) was added to the suspension. The suspension was stirred for 10 minutes under ice-cooling, and then compound 8G (1.06 g, 1.8 mmol) was added. The reaction solution was stirred under ice-cooling for 30 min. The solution was cooled to −50° C., and methanol (2.5 mL) was added. The reaction solution was stirred for 20 min under ice-cooling, and then water was added. The organic layer was separated and washed with water and diluted aqueous sodium bicarbonate, and then dried over anhydrous magnesium sulfate. To the obtained solutions, 4 mol/L hydrochloric acid/ethyl acetate (1 mL) was added and the solution was concentrated. The concenrated solution was 7-amino compound hydrochloride solutions.

On the other hand, (Z)-2-(5-tert-butoxycarbonyl amino)-1,2,4-thiadiazol-3-yl)-2-(fluoromethoxyimino)acetic acid (288 mg, 0.9 mmol) was dissolved in DMA (3 mL). Triethylamine (0.162 mL, 1.17 mmol) was added to the solution, and the solution was cooled to −20° C. To this solution, methanesulfonyl chloride (0.084 mL, 1.08 mmol) was added and stirred for 20 min at this temperature. The solution was obtained as a mixed anhydride solution.

Then, a solution hydrochloride salt of the 7-amino compound was cooled, and 2,6-lutidine (0.314 mL, 2.7 mmol) was added, and then the mixed anhydride solution was added. The reaction solution was stirred under ice-cooling for 20 min, and ethyl acetate and diluted hydrochloric acid were added. The organic layer was separated and washed sequentially with water, brine water, and dried over anhydrous magnesium sulfate. The solvent was removed under reduced pressure, and purified on silica gel chromatography (hexanes-ethyl acetate) to yield Compound 8H (220 mg, 32%, Z:E=15:85).

$^1$H-NMR (CDCl$_3$) δ: 1.49 (s, 9H), 3.44-3.76 (m, 2H), 4.00-4.09 (m, 2H), 5.31-5.35 (m, 1H), 5.59-6.25 (m, 4.15H), 6.88 (d, J=15.6 Hz, 0.85H), 7.23-7.43 (m, 10H), 7.95 (br, 1H).

Step (8): Compound II-8

Compound 8H (220 mg, 0.29 mmol) was dissolved in DMF (1 mL). Sodium bromide (89 mg, 0.86 mmol) and then 2-(ethyl(methyl)amino)acetamide (33 mg, 0.287 mmol) were added, and the solution was stirred at room temperature for 3 hours.

To this reaction solution, ethyl acetate and diluted hydrochloric acid were added. The organic layer was separated and washed sequentially with water and brine, and dried over anhydrous magnesium sulfate. The solvent was removed under reduced pressure, and the residue was dissolved in methylene chloride. Anisole (0.34 mL, 3.12 mmol) was added and the solution was cooled to −30° C. To this solution, titanium tetrachloride (0.344 mL, 3.12 mol) was added under ice-cooling and stirred for 2.5 hours. To this reaction solution, diisopropyl ether, water and acetonitrile were added, and the aqueous layer was separated. The aqueous solution thus obtained was added with HP20SS resin, and the solution was concentrated under reduced pressure, and then purified on HP20SS column chromatography (water-acetonitrile). The fraction containing the desired compound was concentrated under reduced pressure, and freeze-dried to yield Compound II-8 (39 mg, 23%)

$^1$H-NMR (DMSO-d$_6$) δ: 1.25 (t, J=6.9 Hz, 2H), 3.08 (s, 3H), 3.48-3.63 (m, 3H), 3.89-3.94 (m, 3H), 4.10 (br, 2H), 5.32 (d, J=4.8 Hz, 1H), 5.70-5.89 (m, 4H), 7.01 (d, J=15.3 Hz, 1H), 7.69 (s, 1H), 7.94 (s, 1H), 8.21 (s, 2H), 9.74 (d, J=8.4 Hz, 1H).

MS (ESI): 581 [M+H]$^+$

Example 131

Synthesis of Compound II-9

[Chemical Formula 230]

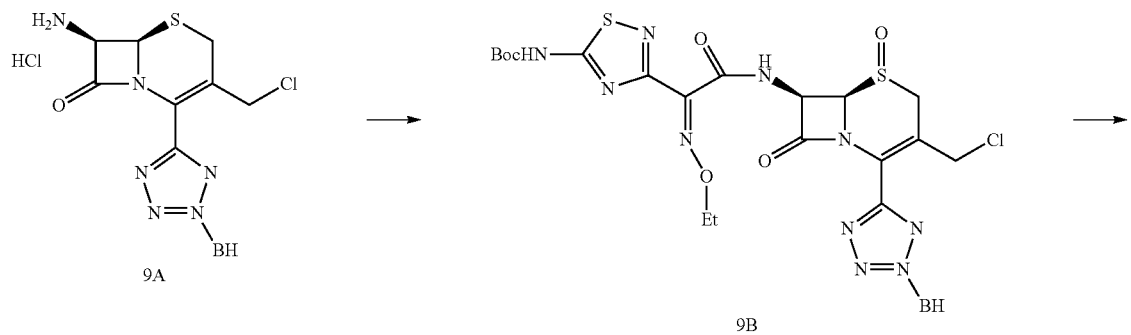

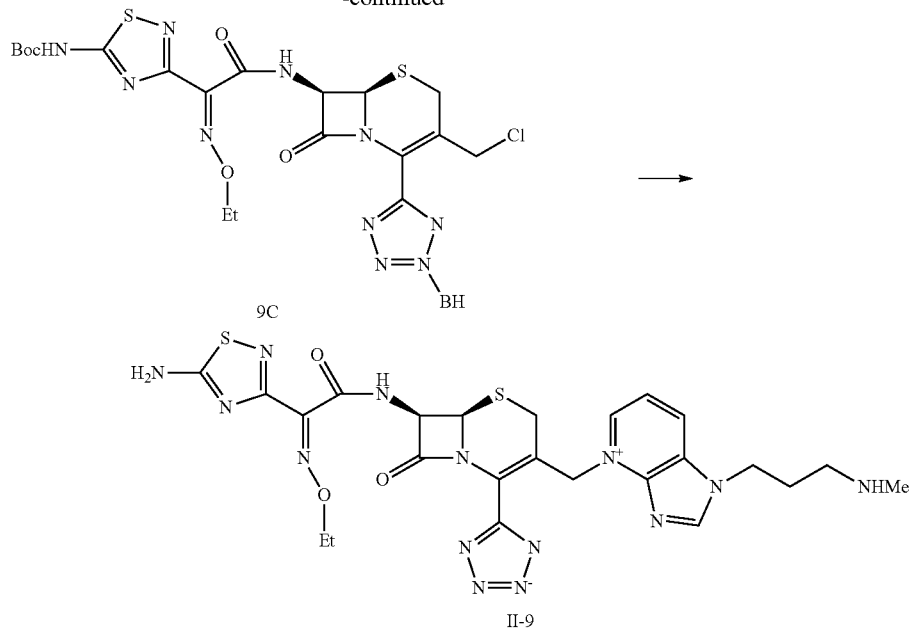

Step (1): Synthesis of Compound 9B (Z)-2-(5-tert-butoxycarbonylamino)-1,2,4-thiadiazol-3-yl)-2-(ethoxyimino)acetic acid (696 mg, 2.2 mmol) was dissolved in DMA (10 mL). Triethylamine (0.36 mL, 2.6 mmol) was added, and the solution was cooled to −20° C. A solution of methanesulfonyl chloride (0.187 mL, 2.4 mmol) was added and stirred at this temperature for 20 min. To this solution, 2,6-lutidine (0.699 mL, 6.0 mmol) and Compound 9A (0.951 g, 2 mmol) were added sequentially. The reaction solution was stirred under ice-cooling for 15 minutes, and ethyl acetate and diluted hydrochloric acid were added. The organic layer was separated and washed sequentially with water and brine, and dried over anhydrous magnesium sulfate. The solvent was removed under reduced pressure. The residue was dissolved in methylene chloride (20 mL), and the solution was cooled to −40° C., and mCPBA (0.637 g, 2.398 mmol) was added. The reaction solution was stirred under ice-cooling for 15 minutes, and sodium thiosulfate (0.316 g, 2 mmol) in water (30 mL) was added. Ethyl acetate was added to this mixture, and the mixture was concentrated under reduced pressure, and methylene chloride was removed. The organic layer was separated, washed twice with diluted sodium bicarbonate and brine, and dried over anhydrous magnesium sulfate. The solvent was removed under reduced pressure, and purified on silica gel column chromatography (hexanes-ethyl acetate) to yield Compound 9B (1.3 g, 86%).

$^1$H-NMR (CDCl$_3$) δ: 1.36 (t, J=6.9 Hz, 3H), 1.56 (s, 9H), 3.52, 3.85 (Abq, J=18.6 Hz, 2H), 4.29-4.41 (m, 2H), 4.36, 4.96 (ABq, J=12.5 Hz, 2H), 4.84 (d, J=3.9 Hz, 1H), 6.15 (dd, J=4.5, 8.4 Hz, 1H), 7.25-7.39 (m, 1H), 8.00 (d, J=8.4 Hz, 1H).

Step (2): Synthesis of Compound 9C

Compound 9B (1.29 g, 1.71 mmol) was dissolved in DMF (10 mL), and the solution was cooled to −40° C. Phosphorus trichloride (0.449 mL, 5.14 mmol) was added to this solution at this temperature, and the solution was stirred for 15 minutes. To this reaction solution, ethyl acetate and diluted hydrochloric acid were added. The organic layer was separated and washed sequentially with water and brine, and dried over anhydrous magnesium sulfate. The solvent was removed under reduced pressure to yield Compound 9C (1.71 g, 100%).

$^1$H-NMR (CDCl$_3$) δ: 1.37 (t, J=6.9 Hz, 3H), 1.46 (s, 9H), 3.56, 3.78 (Abq, J=18.2 Hz, 2H), 4.38-4.48 (m, 2H), 4.39, 4.61 (ABq, J=12.0 Hz, 2H), 5.27 (d, J=5.1 Hz, 1H), 6.21 (dd, J=5.1, 9.0 Hz, 1H), 7.23-7.39 (m, 10H), 7.87 (d, J=8.7 Hz, 1H), 9.63 (br s, 1H).

Step (3): Synthesis of Compound II-9

Compound 9C (621 mg, 0.8 mmol) was dissolved in DMF (2 mL). Sodium bromide (165 mg, 1.6 mmol), 3-(1H-imidazo[4,5-b]pyrydine-1-yl)propyl(methyl)carbamic acid-tert-butyl (232 mg, 0.8 mmol) were added, and the solution was stirred overnight at room temperature. To the reaction solution, ethyl acetate and water were added. The organic layer was separated and washed sequentially with water and brine, and dried over anhydrous magnesium sulfate. The solvent was removed under reduced pressure. The residue was dissolved in methylene chloride, anisole (0.78 mL, 7.14 mmol) was added and the solution was cooled to −30° C. 2 mol/L aluminum chloride in nitroethane (3.57 mL, 7.14 mmol) was added and stirred for 1.5 hours under ice-cooling. Diisopropyl ether, diluted hydrochloric acid and acetonitrile were added to the reaction solution, and the aqueous layer was separated. To the obtained aqueous solution, HP20SS resin was added and concentrated under reduced pressure, and then purified on HP20SS column chromatography (water-acetonitrile). The fraction containing the desired compound was concentrated under reduced pressure and freeze-dried to yield Compound II-9 (210 mg, 45%).

$^1$H-NMR (DMSO-d) δ: 1.21 (t, J=6.9 Hz, 3H), 2.25-2.30 (m, 3H), 2.92 (brt, J=5.7 Hz, 2H), 3.53, 3.60 (Abq, J=18.2 Hz, 2H), 4.14 (q, J=7.2 Hz, 2H), 4.69 (t, j=7.2 Hz, 2H), 5.30 (d, J=5.1 Hz, 1H), 5.62, 6.06 (ABq, J=14.6 Hz, 2H), 5.86 (dd, J=5.1, 8.4 Hz, 1H), 8.01-8.06 (m, 1H), 8.18 (ds, 2H), 9.17 (s, 1H), 9.18 (d, J=6.9 Hz, 1H), 9.24 (d, J=6.3 Hz, 1H), 9.39 (br, 2H), 9.62 (d, J=8.4 Hz, 1H).

Example 132

Synthesis of Compound II-10

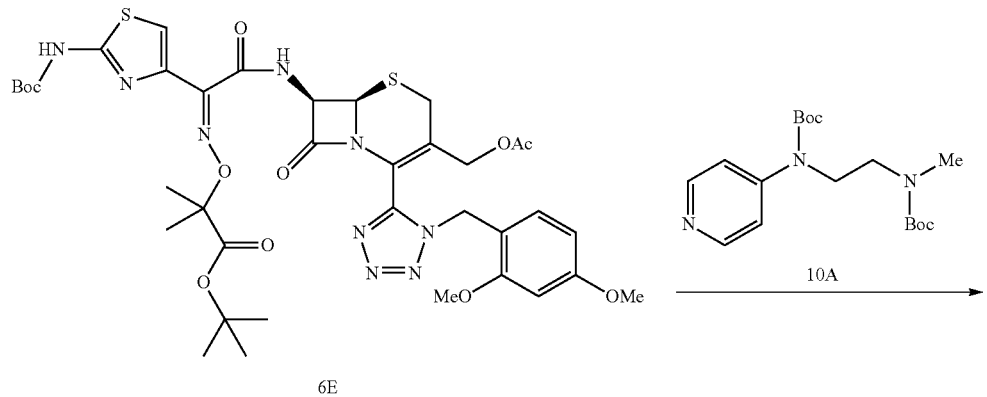

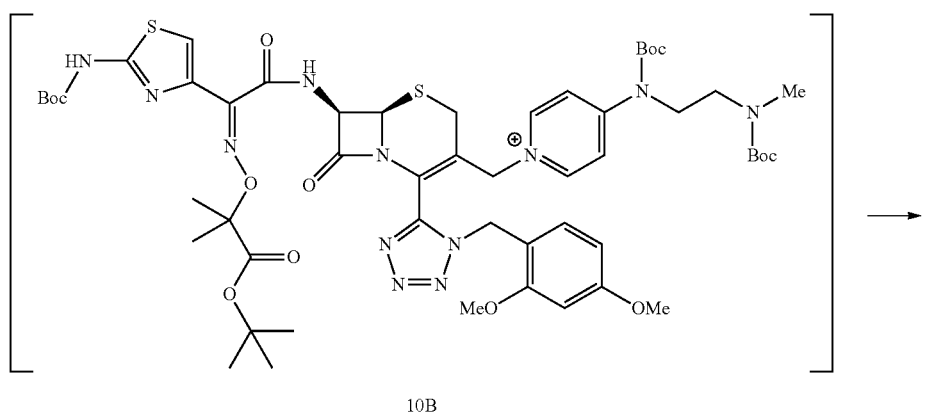

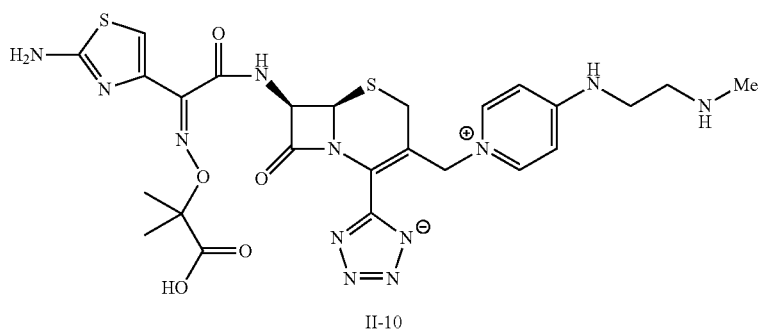

Step (1): Compound 6E→Compound 10B

Compound 6E (300 mg) was dissolved in methylene chloride (3.5 mL), and the solution was cooled to −60° C. Me$_3$Si—I (0.25 mL) was added. After stirring for 15 minutes at room temperature, the solution was concentrated under reduced pressure. The residue was dissolved in DMF (2 mL), pyridine derivative 10A (245 mg) was added and the solution was stirred at room temperature for 2 hours. Isopropyl ether (25 mL) was added and the precipitated oily material was corrected. This material was dissolved in methylene chloride (1 mL), anisole (0.25 mL) and then TFA (6 mL) were added, and the mixture was stirred for 40 min. The mixture was concentrated, and isopropyl ether (20 mL) was added. The precipitation was collected by filtration. The filtrate was purified on HP-20 column chromatography, and the eluted solution was freeze-dried to yield Compound II-10 (60 mg).

$^1$H-NMR (d-DMSO) δ: 1.39 (3H, s), 1.50 (3H, s), 2.50 (3H, s), 3.20, 3.66 (2H, AB-q, J=18.9 Hz), 4.69, 4.97 (2H, AB-q, J=14.1 Hz), 5.36 (1H, d, J=5.1 Hz), 5.83 (1H, dd, J=5.4, 7.2 Hz), 6.74 (1H, s), 6.75-6.79 (1H, m), 7.00 (1H, d, J=5.7 Hz), 7.27 (2H, bs), 8.41 (1H, d, J=6.9 Hz), 8.86 (1H, bs).

MS (ESI): 643.4$^+$ (M+H)$^+$

Example 133

Compound II-11

[Chemical Formula 232]

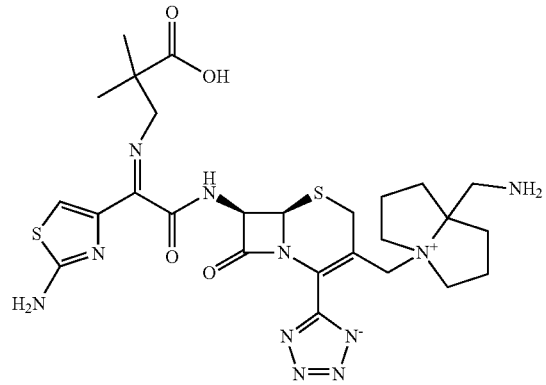

II-11

¹H-NMR (DMSO-D₆) δ: 9.44 (1H, d, J=8.1 Hz), 7.28 (2H, br s), 6.73 (1H, s), 5.84 (1H, dd, J=8.1, 5.2 Hz), 5.42 (1H, d, J=5.2 Hz), 5.18 (1H, d, J=12.9 Hz), 3.96-3.90 (2H, br m), 2.31-1.17 (18H, m), 0.40-0.34 (1H, m).

Elemental analysis for C25H33N11O5S2(H2O)6.1(HCl)0.6

Calcd: C, 39.33; H, 6.05; Cl, 2.79; N, 20.18; S, 8.40(%)
Found: C, 39.61; H, 5.88; Cl, 2.68; N, 19.73; S, 8.25(%)

Example 134

Compound II-12

[Chemical Formula 233]

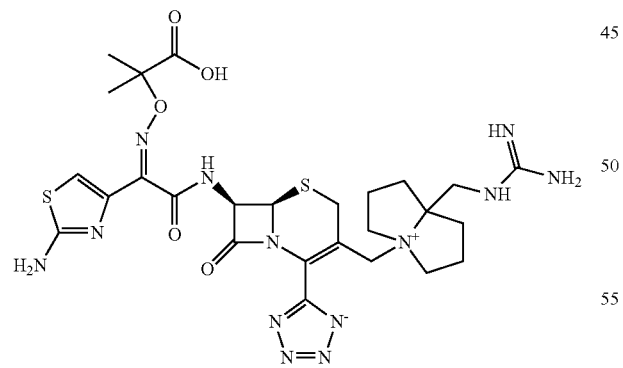

II-12

¹H-NMR (DMSO-DE) δ: 9.44 (1H, d, J=8.4 Hz), 8.32 (1H, br s), 7.52 (4H, br s), 7.29 (2H, br s), 6.73 (1H, s), 5.86 (1H, dd, J=8.4, 5.2 Hz), 5.44 (1H, d, J=5.2 Hz), 5.12 (1H, d, J=12.9 Hz), 4.11-3.94 (2H, m), 2.17-1.90 (8H, m), 1.78-1.65 (2H, m), 1.52-1.28 (9H, m), 0.54-0.46 (1H, m).

Elemental analysis for C26H35N13O5S2(H2O)6(HCl)1.2

Calcd: C, 37.82; H, 5.88; Cl, 5.15; N, 22.05; S, 7.77(%)
Found: C, 37.74; H, 5.68; Cl, 5.24; N, 22.02; S, 7.86(%)

Example 135

Compound II-13

[Chemical Formula 234]

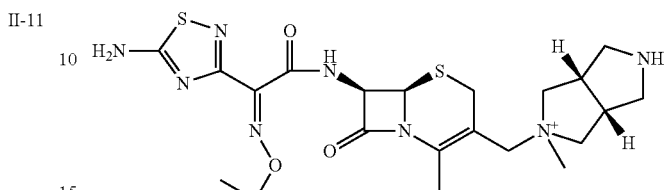

II-13

¹H-NMR (DMSO-d₆) δ: 10.06-10.03 (1H, m), 3.21-8.17 (2H, m), 5.89-5.85 (1H, m), 5.60-5.42 (1H, m), 5.12-5.08 (1H, m) 3.79-2.98 (18H, m), 1.48 (3H, s), 1.42 (3H, s).

MS (m+1)=619.32

Reference Example 1

Synthesis of Intermediates (iii)

[Chemical Formula 235]

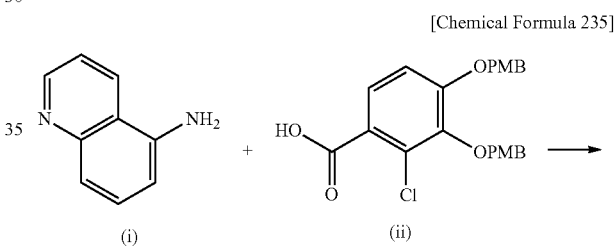

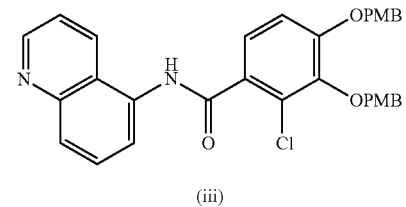

Synthesis of Compound (iii)

To a solution of Compound (II) (0.86 g, 5 mmol) in dichloromethane (25 ml), 1-chloro-N,N,2-trimethylpropyl-1-en-1-amine (0.728 ml, 5.5 mmol) was added at 0° C., and the solution was stirred at room temperature for 35 min. Compound (i) (0.86 g, 6 mmol) was added to the reaction solution at 0° C., and the solution was let stand overnight at room temperature. Aqueous saturated sodium bicarbonate was added to the reaction solution, and the solution was extracted three times with chloroform. The organic layer was washed with brine, dried over anhydrous magnesium sulfate, and filtered. Concentration, washing the solid with diisopropyl ether and filtration yielded Compound (iii) (2.24 g, 80%).

¹H-NMR (CDCl₃) δ: 8.96 (1H, d, J=4.4 Hz), 8.50 (1H, br s), 8.35 (1H, d, J=8.2 Hz), 8.09-8.01 (2H, m), 7.79-7.69 (2H, m), 7.49-7.34 (6H, m), 7.07-7.02 (1H, m), 6.97-6.92 (2H, br nm), 6.86-6.83 (2H, br m), 5.14 (2H, s), 5.02 (2H, s), 3.84 (3H, s), 3.81 (3H, s).

Reference Example 2

Synthesis of Intermediates (vi)

[Chemical Formula 236]

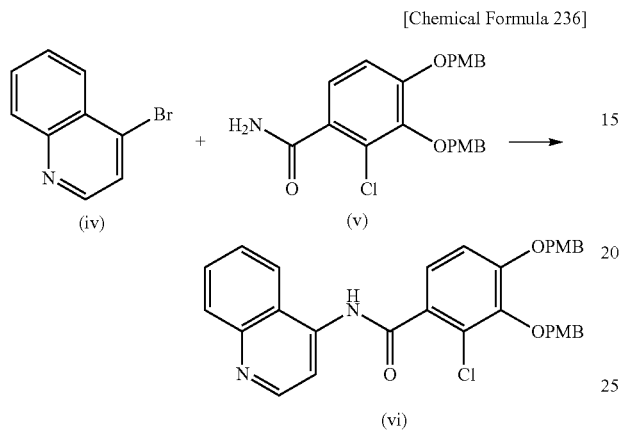

Synthesis of Compound (vi)

To a solution of Compound (v) (1.34 g, 3.15 mmol) in 1,4-dioxane (45 ml), cesium carbonate (2.44 g, 7.50 mmol), (R)-2,2'-bis(diphenylphosphino)-1,1'-binaphythyl (112 mg, 0.18 mmol) and tris(dibenzylidene acetone)bis palladium (82 mg, 0.09 mmol) were added, and the solution was sonicated for 10 min. Compound (iv) was added and heated to reflux overnight. The reaction solution was warmed to room temperature and filtered and concentrated. The residue was purified on silica gel chromatography (hexanes-ethyl acetate) to yield Compound (vi) (453 mg, 27%).

$^1$H-NMR (CDCl$_3$) δ: 9.05 (1H, br s), 8.91 (1H, d, J=5.0 Hz), 8.48 (1H, d, J=5.0 Hz), 8.15 (1H, d, J=8.6 Hz), 7.91 (1H, d, J=8.6 Hz), 7.78-7.72 (2H, m), 7.63-7.57 (1H, m), 7.40-7.34 (5H, m), 7.07 (1H, d, J=8.9 Hz), 6.97-6.92 (2H, m), 6.88-6.84 (2H, m), 5.16 (3H, s), 5.03 (3H, s), 3.84 (4H, s), 3.81 (4H, s).

Example 136

Synthesis of Compound III-1

[Chemical Formula 237]

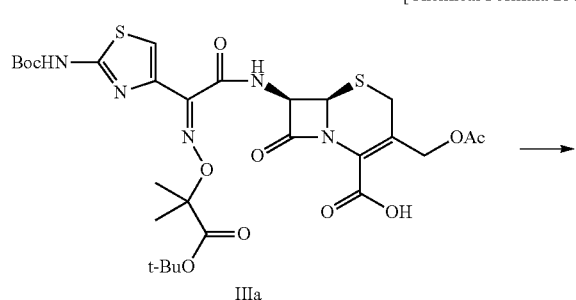

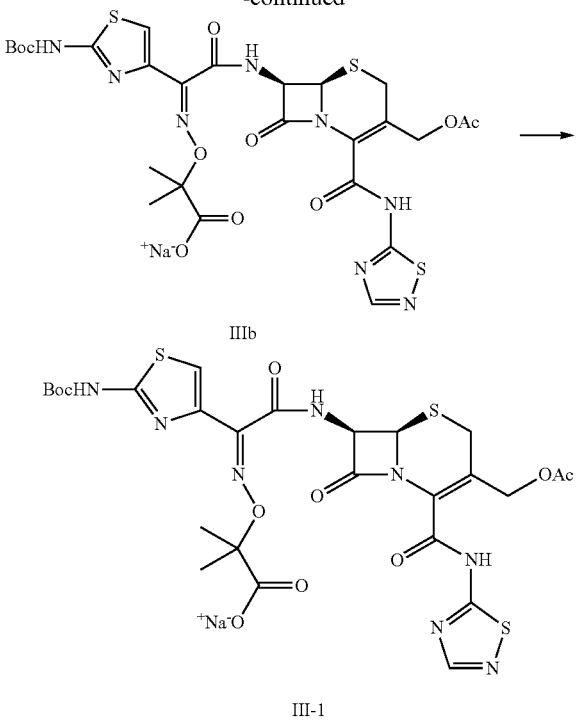

Step (1): Compound IIIa→Compound IIIb

Under nitrogen atmosphere, Compound IIIa (1.02 g, 1.50 mmol) was dissolved in dichloromethane (10.0 mL), and the solution was cooled to 0° C. 1-chloro-N,N,2-trimethyl-1-propenylamine (0.200 g, 1.5 mmol) was added, and the solution was stirred for 40 min. The solution was cooled to −30° C., and 1,2,4-thiadiazol-5-amine (0.303 g, 3.0 mmol) was added, and the solution was stirred for 2 hours. After the reaction was completed, the solution was added with 1 mol/L hydrochloric acid and extracted. The obtained organic layer was washed with purified water, saturated aqueous sodium bicarbonate and then brine, and dried over anhydrous magnesium sulfate. The desiccant was filtered off, and the solvent was removed under reduced pressure. The obtained residue was subjected to silica gel chromatography to yield Compound IIIb (0.525 g, 45.6%).

$^1$H-NMR (CDCl$_3$) δ: 8.46 (d, J=8.8 Hz, 1H), 8.35 (s, 1H), 7.34 (s, 1H), 5.88-5.83 (m, 1H), 5.22-5.18 (m, 2H), 5.07 (d, J=14.2 Hz, 1H), 3.57 (d, J=18.3 Hz, 1H), 3.42 (d, J=18.3 Hz, 1H), 2.11 (s, 3H), 1.59-1.50 (m, 15H), 1.38 (s, 9H).

Step (2): Compound IIIb→Compound III-1

Under nitrogen atmosphere, Compound IIIb (525 mg, 0.685 mmol) was dissolved in dichloromethane (5.00 mL), and the solution was cooled to −20° C. Anisole (0.748 mL, 6.85 mmol) and 2.00 mol/L aluminum chloride-nitromethane solution (3.42 mL, 6.85 mmol) was added, and the solution was stirred at −20° C. for 1 hour. To this solution, 0.2 mol/L hydrochloric acid and diisopropyl ether were added. Acetonitrile and 0.2 mol/L hydrochloric acid were added to dissolve the residue. The aqueous layer was extracted from the organic layer, added with HP20SS and concentrated under reduced pressure. The obtained suspension was subjected to ODS chromatography. The fraction containing the desired compound was concentrated and freeze-dried to yield Compound III-1 (117 mg, 27.0%).

$^1$H-NMR (D$_2$O) δ: 8.43 (s, 1H), 6.97 (s, 1H), 5.94 (d, J=4.7 Hz, 1H), 5.37 (d, J=4.7 Hz, 1H), 5.06 (d, J=13.1 Hz, 1H), 4.86-4.82 (m, 1H), 3.80 (d, J=18.6 Hz, 1H), 3.60 (d, J=18.6 Hz, 1H), 2.08 (s, 3H), 1.52 (s, 3H), 1.49 (s, 3H).

Example 137

Synthesis of Compound II-2

[Chemical Formula 238]

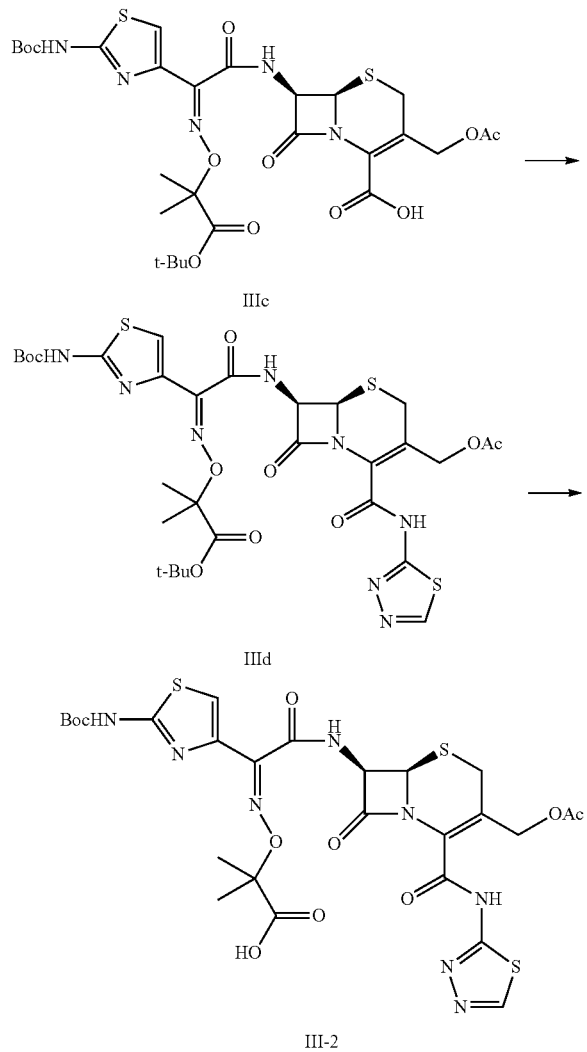

Step (1): Compound IIIc→Compound IIId

Under nitrogen atmosphere, Compound IIIc (1.03 g, 1.50 mol) was dissolved in dichloromethane (10.0 mL), and the solution was cooled to 0° C. 1-chloro-N,N,2-trimethyl-1-propenylamine (0.238 g, 1.2 mmol) was added, and the solution was stirred for 40 min.

The solution was cooled to −40° C., 1,3,4-thiadiazol-2-amine (0.219 g, 2.1 mmol) was added, and the solution was stirred for 2.5 hours and at 0° C. for 2 hours, and then let stand overnight at 4° C. After the reaction was completed, the solution was added with 1 mol/L hydrochloric acid and extracted. The obtained organic layer was washed with purified water, saturated aqueous sodium bicarbonate and brine, and dried over anhydrous magnesium sulfate. The desiccant was filtered off, and the solvent was removed under reduced pressure. The obtained residue was subjected to silica gel chromatography to yield Compound IIId (0.505 g, 43.9%).

$^1$H-NMR (CDCl3) δ: 8.94 (s, 1H), 8.50 (br s, 1H), 8.11 (d, J=8.7 Hz, 1H), 7.30 (s, 1H), 6.05 (dd, J=8.7, 5.0 Hz, 1H), 5.41 (d, J=5.0 Hz, 1H), 5.12 (d, J=13.7 Hz, 1H), 4.93 (d, J=13.7 Hz, 1H), 3.64 (d, J=18.6 Hz, 1H), 3.45 (d, J=18.6 Hz, 1H), 2.07 (s, 3H), 1.60 (s, 3H), 1.56 (s, 3H), 1.49 (s, 9H), 1.41 (s, 9H).

Step (2): Compound IIId→Compound III-2

Under nitrogen atmosphere, Compound IIId (474 mg, 0.618 mmol) was dissolved in dichloromethane (5.00 mL), and the solution was cooled to −20° C. Anisole (0.675 mL, 6.18 mmol) and 2.00 mol/L aluminum chloride-nitromethane solution (3.09 mL, 6.18 mmol) were added, and the solution was stirred at −20° C. for 1 hour.

To this reaction solution, 0.2 mol/L hydrochloric acid and diisopropyl ether were added. Acetonitrile and 0.2 mol/L hydrochloric acid were added to dissolve the residue. The aqueous layer was extracted from the organic layer, added with HP20SS and concentrated under reduced pressure. The obtained suspension was subjected to ODS chromatography. The fraction containing the desired compound was concentrated and freeze-dried to yield Compound III-2 (296 mg, 78.4%)

$^1$H-NMR (DMSO-D) δ: 9.52 (d, J=8.5 Hz, 1H), 9.26 (s, 1H), 7.30 (s, 2H), 6.75 (s, 1H), 5.78 (dd, J=8.5, 4.9 Hz, 1H), 5.19 (d, J=4.9 Hz, 1H), 5.00 (d, J=13.2 Hz, 1H), 4.72 (d, J=13.2 Hz, 1H), 3.70 (d, J=18.7 Hz, 1H), 3.58 (d, J=18.7 Hz, 1H), 2.01 (s, 3H), 1.45 (s, 3H), 1.44 (s, 3H).

Example 138

Synthesis of Compound III-3

[Chemical Formula 239]

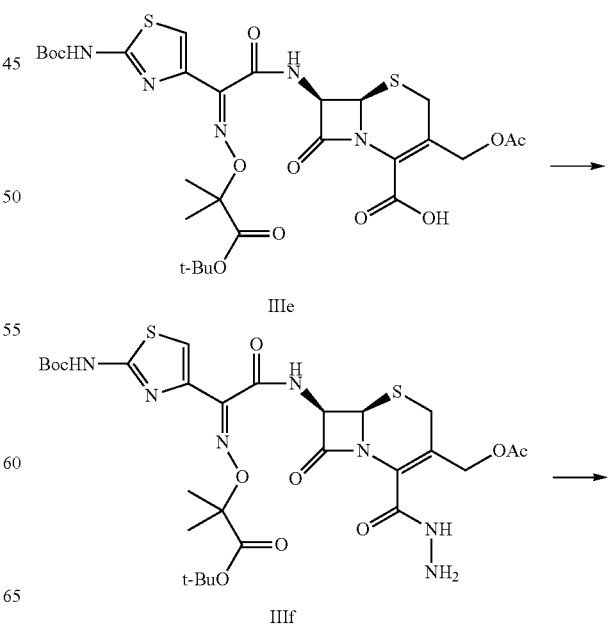

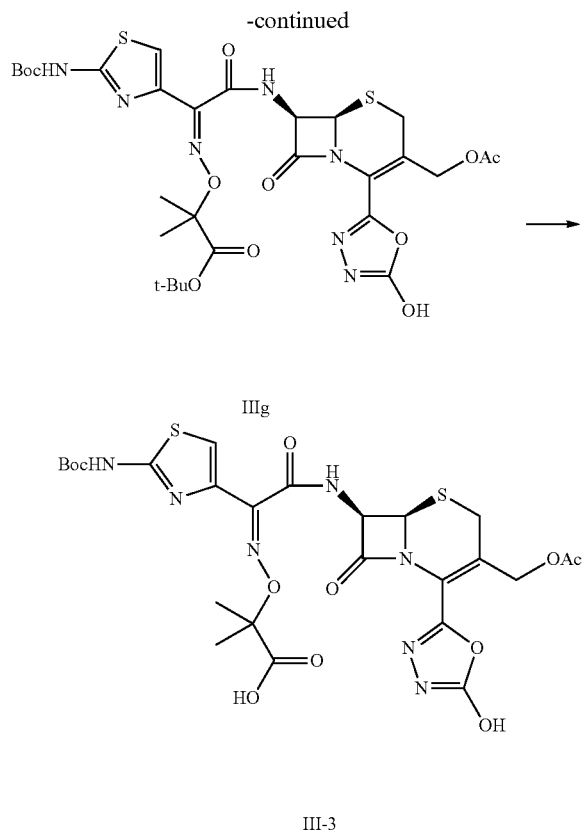

Step (1): Compound IIIe→Compound IIIf

Under nitrogen atmosphere, Compound IIIe (3.42 g, 5.00 mmol) was dissolved in dichloromethane (35.0 mL), and the solution was cooed to 0° C. 1-chloro-N,N,2-trimethyl-1-propenylamine (0.702 g, 0.425 mmol) was added, and the solution was stirred for 40 min.

Separately, hydrazine hydrate (0.375 g, 7.50 mmol) was dissolved in dichloromethane (35.0 mL). Pyridine (0.415 g, 5.25 mmol) was added, and the solution was cooled to −40° C. To this solution, the solution obtained above was added dropwise and stirred at −40° C. After the reaction was completed, purified water was added to this mixture, and the aqueous layer was extracted with ethyl acetate. The obtained organic layer was washed with purified water and then brine, and dried over anhydrous magnesium sulfate. The desiccant was filtered off, and the solvent was removed under reduced pressure. The obtained residue was subjected to silica gel chromatography to yield Compound IIIf (0.630 g, 18.1%).

$^1$H-NMR (DMSO-D$_6$) δ: 11.82 (br s, 1H), 9.59 (s, 1H), 9.53 (d, J=8.5 Hz, 1H), 7.35-7.10 (m, 3H), 5.70 (dd, J=8.5, 4.9 Hz, 1H), 5.10 (d, J=4.9 Hz, 1H), 4.89 (d, J=12.7 Hz, 1H), 4.72 (d, J=12.7 Hz, 1H), 3.56 (d, J=17.9 Hz, 1H), 3.41 (d, J=17.9 Hz, 1H), 1.98 (s, 3H), 1.49-1.42 (m, 15H), 1.38 (s, 9H).

Step (2): Compound IIIf→Compound IIIg

Under nitrogen atmosphere, Compound IIIf (0.600 g, 0.860 mmol) was dissolved in DMF (6.00 mL). CDI (carbonyldiimidazole) (0.153 g, 0.946 mmol) was added, and the solution was stirred at 0° C. for 30 min. To this solution, purified water was added, and the aqueous layer was extracted with ethyl acetate. The organic layer was washed with purified water and then brine, and dried over anhydrous magnesium sulfate. The desiccant was filtered off, the solvent was removed under reduced pressure. The obtained residue was subjected to silica gel chromatography to yield Compound IIIg (0.400 g, 64.3%).

$^1$H-NMR (DMSO-Dr) δ: 12.84 (br s, 1H), 11.84 (s, 1H), 9.56 (d, J=8.3 Hz, 1H), 7.25 (s, 1H), 5.95 (dd, J=8.3, 4.9 Hz, 1H), 5.30 (d, J=4.9 Hz, 1H), 4.93 (d, J=13.0 Hz, 1H), 4.67 (d, J=13.0 Hz, 1H), 3.73 (d, J=18.3 Hz, 1H), 3.59 (d, J=18.3 Hz, 1H), 1.99 (s, 3H), 1.50-1.44 (m, 15H), 1.39 (s, 9H).

Step (3): Compound IIIg→Compound II-3

Under nitrogen atmosphere, Compound IIIg (361 mg, 0.499 mmol) was dissolved in dichloromethane (4.00 mL), and the solution was cooled to −30° C. Anisole (0.327 mL, 2.99 mmol) and 2.00 mol/L aluminum chloride-nitromethane solution (1.50 mL, 2.99 mmol) were added, and the solution was stirred at −30° C. for 20 min. To this solution, purified water and diisopropyl ether were added. Acetonitrile and 2 mol/L hydrochloric acid were added to dissolve the residue. The aqueous layer was extracted from organic layer, added with HP20SS and concentrated under reduced pressure. The obtained suspension was subjected to ODS chromatography. The fraction containing the desired compound was concentrated and freeze-dried to yield Compound II-3 (174 mg, 61.5%).

$^1$H-NMR (DMSO-D)) δ: 12.87 (s, 1H), 9.50 (d, J=8.4 Hz, 1H), 7.32 (br s, 2H), 6.75 (s, 2H), 5.96 (dd, J=8.4, 4.9 Hz, 1H), 5.32 (d, J=4.9 Hz, 1H), 4.97 (d, J=13.0 Hz, 1H), 4.70 (d, J=13.0 Hz, 1H), 3.75 (d, J=18.2 Hz, 1H), 3.62 (d, J=18.2 Hz, 1H), 2.05 (s, 3H), 1.51-1.40 (m, 6H).

Example 139

Synthesis of Compound I-139

Preparation of Compound 15f

[Chemical Formula 240]

Compound 15a (4.29 g, 10 mmol) was suspended in dichloromethane (40 ml), and Compound 15e (1.69 ml, 12 mmol), HOBt (1.62 g, 12 mmol), EDC (2.30 g, 12 mmol) were added sequentially and stirred overnight at room temperature. The reaction mixture was diluted with ethyl acetate, and the organic layer was then washed with aqueous sodium hydroxide water and brine, and dried over magnesium sulfate. The magnesium sulfate was filtered off, and the filtrate was concentrated under reduced pressure. The precipitated solid was corrected by filtration to yield Compound 15f (4.55 g, 86%).

$^1$H-NMR (CDCl$_3$) δ: 7.47 (1H, d, J=8.7 Hz), 7.35-7.34 (4H, m), 7.03 (1H, br s), 6.94-6.92 (3H, m), 6.83 (2H, d, J=8.4 Hz), 5.08 (2H, s), 4.95 (2H, s), 3.83 (3H, s), 3.80 (3H, s), 3.50 (2H, q, J=5.8 Hz), 2.64 (2H, t, J=5.8 Hz), 2.55 (4H, q, J=7.1 Hz), 1.01 (6H, t, J=7.1 Hz).

Compound I-139

[Chemical Formula 241]

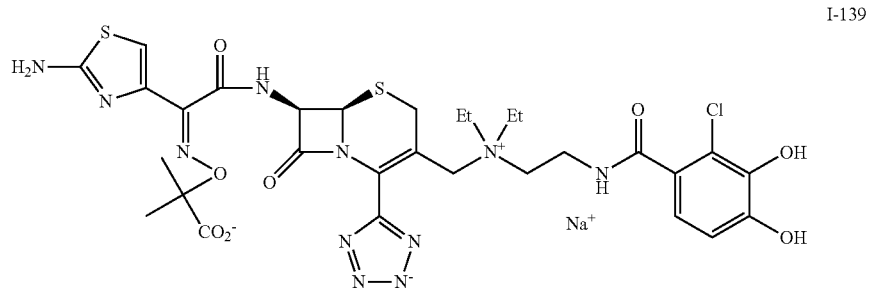

I-139

Using Compound 15f, Compound I-139 was obtained according to similar procedures as described above.

$^1$H-NMR (D$_2$O) δ: 6.96-6.88 (3H, m), 5.92-5.91 (1H, m), 5.58-5.57 (1H, m), 4.15-4.06 (2H, m), 3.79-3.75 (1H, m), 3.60-3.54 (2H, m), 3.33-3.10 (6H, m), 1.50-1.48 (6H, m), 1.11-1.07 (6H, m).

Elemental analysis for: C30H35ClN11O8S2Na(H2O)5.5

Calcd: C, 40.07; H, 5.16; N, 17.13; Cl, 3.94; S, 7.13; Na, 2.56(%)

Found: C, 40.03; H, 5.07; N, 17.26; Cl, 4.06; S, 7.03; Na, 2.44(%)

Test Example 1

Compound (I) of the invention was evaluated for in vitro antimicrobial activity thereof.

(Method)

Measurement of Minimum Inhibitory Concentration (MIC: μg/mL) was conducted according to CLSI (Clinical and Laboratory Standards Institute) method, and the amount of bacteria for inoculation was 5×10$^5$ cfu/mL, and cation-adjusted Mueller Hinton broth containing human apo-transferrin was used as a test medium, and the experiment was conducted using broth microdilution method. The bacteria used are listed below.

TABLE 1

| No. | Species | Strain Name | Enzyme Produced | Strain Type |
|---|---|---|---|---|
| 1 | P. aeruginosa | SR24 | None | Ceftazidime resistance strain |
| 2 | P. aeruginosa | SR27060 | IMP-1 | MBL producing strain (carbapenem resistance strain) |
| 3 | P. aeruginosa | SR24837 | PER-1 | ESBL producing strain |
| 4 | A. baumannii | SR27323 | OXA-23, OXA-58 | OXA-type carbapenemase producing strain (carbapenem resistance strain) |
| 5 | K. pneumoniae | ATCCBAA-1705 | KPC-2 | KPC-type carbapenemase producing strain (carbapenem resistance strain) |
| 6 | E. coli | ATCCBAA-199 | SHV-3 | ESBL producing strain |
| 7 | E. coli | ATCCBAA-200 | SHV-4 | ESBL producing strain |

As a comparative compound, Comparative Compound 1 of the formula:

[Chemical Formula 242]

which is Sodium salt of Compound I-37 disclosed in Patent Document 21 international Publication No. 2010/050468 pamphlet, was used.

(Results)

The test results are shown in Tables 2 to 4. In the table, the values of inhibitory activity are expressed in microgram/mL (μg/ml)

TABLE 2

| Compound | P. aeruginosa | | | A. baumannii | K. pneumoniae | E. coli ATCC BAA-199 | E. coli ATCC BAA-200 |
|---|---|---|---|---|---|---|---|
| | SR24 | SR27060 | SR24837 | SR27323 | ATCCBAA-1705 | | |
| Comparative Compound 1 | 0.5 | 4 | >32 | 1 | 0.125 | 2 | 4 |
| Compound I-1 | 0.5 | 0.5 | 0.5 | 0.5 | ≤0.031 | 0.063 | 0.125 |
| Compound I-2 | 0.25 | 1 | 0.25 | 1 | ≤0.031 | 0.5 | 1 |
| Compound I-3 | 0.5 | 1 | 2 | 0.25 | ≤0.031 | ≤0.031 | 0.063 |
| Compound I-4 | 0.5 | 0.5 | 4 | 0.5 | ≤0.031 | 0.125 | 0.5 |
| Compound I-5 | 0.25 | 0.5 | 2 | 0.125 | 0.063 | 0.5 | 1 |
| Compound I-6 | 0.25 | 0.5 | 1 | 2 | ≤0.031 | 0.25 | 0.5 |
| Compound I-7 | 2 | 4 | 1 | 16 | 0.063 | 0.25 | 0.5 |
| Compound I-9 | 0.25 | 4 | 2 | 1 | 0.063 | 0.25 | 0.5 |
| Compound I-10 | 0.25 | 2 | 2 | 0.5 | ≤0.031 | 0.5 | 1 |
| Compound I-11 | 0.25 | 1 | 0.063 | 0.25 | ≤0.031 | 0.125 | 0.5 |
| Compound I-13 | 0.125 | 0.5 | 2 | 2 | ≤0.031 | 0.5 | 1 |
| Compound I-14 | 0.5 | 1 | 8 | 0.125 | ≤0.031 | 0.25 | 1 |
| Compound I-15 | 0.125 | 0.5 | ≤0.031 | ≤0.031 | ≤0.031 | 0.063 | 0.25 |

TABLE 3

| Compound | P. aeruginosa | | | A. baumannii | K. pneumoniae | E. coli ATCC BAA-199 | E. coli ATCC BAA-200 |
|---|---|---|---|---|---|---|---|
| | SR24 | SR27060 | SR24837 | SR27323 | ATCC BAA-1705 | | |
| Compound I-16 | 0.125 | 0.25 | 1 | 1 | ≤0.031 | 0.25 | 0.25 |
| Compound I-18 | 0.5 | 2 | 1 | 0.125 | ≤0.031 | 0.125 | 0.25 |
| Compound I-22 | ≤0.031 | 0.25 | 0.25 | 0.125 | ≤0.031 | 0.063 | 0.125 |
| Compound I-45 | 0.125 | 0.5 | 0.5 | 0.25 | ≤0.031 | 0.125 | 0.25 |
| Compound I-46 | 0.25 | 0.5 | 1 | 0.5 | ≤0.031 | 0.125 | 0.5 |
| Compound I-47 | 0.125 | 1 | 0.5 | 0.25 | 0.063 | 0.5 | 1 |
| Compound I-48 | ≤0.031 | 0.25 | 0.125 | 0.5 | ≤0.031 | 0.25 | 0.25 |
| Compound I-49 | 0.063 | 1 | 0.25 | 1 | ≤0.031 | 0.25 | 0.5 |
| Compound I-50 | 0.25 | 1 | 2 | 1 | ≤0.031 | 0.25 | 0.5 |
| Compound I-52 | 0.25 | 1 | 2 | 1 | ≤0.031 | 0.125 | 0.5 |
| Compound I-53 | 0.25 | 0.5 | 0.063 | 1 | ≤0.031 | 0.063 | 0.125 |
| Compound I-54 | ≤0.031 | 0.25 | 0.25 | 1 | ≤0.031 | 0.25 | 0.5 |

TABLE 3-continued

| Compound | P. aeruginosa | | A. baumannii | K. pneumoniae | E. coli ATCC BAA-1705 | E. coli ATCC BAA-199 | E. coli ATCC BAA-200 |
|---|---|---|---|---|---|---|---|
| | SR24 | SR27060 | SR24837 | SR27323 | | | |
| Compound I-55 | 0.25 | 1 | 0.5 | 2 | ≤0.031 | 0.25 | 1 |
| Compound I-56 | ≤0.031 | 0.5 | 0.25 | 0.5 | ≤0.031 | 0.125 | 0.25 |

TABLE 4

| Compound | P. aeruginosa | | A. baumannii | K. pneumoniae | E. coli ATCC BAA-1705 | E. coli ATCC BAA-199 | E. coli ATCC BAA-200 |
|---|---|---|---|---|---|---|---|
| | SR24 | SR27060 | SR24837 | SR27323 | | | |
| Compound I-58 | 0.125 | 0.5 | 0.5 | 1 | ≤0.031 | 0.25 | 0.5 |
| Compound I-71 | 0.063 | 0.25 | 1 | 1 | ≤0.031 | 0.25 | 0.5 |
| Compound I-73 | 0.125 | 0.25 | 0.25 | 0.25 | ≤0.031 | 0.063 | 0.125 |
| Compound I-74 | 0.125 | 0.25 | 0.5 | 0.5 | ≤0.031 | 0.063 | 0.125 |
| Compound I-75 | 0.063 | 0.25 | 0.063 | 1 | 0.063 | 0.125 | 0.5 |
| Compound I-76 | 0.125 | 0.5 | 0.125 | 0.5 | ≤0.031 | 0.25 | 0.5 |
| Compound I-77 | ≤0.031 | 0.25 | ≤0.031 | 0.125 | ≤0.031 | ≤0.031 | 0.063 |
| Compound I-78 | 0.125 | 0.25 | 0.125 | 0.25 | ≤0.031 | 0.25 | 0.5 |
| Compound I-79 | ≤0.031 | 0.25 | 0.063 | 0.125 | ≤0.031 | 0.5 | 1 |
| Compound I-80 | ≤0.031 | 0.25 | 0.125 | 2 | ≤0.031 | 0.5 | 1 |
| Compound I-86 | 0.063 | 0.25 | ≤0.031 | 2 | 0.063 | 0.5 | 0.5 |
| Compound I-88 | 0.063 | 0.5 | ≤0.031 | 0.5 | 0.063 | 0.063 | 0.125 |
| Compound I-91 | 0.063 | 0.125 | 0.063 | 0.5 | ≤0.031 | 0.125 | 0.25 |
| Compound I-92 | 0.25 | 2 | 0.25 | 0.5 | ≤0.031 | 0.063 | 0.125 |

Test Example 2

Compound (I) of the invention was evaluated for in vitro antimicrobial activity thereof.
(Method)
Measurement of Minimum Inhibitory Concentration (MIC: μg/mL) was conducted according to CLSI (Clinical and Laboratory Standards Institute) method, and the amount of bacteria for inoculation was $5\times10^5$ cfu/mL, and cation-adjusted Iso-Sensitest broth containing human Apo-transferrin was used as a test medium, and the experiment was conducted using broth microdilution method.

TABLE 5

| No. | Species | Strain Name | Enzyme Produced | Strain Type |
|---|---|---|---|---|
| 1 | E. coli | ATCCBAA-196 | TEM-10 | ESBL producing strain |
| 2 | E. coli | ATCCBAA-200 | SHV-4 | ESBL producing strain |
| 3 | E. coli | SR01337 | TEM-1 | ESBL producing strain |
| 4 | E. cloacae | NCTC13464 | CTX-M group 9 | ESBL producing strain |
| 5 | K. pneumoniae | ATCC700603 | SHV18 | ESBL producing strain |
| 6 | A. baumannii | SR01331 | PER-1, OXA-23.51 | ESBL- &OXA-type carbapenemase producing strain (carbapenem resistance strain) |
| 7 | P. aeruginosa | SR01332 | VIM-11 | MBL producing strain (carbapenem resistance strain) |
| 8 | P. aeruginosa | SR01335 | VIM-1 like | MBL producing strain (carbapenem resistance strain) |

As a comparative compound, Comparative Compound 2 of the formula:

[Chemical Formula 243]

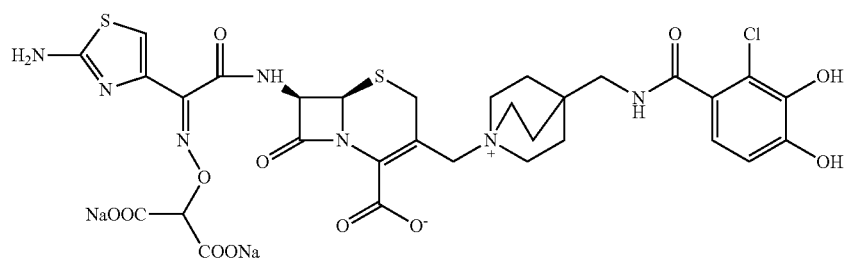

Comparative Compound 2 which is "Compound II-58" disclosed in WO2011/125967 (aforementioned "Patent Document 23") was used.

(Results)

The test results are shown in Tables 6 to 8. In the table, the values of inhibitory activity are expressed in microgram/mL (μg/ml).

TABLE 6

| Compound | E. coli ATCC BAA-196 | E. coli ATCC BAA-200 | E. coli SR01337 | E. cloacae NCTC 13464 | K. pneumoniae ATCC 700603 | A. baumannii SR01331 | P. aeruginosa SR01332 | P. aeruginosa SR01335 |
|---|---|---|---|---|---|---|---|---|
| Comparative Compound 2 | 0.5 | 1 | >32 | 0.5 | 0.5 | >32 | 32 | 4 |
| Compound I-28 | 0.125 | 0.5 | ≤0.031 | 0.5 | 0.125 | 0.5 | 1 | 1 |
| Compound I-29 | ≤0.031 | 0.063 | ≤0.031 | 0.063 | 0.125 | 0.5 | 4 | 2 |
| Compound I-30 | ≤0.031 | 0.063 | ≤0.031 | 0.063 | 0.125 | 1 | 2 | 2 |
| Compound I-31 | 0.063 | 0.25 | ≤0.031 | 0.125 | 0.125 | 0.5 | 1 | 1 |
| Compound I-32 | ≤0.031 | 0.063 | ≤0.031 | 0.063 | ≤0.031 | 0.25 | 4 | 1 |
| Compound I-33 | 0.063 | 0.25 | 0.063 | 0.25 | 0.25 | 0.5 | 2 | 4 |
| Compound I-34 | 0.063 | 0.25 | ≤0.031 | 0.5 | 0.5 | 1 | 4 | 2 |
| Compound I-36 | ≤0.031 | 0.25 | ≤0.031 | 0.125 | 0.5 | 0.5 | 0.5 | 4 |
| Compound I-37 | ≤0.031 | 0.063 | ≤0.031 | ≤0.031 | 0.063 | 0.25 | 0.25 | 0.5 |
| Compound I-38 | 0.063 | 0.25 | ≤0.031 | 0.125 | 0.125 | 0.5 | 0.5 | 1 |
| Compound I-57 | 0.063 | 0.25 | 0.063 | 0.25 | 0.125 | 0.5 | 8 | 1 |
| Compound I-60 | ≤0.031 | 0.063 | ≤0.031 | 0.063 | ≤0.031 | 0.5 | 4 | 1 |
| Compound I-61 | 0.063 | 0.25 | 0.063 | 0.125 | 0.125 | 1 | 4 | 4 |
| Compound I-62 | 0.063 | 0.25 | 0.063 | 0.25 | 0.063 | 0.25 | 8 | 4 |
| Compound I-63 | 0.063 | 0.25 | 0.063 | 0.25 | 0.25 | 1 | 2 | 2 |
| Compound I-64 | ≤0.031 | 0.063 | ≤0.031 | ≤0.031 | ≤0.031 | 0.25 | 0.5 | 4 |

TABLE 7

| Compound | E. coli ATCC BAA-196 | E. coli ATCC BAA-200 | E. coli SR01337 | E. cloacae NCTC 13464 | K. pneumoniae ATCC 700603 | A. baumannii SR01331 | P. aeruginosa SR01332 | P. aeruginosa SR01335 |
|---|---|---|---|---|---|---|---|---|
| Compound I-65 | ≤0.031 | ≤0.031 | ≤0.031 | ≤0.031 | ≤0.031 | 0.125 | 0.25 | 0.5 |

TABLE 7-continued

| | E. coli | | | E. cloacae | K. pneumoniae | A. baumannii | P. aeruginosa | |
|---|---|---|---|---|---|---|---|---|
| | ATCC | ATCC | | | | | | |
| Compound | BAA-196 | BAA-200 | SR01337 | NCTC 13464 | ATCC 700603 | SR01331 | SR01332 | SR01335 |
| Compound I-67 | ≤0.031 | 0.063 | ≤0.031 | 0.063 | ≤0.031 | 0.25 | 2 | 2 |
| Compound I-69 | 0.125 | 0.125 | ≤0.031 | 0.063 | 0.125 | 0.5 | 2 | 2 |
| Compound I-70 | ≤0.031 | 0.125 | ≤0.031 | 0.063 | ≤0.031 | 0.5 | 0.5 | 2 |
| Compound I-82 | 0.125 | 0.25 | ≤0.031 | 0.125 | 0.125 | 0.5 | 4 | 1 |
| Compound I-86 | 0.125 | 1 | ≤0.031 | 0.5 | 0.25 | 0.5 | 8 | 4 |
| Compound I-94 | 0.063 | 0.5 | 0.063 | 0.5 | 0.5 | 0.5 | 2 | 1 |
| Compound I-96 | 0.25 | 1 | 0.125 | 0.5 | 1 | 0.25 | 4 | 2 |
| Compound I-97 | 0.125 | 0.5 | 0.25 | 0.5 | 0.5 | 0.25 | 4 | 1 |
| Compound I-98 | 0.25 | 0.5 | ≤0.031 | 0.125 | 0.25 | 1 | 8 | 2 |
| Compound I-99 | ≤0.031 | 0.063 | ≤0.031 | 0.125 | 0.063 | 0.5 | 4 | 2 |
| Compound I-100 | ≤0.031 | 0.063 | ≤0.031 | 0.25 | 0.125 | 0.25 | 2 | 2 |
| Compound I-101 | ≤0.031 | 0.063 | ≤0.031 | 0.063 | 0.125 | 0.25 | 2 | 1 |
| Compound I-102 | ≤0.031 | 0.063 | ≤0.031 | 0.063 | ≤0.031 | 0.25 | 4 | 1 |
| Compound I-103 | ≤0.031 | 0.125 | ≤0.031 | 0.125 | 0.5 | 0.25 | 2 | 1 |
| Compound I-104 | ≤0.031 | 0.063 | ≤0.031 | 0.125 | 0.125 | 0.5 | 4 | 2 |
| Compound I-105 | 0.063 | 0.25 | ≤0.031 | 0.25 | 0.25 | 2 | 4 | 2 |
| Compound I-106 | ≤0.031 | 0.063 | ≤0.031 | 0.063 | ≤0.031 | 0.5 | 4 | 1 |

TABLE 8

| | E. coli | | | E. cloacae | K. pneumoniae | A. baumannii | P. aeruginosa | |
|---|---|---|---|---|---|---|---|---|
| | ATCC | ATCC | | | | | | |
| Compound | BAA-196 | BAA-200 | SR01337 | NCTC 13464 | ATCC 700603 | SR01331 | SR01332 | SR01335 |
| Compound I-107 | 0.25 | 0.5 | 0.063 | 0.063 | 0.125 | 0.5 | 2 | 2 |
| Compound I-108 | 0.25 | 0.25 | ≤0.031 | 0.125 | 0.25 | 1 | 2 | 2 |
| Compound I-109 | 0.5 | 1 | ≤0.031 | 0.125 | 0.25 | 0.5 | 0.5 | 1 |
| Compound I-110 | 0.5 | | 0.063 | 0.25 | 0.25 | 1 | 8 | 0.5 |
| Compound I-111 | 1 | | 0.125 | 0.25 | 0.5 | 1 | 2 | 2 |
| Compound I-112 | 0.5 | | 0.063 | 0.25 | 0.5 | 1 | 4 | 2 |
| Compound I-113 | 0.125 | 0.25 | ≤0.031 | ≤0.031 | 0.125 | 0.125 | 0.5 | 0.25 |
| Compound I-114 | 0.5 | 1 | ≤0.031 | 0.25 | 1. | 0.5 | 1 | 1 |
| Compound I-115 | 1 | 1 | ≤0.031 | 1 | 0.5 | 0.5 | 2 | 1 |
| Compound I-116 | 0.5 | 1 | ≤0.031 | ≤0.031 | 0.25 | 0.25 | 2 | 1 |
| Compound I-117 | 1 | 1 | 0.063 | 0.5 | 0.25 | 0.5 | 4 | 2 |
| Compound I-118 | 0.25 | 0.25 | ≤0.031 | 0.25 | 0.063 | 0.25 | 8 | 1 |
| Compound I-119 | 0.5 | 0.5 | ≤0.031 | 0.125 | 0.25 | 0.5 | 4 | 2 |
| Compound I-121 | ≤0.031 | ≤0.031 | ≤0.031 | 0.063 | ≤0.031 | 0.125 | 1 | 0.5 |

TABLE 8-continued

| | E. coli | | | | | | | |
|---|---|---|---|---|---|---|---|---|
| | ATCC | ATCC | | E. cloacae | K. pneumoniae | A. baumannii | P. aeruginosa | |
| Compound | BAA-196 | BAA-200 | SR01337 | NCTC 13464 | ATCC 700603 | SR01331 | SR01332 | SR01335 |
| Compound I-122 | 0.125 | 0.25 | ≤0.031 | 0.063 | 0.125 | 0.25 | 4 | 1 |

As shown in the above results, Compounds (I) of the invention have a wide antimicrobial spectrum, in particular, potent antimicrobial spectrum against Gram negative bacteria, and/or effectiveness against multidrug-resistant bacteria, and further to exhibit high stability against beta-lactamase producing Gram negative bacteria.

Formulation Example 1

Powder of a compound of the present invention is formulated to prepare an injecting agent.

INDUSTRIAL APPLICABILITY

The compounds of the present invention have a wide antimicrobial spectrum against Gram negative bacteria and Gram positive bacteria, and are effective as an antimicrobial drug having high stability against beta-lactamase producing Gram negative bacteria. Moreover, the present compounds have good disposition, and high water solubility, and thus particularly effective as an injecting agent.

The invention claimed is:
1. A compound of the formula:

[Chemical Formula 1]

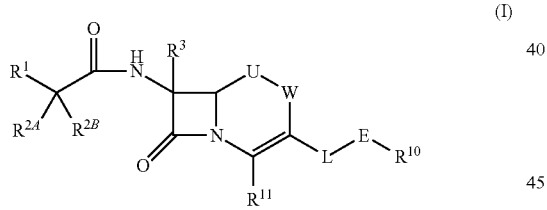

(I)

or an amino-protected compound when the amino group is present on the ring in the 7-side chain, or a pharmaceutically acceptable salt thereof,
wherein
W is —CH$_2$—, —S— or —O—;
a) U is —CH$_2$—, —S—, —S(=O)— or —O— when W is —CH$_2$—; or
b) U is —CH$_2$— when W is —S— or —O—;
L is —CH$_2$—, —CH=CH—, —CH$_2$—CH=CH— or —CH=CH—CH$_2$—;
R$^1$ is a substituted or unsubstituted carbocyclic group or a substituted or unsubstituted heterocyclic group;
with regard to R$^{2A}$ and R$^{2B}$,
a) R$^{2A}$ is a hydrogen atom, a substituted or unsubstituted amino group, —SO$_3$H, a substituted or unsubstituted amino sulfonyl group, carboxyl group, a substituted or unsubstituted (lower alkyl)oxycarbonyl group, a substituted or unsubstituted carbamoyl group, hydroxyl group, or a substituted carbonyloxy group; and R$^{2B}$ is a hydrogen atom, or b) R$^{2A}$ and R$^{2B}$ are taken together to form a substituted or unsubstituted methylidene group or a substituted or unsubstituted hydroxyimino group;
R$^3$ is a hydrogen atom, —OCH$_3$ or —NH—CH(=O);
R$^{11}$ is

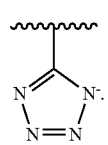

[Chemical Formula 25]

E is a group selected from the following formulae which are substituted or unsubstituted on the ring:

[Chemical Formula 12]

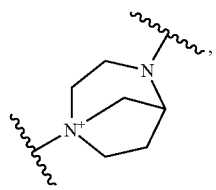

(1)

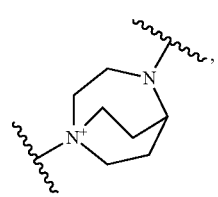

(2)

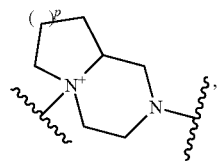

(3)

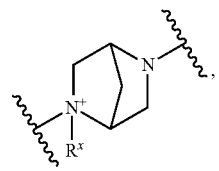

(4)

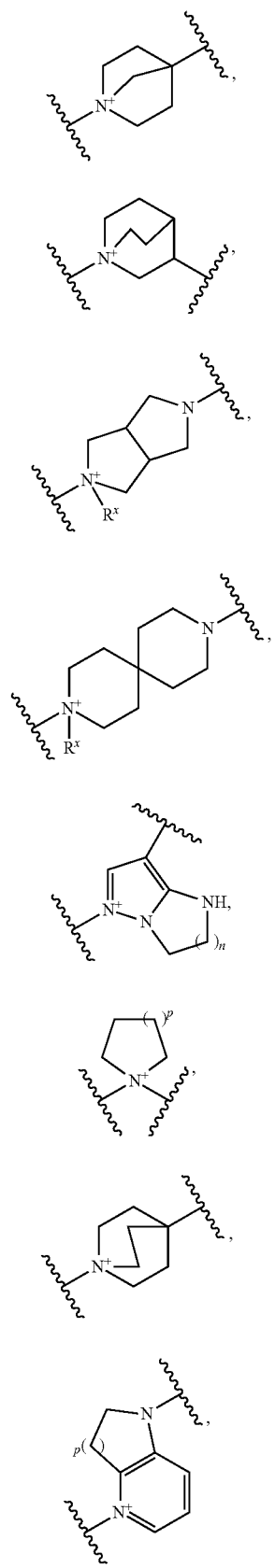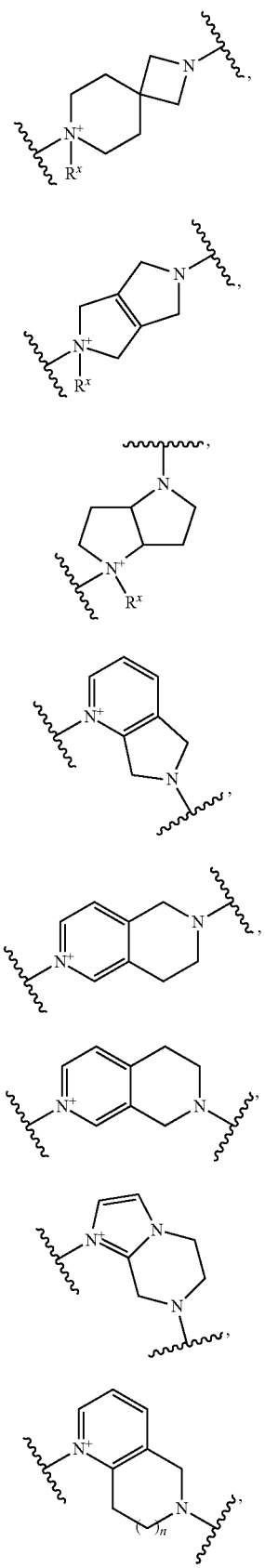

[Chemical Formula 13]
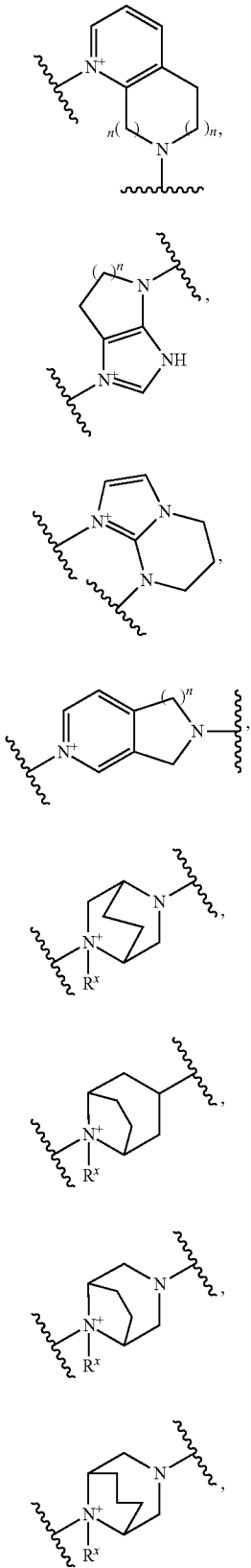
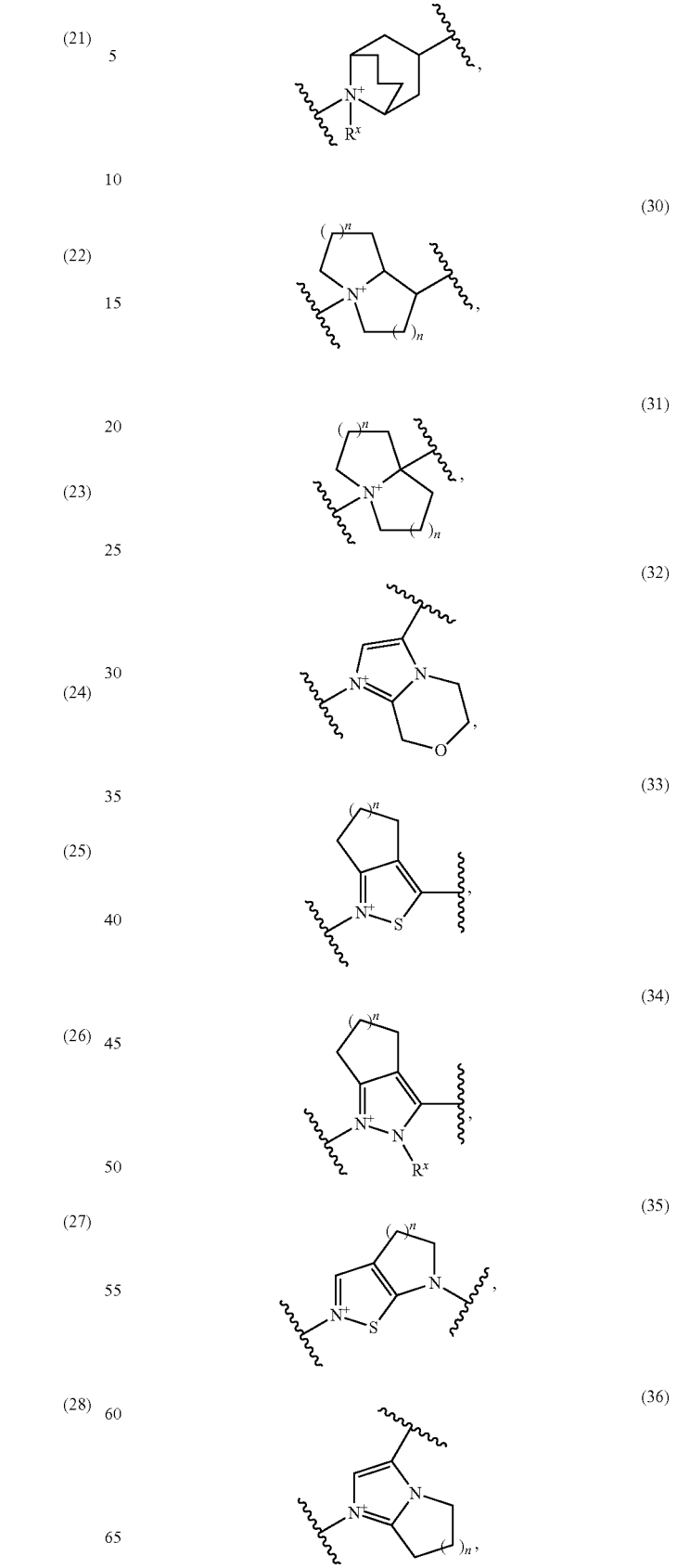

-continued
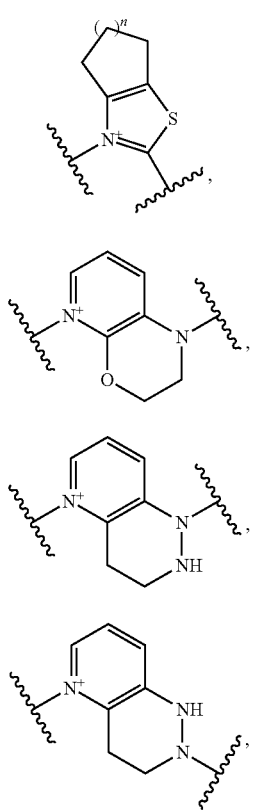
[Chemical Formula 14]
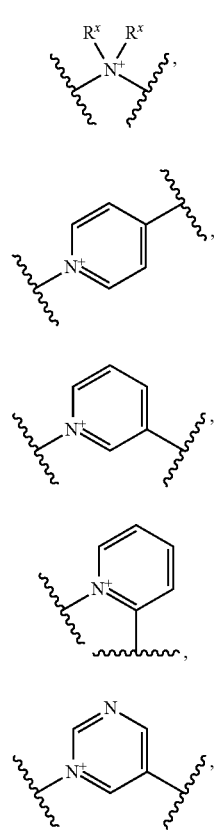
-continued
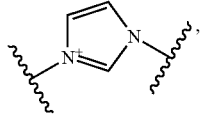
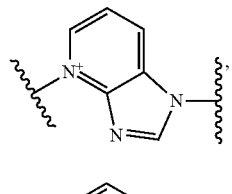
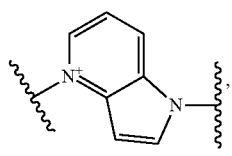
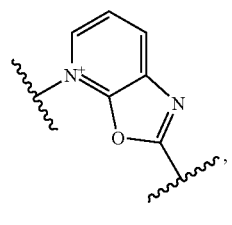
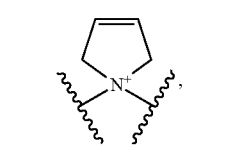
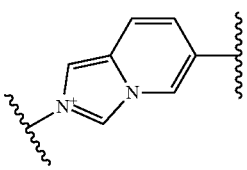
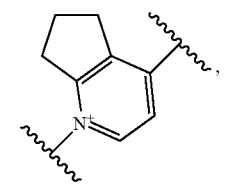
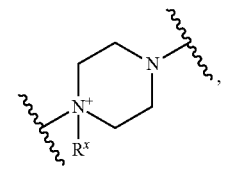
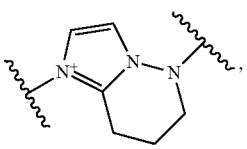

(55) 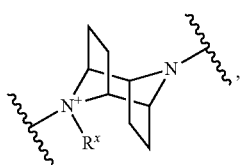
(56) 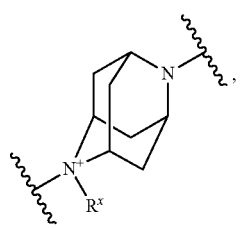
(57) 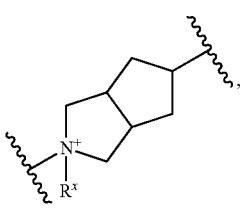
(58) 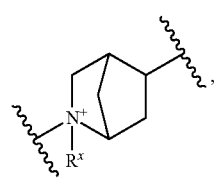
(59) 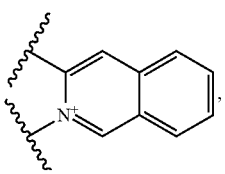
(60) 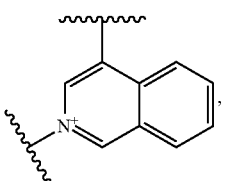
[Chemical Formula 15]
(61) 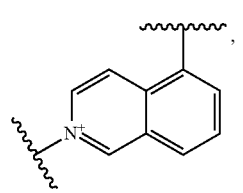
(62) 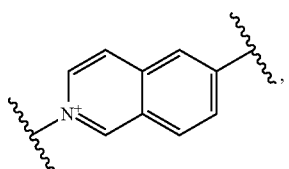
(63) 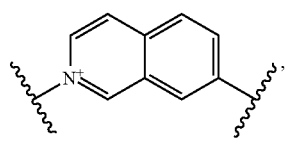
(64) 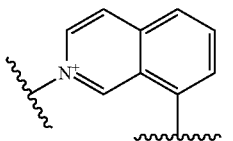
(65) 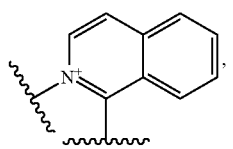
(66) 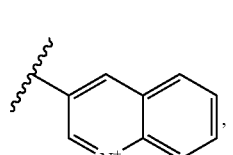
(67) 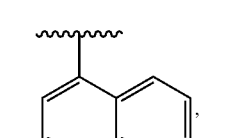
(68) 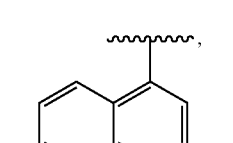
(69) 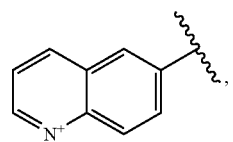
(70) 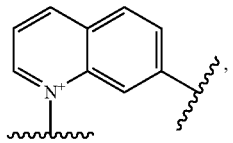
(71)

(72)
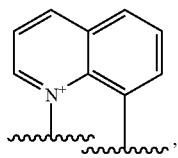

(73)
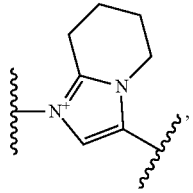

(74)
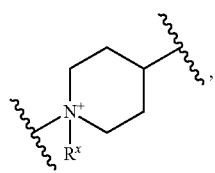

(75)
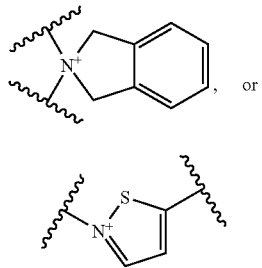, or

(76)
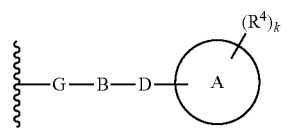

wherein the bond to the quaternary nitrogen atom binds to L, and the other bond binds to $R^{10}$; p is an integer from 1 to 3; n is an integer of 1 or 2; $R^X$ is an optionally substituted lower alkyl group;

$R^{10}$ is $R^{12}$ or a group represented by the formula:

[Chemical Formula 2]

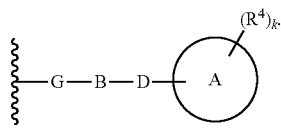

wherein ring A is a benzene ring, or a 6-membered aromatic heterocyclic group having 1-3 nitrogen atoms;

k is an integer from 2 to 5;

each $R^4$ is independently a hydrogen atom, halogen, hydroxyl group, —CN, —C(=O)—$R^5$, —C(=O)—OH, —C(=O)—$OR^5$, or —$OR^5$;

$R^5$ is a lower alkyl group or halo(lower)alkyl group; and

G is a single bond, a substituted or unsubstituted lower alkylene group, a substituted or unsubstituted alkenylene group or a substituted or unsubstituted alkynylene group;

B is a single bond or a 5- or 6-membered heterocyclic group containing at least 1-3 nitrogen atoms;

D is a single bond, —C(=O)—, —O—C(=O)—, —C(=O)—O—, —$NR^6$—, —$NR^6$—C(=O)—, —C(=O)—$NR^6$—, —$NR^6$—C(=O)—$NR^6$—, —O—, —S—, —S(=O)—, —S(=O)$_2$—$NR^6$—, —$NR^6$—S(=O)$_2$—, —$NR^6$—CH$_2$—, —CH$_2$—$NR^6$— or —S(=O)$_2$—;

each $R^6$ is independently a hydrogen atom or a substituted or unsubstituted lower alkyl group;

$R^{12}$ is a hydrogen atom, halogen, hydroxyl group, —SO$_3$H, a substituted or unsubstituted amino group, a substituted or unsubstituted carboxyl group, a substituted or unsubstituted carbamoyl group, a substituted or unsubstituted acyl group, a substituted or unsubstituted amino sulfonyl group, a substituted or unsubstituted lower alkyl group, a substituted or unsubstituted lower alkenyl group, a substituted or unsubstituted lower alkynyl group, a substituted or unsubstituted non-aromatic carbocyclic group or a substituted or unsubstituted non-aromatic heterocyclic group.

2. The compound or an amino-protected compound when the amino group is present on the ring in the 7-side chain, or a pharmaceutically acceptable salt thereof according to claim 1, wherein $R^{10}$ is a group represented by the formula:

[Chemical Formula 3]

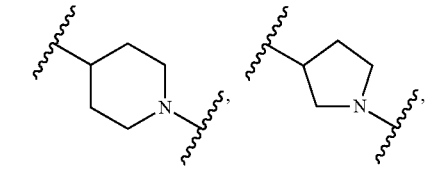

3. The compound or an amino-protected compound when the amino group is present on the ring in the 7-side chain, or a pharmaceutically acceptable salt thereof according to claim 1, wherein $R^{10}$ is $R^{12}$ wherein $R^{12}$ is as defined in claim 1.

4. The compound or an amino-protected compound when the amino group is present on the ring in the 7-side chain, or a pharmaceutically acceptable salt thereof according to claim 1, wherein G is a single bond, —CH$_2$—, —CH$_2$—CH$_2$—, —CH$_2$—CH$_2$—CH$_2$—, —CH=CH—, —CH=CH—CH$_2$—, —CH$_2$—CH=CH—, —CH$_2$—CH(CH$_3$)—, —CH$_2$—CH($^i$Pr)— or —CH$_2$—CH(Ph)— wherein $^i$Pr is isopropyl group and Ph is phenyl group.

5. The compound or an amino-protected compound when the amino group is present on the ring in the 7-side chain, or a pharmaceutically acceptable salt thereof according to claim 1, wherein B is a single bond or a group represented by the formula:

[Chemical Formula 4]

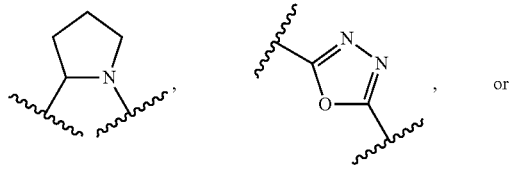

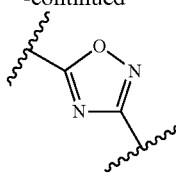

wherein the bond of the left side is attached to G and the bond of the right side is attached to D.

6. The compound or an amino-protected compound when the amino group is present on the ring in the 7-side chain, or a pharmaceutically acceptable salt thereof according to claim 1, wherein D is a single bond, —C(=O)—, —O—C(=O)—, —C(=O)—O—, —NR$^6$—, —NR$^6$—C(=O)—NR$^6$—, —NR$^6$—C(=O)— or —C(=O)—NR$^6$— wherein R$^6$ is as defined in claim 1.

7. The compound or an amino-protected compound when the amino group is present on the ring in the 7-side chain, or a pharmaceutically acceptable salt thereof according to claim 1, wherein the formula:

[Chemical Formula 5]

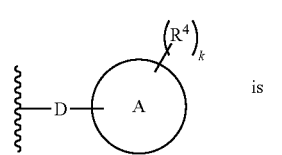

is

[Chemical Formula 6]

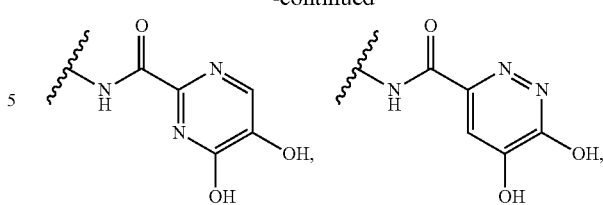

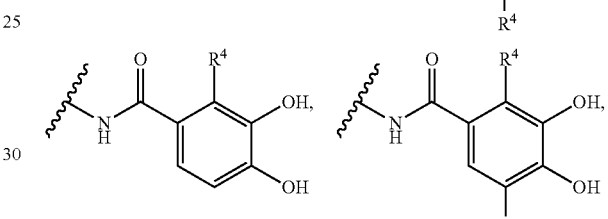

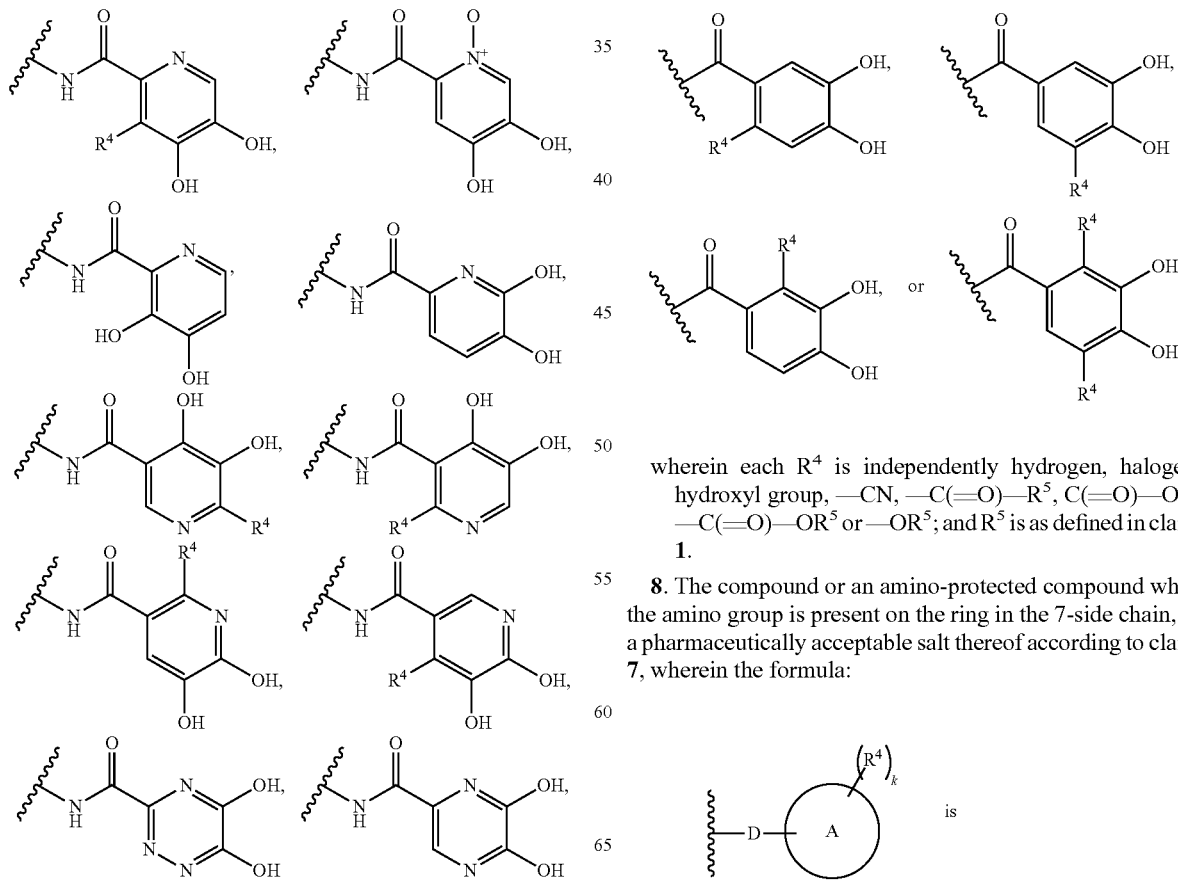

wherein each R$^4$ is independently hydrogen, halogen, hydroxyl group, —CN, —C(=O)—R$^5$, C(=O)—OH, —C(=O)—OR$^5$ or —OR$^5$; and R$^5$ is as defined in claim 1.

8. The compound or an amino-protected compound when the amino group is present on the ring in the 7-side chain, or a pharmaceutically acceptable salt thereof according to claim 7, wherein the formula:

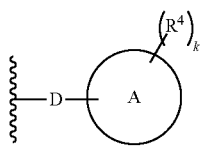

is

281
-continued
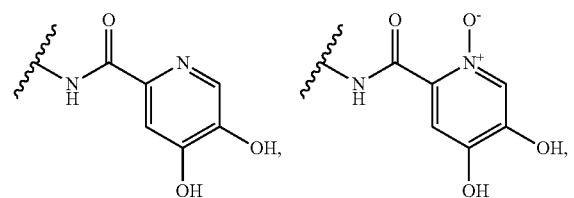
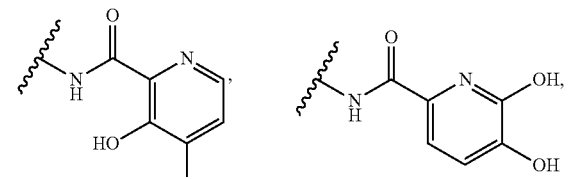
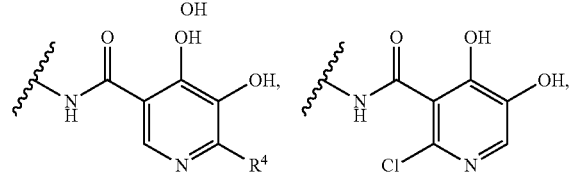
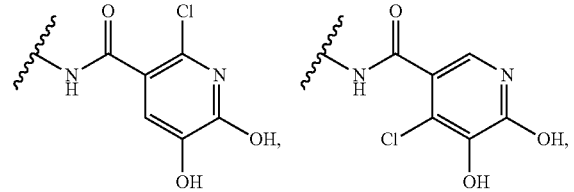
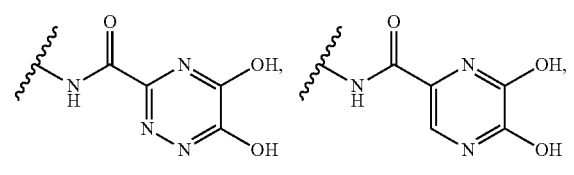
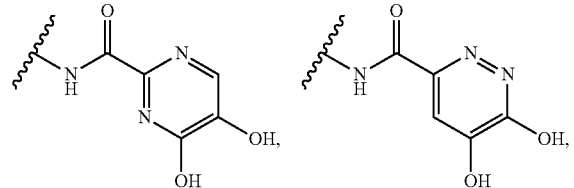
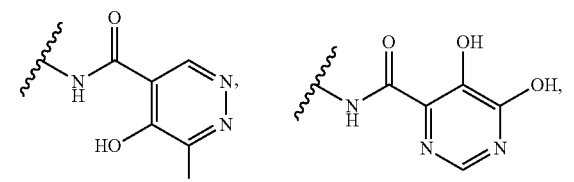
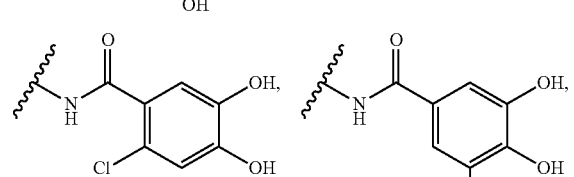
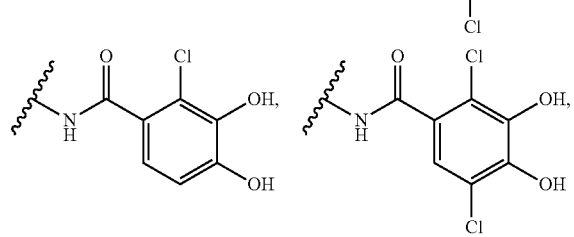
282
-continued
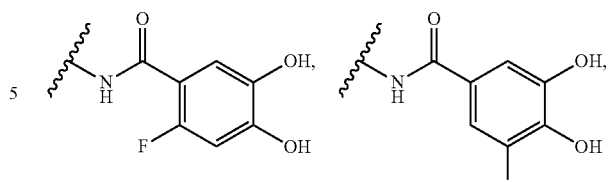
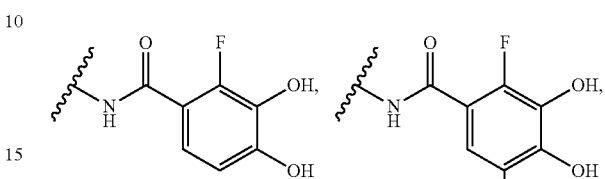
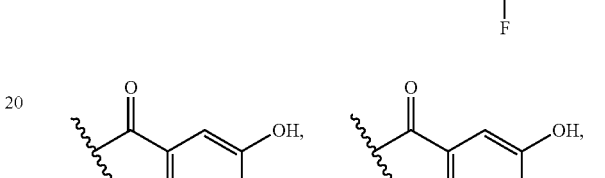
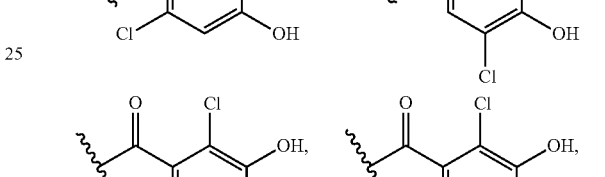
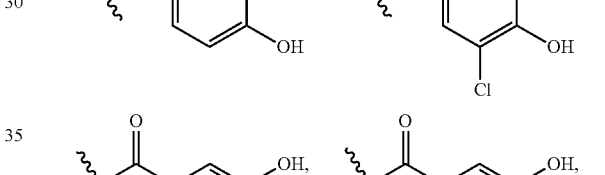
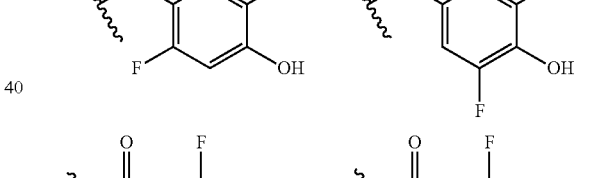
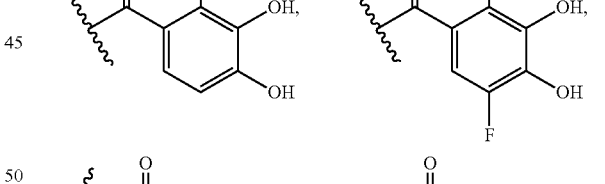
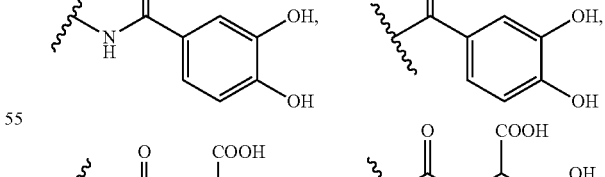
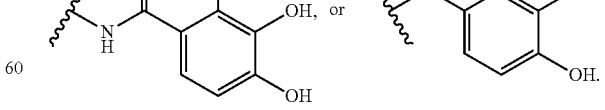
9. The compound or an amino-protected compound when the amino group is present on the ring in the 7-side chain, or a pharmaceutically acceptable salt thereof according to claim 7, wherein the formula:

[Chemical Formula 9]

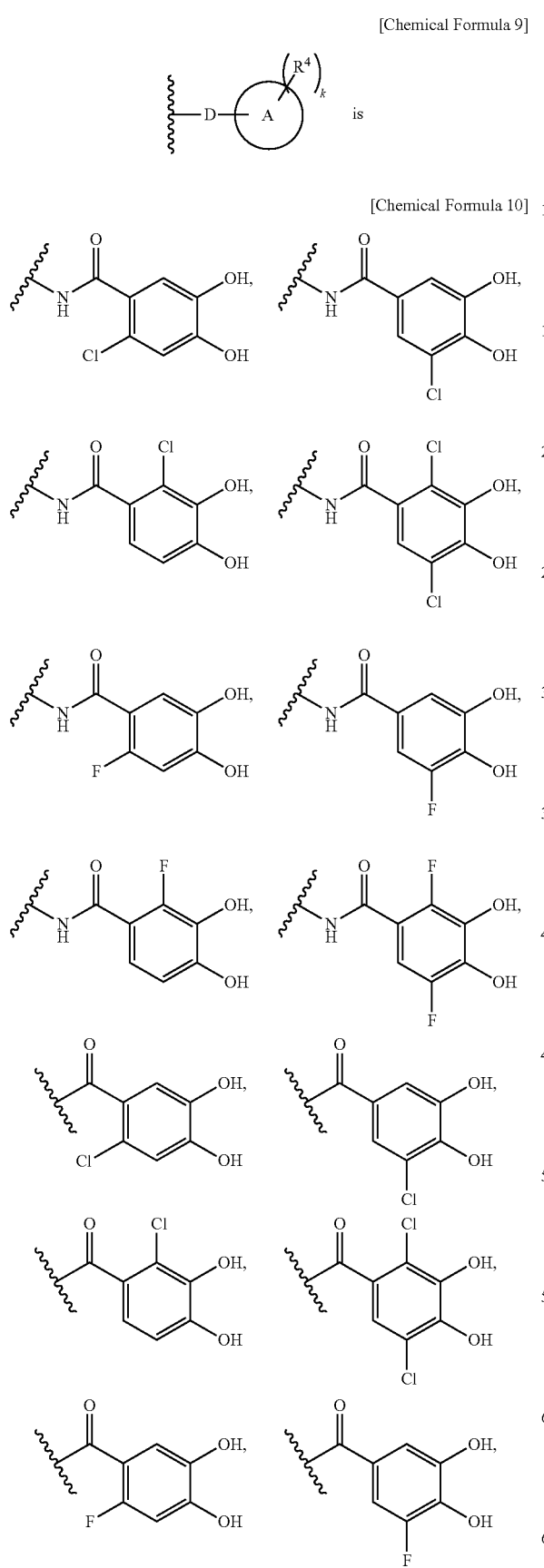

[Chemical Formula 10]

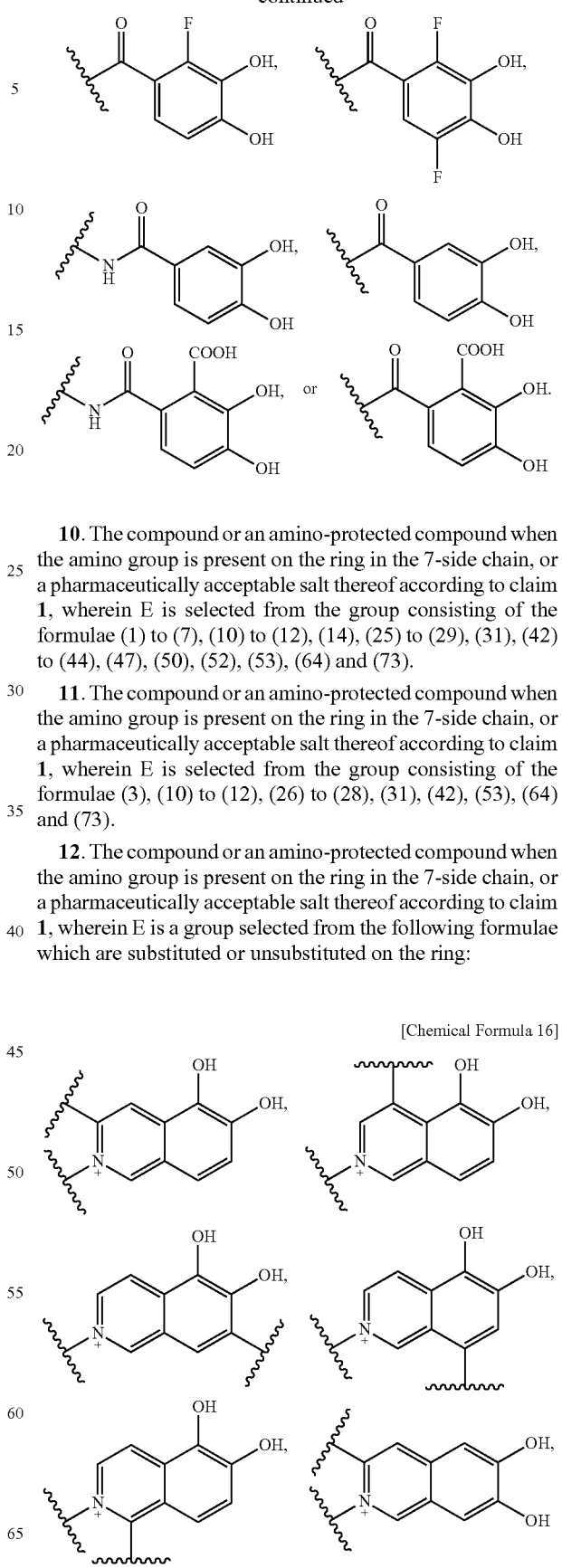

10. The compound or an amino-protected compound when the amino group is present on the ring in the 7-side chain, or a pharmaceutically acceptable salt thereof according to claim 1, wherein E is selected from the group consisting of the formulae (1) to (7), (10) to (12), (14), (25) to (29), (31), (42) to (44), (47), (50), (52), (53), (64) and (73).

11. The compound or an amino-protected compound when the amino group is present on the ring in the 7-side chain, or a pharmaceutically acceptable salt thereof according to claim 1, wherein E is selected from the group consisting of the formulae (3), (10) to (12), (26) to (28), (31), (42), (53), (64) and (73).

12. The compound or an amino-protected compound when the amino group is present on the ring in the 7-side chain, or a pharmaceutically acceptable salt thereof according to claim 1, wherein E is a group selected from the following formulae which are substituted or unsubstituted on the ring:

[Chemical Formula 16]

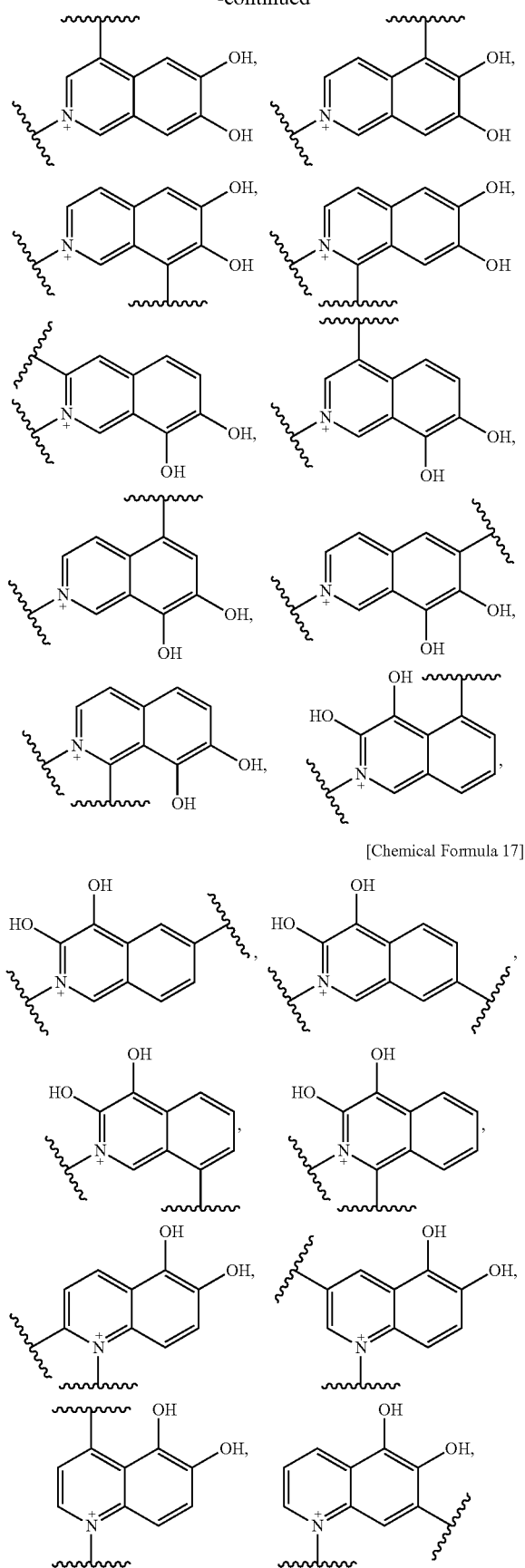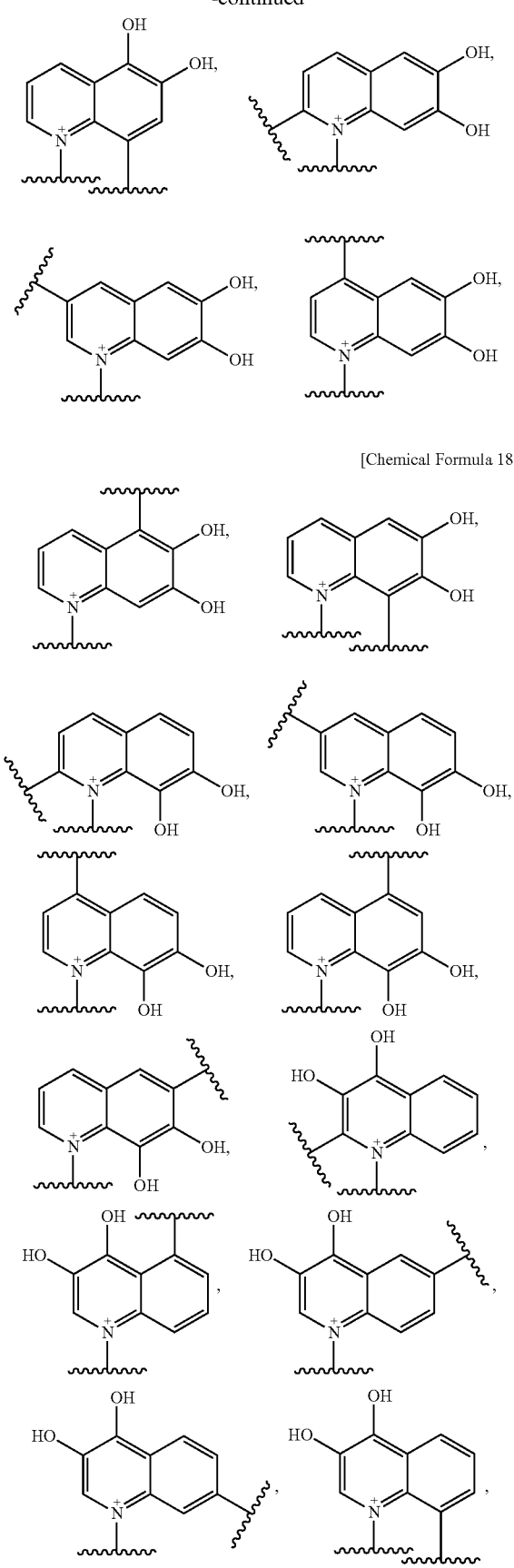
[Chemical Formula 17]
[Chemical Formula 18]

287
-continued

[Chemical Formula 19]

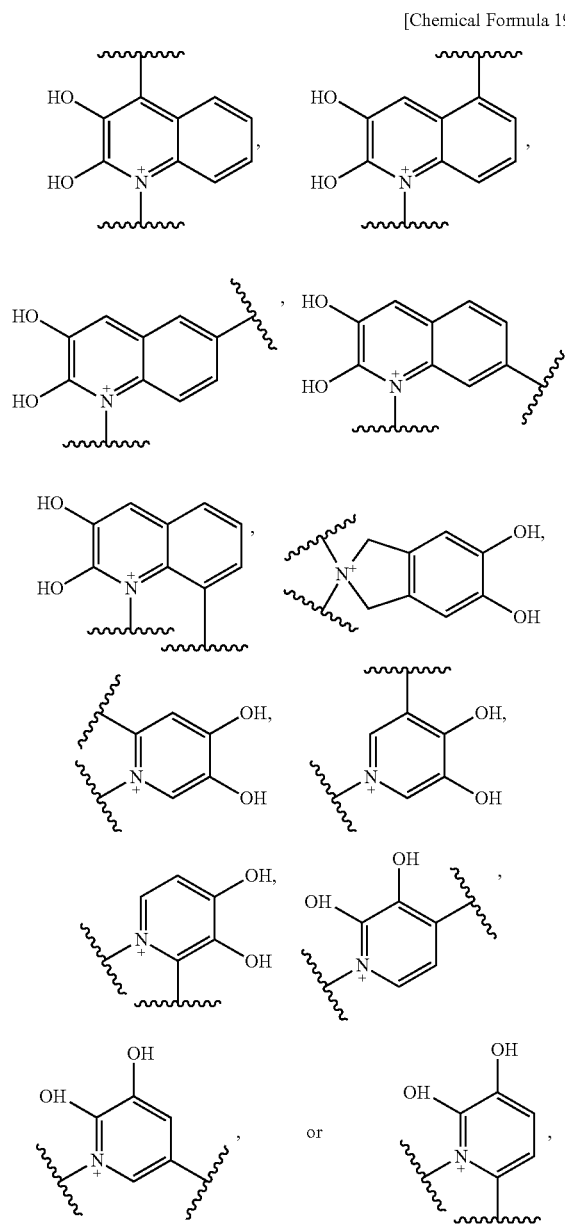

wherein the bond to the quaternary nitrogen atom binds to L, and the other bond binds to $R^{10}$.

13. The compound or an amino-protected compound when the amino group is present on the ring in the 7-side chain, or a pharmaceutically acceptable salt thereof according to claim 1, wherein E-$R^{10}$ is a group selected from the following formulae which are substituted or unsubstituted on the ring:

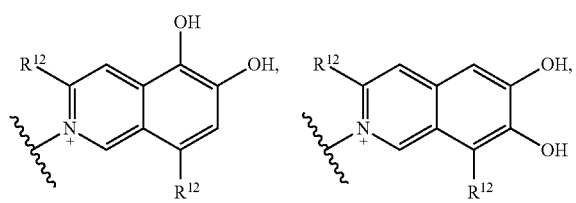

288
-continued

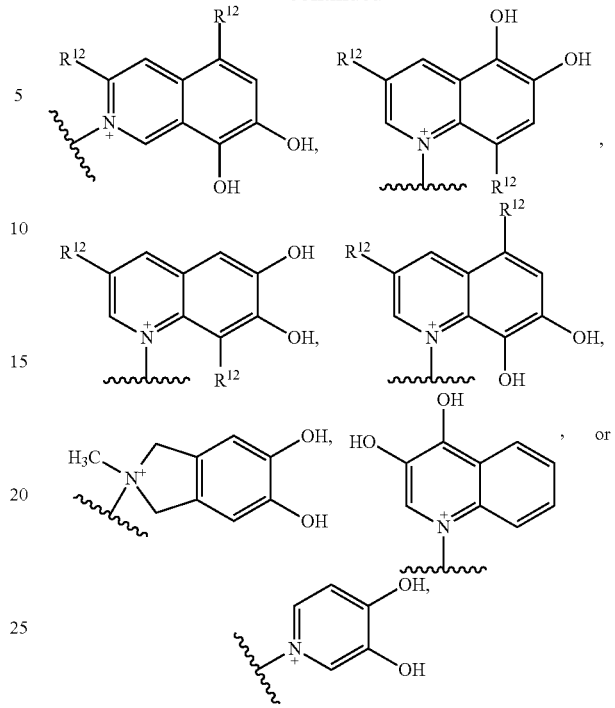

wherein the bond to the quaternary nitrogen atom binds to L, and $R^{12}$ is as defined in claim 1.

14. The compound or an amino-protected compound when the amino group is present on the ring in the 7-side chain, or a pharmaceutically acceptable salt thereof according to claim 1, wherein E-$R^{10}$ is

[Chemical Formula 21]

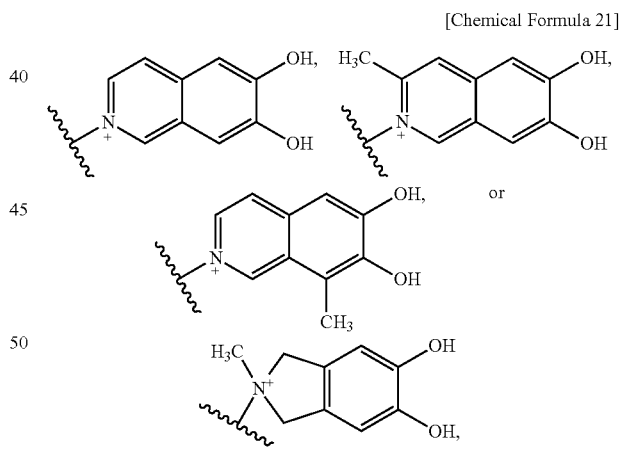

wherein the bond to the quaternary nitrogen atom binds to L.

15. The compound or an amino-protected compound when the amino group is present on the ring in the 7-side chain, or a pharmaceutically acceptable salt thereof according to claim 1, wherein U is —S—.

16. The compound or an amino-protected compound when the amino group is present on the ring in the 7-side chain, or a pharmaceutically acceptable salt thereof according to claim 1, wherein W is —$CH_2$—.

17. The compound or an amino-protected compound when the amino group is present on the ring in the 7-side chain, or a pharmaceutically acceptable salt thereof according to claim 1, wherein $R^3$ is a hydrogen atom or —$OCH_3$.

18. The compound or an amino-protected compound when the amino group is present on the ring in the 7-side chain, or a pharmaceutically acceptable salt thereof according to claim 1, wherein $R^3$ is a substituted or unsubstituted phenyl.

19. The compound or an amino-protected compound when the amino group is present on the ring in the 7-side chain, or a pharmaceutically acceptable salt thereof according to claim 1, wherein $R^1$ is represented by the formula:

[Chemical Formula 26]

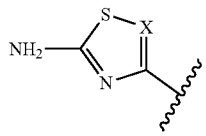

wherein X is N, C(—H) or C(—Cl).

20. The compound or an amino-protected compound when the amino group is present on the ring in the 7-side chain, or a pharmaceutically acceptable salt thereof according to claim 19, wherein X is N.

21. The compound or an amino-protected compound when the amino group is present on the ring in the 7-side chain, or a pharmaceutically acceptable salt thereof according to claim 19, wherein X is C(—H) or C(—Cl).

22. The compound or an amino-protected compound when the amino group is present on the ring in the 7-side chain, or a pharmaceutically acceptable salt thereof according to claim 1, wherein $R^{2A}$ is a hydrogen atom, a substituted or unsubstituted amino group, —$SO_3H$, a substituted or unsubstituted amino sulphonyl group, carboxyl group, a substituted or unsubstituted carbamoyl group, hydroxyl group, or substituted carbonyloxy group, and $R^{2B}$ is a hydrogen atom.

23. The compound or an amino-protected compound when the amino group is present on the ring in the 7-side chain, or a pharmaceutically acceptable salt thereof according to claim 1, wherein $R^{2A}$ is a substituted amino group shown below:

[Chemical Formula 28]

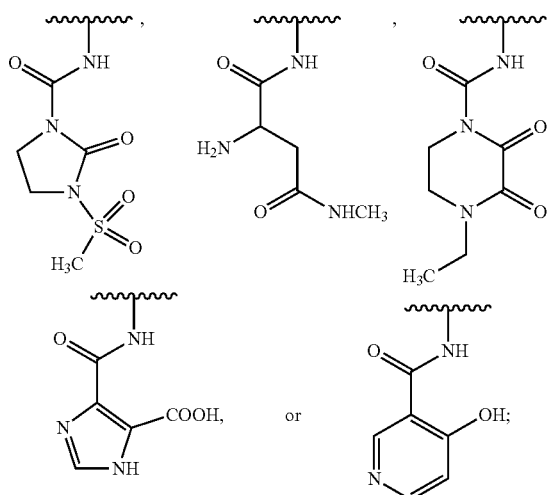

a substituted amino sulfonyl group shown below:

[Chemical Formula 28]

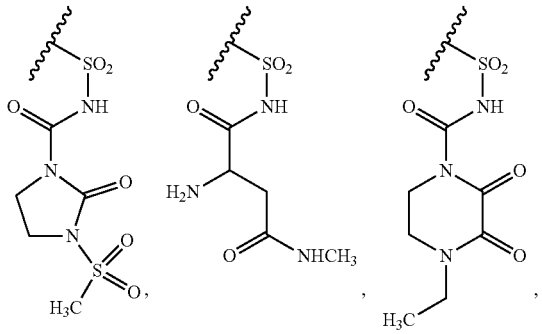

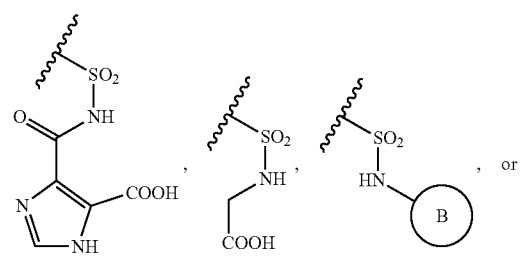

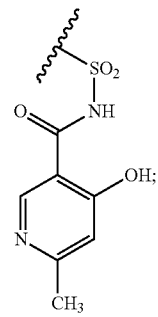

wherein ring B represents a substituted or unsubstituted heterocyclic group;

a substituted carbamoyl group shown below:

[Chemical Formula 29]

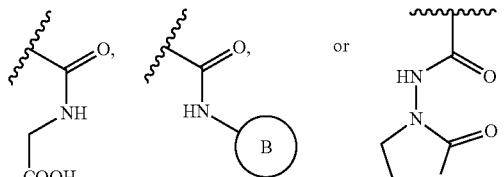

wherein ring B represents a substituted or unsubstituted heterocyclic group; or a substituted carbonyloxy group shown below:

[Chemical Formula 30]

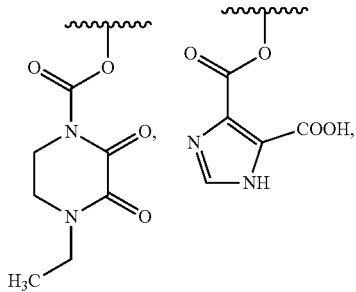

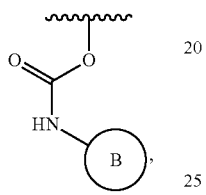

wherein ring B represents a substituted or unsubstituted heterocyclic group.

24. The compound or an amino-protected compound when the amino group is present on the ring in the 7-side chain, or a pharmaceutically acceptable salt thereof according to claim 1, wherein $R^{2A}$ and $R^{2B}$ are taken together to form a substituted methylidene group shown below:

[Chemical Formula 31]

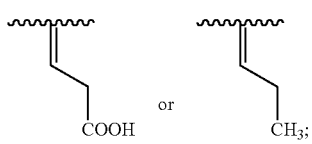

a substituted hydroxyimino group shown below:

[Chemical Formula 32]

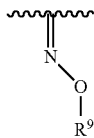

wherein $R^9$ is a substituted or unsubstituted lower alkyl group.

25. The compound or an amino-protected compound when the amino group is present on the ring in the 7-side chain, or a pharmaceutically acceptable salt thereof according to claim 1, wherein $R^{2A}$ and $R^{2B}$ are taken together to form a substituted hydroxyimino group shown below:

[Chemical Formula 33]

wherein $R^7$ and $R^8$ are each independently a hydrogen atom, halogen, hydroxyl group, carboxyl group, a substituted or unsubstituted lower alkyl group, a substituted or unsubstituted carbocyclic group, or a substituted or unsubstituted heterocyclic group, or $R^7$ and $R^8$ may be taken together with a neighboring atom to form a substituted or unsubstituted carbocyclic group or a substituted or unsubstituted heterocyclic group;

Q is a single bond, a substituted or unsubstituted carbocyclic group or a substituted or unsubstituted heterocyclic group; and m is an integer from 0 to 3.

26. A pharmaceutical composition, which comprises a compound or an amino-protected compound when the amino group is present on the ring in the 7-side chain, or a pharmaceutically acceptable salt thereof according to claim 1.

* * * * *